US00RE48345E

(19) United States
(12) Reissued Patent
Chin et al.

(10) Patent Number: US RE48,345 E
(45) Date of Reissued Patent: Dec. 8, 2020

(54) COMPOSITIONS AND METHODS FOR INHIBITING GENE EXPRESSION OF HEPATITIS B VIRUS

(71) Applicant: Arrowhead Pharmaceuticals, Inc., Pasadena, CA (US)

(72) Inventors: Daniel J. Chin, Foster City, CA (US); Jochen Deckert, Kulmbach (DE); Markus Hossbach, Kulmbach (DE); Matthias John, Hallstadt (DE)

(73) Assignee: Arrowhead Pharmaceuticals Inc., Pasadena, CA (US)

(21) Appl. No.: 15/241,733

(22) Filed: Aug. 19, 2016

Related U.S. Patent Documents

Reissue of:
(64) Patent No.: 8,809,293
Issued: Aug. 19, 2014
Appl. No.: 13/535,454
Filed: Jun. 28, 2012

(30) Foreign Application Priority Data

Jun. 30, 2011 (EP) ..... 11172235

(51) Int. Cl.
*C12N 15/11* (2006.01)
*A61K 48/00* (2006.01)
*C07H 21/02* (2006.01)
*C07H 21/04* (2006.01)
*A61K 31/713* (2006.01)
*C12N 15/113* (2010.01)

(52) U.S. Cl.
CPC ..... *A61K 31/713* (2013.01); *C12N 15/1131* (2013.01); *C12N 2310/14* (2013.01); *C12N 2310/315* (2013.01); *C12N 2310/321* (2013.01); *C12N 2310/335* (2013.01); *C12N 2310/3521* (2013.01)

(58) Field of Classification Search
None
See application file for complete search history.

(56) References Cited

U.S. PATENT DOCUMENTS 3,687,808 A 8/1972 Merigan, Jr. et al.
4,469,863 A 9/1984 Ts'o et al.
5,023,243 A 6/1991 Tullis
5,034,506 A 7/1991 Summerton et al.
5,134,066 A 7/1992 Rogers et al.
5,212,295 A 5/1993 Cook
5,214,134 A 5/1993 Weis et al.
5,216,141 A 6/1993 Benner
5,218,105 A 6/1993 Cook et al.
5,264,423 A 11/1993 Cohen et al.
5,264,562 A 11/1993 Matteucci
5,321,131 A 6/1994 Agrawal et al.
5,328,470 A 7/1994 Nabel et al.
5,359,044 A 10/1994 Cook et al.
5,399,676 A 3/1995 Froehler
5,405,939 A 4/1995 Suhadolnik et al.
5,453,496 A 9/1995 Caruthers et al.
5,455,233 A 10/1995 Spielvogel et al.
5,459,255 A 10/1995 Cook et al.
5,466,677 A 11/1995 Baxter et al.
5,466,786 A 11/1995 Buhr et al.
5,470,967 A 11/1995 Huie et al.
5,489,677 A 2/1996 Sanghvi et al.
5,506,351 A 4/1996 McGee
5,519,134 A 5/1996 Acevedo et al.
5,521,302 A 5/1996 Cook
5,539,082 A 7/1996 Nielsen et al.
5,541,307 A 7/1996 Cook et al.
5,552,540 A 9/1996 Haralambidis
5,554,746 A 9/1996 Ravikumar et al.
5,571,902 A 11/1996 Ravikumar et al.
5,578,718 A 11/1996 Cook et al.
5,587,361 A 12/1996 Cook et al.
5,587,469 A 12/1996 Cook et al.
5,587,470 A 12/1996 Cook et al.
5,591,722 A 1/1997 Montgomery et al.
5,594,121 A 1/1997 Froehler et al.
5,596,091 A 1/1997 Switzer
5,597,909 A 1/1997 Urdea et al.
5,602,240 A 2/1997 De Mesmaeker et al.
(Continued)

FOREIGN PATENT DOCUMENTS

CN 101426912 A 5/2009
CN 101948834 A 1/2011
(Continued)

OTHER PUBLICATIONS

"Oligo Calc" http://biotools.nubic.northwestern.edu/OligoCalc.html (accessed Dec. 15, 2017).*
Chen et al. "RNAi for Treating Hepatitis B Viral Infection" Pharmaceutical Research, vol. 25, No. 1, pp. 72-86, Jan. 2008.*
Ortigau et al. "Antisense Effect of Oligodeoxynucleotides with Inverted Terminal Intemucleotidic Linkages: A Minimal Modification Protecting against Nucleolytic Degradation" Antisense Research and Development 2:129-146 (1992).*
Elbashir et al. "Functional anatomy of siRNAs for mediating efficient RNAi in Drosophila melanogaster embryo lysate" EMBO Journal vol. 20 No. 23 pp. 6877-6888, 2001.*
Reynolds et al. "Rational siRNA design for RNA.interference" Nature Biotechnology vol. 22 No. 3 pp. 326-330 Mar. 2004.*
Wooddell, et al.; "Hepatocyte—targeted RNAi Therapeutics for the Treatment of Chronic Hepatitis B Virus infection"; Molecular Therapy; vol. 21; No. 5; pp. 973-985; (2013).
Notice of First Office Action for corresponding China Application 201280031939.3 dated Dec. 3, 2014.
(Continued)

*Primary Examiner* — Bruce R Cambell
(74) *Attorney, Agent, or Firm* — Morrison & Foerster LLP

(57) ABSTRACT

The invention relates to a double-stranded ribonucleic acid (dsRNA) for inhibiting the expression of a Hepatitis B Virus gene. The invention also relates to a pharmaceutical composition comprising the dsRNA or nucleic acid molecules or vectors encoding the same together with a pharmaceutically acceptable carrier; methods for treating diseases caused by Hepatitis B Virus infection using said pharmaceutical composition; and methods for inhibiting the expression of a Hepatitis B Virus gene in a cell.

69 Claims, 38 Drawing Sheets

Specification includes a Sequence Listing.

(56) References Cited

U.S. PATENT DOCUMENTS

| | | | |
|---|---|---|---|
| 5,608,046 | A | 3/1997 | Cook et al. |
| 5,610,289 | A | 3/1997 | Cook et al. |
| 5,646,265 | A | 7/1997 | McGee |
| 5,663,312 | A | 9/1997 | Chaturvedula |
| 5,670,633 | A | 9/1997 | Cook et al. |
| 5,700,920 | A | 12/1997 | Altmann et al. |
| 6,127,533 | A | 10/2000 | Cook et al. |
| 6,166,197 | A | 12/2000 | Cook et al. |
| 6,172,209 | B1 | 1/2001 | Manoharan et al. |
| 6,262,241 | B1 | 7/2001 | Cook et al. |
| 6,271,358 | B1 | 8/2001 | Manoharan et al. |
| 8,232,383 | B2 | 7/2012 | Mcswiggen |
| 8,242,257 | B2 | 8/2012 | Beigelman |
| 8,273,866 | B2 | 9/2012 | Mcswiggen |
| 8,618,277 | B2 | 12/2013 | Beigelman |
| 8,648,185 | B2 | 2/2014 | Mcswigen |
| 8,809,293 | B2 | 8/2014 | Chin et al. |
| 8,828,956 | B2 | 9/2014 | Manoharan |
| 9,181,551 | B2 | 11/2015 | Mcswiggen |
| 9,222,092 | B2 | 12/2015 | Giese |
| 9,260,471 | B2 | 2/2016 | Cancilla |
| 9,290,760 | B2 | 3/2016 | Rajeev |
| 9,352,048 | B2 | 5/2016 | Manoharan |
| 9,566,340 | B2 | 2/2017 | Manoharan |
| 9,695,423 | B2 | 7/2017 | Giese |
| 9,771,588 | B2 | 9/2017 | Mcswiggen |
| 9,790,505 | B2 | 10/2017 | Giese |
| 9,943,604 | B2 | 4/2018 | Seth |
| 9,970,005 | B2 | 5/2018 | Cancilla |
| 10,098,959 | B2 | 10/2018 | Migawa |
| 10,130,651 | B2 | 11/2018 | Wooddell |
| 10,131,907 | B2 | 11/2018 | Forst |
| 10,294,474 | B2 | 5/2019 | Li |
| 10,351,852 | B2 | 7/2019 | Mcswiggen |
| 10,590,418 | B2 | 3/2020 | Kay |
| 2003/0124651 | A1 | 7/2003 | Pasupuleti |
| 2003/0206887 | A1 | 11/2003 | Morissay ..... A61K 38/21 424/93.2 |
| 2005/0032733 | A1 | 2/2005 | McSwiggen |
| 2006/0063731 | A1 | 3/2006 | Lewis |
| 2006/0292691 | A1 | 12/2006 | McSwiggen et al. |
| 2007/0197460 | A1 | 8/2007 | Fougerolles |
| 2008/0113351 | A1 | 5/2008 | Naito et al. |
| 2008/0145346 | A1 | 6/2008 | Ng |
| 2012/0165393 | A1 | 6/2012 | Rozema |
| 2013/0005793 | A1 | 1/2013 | Chin |
| 2013/0150433 | A1 | 6/2013 | Bartz |
| 2013/0281658 | A1 | 10/2013 | Rozema |
| 2016/0152973 | A1 | 6/2016 | Jadhav |
| 2017/0035796 | A1 | 2/2017 | Wooddell |
| 2017/0137821 | A1 | 5/2017 | Limphong |
| 2017/0369883 | A1 | 12/2017 | Swayze |
| 2018/0064819 | A1 | 3/2018 | Li |
| 2018/0371463 | A1 | 12/2018 | Limphong |
| 2019/0022123 | A1 | 1/2019 | Wooddell |
| 2019/0160176 | A1 | 5/2019 | Heyes |
| 2019/0255091 | A1 | 8/2019 | Li |
| 2019/0256849 | A1 | 8/2019 | Li |
| 2019/0292547 | A1 | 9/2019 | Li |

FOREIGN PATENT DOCUMENTS

| | | | |
|---|---|---|---|
| EP | 1752536 | | 2/2007 |
| EP | 1752536 | A1 | 2/2007 |
| EP | 1560840 | B1 | 5/2015 |
| EP | 1931781 | B1 | 7/2016 |
| EP | 3218487 | B1 | 9/2017 |
| JP | H10510435 | A | 10/1998 |
| KR | 10-2007-0110135 | A | 11/2007 |
| RU | 2418068 | C2 | 5/2011 |
| TW | I659040 | B | 5/2019 |
| WO | 91/06309 | | 5/1991 |
| WO | 1991006309 | A1 | 5/1991 |
| WO | 93/07883 | | 4/1993 |
| WO | 1993007883 | A1 | 4/1993 |
| WO | WO-1996/39502 | A1 | 12/1996 |
| WO | 00/22113 | | 4/2000 |
| WO | 2000022113 | A1 | 4/2000 |
| WO | 00/31105 | | 6/2000 |
| WO | 2000031105 | A1 | 6/2000 |
| WO | WO02081494 | A1 | 10/2002 |
| WO | 03/020931 | | 3/2003 |
| WO | 2003020931 | A2 | 3/2003 |
| WO | 2005/065719 | | 7/2005 |
| WO | 2005065719 | A1 | 7/2005 |
| WO | 2005/116204 | | 12/2005 |
| WO | WO-2005/116204 | A1 | 12/2005 |
| WO | 2006/017932 | A1 | 2/2006 |
| WO | 2006017932 | A1 | 2/2006 |
| WO | WO-2006/096018 | A1 | 9/2006 |
| WO | 2007022369 | A2 | 2/2007 |
| WO | WO2009038266 | A1 | 3/2009 |
| WO | 2010/135322 | | 11/2010 |
| WO | 2010135322 | A1 | 11/2010 |
| WO | 2011/003780 | | 1/2011 |
| WO | 2011003780 | A1 | 1/2011 |
| WO | WO-2011/073218 | A1 | 6/2011 |
| WO | WO2011148193 | A1 | 12/2011 |
| WO | WO 2012/024170 | | 2/2012 |
| WO | WO2013003520 | A1 | 1/2013 |
| WO | WO2013159109 | A1 | 10/2013 |
| WO | WO2013176772 | A1 | 11/2013 |
| WO | WO2014037377 | A1 | 3/2014 |
| WO | WO2015050871 | A2 | 4/2015 |
| WO | WO2016057893 | A9 | 5/2016 |
| WO | WO2016077321 | A1 | 5/2016 |
| WO | WO2016077349 | A1 | 5/2016 |
| WO | WO2017015175 | A1 | 1/2017 |
| WO | WO2017019891 | A2 | 2/2017 |
| WO | WO2017027350 | A2 | 2/2017 |
| WO | WO2018027106 | A2 | 2/2018 |
| WO | WO2018044350 | A1 | 3/2018 |

OTHER PUBLICATIONS

Notice on the Second Office Action for corresponding China Application 201280031939.3 dated Aug. 24, 2015.

Notice of Reasons for Rejection for corresponding Japanese Patent Application No. 2014-518986 dated Feb. 24, 2016.

Office Action for corresponding Taiwan Patent Application No. 101123338 dated Mar. 4, 2016.

Zhang, Y-L et al "RNA Interference inhibits hepatitis B virus of different genotypes in vitro and in vivo." BMC Microbial. 2010, vol. 10:214, p. 1-10.

Cone RD et al., "High-efficiency gene transfer into mammalian cells: Generation of helper-free recombinant retrovirus with broad mammalian host range," Proc. Nall. Acad. Sci. USA (1984) 81: 6349-6353.

Crooke et al., "Pharmacokinetic Properties of Several Novel Oligonucleolide Analogs in Mice." J. Pharmacal. Exp. Ther. (1996), 277: 923-927.

Hamm ML et al., "Incorporation of 2'-Deoxy-2'-mercaptocy1idine into Oligonucleotides via Phosphoramidite Chemistry," J. Org. Chem. (1997) 62: 3415-3420.

Kabanov et al., "A new class of antivirals; antisense oligonucleotides combined with a hydrophobic substituent effectively inhibit influenza virus reproduction and synthesis of virus-specific proteins in MOCK cells," FEBS Lett. (1990) 259: 327-330.

Oberhauser et al., "Effective Incorporation of 2"-0-methyl-oligoribonucleotides Into Liposomes and Enhanced Cell Association Through Modification with Thiocholesterol," Nucl. Acids Research (1992) 20: 533-538.

Samukov VV et al., "2-(4-Nitrophenyl)sulfonylethoxycarbonyl (Nsc) Group as a Base-Labile a-Amino Protection for Solid Phase Peptide Synthesis," Tetrahedron Letters (1994) 35(42): 7821-7824.

Genbank Accession No. AP007263; (2005).

Genbank Accession No. AB602818; (2011).

Genbank Accession No. AB644286; (2012).

Genbank Accession No. AB554024; (2011).

(56) References Cited

OTHER PUBLICATIONS

First Substantive Examination Report for corresponding Israeli Patent Application No. 230226 dated Nov. 7, 2016.
Search Report for corresponding Eurasian Application No. 201690497 dated Aug. 12, 2016.
English translation of the Notification of Reasons for Refusal issued in corresponding JP Patent Application No. 2014-518986 dated Jun. 8, 2017, 8 pages.
English translation of the Notice of Reasons for Rejection, issued in Japanese Patent Application No. 2017-073870, dated Apr. 26, 2018, 10 pages.
Kurreck, "siRNA Efficiency: Structure or Sequence—That Is The Question," Journal of Biomedicine and Biotechnology, vol. 2006, pp. 1-7, 2006.
Zhang, Ya-Li et al., "RNA Interference inhibits Hepatitis B Virus of different genotypes in Vitro and in Vivo," BMC Microbiology, vol. 10:214, 2010.
Chen, Z. et al. (Apr. 2005; e-pub. Mar. 20, 2005). "Combination of Small Interfering RNAs Mediates Greater Inhibition of Human Hepatitis B Virus Replication and Antigen Expression," *Journal of Zhejiang University* 6B(4):236-241.
Muzyczka, N. (1992). "Use of Adeno-Associated Virus as a General Transduction Vector for Mammalian Cells," in Current Topics in Microbiology and Immunology, Springer-Verlag, Berlin, Heidelberg, 158:97-129.
Tei, K. et al.(Oct. 1, 2006). "Q&A Regarding Selection of siRNA Sequences," Chapter 4 in Jikken Naruhodo Q&A, Yodosha Co., Ltd., pp. 91-93, English translation provided.
Australian Office Action dated Oct. 11, 2018 for AU Application No. 2017210563 filed on Aug. 3, 2017, 3 pages.
Chinese Office Action dated Oct. 8, 2018 for Chinese Application No. 201610903171.4 filed on Oct. 17, 2016, 6 pages.
Eurasian Office Action dated Jul. 5, 2018 for Eurasian Application No. 201690497 filed on Mar. 28, 2016, 2 pages.
European Search Report dated Nov. 21, 2018 (Partial) for EP Application No. 18187709.3 filed on Aug. 7, 2018, 12 pages.
European Search Report dated Mar. 21, 2019 (Extended) for EP Application No. 18187709.3 filed on Aug. 7, 2018, 13 pages.
European Search Report dated Nov. 10, 2014 for EP Application No. 12804876.6 filed on Jun. 28, 2012, 6 pages.
International Search Report and Written Opinion dated Sep. 24, 2019 for PCT Application No. PCT/US2012/044505 filed Jun. 28, 2012, 10 pages.
Israeli Office Action dated Jul. 29, 2018 for corresponding Israeli Patent Application No. 230226, filed on Feb. 27, 2014, 5 pages.
Korean Office Action dated Aug. 16, 2018 for KR Application No. 10-2013-7031029 filed on Nov. 22, 2013, 9 pages.
Taiwanese Notice of Allowance dated Dec. 6, 2018 for Taiwanese Patent Application No. 101123338 filed on Jun. 28, 2012, 5 pages.
Australian Notice of Allowance dated Sep. 30, 2019 for AU Application No. 2017210563 filed on Aug. 3, 2017, 3 pages.
Canadian Notice of Allowance dated May 27, 2019, for Canadian Application No. 2,833,778, 1 page.
Eurasian Office Action dated Sep. 10, 2019 for Eurasian Application No. 201690497 filed on Mar. 28, 2016, 3 pages.
Indian Office Action dated May 24, 2019 for IN Application No. 9755/DELNP/2013 filed on Nov. 12, 2013, 7 pages.
Israeli Notice of Acceptance dated Aug. 26, 2019 for corresponding Israeli Patent Application No. 230226, filed on Feb. 27, 2014, 6 pages.
Korean Notice of Allowance dated Jun. 20, 2019 for KR Application No. 10-2013-7031029 filed on Nov. 22, 2013, 4 pages.
Eurasian Notice of Allowance dated Jan. 10, 2020, for Eurasian Application No. 201690497 filed on Mar. 28, 2016, 4 pages.
Korean Office Action dated Jan. 10, 2020, for KR Application No. 10-2019-7027444 filed on Sep. 19, 2019, 12 pages.
Ambardekar, V et al. (Feb. 2011). "The Modification of siRNA With 3' Cholesterol to Increase Nuclease Protection and Suppression of Native mRNA by Select siRNA Polyplexes," Biomaterials 32(5):1404-1411.
Haraszti, R.A. et al. (Aug. 2018). "Optimized Cholesterol-SiRNA Chemistry Improves Productive Loading onto Extracellular Vesicles," Molecular Therapy 26(8):1973-1982.
Taiwanese Notice of Allowance dated Feb. 10, 2020 for Taiwanese Patent Application No. 106137891 filed on Jun. 28, 2012, 9 pages.
Canadian Examination Report dated Jul. 17, 2020, for Canadian Application No. 2,833,778, 4 pages.
Korean Office Action dated Jul. 16, 2020, for KR Application No. 10-2019-7027444 filed on Sep. 19, 2019, 5 pages.
Elbashir et al. (The EMBO Journal, 2001 vol. 20, No. 23:6877-6888).*
Akhtar S et al., "Nonviral delivery of synthetic siRNAs in vivo," Journal of Clinical Investigation (2007) 117: 3623-3632.
Atherton E et al., "The Fluorenylmethoxycarbonyl Amino Protecting Group" The Peptides, S. Udenfriend, J. Meienhofer, Eds., Academic Press, Inc. (1987) 9: 1-38.
Berkner KL et al., "Development of adenovirus vectors for the expression of heterologous genes," BioTechniques (1988) 6: 616-629.
Bucchini D et al., "Pancreatic expression of human insulin gene in transgenic mice," Proc. Natl. Acad. Sci. USA (1986) 83: 2511-2515.
Cook PD, "Medicinal Chemistry of Antisense Oligonucleotides-Future Opportunities." Anti-Cancer Drug Design (1991) 6: 585-607.
Chen S-H et al. "Gene therapy for brain tumors: Regression of experimental gliomas by adenovirus-mediated gene transfer in vivo," Proc. Natl. Acad. Sci. USA (1994) 91: 3054-3057.
Cone RD et al., "High-efficiency gene transfer into mammalian cells: Generation of helper-free recombinant retrovirus with broad mammalian host range," Proc. Natl. Acad. Sci. USA (1984) 81: 6349-6353.
Cornetta K et al., "Safety issues related to retroviral-mediated gene transfer in humans," Human Gene Therapy (1991) 2: 5-14.
Crooke et al., "Pharmacokinetic Properties of Several Novel Oligonucleotide Analogs in Mice." J. Pharmacal. Exp. Ther. (1996), 277: 923-927.
Danos O et al., "Safe and efficient generation of recombinant retroviruses with amphotropic and ecotropic host ranges," Proc. Natl. Acad. Sci. USA (1988) 85: 6460-6464.
Delgado C et al., "The Uses and Properties of PEG-Linked Proteins," Critical Reviews in Therapeutic Drug Carrier Systems (1992) 9(3,4): 249-304.
Docherty K et al., "Nutrient regulation of insulin gene expression," FASEB J. (1994) 8:20-24.
Englisch U et al., "Chemically Modified Oligonucleotides as Probes and Inhibitors," Angewandte Chemie, International Edition (1991) 30(6): 613-629.
Gassmann M et al., "Maintenance of an extrachromosomal plasmid vector in mouse embryonic stem cells," Proc. Natl. Acad. Sci. USA (1995) 92: 1292-1296.
Kroschwitz JL, "Monomers," Encyclopedia of Polymer Science and Engineering, John Wiley & Sons, New York, pp. 715-727.
Greene et al. Protective Groups in Organic Synthesis, Chapter 2, 2d ed., John Wiley & Sons, New York, 1991, and Oligonucleotides and Analogues a Practical Approach, Ekstein, F. Ed., IRL Press, N.Y, 1991.
Guzaev AP et al., "A Conformationally Preorganized Universal Solid Support for Efficient Oligonucleotide Synthesis," J. Am. Chem. Soc. (2003) 125: 2380-2381.
Hamm ML et al., "Incorporation of 2'-Deoxy-2'-mercaptocytidine into Oligonucleotides via Phosphoramidite Chemistry," J. Org. Chem. (1997) 62: 3415-3420.
Hsu K-HL et al., "Immunogenicity of Recombinant Adenovirus-Respiratory Syncytial Virus Vaccines with Adenovirus Types 4, 5, and 7 Vectors in Dogs and a Chimpanzee," J. Infectious Disease, (1992) 166: 769-775.
Kabanov et al., "A new class of antivirals; antisense oligonucleotides combined with a hydrophobic substituent effectively inhibit influenza virus reproduction and synthesis of virus-specific proteins in MDCK cells," FEBS Lett. (1990) 259: 327-330.

(56) References Cited

OTHER PUBLICATIONS

Letsinger RL et al., "Cholesteryl-conjugated oligonucleotides: Synthesis, properties, and activity as inhibitors of replication of human immunodeficiency virus in cell culture," Proc. NatL Acad. Sci. USA (1989) 85: 5553-5556.
Li S et al., "Folate-Mediated Targeting of Antisense Oligodeoxynucleotides to Ovarian Cancer Cells," Pharmaceutical Research (1998) 15(10): 1540-1545.
Manoharan M et al., "Chemical Modifications to Improve Uptake and Bioavailability of Antisense Oligonucleotides," Ann. N.Y. Acad. Sci. (1992) 660: 306-309.
Manoharan M et al., "Introduction of a Lipophilic Thioether Tether in the Minor Groove of Nucleic Acids for Antisense Applications," Bioorg. & Med. Chem. Letters (1993) 3: 2765-2770.
Manoharan Met al., "Cholic Acid-Oligonucleotide Conjugates for Antisense Applications," Bioorg. Med. & Chem. Lett. (1994) 4: 1053-1060.
Manoharan M et al., "Oligonucleotide Conjugates: Alteration of the Pharmacokinetic Properties of Antisense Agents," Nucleosides & Nucleotides (1995) 14: 969-973.
Manoharan M et al., "Lipidic Nucleic Acids," Tetrahedron Letters (1995) 36: 3651-3654.
Manoharan M, "Oligonucleotide Conjugates as Potential Antisense Drugs with Improved Uptake, Biodistribution, Targeted Delivery, and Mechanism of Action," Antisense & Nucleic Acid Drug Devel. (2002) 12: 103-128.
Mishra RK et al., "Improved leishmanicidal effect of phosphorothioate antisense oligonucleotides by LDL-mediated delivery," Biochim. et Biophysica Acta (1995) 1264: 229-237.
Nawrot B et al., "Chemical and Structural Diversity of siRNA Molecules," Current Topics in Medicinal Chemistry (2006) 6: 913-925.
Nguyen T et al., "RNAi therapeutics: an update on delivery." Current Opinion in Molecular Therapeutics (2008) 10(2): 158-167.
Oberhauser et al., "Effective Incorporation of 2'-O-methyl-oligoribonucleotides Into Liposomes and Enhanced Cell Association Through Modification with Thiocholesterol," Nucl. Acids Research (1992) 20: 533-538.
Polushin NN et al., "Synthesis of Oligonucleotides Containing 2'-Azido- and 2'-Amino-2'-deoxyuridine Using Phosphotriester Chemistry," Tetrahedron Letters (1996) 37(19): 3227-3230.
Rosenfeld MA et al., "Adenovirus-mediated transfer of a recombinant alpha 1-antitrypsin gene to the lung epithelium in vivo," Science (1991) 252: 431-434.
Saison-Behmoaras et al., "Short Modified Antisense Oligonucleotides Directed Against Ha-ras Point Mutation Induce Selective Cleavage of the mRNA and Inhibit T24 Cells Proliferation," The EMBO Journal (1991) 10: 1111-1118.
Samukov VV et al., "2-(4-Nitrophenyl)sulfonylethoxycarbonyl (Nsc) Group as a Base-Labile α-Amino Protection for Solid Phase Peptide Synthesis," Tetrahedron Letters (1994) 35(42): 7821-7824.
Shea et al., "Synthesis, Hybridization Properties and Antiviral Activity of Lipid-oligodeoxynucleotide Conjugates," Nucl. Acids Research (1990) 18: 3777-3783.
Svinarchuk et al, "Inhibition of HIV proliferation in MT-4 cells by antisense oligonucleotide conjugated to lipophilic groups," Biochimie (1993) 75: 49-54.
Thomson JB et al., "Synthesis and Properties of Diuridine Phosphate Analogues Containing Thio and Amino Modifications," J. Org. Chem. (1996) 61: 6273-6281.
Wagner RW, "The state of the art in antisense research." Nature Medicine (1995) 1(11): 1116-1118.
Williams DJ et al., "Thermodynamic Comparison of the Salt Dependence of Natural RNA Hairpins and RNA Hairpins with Non-Nucleotide Spacers," Biochemistry (1996) 35: 14665-14670.
Zamboni, "Liposomal, Nanoparticle, and Conjugated Formulations of Anticancer Agents," Clin. Cancer Res. (2005) 11: 8230-8234.
Ikeda et al., "Ligand-Targeting Delivery of Therapeutic siRNA," Pharmaceutical Research (2006) 23: 1631-1640.
Rosenfeld MA et al., "In vivo transfer of the human cystic fibrosis transmembrane conductance regulator gene to the airway epithelium" Cell (1992) 68(1): 143-155.
Sanghvi, Antisense Research and Applications, (1993) Chapter 15, p. 289-302, Crooke ST and Lebleu B ed., CRC Press.
Genbank Accession Nos. AP007263, AB 602818, AB644286, and AB554024.
Zhang, Y-L et al "RNA Interference inhibits hepatitis B virus of different genotypes in vitro and in vivo." BMC Microbiol. 2010, vol. 10:214, p. 1-10.

* cited by examiner

Table 1. Core sequences of dsRNAs targeting Hepatitis B Virus gene.

| SEQ ID NO | sense strand sequence (5'-3') | SEQ ID NO | antisense strand sequence (5'-3') |
|---|---|---|---|
| 1 | CAAGGUAUGUUGCCCGUUU | 157 | AAACGGGCAACAUACCUUG |
| 2 | CUGUAGGCAUAAAUUGGUA | 158 | TACCAAUUUAUGCCUACAG |
| 3 | UCUGCGGCGUUUUAUCAUA | 159 | UAUGAUAAAACGCCGCAGA |
| 3 | UCUGCGGCGUUUUAUCAUA | 160 | TAUGAUAAAACGCCGCAGA |
| 4 | ACCUCUGCCUAAUCAUCUC | 161 | GAGAUGAUUAGGCAGAGGU |
| 5 | UUUACUAGUGCCAUUUGUA | 162 | TACAAAUGGCACUAGUAAA |
| 6 | ACCUCUGCCUAAUCAUCUA | 163 | TAGAUGAUUAGGCAGAGGU |
| 7 | CUGUAGGCAUAAAUUGGUC | 164 | GACCAAUUUAUGCCUACAG |
| 8 | UGUCUGCGGCGUUUUAUCA | 165 | UGAUAAAACGCCGCAGACA |
| 8 | UGUCUGCGGCGUUUUAUCA | 166 | TGAUAAAACGCCGCAGACA |
| 9 | UACUAGUGCCAUUUGUUCA | 167 | UGAACAAAUGGCACUAGUA |
| 9 | UACUAGUGCCAUUUGUUCA | 168 | TGAACAAAUGGCACUAGUA |
| 10 | CAACUUUUUCACCUCUGCA | 169 | TGCAGAGGUGAAAAAGUUG |
| 11 | CCAUUUGUUCAGUGGUUCG | 170 | CGAACCACUGAACAAAUGG |
| 12 | CCAAGUGUUUGCUGACGCA | 171 | UGCGUCAGCAAACACUUGG |
| 12 | CCAAGUGUUUGCUGACGCA | 172 | TGCGUCAGCAAACACUUGG |
| 13 | CCAUUUGUUCAGUGGUUCA | 173 | TGAACCACUGAACAAAUGG |
| 14 | UUUACUAGUGCCAUUUGUU | 174 | AACAAAUGGCACUAGUAAA |
| 15 | CACCUCUGCCUAAUCAUCA | 175 | TGAUGAUUAGGCAGAGGUG |
| 16 | CUGGCUCAGUUUACUAGUG | 176 | CACUAGUAAACUGAGCCAG |
| 17 | CAAGGUAUGUUGCCCGUUA | 177 | TAACGGGCAACAUACCUUG |
| 18 | CUGGCUCAGUUUACUAGUA | 178 | TACUAGUAAACUGAGCCAG |
| 19 | GAGGCUGUAGGCAUAAAUU | 179 | AAUUUAUGCCUACAGCCUC |
| 20 | CAGUUUACUAGUGCCAUUU | 180 | AAAUGGCACUAGUAAACUG |
| 21 | AGGUAUGUUGCCCGUUUGU | 181 | ACAAACGGGCAACAUACCU |
| 22 | UAUGUUGCCCGUUUGUCCA | 182 | UGGACAAACGGGCAACAUA |
| 23 | GAGGCUGUAGGCAUAAAUA | 183 | TAUUUAUGCCUACAGCCUC |
| 24 | GUCUGCGGCGUUUUAUCAU | 184 | AUGAUAAAACGCCGCAGAC |
| 25 | CAACUUUUUCACCUCUGCC | 185 | GGCAGAGGUGAAAAAGUUG |
| 26 | CCGUGUGCACUUCGCUUCA | 186 | UGAAGCGAAGUGCACACGG |
| 26 | CCGUGUGCACUUCGCUUCA | 187 | TGAAGCGAAGUGCACACGG |
| 27 | UCAAGGUAUGUUGCCCGUA | 188 | TACGGGCAACAUACCUUGA |
| 28 | CAGUUUACUAGUGCCAUUA | 189 | TAAUGGCACUAGUAAACUG |
| 29 | UGGUGGACUUCUCUCAAUU | 190 | AAUUGAGAGAAGUCCACCA |
| 30 | AGGUAUGUUGCCCGUUUGA | 191 | TCAAACGGGCAACAUACCU |
| 31 | CUGCUCGUGUUACAGGCGG | 192 | CCGCCUGUAACACGAGCAG |
| 32 | UAUGUUGCCCGUUUGUCCU | 193 | AGGACAAACGGGCAACAUA |
| 33 | UCAAGGUAUGUUGCCCGUU | 194 | AACGGGCAACAUACCUUGA |
| 34 | UCUUAUCAACACUUCCGGA | 195 | UCCGGAAGUGUUGAUAAGA |
| 34 | UCUUAUCAACACUUCCGGA | 196 | TCCGGAAGUGUUGAUAAGA |

FIG. 1A

| | | | |
|---|---|---|---|
| 35 | CACCUCUGCCUAAUCAUCU | 197 | AGAUGAUUAGGCAGAGGUG |
| 36 | AUAAGAGGACUCUUGGACU | 198 | AGUCCAAGAGUCCUCUUAU |
| 37 | GUCUGCGGCGUUUUAUCAA | 199 | TUGAUAAAACGCCGCAGAC |
| 38 | GGCGCUGAAUCCCGCGGAC | 200 | GUCCGCGGGAUUCAGCGCC |
| 39 | CGCGUCGCAGAAGAUCUCA | 201 | UGAGAUCUUCUGCGACGCG |
| 40 | AAUGUCAACGACCGACCUU | 202 | AAGGUCGGUCGUUGACAUU |
| 41 | GCUCAGUUUACUAGUGCCA | 203 | UGGCACUAGUAAACUGAGC |
| 42 | UGGUGGACUUCUCUCAAUA | 204 | TAUUGAGAGAAGUCCACCA |
| 43 | AUCGCCGCGUCGCAGAAGA | 205 | UCUUCUGCGACGCGGCGAU |
| 44 | GCCAUUUGUUCAGUGGUUC | 206 | GAACCACUGAACAAAUGGC |
| 45 | CGAUCCAUACUGCGGAACU | 207 | AGUUCCGCAGUAUGGAUCG |
| 46 | UCACCUCUGCCUAAUCAUC | 208 | GAUGAUUAGGCAGAGGUGA |
| 47 | GUGGACUUCUCUCAAUUUU | 209 | AAAAUUGAGAGAAGUCCAC |
| 48 | GGGUCACCAUAUUCUUGGG | 210 | CCCAAGAAUAUGGUGACCC |
| 49 | GCCGCGUCGCAGAAGAUCU | 211 | AGAUCUUCUGCGACGCGGC |
| 50 | UCAAUCGCCGCGUCGCAGA | 212 | UCUGCGACGCGGCGAUUGA |
| 51 | UGGAUGUGUCUGCGGCGUU | 213 | AACGCCGCAGACACAUCCA |
| 52 | UACUGUUCAAGCCUCCAAG | 214 | CUUGGAGGCUUGAACAGUA |
| 53 | GUUUACUAGUGCCAUUUGU | 215 | ACAAAUGGCACUAGUAAAC |
| 54 | ACUAGUGCCAUUUGUUCAG | 216 | CUGAACAAAUGGCACUAGU |
| 55 | CCGCGUCGCAGAAGAUCUC | 217 | GAGAUCUUCUGCGACGCGG |
| 56 | UAUCUUAUCAACACUUCCG | 218 | CGGAAGUGUUGAUAAGAUA |
| 57 | GGCCAAAAUUCGCAGUCCC | 219 | GGGACUGCGAAUUUUGGCC |
| 58 | UUCACCUCUGCCUAAUCAU | 220 | AUGAUUAGGCAGAGGUGAA |
| 59 | CUCAGUUUACUAGUGCCAU | 221 | AUGGCACUAGUAAACUGAG |
| 60 | UGUUGCCCGUUUGUCCUCU | 222 | AGAGGACAAACGGGCAACA |
| 61 | UAGUGCCAUUUGUUCAGUG | 223 | CACUGAACAAAUGGCACUA |
| 62 | AGGCUGUAGGCAUAAAUUG | 224 | CAAUUUAUGCCUACAGCCU |
| 63 | AUGUGUCUGCGGCGUUUUA | 225 | UAAAACGCCGCAGACACAU |
| 63 | AUGUGUCUGCGGCGUUUUA | 226 | TAAAACGCCGCAGACACAU |
| 64 | ACUUCGCUUCACCUCUGCA | 227 | UGCAGAGGUGAAGCGAAGU |
| 65 | CGUGUGCACUUCGCUUCAC | 228 | GUGAAGCGAAGUGCACACG |
| 66 | GUGGUGGACUUCUCUCAAU | 229 | AUUGAGAGAAGUCCACCAC |
| 67 | UGUGUCUGCGGCGUUUUAU | 230 | AUAAAACGCCGCAGACACA |
| 68 | AAGGUAUGUUGCCCGUUUG | 231 | CAAACGGGCAACAUACCUU |
| 69 | UCAACGACCGACCUUGAGG | 232 | CCUCAAGGUCGGUCGUUGA |
| 70 | CAUAAGAGGACUCUUGGAC | 233 | GUCCAAGAGUCCUCUUAUG |
| 71 | GUCAACGACCGACCUUGAG | 234 | CUCAAGGUCGGUCGUUGAC |
| 72 | AUAUUCUUGGGAACAAGAG | 235 | CUCUUGUUCCCAAGAAUAU |
| 73 | UGCUCGUGUUACAGGCGGG | 236 | CCCGCCUGUAACACGAGCA |
| 74 | CAAUCGCCGCGUCGCAGAA | 237 | UUCUGCGACGCGGCGAUUG |
| 75 | ACUGUUCAAGCCUCCAAGC | 238 | GCUUGGAGGCUUGAACAGU |
| 76 | CGCCGCGUCGCAGAAGAUC | 239 | GAUCUUCUGCGACGCGGCG |

FIG. 1B

| | | | |
|---|---|---|---|
| 77 | CAUUUGUUCAGUGGUUCGU | 240 | ACGAACCACUGAACAAAUG |
| 78 | CGCUGAAUCCCGCGGACGA | 241 | UCGUCCGCGGGAUUCAGCG |
| 79 | UGGGUCACCAUAUUCUUGG | 242 | CCAAGAAUAUGGUGACCCA |
| 80 | UCCUCUGCCGAUCCAUACU | 243 | AGUAUGGAUCGGCAGAGGA |
| 81 | AUGUCAACGACCGACCUUG | 244 | CAAGGUCGGUCGUUGACAU |
| 82 | CCUCUGCCUAAUCAUCUCA | 245 | UGAGAUGAUUAGGCAGAGG |
| 83 | ACCGUGUGCACUUCGCUUC | 246 | GAAGCGAAGUGCACACGGU |
| 84 | UGCCGAUCCAUACUGCGGA | 247 | UCCGCAGUAUGGAUCGGCA |
| 85 | CAGAGUCUAGACUCGUGGU | 248 | ACCACGAGUCUAGACUCUG |
| 86 | CUGUUCAAGCCUCCAAGCU | 249 | AGCUUGGAGGCUUGAACAG |
| 87 | GGAGGCUGUAGGCAUAAAU | 250 | AUUUAUGCCUACAGCCUCC |
| 88 | AGGAGGCUGUAGGCAUAAA | 251 | UUUAUGCCUACAGCCUCCU |
| 89 | GGUGGACUUCUCUCAAUUU | 252 | AAAUUGAGAGAAGUCCACC |
| 90 | GCAACUUUUUCACCUCUGC | 253 | GCAGAGGUGAAAAAGUUGC |
| 91 | CUGCUCGUGUUACAGGCGA | 254 | TCGCCUGUAACACGAGCAG |
| 92 | CUAGUGCCAUUUGUUCAGU | 255 | ACUGAACAAAUGGCACUAG |
| 93 | CUGCCGAUCCAUACUGCGG | 256 | CCGCAGUAUGGAUCGGCAG |
| 94 | GUGUGCACUUCGCUUCACC | 257 | GGUGAAGCGAAGUGCACAC |
| 95 | GCUCGUGUUACAGGCGGGC | 258 | GCCCGCCUGUAACACGAGC |
| 96 | CCUAUCUUAUCAACACUUC | 259 | GAAGUGUUGAUAAGAUAGG |
| 97 | UCUCAAUCGCCGCGUCGCA | 260 | UGCGACGCGGCGAUUGAGA |
| 98 | GCCCGUCUGUGCCUUCUCA | 261 | UGAGAAGGCACAGACGGGC |
| 99 | CUAUCUUAUCAACACUUCC | 262 | GGAAGUGUUGAUAAGAUAG |
| 100 | AUGUUGCCCGUUUGUCCUC | 263 | GAGGACAAACGGGCAACAU |
| 101 | GUAUGUUGCCCGUUUGUCC | 264 | GGACAAACGGGCAACAUAC |
| 102 | CUUCGCUUCACCUCUGCAC | 265 | GUGCAGAGGUGAAGCGAAG |
| 103 | UGUGCACUUCGCUUCACCU | 266 | AGGUGAAGCGAAGUGCACA |
| 104 | GCCAAAAUUCGCAGUCCCG | 267 | CGGGACUGCGAAUUUUGGC |
| 105 | CCUGCUCGUGUUACAGGCG | 268 | CGCCUGUAACACGAGCAGG |
| 106 | UGGAGUGUGGAUUCGCACU | 269 | AGUGCGAAUCCACACUCCA |
| 107 | AACGACCGACCUUGAGGCA | 270 | UGCCUCAAGGUCGGUCGUU |
| 108 | ACAGAGUCUAGACUCGUGG | 271 | CCACGAGUCUAGACUCUGU |
| 109 | AAUCGCCGCGUCGCAGAAG | 272 | CUUCUGCGACGCGGCGAUU |
| 110 | GGUAUGUUGCCCGUUUGUC | 273 | GACAAACGGGCAACAUACC |
| 111 | GCCGAUCCAUACUGCGGAA | 274 | UUCCGCAGUAUGGAUCGGC |
| 112 | GCCCUAUCUUAUCAACACU | 275 | AGUGUUGAUAAGAUAGGGC |
| 113 | AGUUUACUAGUGCCAUUUG | 276 | CAAAUGGCACUAGUAAACU |
| 114 | UGUCAACGACCGACCUUGA | 277 | UCAAGGUCGGUCGUUGACA |
| 115 | ACUUCUCUCAAUUUUCUAG | 278 | CUAGAAAAUUGAGAGAAGU |
| 116 | GCGCGGGACGUCCUUUGUC | 279 | GACAAAGGACGUCCCGCGC |
| 117 | UCUAGACUCGUGGUGGACU | 280 | AGUCCACCACGAGUCUAGA |
| 118 | GAUCCAUACUGCGGAACUC | 281 | GAGUUCCGCAGUAUGGAUC |

FIG. 1C

| | | | |
|---|---|---|---|
| 119 | CUCUGCCGAUCCAUACUGC | 282 | GCAGUAUGGAUCGGCAGAG |
| 120 | UCUGCCGAUCCAUACUGCG | 283 | CGCAGUAUGGAUCGGCAGA |
| 121 | CCUCUGCCGAUCCAUACUG | 284 | CAGUAUGGAUCGGCAGAGG |
| 122 | GCACCUCUCUUUACGCGGU | 285 | ACCGCGUAAAGAGAGGUGC |
| 123 | AAGAACUCCCUCGCCUCGC | 286 | GCGAGGCGAGGGAGUUCUU |
| 124 | GAACUCCCUCGCCUCGCAG | 287 | CUGCGAGGCGAGGGAGUUC |
| 125 | UCUCUCAAUUUUCUAGGGC | 288 | GCCCUAGAAAAUUGAGAGA |
| 126 | GGGCGCACCUCUCUUUACG | 289 | CGUAAAGAGAGGUGCGCCC |
| 127 | CCGAUCCAUACUGCGGAAC | 290 | GUUCCGCAGUAUGGAUCGG |
| 128 | AACUCCCUCGCCUCGCAGA | 291 | UCUGCGAGGCGAGGGAGUU |
| 129 | CUCCUCUGCCGAUCCAUAC | 292 | GUAUGGAUCGGCAGAGGAG |
| 130 | GGAGUGUGGAUUCGCACUC | 293 | GAGUGCGAAUCCACACUCC |
| 131 | CGGGCGCACCUCUCUUUAC | 294 | GUAAAGAGAGGUGCGCCCG |
| 132 | GUCUCAAUCGCCGCGUCGC | 295 | GCGACGCGGCGAUUGAGAC |
| 133 | AUCCAUACUGCGGAACUCC | 296 | GGAGUUCCGCAGUAUGGAU |
| 134 | CGCACCUCUCUUUACGCGG | 297 | CCGCGUAAAGAGAGGUGCG |
| 135 | CAACGACCGACCUUGAGGC | 298 | GCCUCAAGGUCGGUCGUUG |
| 136 | CCAUACUGCGGAACUCCUA | 299 | UAGGAGUUCCGCAGUAUGG |
| 137 | UGAAUCCCGCGGACGACCC | 300 | GGGUCGUCCGCGGGAUUCA |
| 138 | AGAACUCCCUCGCCUCGCA | 301 | UGCGAGGCGAGGGAGUUCU |
| 139 | GGCGCACCUCUCUUUACGC | 302 | GCGUAAAGAGAGGUGCGCC |
| 140 | GCGCACCUCUCUUUACGCG | 303 | CGCGUAAAGAGAGGUGCGC |
| 141 | GCUGAAUCCCGCGGACGAC | 304 | GUCGUCCGCGGGAUUCAGC |
| 142 | CACUUCGCUUCACCUCUGC | 305 | GCAGAGGUGAAGCGAAGUG |
| 143 | CUCAAUCGCCGCGUCGCAG | 306 | CUGCGACGCGGCGAUUGAG |
| 144 | UCCCGUCGGCGCUGAAUCC | 307 | GGAUUCAGCGCCGACGGGA |
| 145 | CUGAAUCCCGCGGACGACC | 308 | GGUCGUCCGCGGGAUUCAG |
| 146 | AGAGUCUAGACUCGUGGUG | 309 | CACCACGAGUCUAGACUCU |
| 147 | UCCAUACUGCGGAACUCCU | 310 | AGGAGUUCCGCAGUAUGGA |
| 148 | GCGCUGAAUCCCGCGGACG | 311 | CGUCCGCGGGAUUCAGCGC |
| 149 | AGUGUGGAUUCGCACUCCU | 312 | AGGAGUGCGAAUCCACACU |
| 150 | CCCUGCUCGUGUUACAGGC | 313 | GCCUGUAACACGAGCAGGG |
| 151 | GAAUCCCGCGGACGACCCG | 314 | CGGGUCGUCCGCGGGAUUC |
| 152 | AAGCUGUGCCUUGGGUGGC | 315 | GCCACCCAAGGCACAGCUU |
| 153 | GCCCUGCUCGUGUUACAGG | 316 | CCUGUAACACGAGCAGGGC |
| 154 | GUCCCGUCGGCGCUGAAUC | 317 | GAUUCAGCGCCGACGGGAC |
| 155 | AUCUUAUCAACACUUCCGG | 318 | CCGGAAGUGUUGAUAAGAU |
| 156 | CUUAUCAACACUUCCGGAA | 319 | UUCCGGAAGUGUUGAUAAG |
| 156 | CUUAUCAACACUUCCGGAA | 320 | TUCCGGAAGUGUUGAUAAG |

FIG. 1D

Table 2. Activity testing in psiCHECK2 reporter system in COS7 cells.

| | | | | Activity testing in psiCHECK2 reporter system in COS7 cells | | | |
|---|---|---|---|---|---|---|---|
| | | | | 10 nM siRNA | | 1 nM siRNA | |
| SEQ ID NO | sense strand sequence (5'-3') | SEQ ID NO | antisense strand sequence (5'-3') | mean remaining mRNA (%) | standard deviation (%) | mean remaining mRNA (%) | standard deviation (%) |
| 321 | caAGGuAuGuuGcccGuuudTsdT | 485 | AAACGGGcAAcAuACCUUGdTsdT | 13 | 1 | 13 | 1 |
| 322 | CfuGfuAfgGfcAfuAfaAfuUfgGfuAf(invdT) | 486 | pdTAfcCfaAfuUfuAfuGfcCfuAfcAfgdTsdT | 8 | 2 | 14 | 2 |
| 323 | ucuGcGGcGuuuuAucAuAdTsdT | 487 | uAUGAuAAAACGCCGcAGAdTsdT | 15 | 7 | 29 | 11 |
| 324 | UfcUfgCfgGfcGfuUfuUfaUfcAfuAf(invdT) | 488 | pdTAfuGfaUfaAfaAfcGfcCfgCfaGfadTsdT | 6 | 2 | 15 | 4 |
| 325 | accucuGccuAAucAucucdTsdT | 489 | GAGAUGAUuAGGcAGAGGUdTsdT | 17 | 1 | 16 | 2 |
| 326 | UfuUfaCfuAfgUfgCfcAfuUfuGfuAf(invdT) | 490 | pdTAfcAfaAfuGfgCfaCfuAfgUfaAfadTsdT | 8 | 0 | 17 | 1 |
| 327 | AfcCfuCfuGfcCfuAfaUfcAfuCfuAf(invdT) | 491 | pdTAfgAfuGfaUfuAfgGfcAfgAfgGfudTsdT | 6 | 2 | 19 | 3 |
| 328 | cuGuAGGcAuAAAuuGGucdTsdT | 492 | GACcAAUUuAUGCCuAcAGdTsdT | 23 | 2 | 28 | 6 |
| 329 | ugucuGcGGcGuuuuAucAdTsdT | 493 | UGAuAAAACGCCGcAGAcAdTsdT | 33 | 3 | 34 | 10 |
| 330 | UfgUfcUfgCfgGfcGfuUfuUfaUfcAf(invdT) | 494 | pdTGfaUfaAfaAfcGfcCfgCfaGfaCfadTsdT | 6 | 0 | 20 | 3 |
| 331 | uacuAGuGccAuuuGuucAdTsdT | 495 | UGAAcAAAUGGcACuAGuAdTsdT | 18 | 3 | 20 | 2 |
| 332 | UfaCfuAfgUfgCfcAfuUfuGfuUfcAf(invdT) | 496 | pdTGfaAfcAfaAfuGfgCfaCfuAfgUfadTsdT | 6 | 2 | 21 | 4 |
| 333 | CfaAfcUfuUfuUfcAfcCfuCfuGfcAf(invdT) | 497 | pdTGfcAfgAfgGfuGfaAfaAfaGfuUfgdTsdT | 6 | 2 | 21 | 3 |
| 334 | ccAuuuGuucAGuGGuucGdTsdT | 498 | CGAACcACUGAAcAAAUGGdTsdT | 12 | 1 | 21 | 1 |
| 335 | ccAAGuGuuuGcuGAcGcAdTsdT | 499 | UGCGUcAGcAAAcACUUGGdTsdT | 18 | 2 | 23 | 4 |
| 336 | CfcAfaGfuGfuUfuGfcUfgAfcGfcAf(invdT) | 500 | pdTGfcGfuCfaGfcAfaAfcAfcUfuGfgdTsdT | 8 | 1 | 23 | 5 |
| 337 | CfcAfuUfuGfuUfcAfgUfgGfuUfcAf(invdT) | 501 | pdTGfaAfcCfaCfuGfaAfcAfaAfuGfgdTsdT | 7 | 2 | 24 | 3 |
| 338 | uuuAcuAGuGccAuuuGuudTsdT | 502 | AAcAAAUGGcACuAGuAAAdTsdT | 21 | 2 | 24 | 4 |
| 339 | CfaCfcUfcUfgCfcUfaAfuCfaUfcAf(invdT) | 503 | pdTGfaUfgAfuUfaGfgCfaGfaGfgUfgdTsdT | 9 | 0 | 25 | 2 |
| 340 | cuGGcucAGuuuAcuAGuGdTsdT | 504 | cACuAGuAAACUGAGCcAGdTsdT | 34 | 3 | 29 | 7 |
| 341 | CfaAfgGfuAfuGfuUfgCfcCfgUfuAf(invdT) | 505 | pdTAfaCfgGfgCfaAfcAfuAfcCfuUfgdTsdT | 8 | 0 | 31 | 3 |
| 342 | CfuGfgCfuCfaGfuUfuAfcUfaGfuAf(invdT) | 506 | pdTAfcUfaGfuAfaAfcUfgAfgCfcAfgdTsdT | 11 | 3 | 32 | 5 |
| 343 | gaGGcuGuAGGcAuAAAuudTsdT | 507 | AAUUuAUGCCuAcAGCCUCdTsdT | 16 | 1 | 32 | 8 |
| 344 | caGuuuAcuAGuGccAuuudTsdT | 508 | AAAUGGcACuAGuAAACUGdTsdT | 37 | 1 | 33 | 8 |

FIG. 2A

| | | | | | | | |
|---|---|---|---|---|---|---|---|
| 345 | agGuAuGuuGcccGuuuGudTsdT | 509 | AcAAACGGGcAAcAuACCUdTsdT | 33 | 3 | 34 | 4 |
| 346 | UfaUfgUfuGfcCfcGfuUfuGfuCfcAf(invdT) | 510 | pdTGfgAfcAfaAfcGfgGfcAfaCfaUfadTsdT | 9 | 3 | 35 | 5 |
| 347 | GfaGfgCfuGfuAfgGfcAfuAfaAfuAf(invdT) | 511 | pdTAfuUfuAfuGfcCfuAfcAfgCfcUfcdTsdT | 9 | 1 | 36 | 4 |
| 348 | gucuGcGGcGuuuuAucAudTsdT | 512 | AUGAuAAAACGCCGcAGACdTsdT | 26 | 3 | 36 | 14 |
| 349 | caAcuuuuucAccucuGccdTsdT | 513 | GGcAGAGGUGAAAAAGUUGdTsdT | 24 | 2 | 37 | 9 |
| 350 | ccGuGuGcAcuucGcuucAdTsdT | 514 | UGAAGCGAAGUGcAcACGGdTsdT | 13 | 1 | 16 | 5 |
| 351 | CfcGfuGfuGfcAfcUfuCfgCfuUfcAf(invdT) | 515 | pdTGfaAfgCfgAfaGfuGfcAfcAfcGfgdTsdT | 13 | 2 | 38 | 4 |
| 352 | UfcAfaGfgUfaUfgUfuGfcCfcGfuAf(invdT) | 516 | pdTAfcGfgGfcAfaCfaUfaCfcUfuGfadTsdT | 12 | 1 | 38 | 4 |
| 353 | CfaGfuUfuAfcUfaGfuGfcCfaUfuAf(invdT) | 517 | pdTAfaUfgGfcAfcUfaGfuAfaAfcUfgdTsdT | 12 | 2 | 38 | 5 |
| 354 | ugGuGGAcuucucucAAuudTsdT | 518 | AAUUGAGAGAAGUCcACcAdTsdT | 24 | 6 | 39 | 16 |
| 355 | AfgGfuAfuGfuUfgCfcCfgUfuUfgAf(invdT) | 519 | pdTCfaAfaCfgGfgCfaAfcAfuAfcCfudTsdT | 18 | 1 | 40 | 4 |
| 356 | cuGcucGuGuuAcAGGcGGdTsdT | 520 | CCGCCUGuAAcACGAGcAGdTsdT | 26 | 2 | 40 | 11 |
| 357 | uauGuuGcccGuuuGuccudTsdT | 521 | AGGAcAAACGGGcAAcAuAdTsdT | 42 | 1 | 40 | 3 |
| 358 | ucAAGGuAuGuuGcccGuudTsdT | 522 | AACGGGcAAcAuACCUUGAdTsdT | 31 | 4 | 42 | 12 |
| 359 | ucuuAucAAcAcuuccGGAdTsdT | 523 | UCCGGAAGUGUUGAuAAGAdTsdT | 35 | 2 | 43 | 38 |
| 360 | UfcUfuAfuCfaAfcAfcUfuCfcGfgAf(invdT) | 524 | pdTCfcGfgAfaGfuGfuUfgAfuAfaGfadTsdT | 32 | 2 | 46 | 3 |
| 361 | caccucuGccuAAucAucudTsdT | 525 | AGAUGAUuAGGcAGAGGUGdTsdT | 31 | 3 | 47 | 8 |
| 362 | auAAGAGGAcucuuGGAcudTsdT | 526 | AGUCcAAGAGUCCUCUuAUdTsdT | 28 | 1 | 49 | 6 |
| 363 | GfuCfuGfcGfgCfgUfuUfuAfuCfaAf(invdT) | 527 | pdTUfgAfuAfaAfaCfgCfcGfcAfgAfcdTsdT | 15 | 0 | 51 | 4 |
| 364 | ggcGcuGAAucccGcGGAcdTsdT | 528 | GUCCGCGGGAUUcAGCGCCdTsdT | 24 | 3 | 51 | 10 |
| 365 | cgcGucGcAGAAGAucucAdTsdT | 529 | UGAGAUCUUCUGCGACGCGdTsdT | 46 | 3 | 53 | 6 |
| 366 | aauGucAAcGAccGAccuudTsdT | 530 | AAGGUCGGUCGUUGAcAUUdTsdT | 40 | 1 | 54 | 8 |
| 367 | gcucAGuuuAcuAGuGccAdTsdT | 531 | UGGcACuAGuAAACUGAGCdTsdT | 37 | 5 | 51 | 4 |
| 368 | UfgGfuGfgAfcUfuCfuCfuCfaAfuAf(invdT) | 532 | pdTAfuUfgAfgAfgAfaGfuCfcAfcCfadTsdT | 20 | 4 | 58 | 6 |
| 369 | aucGccGcGucGcAGAAGAdTsdT | 533 | UCUUCUGCGACGCGGCGAUdTsdT | 57 | 6 | 58 | 1 |
| 370 | gccAuuuGuucAGuGGuucdTsdT | 534 | GAACcACUGAAcAAAUGGCdTsdT | 36 | 3 | 60 | 6 |
| 371 | cgAuccAuAcuGcGGAAcudTsdT | 535 | AGUUCCGcAGuAUGGAUCGdTsdT | 43 | 8 | 61 | 9 |
| 372 | ucAccucuGccuAAucAucdTsdT | 536 | GAUGAUuAGGcAGAGGUGAdTsdT | 48 | 4 | 61 | 10 |
| 373 | guGGAcuucucucAAuuuudTsdT | 537 | AAAAUUGAGAGAAGUCcACdTsdT | 31 | 4 | 61 | 5 |
| 374 | ggGucAccAuAuucuuGGGdTsdT | 538 | CCcAAGAAuAUGGUGACCCdTsdT | 58 | 6 | 62 | 10 |
| 375 | gccGcGucGcAGAAGAucudTsdT | 539 | AGAUCUUCUGCGACGCGGCdTsdT | 59 | 3 | 64 | 7 |

FIG. 2B

| | | | | | | | |
|---|---|---|---|---|---|---|---|
| 376 | ucAAucGccGcGucGcAGAdTsdT | 540 | UCUGCGACGCGGCGAUUGAdTsdT | 59 | 1 | 64 | 9 |
| 377 | ugGAuGuGucuGcGGcGuudTsdT | 541 | AACGCCGcAGAcAcAUCcAdTsdT | 44 | 8 | 65 | 12 |
| 378 | uacuGuucAAGccuccAAGdTsdT | 542 | CUUGGAGGCUUGAAcAGuAdTsdT | 51 | 2 | 65 | 32 |
| 379 | guuuAcuAGuGccAuuuGudTsdT | 543 | AcAAAUGGcACuAGuAAACdTsdT | 44 | 5 | 66 | 6 |
| 380 | acuAGuGccAuuuGuucAGdTsdT | 544 | CUGAAcAAAUGGcACuAGUdTsdT | 56 | 0 | 66 | 5 |
| 381 | ccGcGucGcAGAAGAucucdTsdT | 545 | GAGAUCUUCUGCGACGCGGdTsdT | 59 | 3 | 67 | 11 |
| 382 | uaucuuAucAAcAcuuccGdTsdT | 546 | CGGAAGUGUUGAuAAGAuAdTsdT | 37 | 1 | 67 | 51 |
| 383 | ggccAAAAuucGcAGucccdTsdT | 547 | GGGACUGCGAAUUUUGGCCdTsdT | 49 | 6 | 67 | 7 |
| 384 | uucAccucuGccuAAucAudTsdT | 548 | AUGAUuAGGcAGAGGUGAAdTsdT | 50 | 4 | 68 | 7 |
| 385 | cucAGuuuAcuAGuGccAudTsdT | 549 | AUGGcACuAGuAAACUGAGdTsdT | 52 | 2 | 68 | 6 |
| 386 | uguuGcccGuuuGuccucudTsdT | 550 | AGAGGAcAAACGGGcAAcAdTsdT | 50 | 2 | 69 | 4 |
| 387 | uaGuGccAuuuGuucAGuGdTsdT | 551 | cACUGAAcAAAUGGcACuAdTsdT | 46 | 1 | 70 | 8 |
| 388 | agGcuGuAGGcAuAAAuuGdTsdT | 552 | cAAUUuAUGCCuAcAGCCUdTsdT | 69 | 3 | 71 | 13 |
| 389 | auGuGucuGcGGcGuuuuAdTsdT | 553 | uAAAACGCCGcAGAcAcAUdTsdT | 17 | 6 | 33 | 12 |
| 390 | AfuGfuGfuCfuGfcGfgCfgUfuUfuAf(invdT) | 554 | pdTAfaAfaCfgCfcGfcAfgAfcAfcAfudTsdT | 24 | 3 | 72 | 4 |
| 391 | acuucGcuucAccucuGcAdTsdT | 555 | UGcAGAGGUGAAGCGAAGUdTsdT | 49 | 4 | 73 | 4 |
| 392 | cguGuGcAcuucGcuucAcdTsdT | 556 | GUGAAGCGAAGUGcAcACGdTsdT | 45 | 3 | 73 | 10 |
| 393 | guGGuGGAcuucucucAAudTsdT | 557 | AUUGAGAGAAGUCcACcACdTsdT | 47 | 5 | 73 | 5 |
| 394 | uguGucuGcGGcGuuuuAudTsdT | 558 | AuAAAACGCCGcAGAcAcAdTsdT | 62 | 8 | 75 | 14 |
| 395 | aaGGuAuGuuGcccGuuuGdTsdT | 559 | cAAACGGGcAAcAuACCUUdTsdT | 61 | 3 | 76 | 2 |
| 396 | ucAAcGAccGAccuuGAGGdTsdT | 560 | CCUcAAGGUCGGUCGUUGAdTsdT | 57 | 1 | 76 | 16 |
| 397 | cauAAGAGGAcucuuGGAcdTsdT | 561 | GUCcAAGAGUCCUCUuAUGdTsdT | 62 | 4 | 76 | 4 |
| 398 | gucAAcGAccGAccuuGAGdTsdT | 562 | CUcAAGGUCGGUCGUUGACdTsdT | 55 | 2 | 77 | 13 |
| 399 | auAuucuuGGGAAcAAGAGdTsdT | 563 | CUCUUGUUCCcAAGAAuAUdTsdT | 56 | 5 | 77 | 11 |
| 400 | ugcucGuGuuAcAGGcGGGdTsdT | 564 | CCCGCCUGuAAcACGAGcAdTsdT | 61 | 5 | 78 | 4 |
| 401 | caAucGccGcGucGcAGAAdTsdT | 565 | UUCUGCGACGCGGCGAUUGdTsdT | 65 | 1 | 78 | 4 |
| 402 | acuGuucAAGccuccAAGcdTsdT | 566 | GCUUGGAGGCUUGAAcAGUdTsdT | 86 | 3 | 78 | 5 |
| 403 | cgccGcGucGcAGAAGAucdTsdT | 567 | GAUCUUCUGCGACGCGGCGdTsdT | 71 | 3 | 79 | 2 |
| 404 | cauuuGuucAGuGGuucGudTsdT | 568 | ACGAACcACUGAAcAAAUGdTsdT | 54 | 5 | 80 | 4 |
| 405 | cgcuGAAucccGcGGAcGAdTsdT | 569 | UCGUCCGCGGGAUUcAGCGdTsdT | 62 | 2 | 80 | 7 |

FIG. 2C

| | | | | | | | |
|---|---|---|---|---|---|---|---|
| 406 | ugGGucAccAuAuucuuGGdTsdT | 570 | CcAAGAAuAUGGUGACCcAdTsdT | 75 | 2 | 80 | 16 |
| 407 | uccucuGccGAuccAuAcudTsdT | 571 | AGuAUGGAUCGGcAGAGGAdTsdT | 73 | 2 | 81 | 3 |
| 408 | auGucAAcGAccGAccuuGdTsdT | 572 | cAAGGUCGGUCGUUGAcAUdTsdT | 69 | 8 | 81 | 7 |
| 409 | ccucuGccuAAucAucucAdTsdT | 573 | UGAGAUGAUuAGGcAGAGGdTsdT | 81 | 4 | 81 | 4 |
| 410 | accGuGuGcAcuucGcuucdTsdT | 574 | GAAGCGAAGUGcAcACGGUdTsdT | 46 | 5 | 81 | 7 |
| 411 | ugccGAuccAuAcuGcGGAdTsdT | 575 | UCCGcAGuAUGGAUCGGcAdTsdT | 61 | 8 | 81 | 5 |
| 412 | caGAGucuAGAcucGuGGudTsdT | 576 | ACcACGAGUCuAGACUCUGdTsdT | 65 | 9 | 81 | 5 |
| 413 | cuGuucAAGccuccAAGcudTsdT | 577 | AGCUUGGAGGCUUGAAcAGdTsdT | 82 | 3 | 82 | 21 |
| 414 | ggAGGcuGuAGGcAuAAAudTsdT | 578 | AUUuAUGCCuAcAGCCUCCdTsdT | 68 | 2 | 82 | 12 |
| 415 | agGAGGcuGuAGGcAuAAAdTsdT | 579 | UUuAUGCCuAcAGCCUCCUdTsdT | 55 | 4 | 83 | 5 |
| 416 | gguGGAcuucucucAAuuudTsdT | 580 | AAAUUGAGAGAAGUCcACCdTsdT | 62 | 7 | 84 | 2 |
| 417 | gcAAcuuuuucAccucuGcdTsdT | 581 | GcAGAGGUGAAAAAGUUGCdTsdT | 93 | 1 | 85 | 5 |
| 418 | CfuGfcUfcGfuGfuUfaCfaGfgCfgAf(invdT) | 582 | pdTCfgCfcUfgUfaAfcAfcGfaGfcAfgdTsdT | 56 | 1 | 86 | 2 |
| 419 | cuAGuGccAuuuGuucAGudTsdT | 583 | ACUGAAcAAAUGGcACuAGdTsdT | 66 | 0 | 86 | 6 |
| 420 | cuGccGAuccAuAcuGcGGdTsdT | 584 | CCGcAGuAUGGAUCGGcAGdTsdT | 73 | 8 | 86 | 5 |
| 421 | guGuGcAcuucGcuucAccdTsdT | 585 | GGUGAAGCGAAGUGcAcACdTsdT | 54 | 4 | 87 | 4 |
| 422 | gcucGuGuuAcAGGcGGGcdTsdT | 586 | GCCCGCCUGuAAcACGAGCdTsdT | 91 | 4 | 87 | 5 |
| 423 | ccuAucuuAucAAcAcuucdTsdT | 587 | GAAGUGUUGAuAAGAuAGGdTsdT | 37 | 2 | 88 | 45 |
| 424 | ucucAAucGccGcGucGcAdTsdT | 588 | UGCGACGCGGCGAUUGAGAdTsdT | 79 | 4 | 88 | 6 |
| 425 | gcccGucuGuGccuucucAdTsdT | 589 | UGAGAAGGcAcAGACGGGCdTsdT | 85 | 4 | 88 | 16 |
| 426 | cuAucuuAucAAcAcuuccdTsdT | 590 | GGAAGUGUUGAuAAGAuAGdTsdT | 43 | 3 | 90 | 23 |
| 427 | auGuuGcccGuuuGuccucdTsdT | 591 | GAGGAcAAACGGGcAAcAUdTsdT | 87 | 5 | 90 | 4 |
| 428 | guAuGuuGcccGuuuGuccdTsdT | 592 | GGAcAAACGGGcAAcAuACdTsdT | 88 | 4 | 90 | 11 |
| 429 | cuucGcuucAccucuGcAcdTsdT | 593 | GUGcAGAGGUGAAGCGAAGdTsdT | 69 | 7 | 91 | 5 |
| 430 | uguGcAcuucGcuucAccudTsdT | 594 | AGGUGAAGCGAAGUGcAcAdTsdT | 76 | 3 | 91 | 14 |
| 431 | gccAAAAuucGcAGucccGdTsdT | 595 | CGGGACUGCGAAUUUUGGCdTsdT | 81 | 3 | 92 | 3 |
| 432 | ccuGcucGuGuuAcAGGcGdTsdT | 596 | CGCCUGuAAcACGAGcAGGdTsdT | 86 | 3 | 92 | 1 |
| 433 | ugGAGuGuGGAuucGcAcudTsdT | 597 | AGUGCGAAUCcAcACUCcAdTsdT | 87 | 4 | 92 | 3 |
| 434 | aacGAccGAccuuGAGGcAdTsdT | 598 | UGCCUcAAGGUCGGUCGUUdTsdT | 83 | 9 | 92 | 3 |
| 435 | acAGAGucuAGAcucGuGGdTsdT | 599 | CcACGAGUCuAGACUCUGUdTsdT | 89 | 4 | 92 | 4 |

FIG. 2D

| | | | | | | | |
|---|---|---|---|---|---|---|---|
| 436 | aaucGccGcGucGcAGAAGdTsdT | 600 | CUUCUGCGACGCGGCGAUUdTsdT | 85 | 6 | 92 | 2 |
| 437 | gguAuGuuGcccGuuuGucdTsdT | 601 | GAcAAACGGGcAAcAuACCdTsdT | 80 | 2 | 93 | 3 |
| 438 | gccGAuccAuAcuGcGGAAdTsdT | 602 | UUCCGcAGuAUGGAUCGGCdTsdT | 79 | 3 | 93 | 3 |
| 439 | gcccuAucuuAucAAcAcudTsdT | 603 | AGUGUUGAuAAGAuAGGGCdTsdT | 84 | 4 | 94 | 50 |
| 440 | aguuuAcuAGuGccAuuuGdTsdT | 604 | cAAAUGGcACuAGuAAACUdTsdT | 89 | 7 | 95 | 8 |
| 441 | ugucAAcGAccGAccuuGAdTsdT | 605 | UcAAGGUCGGUCGUUGAcAdTsdT | 84 | 5 | 95 | 8 |
| 442 | acuucucucAAuuuucuAGdTsdT | 606 | CuAGAAAAUUGAGAGAAGUdTsdT | 103 | 3 | 95 | 6 |
| 443 | gcGcGGGAcGuccuuuGucdTsdT | 607 | GAcAAAGGACGUCCCGCGCdTsdT | 88 | 4 | 97 | 3 |
| 444 | ucuAGAcucGuGGuGGAcudTsdT | 608 | AGUCcACcACGAGUCuAGAdTsdT | 90 | 5 | 97 | 2 |
| 445 | gauccAuAcuGcGGAAcucdTsdT | 609 | GAGUUCCGcAGuAUGGAUCdTsdT | 73 | 6 | 98 | 4 |
| 446 | cucuGccGAuccAuAcuGcdTsdT | 610 | GcAGuAUGGAUCGGcAGAGdTsdT | 100 | 5 | 99 | 7 |
| 447 | ucuGccGAuccAuAcuGcGdTsdT | 611 | CGcAGuAUGGAUCGGcAGAdTsdT | 88 | 6 | 99 | 4 |
| 448 | ccucuGccGAuccAuAcuGdTsdT | 612 | cAGuAUGGAUCGGcAGAGGdTsdT | 98 | 11 | 99 | 5 |
| 449 | gcAccucucuuuAcGcGGudTsdT | 613 | ACCGCGuAAAGAGAGGUGCdTsdT | 82 | 7 | 100 | 4 |
| 450 | aaGAAcucccucGccucGcdTsdT | 614 | GCGAGGCGAGGGAGUUCUUdTsdT | 97 | 6 | 100 | 1 |
| 451 | gaAcucccucGccucGcAGdTsdT | 615 | CUGCGAGGCGAGGGAGUUCdTsdT | 100 | 2 | 100 | 2 |
| 452 | ucucucAAuuuucuAGGGcdTsdT | 616 | GCCCuAGAAAAUUGAGAGAdTsdT | 102 | 4 | 100 | 8 |
| 453 | ggGcGcAccucucuuuAcGdTsdT | 617 | CGuAAAGAGAGGUGCGCCCdTsdT | 80 | 4 | 100 | 3 |
| 454 | ccGAuccAuAcuGcGGAAcdTsdT | 618 | GUUCCGcAGuAUGGAUCGGdTsdT | 83 | 5 | 101 | 3 |
| 455 | aacucccucGccucGcAGAdTsdT | 619 | UCUGCGAGGCGAGGGAGUUdTsdT | 100 | 2 | 101 | 2 |
| 456 | cuccucuGccGAuccAuAcdTsdT | 620 | GuAUGGAUCGGcAGAGGAGdTsdT | 93 | 2 | 101 | 2 |
| 457 | ggAGuGuGGAuucGcAcucdTsdT | 621 | GAGUGCGAAUCcAcACUCCdTsdT | 97 | 5 | 101 | 3 |
| 458 | cgGGcGcAccucucuuuAcdTsdT | 622 | GuAAAGAGAGGUGCGCCCGdTsdT | 83 | 6 | 101 | 6 |
| 459 | gucucAAucGccGcGucGcdTsdT | 623 | GCGACGCGGCGAUUGAGACdTsdT | 92 | 4 | 102 | 9 |
| 460 | auccAuAcuGcGGAAcuccdTsdT | 624 | GGAGUUCCGcAGuAUGGAUdTsdT | 88 | 3 | 102 | 7 |
| 461 | cgcAccucucuuuAcGcGGdTsdT | 625 | CCGCGuAAAGAGAGGUGCGdTsdT | 78 | 1 | 102 | 10 |
| 462 | caAcGAccGAccuuGAGGcdTsdT | 626 | GCCUcAAGGUCGGUCGUUGdTsdT | 88 | 4 | 102 | 8 |
| 463 | ccAuAcuGcGGAAcuccuAdTsdT | 627 | uAGGAGUUCCGcAGuAUGGdTsdT | 85 | 3 | 102 | 5 |
| 464 | ugAAucccGcGGAcGAcccdTsdT | 628 | GGGUCGUCCGCGGGAUUcAdTsdT | 92 | 4 | 103 | 3 |
| 465 | agAAcucccucGccucGcAdTsdT | 629 | UGCGAGGCGAGGGAGUUCUdTsdT | 94 | 5 | 103 | 2 |

FIG. 2E

| | | | | | | | |
|---|---|---|---|---|---|---|---|
| 466 | ggcGcAccucucuuuAcGcdTsdT | 630 | GCGuAAAGAGAGGUGCGCCdTsdT | 97 | 7 | 103 | 10 |
| 467 | gcGcAccucucuuuAcGcGdTsdT | 631 | CGCGuAAAGAGAGGUGCGCdTsdT | 99 | 5 | 104 | 7 |
| 468 | gcuGAAucccGcGGAcGAcdTsdT | 632 | GUCGUCCGCGGGAUUcAGCdTsdT | 84 | 2 | 104 | 3 |
| 469 | cacuucGcuucAccucuGcdTsdT | 633 | GcAGAGGUGAAGCGAAGUGdTsdT | 90 | 4 | 105 | 12 |
| 470 | cucAAucGccGcGucGcAGdTsdT | 634 | CUGCGACGCGGCGAUUGAGdTsdT | 99 | 3 | 105 | 14 |
| 471 | ucccGucGGcGcuGAAuccdTsdT | 635 | GGAUUcAGCGCCGACGGGAdTsdT | 91 | 3 | 106 | 7 |
| 472 | cuGAAucccGcGGAcGAccdTsdT | 636 | GGUCGUCCGCGGGAUUcAGdTsdT | 96 | 2 | 106 | 6 |
| 473 | agAGucuAGAcucGuGGuGdTsdT | 637 | cACcACGAGUCuAGACUCUdTsdT | 93 | 4 | 107 | 9 |
| 474 | uccAuAcuGcGGAAcuccudTsdT | 638 | AGGAGUUCCGcAGuAUGGAdTsdT | 91 | 4 | 107 | 7 |
| 475 | gcGcuGAAucccGcGGAcGdTsdT | 639 | CGUCCGCGGGAUUcAGCGCdTsdT | 90 | 3 | 108 | 3 |
| 476 | aguGuGGAuucGcAcuccudTsdT | 640 | AGGAGUGCGAAUCcAcACUdTsdT | 94 | 4 | 111 | 3 |
| 477 | cccuGcucGuGuuAcAGGcdTsdT | 641 | GCCUGuAAcACGAGcAGGGdTsdT | 99 | 11 | 111 | 10 |
| 478 | gaAucccGcGGAcGAcccGdTsdT | 642 | CGGGUCGUCCGCGGGAUUCdTsdT | 96 | 3 | 115 | 5 |
| 479 | aaGcuGuGccuuGGGuGGcdTsdT | 643 | GCcACCcAAGGcAcAGCUUdTsdT | 99 | 5 | 116 | 53 |
| 480 | gcccuGcucGuGuuAcAGGdTsdT | 644 | CCUGuAAcACGAGcAGGGCdTsdT | 96 | 5 | 116 | 11 |
| 481 | gucccGucGGcGcuGAAucdTsdT | 645 | GAUUcAGCGCCGACGGGACdTsdT | 93 | 2 | 118 | 4 |
| 482 | aucuuAucAAcAcuuccGGdTsdT | 646 | CCGGAAGUGUUGAuAAGAUdTsdT | 76 | 3 | 126 | 23 |
| 483 | cuuAucAAcAcuuccGGAAdTsdT | 647 | UUCCGGAAGUGUUGAuAAGdTsdT | 39 | 6 | 42 | 3 |

FIG. 2F

Table 3. Serum stability of dsRNAs targeting Hepatitis B Virus.

| SEQ ID No. Pair | Mouse Serum | | Human Serum | | Cynomologous Serum | |
|---|---|---|---|---|---|---|
| | sense $t_{1/2}$ (hr) | antisense $t_{1/2}$ (hr) | sense $t_{1/2}$ (hr) | antisense $t_{1/2}$ (hr) | sense $t_{1/2}$ (hr) | antisense $t_{1/2}$ (hr) |
| 321/485 | 26.4 | 0.5 | >48 | 2.1 | n.d. | n.d. |
| 325/489 | 27.2 | 6.7 | >48 | 8.8 | n.d. | n.d. |
| 350/514 | 11.3 | 2.6 | >48 | 17.0 | n.d. | n.d. |
| 326/490 | >48 | 11.7 | >48 | 43.9 | >48 | 5.5 |
| 324/488 | >48 | 13.3 | >48 | 44.7 | >48 | 6.4 |
| 328/492 | 19.1 | 9.9 | >48 | >48 | n.d. | n.d. |
| 322/486 | >48 | 14.5 | >48 | >48 | >48 | 6.5 |
| 327/491 | >48 | 16.0 | >48 | >48 | >48 | 8.1 |

FIG. 3

Table 4. Core sequences of dsRNAs targeting Hepatitis B Virus gene and their modified counterparts.

| core sequence | | | | modified sequence | | | |
|---|---|---|---|---|---|---|---|
| SEQ ID No. | sense strand sequence (5′-3′) | SEQ ID No. | antisense strand sequence (5′-3′) | SEQ ID No. | sense strand sequence (5′-3′) | SEQ ID No. | antisense strand sequence (5′-3′) |
| 1 | CAAGGUAUGUUGCCCGUUU | 157 | AAACGGGCAACAUACCUUG | 321 | caAGGuAuGuuGcccGuuudTsdT | 485 | AAACGGGcAAcAuACCUUGdTsdT |
| 2 | CUGUAGGCAUAAAUUGGUA | 158 | TACCAAUUUAUGCCUACAG | 322 | CfuGfuAfgGfcAfuAfaAfuUfgGfuAf(invdT) | 486 | pdTAfcCfaAfuUfuAfuGfcCfuAfcAfgdTsdT |
| 3 | UCUGCGGCGUUUUAUCAUA | 159 | UAUGAUAAAACGCCGCAGA | 323 | ucuGcGGcGuuuuAucAuAdTsdT | 487 | uAUGAuAAAACGCCGcAGAdTsdT |
| 3 | UCUGCGGCGUUUUAUCAUA | 160 | TAUGAUAAAACGCCGCAGA | 324 | UfcUfgCfgGfcGfuUfuUfaUfcAfuAf(invdT) | 488 | pdTAfuGfaUfaAfaAfcGfcCfgCfaGfadTsdT |
| 4 | ACCUCUGCCUAAUCAUCUC | 161 | GAGAUGAUUAGGCAGAGGU | 325 | accucuGccuAAucAucucdTsdT | 489 | GAGAUGAUuAGGcAGAGGUdTsdT |
| 5 | UUUACUAGUGCCAUUUGUA | 162 | TACAAAUGGCACUAGUAAA | 326 | UfuUfaCfuAfgUfgCfcAfuUfuGfuAf(invdT) | 490 | pdTAfcAfaAfuGfgCfaCfuAfgUfaAfadTsdT |
| 6 | ACCUCUGCCUAAUCAUCUA | 163 | TAGAUGAUUAGGCAGAGGU | 327 | AfcCfuCfuGfcCfuAfaUfcAfuCfuAf(invdT) | 491 | pdTAfgAfuGfaUfuAfgGfcAfgAfgGfudTsdT |
| 7 | CUGUAGGCAUAAAUUGGUC | 164 | GACCAAUUUAUGCCUACAG | 328 | cuGuAGGcAuAAAuuGGucdTsdT | 492 | GACcAAUUuAUGCCuAcAGdTsdT |
| 8 | UGUCUGCGGCGUUUUAUCA | 165 | UGAUAAAACGCCGCAGACA | 329 | ugucuGcGGcGuuuuAucAdTsdT | 493 | UGAuAAAACGCCGcAGAcAdTsdT |
| 8 | UGUCUGCGGCGUUUUAUCA | 166 | TGAUAAAACGCCGCAGACA | 330 | UfgUfcUfgCfgGfcGfuUfuUfaUfcAf(invdT) | 494 | pdTGfaUfaAfaAfcGfcCfgCfaGfaCfadTsdT |
| 9 | UACUAGUGCCAUUUGUUCA | 167 | UGAACAAAUGGCACUAGUA | 331 | uacuAGuGccAuuuGuucAdTsdT | 495 | UGAAcAAAUGGcACuAGuAdTsdT |
| 9 | UACUAGUGCCAUUUGUUCA | 168 | TGAACAAAUGGCACUAGUA | 332 | UfaCfuAfgUfgCfcAfuUfuGfuUfcAf(invdT) | 496 | pdTGfaAfcAfaAfuGfgCfaCfuAfgUfadTsdT |
| 10 | CAACUUUUUCACCUCUGCA | 169 | TGCAGAGGUGAAAAAGUUG | 333 | CfaAfcUfuUfuUfcAfcCfuCfuGfcAf(invdT) | 497 | pdTGfcAfgAfgGfuGfaAfaAfaGfuUfgdTsdT |

FIG. 4A

| | | | | | | | |
|---|---|---|---|---|---|---|---|
| 11 | CCAUUUGUUCAGUGGUUCG | 170 | CGAACCACUGAACAAAUGG | 334 | ccAuuuGuucAGuGGuucGdTsdT | 498 | CGAACcACUGAAcAAAUGGdTsdT |
| 12 | CCAAGUGUUUGCUGACGCA | 171 | UGCGUCAGCAAACACUUGG | 335 | ccAAGuGuuuGcuGAcGcAdTsdT | 499 | UGCGUcAGcAAAcACUUGGdTsdT |
| 12 | CCAAGUGUUUGCUGACGCA | 172 | TGCGUCAGCAAACACUUGG | 336 | CfcAfaGfuGfuUfuGfcUfgAfcGfcAf(invdT) | 500 | pdTGfcGfuCfaGfcAfaAfcAfcUfuGfgdTsdT |
| 13 | CCAUUUGUUCAGUGGUUCA | 173 | TGAACCACUGAACAAAUGG | 337 | CfcAfuUfuGfuUfcAfgUfgGfuUfcAf(invdT) | 501 | pdTGfaAfcCfaCfuGfaAfcAfaAfuGfgdTsdT |
| 14 | UUUACUAGUGCCAUUUGUU | 174 | AACAAAUGGCACUAGUAAA | 338 | uuuAcuAGuGccAuuuGuudTsdT | 502 | AAcAAAUGGcACuAGuAAAdTsdT |
| 15 | CACCUCUGCCUAAUCAUCA | 175 | TGAUGAUUAGGCAGAGGUG | 339 | CfaCfcUfcUfgCfcUfaAfuCfaUfcAf(invdT) | 503 | pdTGfaUfgAfuUfaGfgCfaGfaGfgUfgdTsdT |
| 16 | CUGGCUCAGUUUACUAGUG | 176 | CACUAGUAAACUGAGCCAG | 340 | cuGGcucAGuuuAcuAGuGdTsdT | 504 | cACuAGuAAACUGAGCcAGdTsdT |
| 17 | CAAGGUAUGUUGCCCGUUA | 177 | TAACGGGCAACAUACCUUG | 341 | CfaAfgGfuAfuGfuUfgCfcCfgUfuAf(invdT) | 505 | pdTAfaCfgGfgCfaAfcAfuAfcCfuUfgdTsdT |
| 18 | CUGGCUCAGUUUACUAGUA | 178 | TACUAGUAAACUGAGCCAG | 342 | CfuGfgCfuCfaGfuUfuAfcUfaGfuAf(invdT) | 506 | pdTAfcUfaGfuAfaAfcUfgAfgCfcAfgdTsdT |
| 19 | GAGGCUGUAGGCAUAAAUU | 179 | AAUUUAUGCCUACAGCCUC | 343 | gaGGcuGuAGGcAuAAAuudTsdT | 507 | AAUUuAUGCCuAcAGCCUCdTsdT |
| 20 | CAGUUUACUAGUGCCAUUU | 180 | AAAUGGCACUAGUAAACUG | 344 | caGuuuAcuAGuGccAuuudTsdT | 508 | AAAUGGcACuAGuAAACUGdTsdT |
| 21 | AGGUAUGUUGCCCGUUUGU | 181 | ACAAACGGGCAACAUACCU | 345 | agGuAuGuuGcccGuuuGudTsdT | 509 | AcAAACGGGcAAcAuACCUdTsdT |
| 22 | UAUGUUGCCCGUUUGUCCA | 182 | UGGACAAACGGGCAACAUA | 346 | UfaUfgUfuGfcCfcGfuUfuGfuCfcAf(invdT) | 510 | pdTGfgAfcAfaAfcGfgGfcAfaCfaUfadTsdT |
| 23 | GAGGCUGUAGGCAUAAAUA | 183 | TAUUUAUGCCUACAGCCUC | 347 | GfaGfgCfuGfuAfgGfcAfuAfaAfuAf(invdT) | 511 | pdTAfuUfuAfuGfcCfuAfcAfgCfcUfcdTsdT |
| 24 | GUCUGCGGCGUUUUAUCAU | 184 | AUGAUAAAACGCCGCAGAC | 348 | gucuGcGGcGuuuuAucAudTsdT | 512 | AUGAuAAAACGCCGcAGACdTsdT |
| 25 | CAACUUUUUCACCUCUGCC | 185 | GGCAGAGGUGAAAAAGUUG | 349 | caAcuuuuucAccucuGccdTsdT | 513 | GGcAGAGGUGAAAAAGUUGdTsdT |

FIG. 4B

| | | | | | | | |
|---|---|---|---|---|---|---|---|
| 26 | CCGUGUGCACUUCGCUUCA | 186 | UGAAGCGAAGUGCACACGG | 350 | ccGuGuGcAcuucGcuucAdTsdT | 514 | UGAAGCGAAGUGcAcACGGdTsdT |
| 26 | CCGUGUGCACUUCGCUUCA | 187 | TGAAGCGAAGUGCACACGG | 351 | CfcGfuGfuGfcAfcUfuCfgCfuUfcAf(invdT) | 515 | pdTGfaAfgCfgAfaGfuGfcAfcAfcGfgdTsdT |
| 27 | UCAAGGUAUGUUGCCCGUA | 188 | TACGGGCAACAUACCUUGA | 352 | UfcAfaGfgUfaUfgUfuGfcCfcGfuAf(invdT) | 516 | pdTAfcGfgGfcAfaCfaUfaCfcUfuGfadTsdT |
| 28 | CAGUUUACUAGUGCCAUUA | 189 | TAAUGGCACUAGUAAACUG | 353 | CfaGfuUfuAfcUfaGfuGfcCfaUfuAf(invdT) | 517 | pdTAfaUfgGfcAfcUfaGfuAfaAfcUfgdTsdT |
| 29 | UGGUGGACUUCUCUCAAUU | 190 | AAUUGAGAGAAGUCCACCA | 354 | ugGuGGAcuucucucAAuudTsdT | 518 | AAUUGAGAGAAGUCcACcAdTsdT |
| 30 | AGGUAUGUUGCCCGUUUGA | 191 | TCAAACGGGCAACAUACCU | 355 | AfgGfuAfuGfuUfgCfcCfgUfuUfgAf(invdT) | 519 | pdTCfaAfaCfgGfgCfaAfcAfuAfcCfudTsdT |
| 31 | CUGCUCGUGUUACAGGCGG | 192 | CCGCCUGUAACACGAGCAG | 356 | cuGcucGuGuuAcAGGcGGdTsdT | 520 | CCGCCUGuAAcACGAGcAGdTsdT |
| 32 | UAUGUUGCCCGUUUGUCCU | 193 | AGGACAAACGGGCAACAUA | 357 | uauGuuGcccGuuuGuccudTsdT | 521 | AGGAcAAACGGGcAAcAuAdTsdT |
| 33 | UCAAGGUAUGUUGCCCGUU | 194 | AACGGGCAACAUACCUUGA | 358 | ucAAGGuAuGuuGcccGuudTsdT | 522 | AACGGGcAAcAuACCUUGAdTsdT |
| 34 | UCUUAUCAACACUUCCGGA | 195 | UCCGGAAGUGUUGAUAAGA | 359 | ucuuAucAAcAcuuccGGAdTsdT | 523 | UCCGGAAGUGUUGAuAAGAdTsdT |
| 34 | UCUUAUCAACACUUCCGGA | 196 | TCCGGAAGUGUUGAUAAGA | 360 | UfcUfuAfuCfaAfcAfcUfuCfcGfgAf(invdT) | 524 | pdTCfcGfgAfaGfuGfuUfgAfuAfaGfadTsdT |
| 35 | CACCUCUGCCUAAUCAUCU | 197 | AGAUGAUUAGGCAGAGGUG | 361 | caccucuGccuAAucAucudTsdT | 525 | AGAUGAUuAGGcAGAGGUGdTsdT |
| 36 | AUAAGAGGACUCUUGGACU | 198 | AGUCCAAGAGUCCUCUUAU | 362 | auAAGAGGAcucuuGGAcudTsdT | 526 | AGUCcAAGAGUCCUCUuAUdTsdT |
| 37 | GUCUGCGGCGUUUUAUCAA | 199 | TUGAUAAAACGCCGCAGAC | 363 | GfuCfuGfcGfgCfgUfuUfuAfuCfaAf(invdT) | 527 | pdTUfgAfuAfaAfaCfgCfcGfcAfgAfcdTsdT |
| 38 | GGCGCUGAAUCCCGCGGAC | 200 | GUCCGCGGGAUUCAGCGCC | 364 | ggcGcuGAAucccGcGGAcdTsdT | 528 | GUCCGCGGGAUUcAGCGCCdTsdT |
| 39 | CGCGUCGCAGAAGAUCUCA | 201 | UGAGAUCUUCUGCGACGCG | 365 | cgcGucGcAGAAGAucucAdTsdT | 529 | UGAGAUCUUCUGCGACGCGdTsdT |

FIG. 4C

| | | | | | | | |
|---|---|---|---|---|---|---|---|
| 40 | AAUGUCAACGACCGACCUU | 202 | AAGGUCGGUCGUUGACAUU | 366 | aauGucAAcGAccGAccuudTsdT | 530 | AAGGUCGGUCGUUGAcAUUdTsdT |
| 41 | GCUCAGUUUACUAGUGCCA | 203 | UGGCACUAGUAAACUGAGC | 367 | gcucAGuuuAcuAGuGccAdTsdT | 531 | UGGcACuAGuAAACUGAGCdTsdT |
| 42 | UGGUGGACUUCUCUCAAUA | 204 | TAUUGAGAGAAGUCCACCA | 368 | UfgGfuGfgAfcUfuCfuCfuCfaAfuAf(invdT) | 532 | pdTAfuUfgAfgAfgAfaGfuCfcAfcCfadTsdT |
| 43 | AUCGCCGCGUCGCAGAAGA | 205 | UCUUCUGCGACGCGGCGAU | 369 | aucGccGcGucGcAGAAGAdTsdT | 533 | UCUUCUGCGACGCGGCGAUdTsdT |
| 44 | GCCAUUUGUUCAGUGGUUC | 206 | GAACCACUGAACAAAUGGC | 370 | gccAuuuGuucAGuGGuucdTsdT | 534 | GAACcACUGAAcAAAUGGCdTsdT |
| 45 | CGAUCCAUACUGCGGAACU | 207 | AGUUCCGCAGUAUGGAUCG | 371 | cgAuccAuAcuGcGGAAcudTsdT | 535 | AGUUCCGcAGuAUGGAUCGdTsdT |
| 46 | UCACCUCUGCCUAAUCAUC | 208 | GAUGAUUAGGCAGAGGUGA | 372 | ucAccucuGccuAAucAucdTsdT | 536 | GAUGAUuAGGcAGAGGUGAdTsdT |
| 47 | GUGGACUUCUCUCAAUUUU | 209 | AAAAUUGAGAGAAGUCCAC | 373 | guGGAcuucucucAAuuuudTsdT | 537 | AAAAUUGAGAGAAGUCcACdTsdT |
| 48 | GGGUCACCAUAUUCUUGGG | 210 | CCCAAGAAUAUGGUGACCC | 374 | ggGucAccAuAuucuuGGGdTsdT | 538 | CCcAAGAAuAUGGUGACCCdTsdT |
| 49 | GCCGCGUCGCAGAAGAUCU | 211 | AGAUCUUCUGCGACGCGGC | 375 | gccGcGucGcAGAAGAucudTsdT | 539 | AGAUCUUCUGCGACGCGGCdTsdT |
| 50 | UCAAUCGCCGCGUCGCAGA | 212 | UCUGCGACGCGGCGAUUGA | 376 | ucAAucGccGcGucGcAGAdTsdT | 540 | UCUGCGACGCGGCGAUUGAdTsdT |
| 51 | UGGAUGUGUCUGCGGCGUU | 213 | AACGCCGCAGACACAUCCA | 377 | ugGAuGuGucuGcGGcGudTsdT | 541 | AACGCCGcAGAcAcAUCcAdTsdT |
| 52 | UACUGUUCAAGCCUCCAAG | 214 | CUUGGAGGCUUGAACAGUA | 378 | uacuGuucAAGccuccAAGdTsdT | 542 | CUUGGAGGCUUGAAcAGUAdTsdT |
| 53 | GUUUACUAGUGCCAUUUGU | 215 | ACAAAUGGCACUAGUAAAC | 379 | guuuAcuAGuGccAuuuGudTsdT | 543 | AcAAAUGGcACuAGuAAACdTsdT |
| 54 | ACUAGUGCCAUUUGUUCAG | 216 | CUGAACAAAUGGCACUAGU | 380 | acuAGuGccAuuuGuucAGdTsdT | 544 | CUGAAcAAAUGGcACuAGUdTsdT |
| 55 | CCGCGUCGCAGAAGAUCUC | 217 | GAGAUCUUCUGCGACGCGG | 381 | ccGcGucGcAGAAGAucucdTsdT | 545 | GAGAUCUUCUGCGACGCGGdTsdT |

FIG. 4D

| | | | | | | | |
|---|---|---|---|---|---|---|---|
| 56 | UAUCUUAUCAACACUUCCG | 218 | CGGAAGUGUUGAUAAGAUA | 382 | uaucuuAucAAcAcuuccGdTsdT | 546 | CGGAAGUGUUGAuAAGAuAdTsdT |
| 57 | GGCCAAAAUUCGCAGUCCC | 219 | GGGACUGCGAAUUUUGGCC | 383 | ggccAAAAuucGcAGucccdTsdT | 547 | GGGACUGCGAAUUUUGGCCdTsdT |
| 58 | UUCACCUCUGCCUAAUCAU | 220 | AUGAUUAGGCAGAGGUGAA | 384 | uucAccucuGccuAAucAudTsdT | 548 | AUGAUuAGGcAGAGGUGAAdTsdT |
| 59 | CUCAGUUUACUAGUGCCAU | 221 | AUGGCACUAGUAAACUGAG | 385 | cucAGuuuAcuAGuGccAudTsdT | 549 | AUGGcACuAGuAAACUGAGdTsdT |
| 60 | UGUUGCCCGUUUGUCCUCU | 222 | AGAGGACAAACGGGCAACA | 386 | uguuGcccGuuuGuccucudTsdT | 550 | AGAGGAcAAACGGGcAAcAdTsdT |
| 61 | UAGUGCCAUUUGUUCAGUG | 223 | CACUGAACAAAUGGCACUA | 387 | uaGuGccAuuuGuucAGuGdTsdT | 551 | cACUGAAcAAAUGGcACuAdTsdT |
| 62 | AGGCUGUAGGCAUAAAUUG | 224 | CAAUUUAUGCCUACAGCCU | 388 | agGcuGuAGGcAuAAAuuGdTsdT | 552 | cAAUUuAUGCCuAcAGCCUdTsdT |
| 63 | AUGUGUCUGCGGCGUUUUA | 225 | UAAAACGCCGCAGACACAU | 389 | auGuGucuGcGGcGuuuuAdTsdT | 553 | uAAAACGCCGcAGAcAcAUdTsdT |
| 63 | AUGUGUCUGCGGCGUUUUA | 226 | TAAAACGCCGCAGACACAU | 390 | AfuGfuGfuCfuGfcGfgCfgUfuUfuAf(invdT) | 554 | pdTAfaAfaCfgCfcGfcAfgAfcAfcAfudTsdT |
| 64 | ACUUCGCUUCACCUCUGCA | 227 | UGCAGAGGUGAAGCGAAGU | 391 | acuucGcuucAccucuGcAdTsdT | 555 | UGcAGAGGUGAAGCGAAGUdTsdT |
| 65 | CGUGUGCACUUCGCUUCAC | 228 | GUGAAGCGAAGUGCACACG | 392 | cguGuGcAcuucGcuucAcdTsdT | 556 | GUGAAGCGAAGUGcAcACGdTsdT |
| 66 | GUGGUGGACUUCUCUCAAU | 229 | AUUGAGAGAAGUCCACCAC | 393 | guGGuGGAcuucucucAAudTsdT | 557 | AUUGAGAGAAGUCcACcACdTsdT |
| 67 | UGUGUCUGCGGCGUUUUAU | 230 | AUAAAACGCCGCAGACACA | 394 | uguGucuGcGGcGuuuuAudTsdT | 558 | AuAAAACGCCGcAGAcAcAdTsdT |
| 68 | AAGGUAUGUUGCCCGUUUG | 231 | CAAACGGGCAACAUACCUU | 395 | aaGGuAuGuuGcccGuuuGdTsdT | 559 | cAAACGGGcAAcAuACCUUdTsdT |
| 69 | UCAACGACCGACCUUGAGG | 232 | CCUCAAGGUCGGUCGUUGA | 396 | ucAAcGAccGAccuuGAGGdTsdT | 560 | CCUcAAGGUCGGUCGUUGAdTsdT |
| 70 | CAUAAGAGGACUCUUGGAC | 233 | GUCCAAGAGUCCUCUUAUG | 397 | cauAAGAGGAcucuuGGAcdTsdT | 561 | GUCcAAGAGUCCUCUuAUGdTsdT |

FIG. 4E

| | | | | | | | |
|---|---|---|---|---|---|---|---|
| 71 | GUCAACGACCGACCUUGAG | 234 | CUCAAGGUCGGUCGUUGAC | 398 | gucAAcGAccGAccuuGAGdTsdT | 562 | CUcAAGGUCGGUCGUUGACdTsdT |
| 72 | AUAUUCUUGGGAACAAGAG | 235 | CUCUUGUUCCCAAGAAUAU | 399 | auAuucuuGGGAAcAAGAGdTsdT | 563 | CUCUUGUUCCcAAGAAuAUdTsdT |
| 73 | UGCUCGUGUUACAGGCGGG | 236 | CCCGCCUGUAACACGAGCA | 400 | ugcucGuGuuAcAGGcGGGdTsdT | 564 | CCCGCCUGuAAcACGAGcAdTsdT |
| 74 | CAAUCGCCGCGUCGCAGAA | 237 | UUCUGCGACGCGGCGAUUG | 401 | caAucGccGcGucGcAGAAdTsdT | 565 | UUCUGCGACGCGGCGAUUGdTsdT |
| 75 | ACUGUUCAAGCCUCCAAGC | 238 | GCUUGGAGGCUUGAACAGU | 402 | acuGuucAAGccuccAAGcdTsdT | 566 | GCUUGGAGGCUUGAAcAGUdTsdT |
| 76 | CGCCGCGUCGCAGAAGAUC | 239 | GAUCUUCUGCGACGCGGCG | 403 | cgccGcGucGcAGAAGAucdTsdT | 567 | GAUCUUCUGCGACGCGGCGdTsdT |
| 77 | CAUUUGUUCAGUGGUUCGU | 240 | ACGAACCACUGAACAAAUG | 404 | cauuuGuucAGuGGuucGudTsdT | 568 | ACGAACcACUGAAcAAAUGdTsdT |
| 78 | CGCUGAAUCCCGCGGACGA | 241 | UCGUCCGCGGGAUUCAGCG | 405 | cgcuGAAucccGcGGAcGAdTsdT | 569 | UCGUCCGCGGGAUUcAGCGdTsdT |
| 79 | UGGGUCACCAUAUUCUUGG | 242 | CCAAGAAUAUGGUGACCCA | 406 | ugGGucAccAuAuucuuGGdTsdT | 570 | CcAAGAAuAUGGUGACCcAdTsdT |
| 80 | UCCUCUGCCGAUCCAUACU | 243 | AGUAUGGAUCGGCAGAGGA | 407 | uccucuGccGAuccAuAcudTsdT | 571 | AGuAUGGAUCGGcAGAGGAdTsdT |
| 81 | AUGUCAACGACCGACCUUG | 244 | CAAGGUCGGUCGUUGACAU | 408 | auGucAAcGAccGAccuuGdTsdT | 572 | cAAGGUCGGUCGUUGAcAUdTsdT |
| 82 | CCUCUGCCUAAUCAUCUCA | 245 | UGAGAUGAUUAGGCAGAGG | 409 | ccucuGccuAAucAucucAdTsdT | 573 | UGAGAUGAUuAGGcAGAGGdTsdT |
| 83 | ACCGUGUGCACUUCGCUUC | 246 | GAAGCGAAGUGCACACGGU | 410 | accGuGuGcAcuucGcuucdTsdT | 574 | GAAGCGAAGUGcAcACGGUdTsdT |
| 84 | UGCCGAUCCAUACUGCGGA | 247 | UCCGCAGUAUGGAUCGGCA | 411 | ugccGAuccAuAcuGcGGAdTsdT | 575 | UCCGcAGuAUGGAUCGGcAdTsdT |
| 85 | CAGAGUCUAGACUCGUGGU | 248 | ACCACGAGUCUAGACUCUG | 412 | caGAGucuAGAcucGuGGudTsdT | 576 | ACcACGAGUCuAGACUCUGdTsdT |
| 86 | CUGUUCAAGCCUCCAAGCU | 249 | AGCUUGGAGGCUUGAACAG | 413 | cuGuucAAGccuccAAGcudTsdT | 577 | AGCUUGGAGGCUUGAAcAGdTsdT |

FIG. 4F

| | | | | | | | |
|---|---|---|---|---|---|---|---|
| 87 | GGAGGCUGUAGGCAUAAAU | 250 | AUUUAUGCCUACAGCCUCC | 414 | ggAGGcuGuAGGcAuAAAudTsdT | 578 | AUUuAUGCCuAcAGCCUCCdTsdT |
| 88 | AGGAGGCUGUAGGCAUAAA | 251 | UUUAUGCCUACAGCCUCCU | 415 | agGAGGcuGuAGGcAuAAAdTsdT | 579 | UUuAUGCCuAcAGCCUCCUdTsdT |
| 89 | GGUGGACUUCUCUCAAUUU | 252 | AAAUUGAGAGAAGUCCACC | 416 | gguGGAcuucucucAAuuudTsdT | 580 | AAAUUGAGAGAAGUCcACCdTsdT |
| 90 | GCAACUUUUUCACCUCUGC | 253 | GCAGAGGUGAAAAAGUUGC | 417 | gcAAcuuuuucAccucuGcdTsdT | 581 | GcAGAGGUGAAAAAGUUGCdTsdT |
| 91 | CUGCUCGUGUUACAGGCGA | 254 | TCGCCUGUAACACGAGCAG | 418 | CfuGfcUfcGfuGfuUfaCfaGfgCfgAf(invdT) | 582 | pdTCfgCfcUfgUfaAfcAfcGfaGfcAfgdTsdT |
| 92 | CUAGUGCCAUUUGUUCAGU | 255 | ACUGAACAAAUGGCACUAG | 419 | cuAGuGccAuuuGuucAGudTsdT | 583 | ACUGAAcAAAUGGcACuAGdTsdT |
| 93 | CUGCCGAUCCAUACUGCGG | 256 | CCGCAGUAUGGAUCGGCAG | 420 | cuGccGAuccAuAcuGcGGdTsdT | 584 | CCGcAGuAUGGAUCGGcAGdTsdT |
| 94 | GUGUGCACUUCGCUUCACC | 257 | GGUGAAGCGAAGUGCACAC | 421 | guGuGcAcuucGcuucAccdTsdT | 585 | GGUGAAGCGAAGUGcAcACdTsdT |
| 95 | GCUCGUGUUACAGGCGGGC | 258 | GCCCGCCUGUAACACGAGC | 422 | gcucGuGuuAcAGGcGGGcdTsdT | 586 | GCCCGCCUGuAAcACGAGCdTsdT |
| 96 | CCUAUCUUAUCAACACUUC | 259 | GAAGUGUUGAUAAGAUAGG | 423 | ccuAucuuAucAAcAcuuccdTsdT | 587 | GAAGUGUUGAuAAGAuAGGdTsdT |
| 97 | UCUCAAUCGCCGCGUCGCA | 260 | UGCGACGCGGCGAUUGAGA | 424 | ucucAAucGccGcGucGcAdTsdT | 588 | UGCGACGCGGCGAUUGAGAdTsdT |
| 98 | GCCCGUCUGUGCCUUCUCA | 261 | UGAGAAGGCACAGACGGGC | 425 | gcccGucuGuGccuucucAdTsdT | 589 | UGAGAAGGcAcAGACGGGCdTsdT |
| 99 | CUAUCUUAUCAACACUUCC | 262 | GGAAGUGUUGAUAAGAUAG | 426 | cuAucuuAucAAcAcuuccdTsdT | 590 | GGAAGUGUUGAuAAGAuAGdTsdT |
| 100 | AUGUUGCCCGUUUGUCCUC | 263 | GAGGACAAACGGGCAACAU | 427 | auGuuGcccGuuuGuccucdTsdT | 591 | GAGGAcAAACGGGcAAcAUdTsdT |
| 101 | GUAUGUUGCCCGUUUGUCC | 264 | GGACAAACGGGCAACAUAC | 428 | guAuGuuGcccGuuuGuccdTsdT | 592 | GGAcAAACGGGcAAcAuACdTsdT |
| 102 | CUUCGCUUCACCUCUGCAC | 265 | GUGCAGAGGUGAAGCGAAG | 429 | cuucGcuucAccucuGcAcdTsdT | 593 | GUGcAGAGGUGAAGCGAAGdTsdT |

FIG. 4G

| | | | | | | | |
|---|---|---|---|---|---|---|---|
| 103 | UGUGCACUUCGCUUCACCU | 266 | AGGUGAAGCGAAGUGCACA | 430 | uguGcAcuucGcuucAccudTsdT | 594 | AGGUGAAGCGAAGUGcAcAdTsdT |
| 104 | GCCAAAAUUCGCAGUCCCG | 267 | CGGGACUGCGAAUUUUGGC | 431 | gccAAAAuucGcAGucccGdTsdT | 595 | CGGGACUGCGAAUUUUGGCdTsdT |
| 105 | CCUGCUCGUGUUACAGGCG | 268 | CGCCUGUAACACGAGCAGG | 432 | ccuGcucGuGuuAcAGGcGdTsdT | 596 | CGCCUGuAAcACGAGcAGGdTsdT |
| 106 | UGGAGUGUGGAUUCGCACU | 269 | AGUGCGAAUCCACACUCCA | 433 | ugGAGuGuGGAuucGcAcudTsdT | 597 | AGUGCGAAUCcAcACUCcAdTsdT |
| 107 | AACGACCGACCUUGAGGCA | 270 | UGCCUCAAGGUCGGUCGUU | 434 | aacGAccGAccuuGAGGcAdTsdT | 598 | UGCCUcAAGGUCGGUCGUUdTsdT |
| 108 | ACAGAGUCUAGACUCGUGG | 271 | CCACGAGUCUAGACUCUGU | 435 | acAGAGucuAGAcucGuGGdTsdT | 599 | CcACGAGUCuAGACUCUGUdTsdT |
| 109 | AAUCGCCGCGUCGCAGAAG | 272 | CUUCUGCGACGCGGCGAUU | 436 | aaucGccGcGucGcAGAAGdTsdT | 600 | CUUCUGCGACGCGGCGAUUdTsdT |
| 110 | GGUAUGUUGCCCGUUUGUC | 273 | GACAAACGGGCAACAUACC | 437 | gguAuGuuGcccGuuuGucdTsdT | 601 | GAcAAACGGGcAAcAuACCdTsdT |
| 111 | GCCGAUCCAUACUGCGGAA | 274 | UUCCGCAGUAUGGAUCGGC | 438 | gccGAuccAuAcuGcGGAAdTsdT | 602 | UUCCGcAGuAUGGAUCGGCdTsdT |
| 112 | GCCCUAUCUUAUCAACACU | 275 | AGUGUUGAUAAGAUAGGGC | 439 | gcccuAucuuAucAAcAcudTsdT | 603 | AGUGUUGAuAAGAuAGGGCdTsdT |
| 113 | AGUUUACUAGUGCCAUUUG | 276 | CAAAUGGCACUAGUAAACU | 440 | aguuuAcuAGuGccAuuuGdTsdT | 604 | cAAAUGGcACuAGuAAACUdTsdT |
| 114 | UGUCAACGACCGACCUUGA | 277 | UCAAGGUCGGUCGUUGACA | 441 | ugucAAcGAccGAccuuGAdTsdT | 605 | UcAAGGUCGGUCGUUGAcAdTsdT |
| 115 | ACUUCUCUCAAUUUUCUAG | 278 | CUAGAAAAUUGAGAGAAGU | 442 | acuucucucAAuuuucuAGdTsdT | 606 | CuAGAAAAUUGAGAGAAGUdTsdT |
| 116 | GCGCGGGACGUCCUUUGUC | 279 | GACAAAGGACGUCCCGCGC | 443 | gcGcGGGAcGuccuuuGucdTsdT | 607 | GAcAAAGGACGUCCCGCGCdTsdT |
| 117 | UCUAGACUCGUGGUGGACU | 280 | AGUCCACCACGAGUCUAGA | 444 | ucuAGAcucGuGGuGGAcudTsdT | 608 | AGUCcACcACGAGUCuAGAdTsdT |
| 118 | GAUCCAUACUGCGGAACUC | 281 | GAGUUCCGCAGUAUGGAUC | 445 | gauccAuAcuGcGGAAcucdTsdT | 609 | GAGUUCCGcAGuAUGGAUCdTsdT |

FIG. 4H

| | | | | | | | |
|---|---|---|---|---|---|---|---|
| 119 | CUCUGCCGAUCCAUACUGC | 282 | GCAGUAUGGAUCGGCAGAG | 446 | cucuGccGAuccAuAcuGcdTsdT | 610 | GcAGuAUGGAUCGGcAGAGdTsdT |
| 120 | UCUGCCGAUCCAUACUGCG | 283 | CGCAGUAUGGAUCGGCAGA | 447 | ucuGccGAuccAuAcuGcGdTsdT | 611 | CGcAGuAUGGAUCGGcAGAdTsdT |
| 121 | CCUCUGCCGAUCCAUACUG | 284 | CAGUAUGGAUCGGCAGAGG | 448 | ccucuGccGAuccAuAcuGdTsdT | 612 | cAGuAUGGAUCGGcAGAGGdTsdT |
| 122 | GCACCUCUCUUUACGCGGU | 285 | ACCGCGUAAAGAGAGGUGC | 449 | gcAccucucuuuAcGcGGudTsdT | 613 | ACCGCGuAAAGAGAGGUGCdTsdT |
| 123 | AAGAACUCCCUCGCCUCGC | 286 | GCGAGGCGAGGGAGUUCUU | 450 | aaGAAcucccucGccucGcdTsdT | 614 | GCGAGGCGAGGGAGUUCUUdTsdT |
| 124 | GAACUCCCUCGCCUCGCAG | 287 | CUGCGAGGCGAGGGAGUUC | 451 | gaAcucccucGccucGcAGdTsdT | 615 | CUGCGAGGCGAGGGAGUUCdTsdT |
| 125 | UCUCUCAAUUUUCUAGGGC | 288 | GCCCUAGAAAAUUGAGAGA | 452 | ucucucAAuuuucuAGGGcdTsdT | 616 | GCCCuAGAAAAUUGAGAGAdTsdT |
| 126 | GGGCGCACCUCUCUUUACG | 289 | CGUAAAGAGAGGUGCGCCC | 453 | ggGcGcAccucucuuuAcGdTsdT | 617 | CGuAAAGAGAGGUGCGCCCdTsdT |
| 127 | CCGAUCCAUACUGCGGAAC | 290 | GUUCCGCAGUAUGGAUCGG | 454 | ccGAuccAuAcuGcGGAAcdTsdT | 618 | GUUCCGcAGuAUGGAUCGGdTsdT |
| 128 | AACUCCCUCGCCUCGCAGA | 291 | UCUGCGAGGCGAGGGAGUU | 455 | aacucccucGccucGcAGAdTsdT | 619 | UCUGCGAGGCGAGGGAGUUdTsdT |
| 129 | CUCCUCUGCCGAUCCAUAC | 292 | GUAUGGAUCGGCAGAGGAG | 456 | cuccucuGccGAuccAuAcdTsdT | 620 | GuAUGGAUCGGcAGAGGAGdTsdT |
| 130 | GGAGUGUGGAUUCGCACUC | 293 | GAGUGCGAAUCCACACUCC | 457 | ggAGuGuGGAuucGcAcucdTsdT | 621 | GAGUGCGAAUCcAcACUCCdTsdT |
| 131 | CGGGCGCACCUCUCUUUAC | 294 | GUAAAGAGAGGUGCGCCCG | 458 | cgGGcGcAccucucuuuAcdTsdT | 622 | GuAAAGAGAGGUGCGCCCGdTsdT |
| 132 | GUCUCAAUCGCCGCGUCGC | 295 | GCGACGCGGCGAUUGAGAC | 459 | gucucAAucGccGcGucGcdTsdT | 623 | GCGACGCGGCGAUUGAGACdTsdT |
| 133 | AUCCAUACUGCGGAACUCC | 296 | GGAGUUCCGCAGUAUGGAU | 460 | auccAuAcuGcGGAAcuccdTsdT | 624 | GGAGUUCCGcAGuAUGGAUdTsdT |
| 134 | CGCACCUCUCUUUACGCGG | 297 | CCGCGUAAAGAGAGGUGCG | 461 | cgcAccucucuuuAcGcGGdTsdT | 625 | CCGCGuAAAGAGAGGUGCGdTsdT |

FIG. 4I

| | | | | | | | |
|---|---|---|---|---|---|---|---|
| 135 | CAACGACCGACCUUGAGGC | 298 | GCCUCAAGGUCGGUCGUUG | 462 | caAcGAccGAccuuGAGGcdTsdT | 626 | GCCUcAAGGUCGGUCGUUGdTsdT |
| 136 | CCAUACUGCGGAACUCCUA | 299 | UAGGAGUUCCGCAGUAUGG | 463 | ccAuAcuGcGGAAcuccuAdTsdT | 627 | uAGGAGUUCCGcAGuAUGGdTsdT |
| 137 | UGAAUCCCGCGGACGACCC | 300 | GGGUCGUCCGCGGGAUUCA | 464 | ugAAucccGcGGAcGAcccdTsdT | 628 | GGGUCGUCCGCGGGAUUcAdTsdT |
| 138 | AGAACUCCCUCGCCUCGCA | 301 | UGCGAGGCGAGGGAGUUCU | 465 | agAAcucccucGccucGcAdTsdT | 629 | UGCGAGGCGAGGGAGUUCUdTsdT |
| 139 | GGCGCACCUCUCUUUACGC | 302 | GCGUAAAGAGAGGUGCGCC | 466 | ggcGcAccucucuuuAcGcdTsdT | 630 | GCGuAAAGAGAGGUGCGCCdTsdT |
| 140 | GCGCACCUCUCUUUACGCG | 303 | CGCGUAAAGAGAGGUGCGC | 467 | gcGcAccucucuuuAcGcGdTsdT | 631 | CGCGuAAAGAGAGGUGCGCdTsdT |
| 141 | GCUGAAUCCCGCGGACGAC | 304 | GUCGUCCGCGGGAUUCAGC | 468 | gcuGAAucccGcGGAcGAcdTsdT | 632 | GUCGUCCGCGGGAUUcAGCdTsdT |
| 142 | CACUUCGCUUCACCUCUGC | 305 | GCAGAGGUGAAGCGAAGUG | 469 | cacuucGcuucAccucuGcdTsdT | 633 | GcAGAGGUGAAGCGAAGUGdTsdT |
| 143 | CUCAAUCGCCGCGUCGCAG | 306 | CUGCGACGCGGCGAUUGAG | 470 | cucAAucGccGcGucGcAGdTsdT | 634 | CUGCGACGCGGCGAUUGAGdTsdT |
| 144 | UCCCGUCGGCGCUGAAUCC | 307 | GGAUUCAGCGCCGACGGGA | 471 | ucccGucGGcGcuGAAuccdTsdT | 635 | GGAUUcAGCGCCGACGGGAdTsdT |
| 145 | CUGAAUCCCGCGGACGACC | 308 | GGUCGUCCGCGGGAUUCAG | 472 | cuGAAucccGcGGAcGAccdTsdT | 636 | GGUCGUCCGCGGGAUUcAGdTsdT |
| 146 | AGAGUCUAGACUCGUGGUG | 309 | CACCACGAGUCUAGACUCU | 473 | agAGucuAGAcucGuGGuGdTsdT | 637 | cACcACGAGUCuAGACUCUdTsdT |
| 147 | UCCAUACUGCGGAACUCCU | 310 | AGGAGUUCCGCAGUAUGGA | 474 | uccAuAcuGcGGAAcuccudTsdT | 638 | AGGAGUUCCGcAGuAUGGAdTsdT |
| 148 | GCGCUGAAUCCCGCGGACG | 311 | CGUCCGCGGGAUUCAGCGC | 475 | gcGcuGAAucccGcGGAcGdTsdT | 639 | CGUCCGCGGGAUUcAGCGCdTsdT |
| 149 | AGUGUGGAUUCGCACUCCU | 312 | AGGAGUGCGAAUCCACACU | 476 | aguGuGGAuucGcAcuccudTsdT | 640 | AGGAGUGCGAAUCcAcACUdTsdT |
| 150 | CCCUGCUCGUGUUACAGGC | 313 | GCCUGUAACACGAGCAGGG | 477 | cccuGcucGuGuuAcAGGcdTsdT | 641 | GCCUGuAAcACGAGcAGGGdTsdT |

FIG. 4J

| | | | | | | | |
|---|---|---|---|---|---|---|---|
| 151 | GAAUCCCGCGGACGACCCG | 314 | CGGGUCGUCCGCGGGAUUC | 478 | gaAucccGcGGAcGAcccGdTsdT | 642 | CGGGUCGUCCGCGGGAUUCdTsdT |
| 152 | AAGCUGUGCCUUGGGUGGC | 315 | GCCACCCAAGGCACAGCUU | 479 | aaGcuGuGccuuGGGuGGcdTsdT | 643 | GCcACCcAAGGcAcAGCUUdTsdT |
| 153 | GCCCUGCUCGUGUUACAGG | 316 | CCUGUAACACGAGCAGGGC | 480 | gcccuGcucGuGuuAcAGGdTsdT | 644 | CCUGuAAcACGAGcAGGGCdTsdT |
| 154 | GUCCCGUCGGCGCUGAAUC | 317 | GAUUCAGCGCCGACGGGAC | 481 | gucccGucGGcGcuGAAucdTsdT | 645 | GAUUcAGCGCCGACGGGACdTsdT |
| 155 | AUCUUAUCAACACUUCCGG | 318 | CCGGAAGUGUUGAUAAGAU | 482 | aucuuAucAAcAcuuccGGdTsdT | 646 | CCGGAAGUGUUGAuAAGAUdTsdT |
| 156 | CUUAUCAACACUUCCGGAA | 319 | UUCCGGAAGUGUUGAUAAG | 483 | cuuAucAAcAcuuccGGAAdTsdT | 647 | UUCCGGAAGUGUUGAuAAGdTsdT |
| 156 | CUUAUCAACACUUCCGGAA | 320 | TUCCGGAAGUGUUGAUAAG | 484 | CfuUfaUfcAfaCfaCfuUfcCfgGfaAf(invdT) | 648 | pdTUfcCfgGfaAfgUfgUfuGfaUfaAfgdTsdT |

FIG. 4K

Table 5. Target site sequences of dsRNAs targeting Hepatitis B Virus

| position of 17mer in acc. AM282986.1 | Unmodified dsRNAs of table 1 | | Modified dsRNAs of table 2 | | 17mer target site sequence (5'-3') | | genotype coverage [%] | | | |
|---|---|---|---|---|---|---|---|---|---|---|
| | SEQ ID | SEQ ID | SEQ ID | SEQ ID | SEQ ID | | A | B | C | D |
| | No. pair | No. pair | No. pair | No. pair | No. | | (n=332) | (n=615) | (n=1332) | (n=475) |
| 456 | 1/157 | 17/177 | 321/485 | 341/505 | 649 | AAGGUAUGUUGCCCGUU | 91.3 | 94.3 | 94.9 | 78.3 |
| 383 | 3/159 | 3/160 | 323/487 | 324/488 | 650 | CUGCGGCGUUUUAUCAU | 96.7 | 95.9 | 95.9 | 94.3 |
| 1828 | 4/161 | 6/163 | 325/489 | 327/491 | 651 | CCUCUGCCUAAUCAUCU | 95.5 | 81.8 | 96.8 | 92.8 |
| 1782 | 7/164 | 2/158 | 328/492 | 322/486 | 652 | UGUAGGCAUAAAUUGGU | 97.9 | 96.1 | 95.9 | 97.5 |
| 381 | 8/165 | 8/166 | 329/493 | 330/494 | 653 | GUCUGCGGCGUUUUAUC | 96.4 | 84.9 | 94 | 93.9 |
| 679 | 9/167 | 9/168 | 331/495 | 332/496 | 654 | ACUAGUGCCAUUUGUUC | 96.4 | 90.4 | 94.9 | 94.7 |
| 687 | 11/170 | 13/173 | 334/498 | 337/501 | 655 | CAUUUGUUCAGUGGUUC | 96.7 | 90.4 | 96.1 | 97.7 |
| 1177 | 12/171 | 12/172 | 335/499 | 336/500 | 656 | CAAGUGUUUGCUGACGC | 91.3 | 95.9 | 91.8 | 77.5 |
| 677 | 14/174 | 5/162 | 338/502 | 326/490 | 657 | UUACUAGUGCCAUUUGU | 95.5 | 88.9 | 94.2 | 94.7 |
| 668 | 16/176 | 18/178 | 340/504 | 342/506 | 658 | UGGCUCAGUUUACUAGU | 97 | 94.6 | 91 | 94.7 |
| 1778 | 19/179 | 23/183 | 343/507 | 347/511 | 659 | AGGCUGUAGGCAUAAAU | 97.9 | 95.8 | 96.2 | 97.5 |
| 674 | 20/180 | 28/189 | 344/508 | 353/517 | 660 | AGUUUACUAGUGCCAUU | 95.2 | 88.3 | 93.8 | 93.9 |
| 458 | 21/181 | 30/191 | 345/509 | 355/519 | 661 | GGUAUGUUGCCCGUUUG | 94.6 | 96.1 | 98.1 | 80.2 |
| 382 | 24/184 | 37/199 | 348/512 | 363/527 | 662 | UCUGCGGCGUUUUAUCA | 96.7 | 95.6 | 95.3 | 95.8 |
| 1818 | 25/185 | 10/169 | 349/513 | 333/497 | 663 | AACUUUUUCACCUCUGC | 96.1 | 92 | 96.5 | 84.8 |
| 1576 | 26/186 | 26/187 | 350/514 | 351/515 | 664 | CGUGUGCACUUCGCUUC | 97.6 | 98.4 | 98.3 | 95.6 |
| 258 | 29/190 | 42/204 | 354/518 | 368/532 | 665 | GGUGGACUUCUCUCAAU | 91.9 | 83.6 | 97.3 | 90.5 |
| 189 | 31/192 | 91/254 | 356/520 | 418/582 | 666 | UGCUCGUGUUACAGGCG | 93.7 | 93 | 93.8 | 76 |
| 461 | 32/193 | 22/182 | 357/521 | 346/510 | 667 | AUGUUGCCCGUUUGUCC | 95.5 | 96.1 | 98.4 | 79.8 |
| 455 | 33/194 | 27/188 | 358/522 | 352/516 | 668 | CAAGGUAUGUUGCCCGU | 91 | 95.4 | 93.5 | 93.3 |
| 2317 | 34/195 | 34/196 | 359/523 | 360/524 | 669 | CUUAUCAACACUUCCGG | 89.8 | 89.8 | 94.8 | 77.7 |
| 1827 | 35/197 | 15/175 | 361/525 | 339/503 | 670 | ACCUCUGCCUAAUCAUC | 95.8 | 82.1 | 96.5 | 92.8 |
| 1655 | 36/198 | | 362/526 | | 671 | UAAGAGGACUCUUGGAC | 92.2 | 88.1 | 90.2 | 91.4 |
| 1438 | 38/200 | | 364/528 | | 672 | GCGCUGAAUCCCGCGGA | 95.5 | 94.1 | 92 | 79.6 |

FIG. 5A

| | | | | | | | | | |
|---|---|---|---|---|---|---|---|---|---|
| 2419 | 39/201 | | 365/529 | | 673 | GCGUCGCAGAAGAUCUC | 94.6 | 89.6 | 92.3 | 83.2 |
| 1680 | 40/202 | | 366/530 | | 674 | AUGUCAACGACCGACCU | 96.7 | 83.9 | 93.6 | 93.5 |
| 671 | 41/203 | | 367/531 | | 675 | CUCAGUUUACUAGUGCC | 96.7 | 94.8 | 92.6 | 94.7 |
| 2414 | 43/205 | | 369/533 | | 676 | UCGCCGCGUCGCAGAAG | 88.6 | 84.1 | 95.1 | 92.4 |
| 686 | 44/206 | | 370/534 | | 677 | CCAUUUGUUCAGUGGUU | 96.7 | 90.4 | 96 | 97.5 |
| 1263 | 45/207 | | 371/535 | | 678 | GAUCCAUACUGCGGAAC | 97.3 | 89.9 | 93.8 | 95.6 |
| 1826 | 46/208 | | 372/536 | | 679 | CACCUCUGCCUAAUCAU | 96.1 | 81.8 | 96.5 | 91.6 |
| 260 | 47/209 | | 373/537 | | 680 | UGGACUUCUCUCAAUUU | 91.6 | 83.4 | 97.3 | 90.7 |
| 2821 | 48/210 | | 374/538 | | 681 | GGUCACCAUAUUCUUGG | 86.7 | 95.4 | 96.5 | 85.3 |
| 2417 | 49/211 | | 375/539 | | 682 | CCGCGUCGCAGAAGAUC | 94.9 | 94.8 | 95 | 92.2 |
| 2411 | 50/212 | | 376/540 | | 683 | CAAUCGCCGCGUCGCAG | 87.7 | 84.6 | 94.3 | 90.9 |
| 375 | 51/213 | | 377/541 | | 684 | GGAUGUGUCUGCGGCGU | 95.2 | 85.7 | 94.5 | 93.7 |
| 1859 | 52/214 | | 378/542 | | 685 | ACUGUUCAAGCCUCCAA | 68.4 | 91.9 | 97 | 96.4 |
| 676 | 53/215 | | 379/543 | | 686 | UUUACUAGUGCCAUUUG | 95.5 | 88.9 | 94.1 | 94.7 |
| 680 | 54/216 | | 380/544 | | 687 | CUAGUGCCAUUUGUUCA | 96.1 | 90.2 | 94.9 | 94.7 |
| 2418 | 55/217 | | 381/545 | | 688 | CGCGUCGCAGAAGAUCU | 95.2 | 94.8 | 95 | 92.4 |
| 2315 | 56/218 | | 382/546 | | 689 | AUCUUAUCAACACUUCC | 90.1 | 89.8 | 94.8 | 78.3 |
| 303 | 57/219 | | 383/547 | | 690 | GCCAAAAUUCGCAGUCC | 98.5 | 97.2 | 85.7 | 94.7 |
| 1825 | 58/220 | | 384/548 | | 691 | UCACCUCUGCCUAAUCA | 96.7 | 82 | 96.6 | 92 |
| 672 | 59/221 | | 385/549 | | 692 | UCAGUUUACUAGUGCCA | 94.9 | 88.5 | 93.8 | 94.1 |
| 463 | 60/222 | | 386/550 | | 693 | GUUGCCCGUUUGUCCUC | 94.9 | 95.1 | 98.4 | 78.9 |
| 682 | 61/223 | | 387/551 | | 694 | AGUGCCAUUUGUUCAGU | 96.1 | 89.9 | 94.8 | 94.5 |
| 1779 | 62/224 | | 388/552 | | 695 | GGCUGUAGGCAUAAAUU | 97.9 | 96.3 | 96.3 | 97.7 |
| 378 | 63/225 | 63/226 | 389/553 | 390/554 | 696 | UGUGUCUGCGGCGUUUU | 96.7 | 84.9 | 93.5 | 94.3 |
| 1584 | 64/227 | | 391/555 | | 697 | CUUCGCUUCACCUCUGC | 97.6 | 98.4 | 97.9 | 95.4 |
| 1577 | 65/228 | | 392/556 | | 698 | GUGUGCACUUCGCUUCA | 97.6 | 98.2 | 98.5 | 95.4 |
| 257 | 66/229 | | 393/557 | | 699 | UGGUGGACUUCUCUCAA | 91.9 | 83.6 | 97.1 | 90.5 |
| 379 | 67/230 | | 394/558 | | 700 | GUGUCUGCGGCGUUUUA | 96.1 | 84.9 | 93.6 | 94.1 |
| 457 | 68/231 | | 395/559 | | 701 | AGGUAUGUUGCCCGUUU | 91.3 | 94.8 | 96.7 | 79.2 |

FIG. 5B

| | | | | | | | | |
|---|---|---|---|---|---|---|---|---|
| 1684 | 69/232 | 396/560 | 702 | CAACGACCGACCUUGAG | 96.4 | 85.4 | 94.1 | 93.3 |
| 1654 | 70/233 | 397/561 | 703 | AUAAGAGGACUCUUGGA | 92.2 | 87.8 | 90.2 | 91.2 |
| 1683 | 71/234 | 398/562 | 704 | UCAACGACCGACCUUGA | 96.7 | 85.7 | 94.2 | 93.1 |
| 2829 | 72/235 | 399/563 | 705 | UAUUCUUGGGAACAAGA | 87 | 96.7 | 97.1 | 85.1 |
| 190 | 73/236 | 400/564 | 706 | GCUCGUGUUACAGGCGG | 94.9 | 93.3 | 94 | 76 |
| 2412 | 74/237 | 401/565 | 707 | AAUCGCCGCGUCGCAGA | 88 | 85.7 | 95.1 | 92.8 |
| 1860 | 75/238 | 402/566 | 708 | CUGUUCAAGCCUCCAAG | 68.4 | 91.7 | 97 | 96.4 |
| 2416 | 76/239 | 403/567 | 709 | GCCGCGUCGCAGAAGAU | 88.3 | 83.6 | 93.8 | 90.7 |
| 688 | 77/240 | 404/568 | 710 | AUUUGUUCAGUGGUUCG | 96.7 | 90.6 | 96.1 | 97.7 |
| 1440 | 78/241 | 405/569 | 711 | GCUGAAUCCCGCGGACG | 95.8 | 95.3 | 92.8 | 79.8 |
| 2820 | 79/242 | 406/570 | 712 | GGGUCACCAUAUUCUUG | 86.4 | 95.3 | 96.8 | 85.3 |
| 1255 | 80/243 | 407/571 | 713 | CCUCUGCCGAUCCAUAC | 97.6 | 90.2 | 94.9 | 88.8 |
| 1681 | 81/244 | 408/572 | 714 | UGUCAACGACCGACCUU | 96.7 | 85.7 | 94.3 | 93.7 |
| 1829 | 82/245 | 409/573 | 715 | CUCUGCCUAAUCAUCUC | 95.8 | 82.8 | 97 | 89.3 |
| 1575 | 83/246 | 410/574 | 716 | CCGUGUGCACUUCGCUU | 97.6 | 98.5 | 98.3 | 95.8 |
| 1260 | 84/247 | 411/575 | 717 | GCCGAUCCAUACUGCGG | 97 | 88.6 | 92.9 | 95.2 |
| 243 | 85/248 | 412/576 | 718 | AGAGUCUAGACUCGUGG | 93.7 | 96.9 | 95.7 | 96 |
| 1861 | 86/249 | 413/577 | 719 | UGUUCAAGCCUCCAAGC | 68.4 | 91.7 | 96.9 | 96.4 |
| 1777 | 87/250 | 414/578 | 720 | GAGGCUGUAGGCAUAAA | 97.9 | 95.8 | 96.3 | 97.7 |
| 1776 | 88/251 | 415/579 | 721 | GGAGGCUGUAGGCAUAA | 96.7 | 95.4 | 96.2 | 97.7 |
| 259 | 89/252 | 416/580 | 722 | GUGGACUUCUCUCAAUU | 91.9 | 83.7 | 97.5 | 90.7 |
| 1817 | 90/253 | 417/581 | 723 | CAACUUUUUCACCUCUG | 95.8 | 91.7 | 96.2 | 84.4 |
| 681 | 92/255 | 419/583 | 724 | UAGUGCCAUUUGUUCAG | 96.1 | 89.9 | 94.9 | 94.7 |
| 1259 | 93/256 | 420/584 | 725 | UGCCGAUCCAUACUGCG | 96.7 | 88.5 | 92.8 | 94.9 |
| 1578 | 94/257 | 421/585 | 726 | UGUGCACUUCGCUUCAC | 97.6 | 98 | 98.6 | 95.8 |
| 191 | 95/258 | 422/586 | 727 | CUCGUGUUACAGGCGGG | 94.9 | 92.7 | 92.5 | 96 |
| 2313 | 96/259 | 423/587 | 728 | CUAUCUUAUCAACACUU | 90.1 | 89.4 | 95.3 | 78.3 |
| 2409 | 97/260 | 424/588 | 729 | CUCAAUCGCCGCGUCGC | 88.6 | 85.2 | 96.7 | 93.1 |
| 1548 | 98/261 | 425/589 | 730 | CCCGUCUGUGCCUUCUC | 97.9 | 96.7 | 95.7 | 98.1 |

FIG. 5C

| | | | | | | | | |
|---|---|---|---|---|---|---|---|---|
| 2314 | 99/262 | 426/590 | 731 | UAUCUUAUCAACACUUC | 90.1 | 89.8 | 94.9 | 78.3 |
| 462 | 100/263 | 427/591 | 732 | UGUUGCCCGUUUGUCCU | 95.2 | 95.3 | 98.4 | 79.2 |
| 460 | 101/264 | 428/592 | 733 | UAUGUUGCCCGUUUGUC | 95.5 | 96.1 | 98.3 | 79.6 |
| 1585 | 102/265 | 429/593 | 734 | UUCGCUUCACCUCUGCA | 97.3 | 98.4 | 97.8 | 94.7 |
| 1579 | 103/266 | 430/594 | 735 | GUGCACUUCGCUUCACC | 97.9 | 98.4 | 98.6 | 95.8 |
| 304 | 104/267 | 431/595 | 736 | CCAAAAUUCGCAGUCCC | 98.5 | 97.4 | 85.9 | 95.2 |
| 188 | 105/268 | 432/596 | 737 | CUGCUCGUGUUACAGGC | 93.7 | 93 | 93.8 | 75.8 |
| 2267 | 106/269 | 433/597 | 738 | GGAGUGUGGAUUCGCAC | 93.7 | 96.4 | 94.4 | 97.3 |
| 1686 | 107/270 | 434/598 | 739 | ACGACCGACCUUGAGGC | 96.4 | 85.9 | 93.8 | 93.1 |
| 242 | 108/271 | 435/599 | 740 | CAGAGUCUAGACUCGUG | 93.1 | 96.7 | 94.9 | 92.6 |
| 2413 | 109/272 | 436/600 | 741 | AUCGCCGCGUCGCAGAA | 88.6 | 84.1 | 95 | 92.8 |
| 459 | 110/273 | 437/601 | 742 | GUAUGUUGCCCGUUUGU | 95.2 | 95.9 | 98.3 | 79.6 |
| 1261 | 111/274 | 438/602 | 743 | CCGAUCCAUACUGCGGA | 97.3 | 89.8 | 94.1 | 96 |
| 2311 | 112/275 | 439/603 | 744 | CCCUAUCUUAUCAACAC | 93.7 | 88.9 | 95.3 | 78.3 |
| 675 | 113/276 | 440/604 | 745 | GUUUACUAGUGCCAUUU | 95.2 | 88.6 | 93.8 | 93.9 |
| 1682 | 114/277 | 441/605 | 746 | GUCAACGACCGACCUUG | 97 | 85.7 | 94.4 | 93.1 |
| 264 | 115/278 | 442/606 | 747 | CUUCUCUCAAUUUUCUA | 90.7 | 82 | 96.4 | 88.2 |
| 1408 | 116/279 | 443/607 | 748 | CGCGGGACGUCCUUUGU | 95.5 | 96.9 | 95.9 | 94.5 |
| 248 | 117/280 | 444/608 | 749 | CUAGACUCGUGGUGGAC | 95.5 | 97.2 | 96.5 | 97.1 |
| 1264 | 118/281 | 445/609 | 750 | AUCCAUACUGCGGAACU | 97.9 | 89.4 | 94.1 | 95.6 |
| 1257 | 119/282 | 446/610 | 751 | UCUGCCGAUCCAUACUG | 96.7 | 88.5 | 91.1 | 86.9 |
| 1258 | 120/283 | 447/611 | 752 | CUGCCGAUCCAUACUGC | 96.7 | 92.5 | 92.2 | 88.4 |
| 1256 | 121/284 | 448/612 | 753 | CUCUGCCGAUCCAUACU | 96.7 | 88.1 | 90.7 | 86.5 |
| 1527 | 122/285 | 449/613 | 754 | CACCUCUCUUUACGCGG | 95.8 | 94.6 | 95.9 | 98.3 |
| 2381 | 123/286 | 450/614 | 755 | AGAACUCCCUCGCCUCG | 91.6 | 95.8 | 97.3 | 89.9 |
| 2383 | 124/287 | 451/615 | 756 | AACUCCCUCGCCUCGCA | 97.3 | 95.8 | 97.3 | 90.5 |
| 267 | 125/288 | 452/616 | 757 | CUCUCAAUUUUCUAGGG | 90.1 | 82.3 | 96.4 | 87.6 |
| 1523 | 126/289 | 453/617 | 758 | GGCGCACCUCUCUUUAC | 95.5 | 95.1 | 95.6 | 97.9 |
| 1262 | 127/290 | 454/618 | 759 | CGAUCCAUACUGCGGAA | 97.6 | 89.9 | 94 | 95.8 |

FIG. 5D

| | | | | | | | | |
|---|---|---|---|---|---|---|---|---|
| 2384 | 128/291 | 455/619 | 760 | ACUCCCUCGCCUCGCAG | 97.6 | 95.8 | 96.9 | 90.1 |
| 1254 | 129/292 | 456/620 | 761 | UCCUCUGCCGAUCCAUA | 97.6 | 89.6 | 94.7 | 89.1 |
| 2268 | 130/293 | 457/621 | 762 | GAGUGUGGAUUCGCACU | 93.7 | 93.8 | 93.5 | 97.3 |
| 1522 | 131/294 | 458/622 | 763 | GGGCGCACCUCUCUUUA | 95.5 | 95.1 | 95.6 | 97.9 |
| 2408 | 132/295 | 459/623 | 764 | UCUCAAUCGCCGCGUCG | 88.6 | 84.4 | 96.4 | 93.1 |
| 1265 | 133/296 | 460/624 | 765 | UCCAUACUGCGGAACUC | 97.6 | 88.5 | 91.2 | 95.2 |
| 1526 | 134/297 | 461/625 | 766 | GCACCUCUCUUUACGCG | 95.5 | 94.8 | 95.8 | 98.3 |
| 1685 | 135/298 | 462/626 | 767 | AACGACCGACCUUGAGG | 96.4 | 85.2 | 94.1 | 93.3 |
| 1267 | 136/299 | 463/627 | 768 | CAUACUGCGGAACUCCU | 97.6 | 88.1 | 90.1 | 95.2 |
| 1443 | 137/300 | 464/628 | 769 | GAAUCCCGCGGACGACC | 95.5 | 95.4 | 92.3 | 79.2 |
| 2382 | 138/301 | 465/629 | 770 | GAACUCCCUCGCCUCGC | 97.3 | 96.1 | 97.9 | 91.6 |
| 1524 | 139/302 | 466/630 | 771 | GCGCACCUCUCUUUACG | 95.2 | 95 | 95.6 | 97.9 |
| 1525 | 140/303 | 467/631 | 772 | CGCACCUCUCUUUACGC | 95.2 | 94.8 | 95.8 | 98.3 |
| 1441 | 141/304 | 468/632 | 773 | CUGAAUCCCGCGGACGA | 95.8 | 95.3 | 94.1 | 79.6 |
| 1583 | 142/305 | 469/633 | 774 | ACUUCGCUUCACCUCUG | 97.6 | 98.4 | 98.2 | 96.6 |
| 2410 | 143/306 | 470/634 | 775 | UCAAUCGCCGCGUCGCA | 88 | 84.6 | 94.8 | 92 |
| 1431 | 144/307 | 471/635 | 776 | CCCGUCGGCGCUGAAUC | 87.7 | 93.5 | 87.7 | 94.7 |
| 1442 | 145/308 | 472/636 | 777 | UGAAUCCCGCGGACGAC | 95.8 | 95.4 | 92.3 | 78.9 |
| 244 | 146/309 | 473/637 | 778 | GAGUCUAGACUCGUGGU | 93.7 | 96.7 | 96 | 95.8 |
| 1266 | 147/310 | 474/638 | 779 | CCAUACUGCGGAACUCC | 97.6 | 88.3 | 89.9 | 95.2 |
| 1439 | 148/311 | 475/639 | 780 | CGCUGAAUCCCGCGGAC | 95.8 | 94.8 | 92.1 | 79.8 |
| 2270 | 149/312 | 476/640 | 781 | GUGUGGAUUCGCACUCC | 96.1 | 94.6 | 94.6 | 97.7 |
| 187 | 150/313 | 477/641 | 782 | CCUGCUCGUGUUACAGG | 93.7 | 93.2 | 94.1 | 76 |
| 1444 | 151/314 | 478/642 | 783 | AAUCCCGCGGACGACCC | 95.5 | 95.4 | 92.4 | 79.2 |
| 1875 | 152/315 | 479/643 | 784 | AGCUGUGCCUUGGGUGG | 73.8 | 96.1 | 96.4 | 96.2 |
| 186 | 153/316 | 480/644 | 785 | CCCUGCUCGUGUUACAG | 93.7 | 93 | 93.9 | 76 |
| 1430 | 154/317 | 481/645 | 786 | UCCCGUCGGCGCUGAAU | 87.3 | 93.5 | 87.6 | 94.7 |
| 2316 | 155/318 | 482/646 | 787 | UCUUAUCAACACUUCCG | 89.8 | 89.8 | 94.8 | 77.7 |
| 2318 | 156/319 156/320 | 483/647 484/648 | 788 | UUAUCAACACUUCCGGA | 89.8 | 89.9 | 94.7 | 77.7 |

FIG. 5E

Table 6. NCBI Genbank accession Nos. of Hepatitis B Virus genomic sequences

Genotype A

| | | | | | | | |
|---|---|---|---|---|---|---|---|
| FJ692613 | FJ692587 | AF090838 | FJ692590 | DQ020003 | AF090839 | GQ477476 | GQ477473 |
| FJ692584 | EU859907 | AJ131570 | EU859910 | FJ349223 | FJ023662 | AY862867 | EU859928 |
| AY233287 | AY233279 | FJ692609 | AF297624 | AB270536 | GQ331048 | AM295795 | FJ692555 |
| EU859904 | FJ692610 | FJ692563 | GQ477496 | EU859934 | FJ692582 | AB453982 | EU594391 |
| FJ692579 | EU859927 | EU859942 | EU859930 | GQ477492 | AY233281 | EU594394 | FJ692588 |
| AY738141 | GQ477481 | AY934765 | AM184126 | AF143305 | EU859902 | EU859951 | AY934773 |
| GQ477482 | AY738142 | AY161141 | GQ331046 | DQ788725 | FM199974 | FJ692570 | FJ692575 |
| FJ692559 | AB453988 | AY373428 | EU859950 | EU859914 | EU859922 | GQ331047 | AY233276 |
| EU859924 | AM410963 | GQ477498 | FJ692571 | EU859948 | GQ477479 | AF143301 | EU859954 |
| GQ414522 | DQ298164 | GQ477465 | EU594395 | FJ692569 | GQ477484 | FJ692607 | EU859908 |
| FJ904434 | AJ131573 | AF418674 | AB453983 | FJ692594 | EF208113 | AF143303 | EU859898 |
| FJ692565 | AB241115 | AM184125 | GQ477477 | DQ315784 | EU859947 | EU859931 | FJ692556 |
| EU859944 | EF208115 | EU185786 | AB222707 | EU054331 | FJ692566 | AF297625 | GQ477470 |
| EU859918 | EU859941 | FJ692572 | AF043580 | GQ477501 | DQ298162 | GQ477497 | AY233288 |
| DQ788729 | FJ692560 | EU859953 | DQ315786 | AB126580 | GQ477460 | AY903452 | AY934770 |
| FJ692598 | AY934766 | AY934774 | FJ692596 | FJ692603 | U87746 | EU859911 | AY233275 |
| AY934763 | AB246317 | AY077735 | EU859916 | EU859909 | AB194952 | FJ692591 | FJ692576 |
| DQ298161 | GQ477466 | AB453980 | DQ788727 | FJ692574 | AF090841 | FJ692606 | AF043560 |
| AB194951 | FJ904411 | AM295797 | FJ692601 | EU859955 | AF143299 | GQ477504 | EU594392 |
| EU859938 | EU185788 | FM199979 | GQ477503 | AY233277 | AY233284 | AF143300 | AB453987 |
| GQ477463 | AY233282 | GQ477489 | AF143307 | AY934772 | GQ477480 | FJ692583 | EU859900 |
| AF090842 | FJ692581 | GQ477474 | EU859936 | FJ692589 | AY738143 | AY233280 | AY233283 |
| EU859944 | EU859901 | AM282986 | AF297622 | EU594390 | AM494718 | GQ477464 | FJ692580 |
| EU859925 | FM199977 | AF143302 | GQ477490 | FJ692554 | EU859926 | GQ477499 | AY738139 |
| FJ692558 | AM295799 | FJ692593 | AY902775 | EU859929 | AY128092 | AY373429 | EU185789 |
| AY738140 | GQ477487 | AY233290 | EU594393 | GQ477472 | FJ692611 | AY934764 | AB222708 |
| GQ477483 | EU859921 | AY934768 | EU859956 | AB453986 | AY233278 | FJ692562 | GQ477485 |
| FJ692578 | GQ477467 | EU859913 | AY233274 | GQ477500 | EU859906 | EU859943 | GQ477478 |
| EU859905 | GQ161813 | FJ692604 | FJ692577 | FJ692602 | AY233285 | EU410082 | EU859923 |
| FJ692585 | EF208114 | FJ349224 | AY934771 | FJ692595 | FJ692586 | FJ692608 | EU859903 |
| AY233286 | AY934767 | EU859933 | AY233289 | EU859949 | EU185787 | AF143306 | FJ349222 |
| FJ692612 | EU859940 | GQ477468 | GQ477471 | FJ692568 | AF418675 | FJ692600 | AB330371 |
| GQ477462 | FJ692561 | GQ477495 | EU859899 | EU859915 | GQ477494 | GQ477502 | AB330372 |
| EU859925 | AB241114 | AM295800 | FJ692557 | DQ315785 | GQ477469 | DQ788726 | AB330373 |
| EU086721 | DQ298165 | GQ477475 | FM199981 | GQ184323 | EU859932 | EU859917 | AJ627226 |
| AB194950 | AY034878 | GQ477488 | AB453985 | AF143304 | FJ692605 | FJ692597 | AJ627227 |
| EU859939 | EU859920 | AM295796 | EU366129 | GQ477493 | EU859912 | EU747320 | AJ627228 |
| AF143308 | GQ477486 | AB453981 | AF297623 | AF297621 | AY934769 | FM199980 | AP007263 |
| FJ692599 | FM199976 | FJ692573 | GQ477491 | EU859935 | FJ692592 | AB453984 | EU304331 |
| DQ788728 | AM295798 | EU859952 | EU859937 | DQ020002 | GQ184324 | AB453979 | EU414132 |
| EU859919 | FJ692567 | EU414134 | DQ298163 | AF090840 | EU859945 | S50225 | V00866 |
| FJ692564 | AB453989 | FM199978 | EU859946 | GQ477461 | AF143298 | | |

FIG. 6A

Genotype B

| | | | | | | | |
|---|---|---|---|---|---|---|---|
| EU306702 | GU332692 | AB073842 | AY800389 | AY206377 | AB106884 | AB073843 | FJ386688 |
| GU332701 | AB073822 | AB493832 | DQ463798 | FJ386636 | EU939630 | EU939633 | AJ131574 |
| EF473975 | AY596102 | GQ924634 | EU939670 | D23678 | FJ386656 | DQ463787 | AB073840 |
| FJ787444 | DQ904357 | AY167098 | AY596103 | DQ993680 | AB116083 | FJ386655 | AB219429 |
| D23679 | EU882001 | AB116082 | AB073823 | EF473974 | GQ377641 | AY293309 | DQ361535 |
| DQ993681 | GQ924608 | AB205122 | GQ377596 | AY781187 | AF121243 | U87747 | AB493830 |
| AY033072 | GQ924654 | EU306670 | GQ377537 | AY163870 | GQ924635 | EU564822 | DQ993710 |
| GQ924628 | EU939671 | EU939631 | EU919175 | EU306703 | FJ386676 | EU522074 | AB365445 |
| EU919174 | DQ463799 | AB106885 | GU332693 | GU332700 | AB493833 | AB205120 | EU882003 |
| FJ562311 | GQ377556 | GQ924648 | AY033073 | FJ562222 | FJ562262 | FJ386675 | FJ386582 |
| FJ386615 | GQ377568 | EU305543 | EU564823 | GQ377549 | FJ562312 | AB073847 | M54923 |
| EU939673 | DQ993683 | AB219428 | GQ377588 | GU332702 | GU332691 | AB287317 | EU660233 |
| GQ924656 | FJ386669 | AB073841 | AY217370 | EU306701 | EU939672 | EU305545 | AF121247 |
| GU332690 | GU332703 | FJ032344 | GQ924617 | FJ386634 | FJ386648 | AP011087 | GQ377573 |
| EF103278 | GQ377622 | GQ924637 | FJ386608 | FJ386668 | EU882002 | FJ032342 | EU522073 |
| GQ377602 | EU306700 | AB205121 | FJ386654 | AY206375 | DQ993711 | GQ377639 | FJ562246 |
| EU919176 | EU796068 | AY330917 | EU939632 | DQ993682 | FJ386583 | GQ924611 | EU564825 |
| AB300364 | EF473977 | GQ377643 | DQ448628 | GQ377569 | GQ924631 | AY800391 | X97851 |
| GQ377595 | FJ562260 | EU522075 | EF473976 | AB073821 | DQ993698 | EU939634 | DQ993684 |
| AY220698 | AB493831 | FJ562240 | FJ032358 | GQ377594 | AY217356 | EU939668 | AY206373 |
| GQ377625 | GU332697 | GQ924610 | AY217357 | EU306695 | EU306706 | AB471854 | AB493829 |
| AF479684 | EU919171 | EU939669 | DQ975271 | EU939629 | EU579441 | AY217368 | AB219430 |
| GU332704 | GQ377592 | EU939635 | DQ993699 | EU939675 | DQ993685 | AY596105 | EF473972 |
| EU306707 | AB073827 | AY800390 | GQ924630 | EU881998 | EU919173 | GQ924653 | DQ993686 |
| AY781183 | EU564824 | AY163869 | AB073826 | FJ386584 | EU306696 | FJ386610 | AF121245 |
| EU882004 | GQ377644 | GQ377638 | GU332696 | FJ349296 | GU332695 | EU939676 | AB073839 |
| FJ349236 | EU522072 | EU305544 | DQ377158 | AY596106 | FJ562316 | EU306705 | EU660231 |
| EU939674 | X97850 | AB287316 | GQ377604 | EF473971 | AB287329 | GU332706 | EU139543 |
| EU939628 | EU660232 | AB073846 | EU919170 | AB100695 | GQ377590 | FJ562224 | EU158262 |
| GQ924651 | AF121246 | AP011086 | GQ205440 | GU332705 | AB073825 | AB205119 | AB246335 |
| EU330998 | AB493835 | GU332707 | GQ377606 | AB287314 | EU660230 | AY217364 | AB073829 |
| EU306677 | AF282918 | EU939677 | GU332694 | DQ993708 | AY206380 | AY596109 | GQ377561 |
| EU939636 | AY206390 | AY596104 | AY217355 | AY800392 | FJ386660 | EU881997 | AB033555 |
| DQ993709 | EU487256 | AY217369 | AB241116 | EU939637 | EU306709 | GQ924603 | FJ386681 |
| AY217374 | AB241117 | AB471855 | GQ924632 | EU158263 | DQ995803 | DQ463792 | AY217358 |
| EU796071 | DQ993687 | AB073824 | EU487257 | EU330999 | FJ562289 | FJ562254 | DQ993696 |
| AP011085 | AB073858 | AB287328 | AY206391 | FJ562219 | D00329 | GU332699 | FJ518812 |
| AB287315 | EF473973 | EU306697 | AP011084 | EU564826 | AB073855 | EU439022 | AY167093 |
| EU305547 | EU306704 | FJ562259 | GQ377550 | AB073838 | AP011095 | DQ980548 | AP011089 |
| AB073845 | GQ377626 | EU919172 | AB073844 | AF121244 | DQ448620 | AB287325 | AB073849 |
| AB287319 | EU330994 | AY217365 | EU330995 | DQ993697 | GQ924641 | FM209516 | AB368295 |
| FJ562234 | EU570070 | AB073854 | AF121248 | AY217359 | EU939664 | EU306698 | GQ377629 |
| EU939666 | AB300371 | DQ448621 | AB073834 | AB033554 | EU939638 | AB287327 | AB493827 |
| FJ386600 | EU439023 | AY220703 | DQ993704 | FJ386680 | AY167102 | EU439020 | DQ995801 |

FIG. 6B

| | | | | | | | |
|---|---|---|---|---|---|---|---|
| DQ993705 | AB073828 | AP011094 | AY167101 | GQ377582 | DQ993707 | AF100308 | DQ448622 |
| AY167100 | AB287324 | EU306708 | GU357842 | AB073837 | AB010289 | AY217366 | FJ032352 |
| AB073835 | EU330989 | DQ995802 | EU939667 | EU306679 | FJ562236 | AY766463 | AB073857 |
| AF121249 | GU332698 | AB300370 | AP011088 | EU919161 | X98073 | EU939678 | GQ924621 |
| AB231909 | EU939627 | EU919162 | AB287318 | EU306684 | FJ386683 | FJ386642 | DQ993695 |
| AB246339 | DQ463793 | EU570071 | AB073848 | EU330996 | DQ993694 | DQ463790 | FJ518811 |
| FJ386682 | EU939639 | DQ448623 | EU306699 | EF494381 | EU939663 | AB073850 | AY217361 |
| AF282917 | EU939665 | GQ377542 | FJ562257 | FJ386684 | AY596110 | D23677 | DQ463797 |
| X98072 | EU330997 | AB073856 | GQ377558 | DQ448619 | AB195935 | GQ924626 | GQ924606 |
| GQ377634 | GQ377614 | DQ463791 | FJ032349 | DQ463800 | DQ993700 | AB116090 | AB212626 |
| FJ562296 | EU306678 | EU939679 | AB246340 | AB073830 | FJ787476 | EU570069 | AY596111 |
| FJ562237 | AB073836 | AY217367 | EU306710 | EU570075 | AB115551 | AF121250 | AB195934 |
| EU305548 | AY206383 | AF100309 | X98074 | EU306683 | AB117759 | AB287320 | FJ787477 |
| AB195933 | AB302095 | AY518556 | D00330 | GQ377612 | AB010292 | GQ377564 | DQ993701 |
| DQ993706 | FJ032353 | AB287326 | FJ562231 | FJ562303 | AP011090 | EU660224 | GQ924647 |
| GQ924640 | AP011096 | EU439021 | GU168597 | GQ924646 | DQ448625 | EU331000 | FJ386658 |
| EU939662 | AB246341 | GQ377565 | AY217363 | GQ924624 | GQ924644 | EU330993 | EU589335 |
| GQ377613 | EF494380 | AB287321 | EU547563 | AB010290 | DQ993702 | GQ924638 | GQ377547 |
| EU306682 | GU168596 | AF121251 | DQ463795 | DQ995804 | EU350409 | FM209513 | AB073853 |
| EU330990 | D00331 | EF134945 | FJ562253 | AB073852 | AB212625 | EU439019 | EU796067 |
| AB073831 | X98075 | GQ924627 | EU522066 | DQ448627 | AY596112 | AB219427 | AP011093 |
| DQ463801 | DQ463796 | DQ448624 | GQ377566 | FJ032357 | GQ377587 | GU168595 | AY220704 |
| GQ377525 | GQ924607 | FJ032354 | AB287322 | EU796066 | AB073832 | X98076 | DQ448626 |
| AY167097 | AY217360 | AP011091 | EF134946 | AP011092 | DQ463802 | FJ562321 | AB010291 |
| FJ562322 | EU331001 | AB073851 | EU595030 | DQ463789 | GQ377610 | EU306712 | FJ386666 |
| EU306711 | GQ377539 | GQ377519 | AY206387 | EU939661 | EU306681 | AB246342 | AB486012 |
| GQ924625 | GQ924659 | AB219426 | DQ463788 | AB493834 | FJ023634 | D50521 | AB302943 |
| EU595031 | DQ463794 | FM209512 | GQ924645 | AB493836 | FJ023635 | D50522 | AB302944 |
| AY167089 | EU939681 | GQ924639 | AB014366 | AF461360 | FJ023636 | FJ023631 | AB302945 |
| EU439024 | AY217362 | EU330992 | AB031267 | AJ627225 | FJ023637 | FJ023632 | AB362933 |
| EU660227 | X98077 | EU306680 | AB302942 | AY167094 | FJ023638 | FJ023633 | AB493828 |
| AY220697 | AJ131133 | AB073833 | EU522067 | AB246343 | AF233236 | GQ377567 | GU168594 |
| AB287323 | EF494382 | DQ993703 | GQ475340 | EU439018 | EU939660 | FJ787475 | |

Genotype C

| | | | | | | | |
|---|---|---|---|---|---|---|---|
| FJ562331 | EU439009 | EU916218 | FJ386580 | FJ386617 | FJ386677 | GQ475351 | AB250109 |
| AY781186 | D23684 | EU570067 | EU939547 | EU439015 | AB195947 | AF537372 | AB111117 |
| FJ562282 | FJ023664 | AB300366 | AY373432 | FJ032347 | EU939586 | GQ377640 | GQ924614 |
| GQ377620 | AF411411 | GQ475311 | FJ787464 | EU305540 | GQ227696 | AY330914 | DQ089764 |
| GQ475331 | EU939567 | GQ377600 | FJ787438 | EU916224 | FJ787458 | EU919168 | EU872003 |
| FJ562223 | FJ386637 | EU306722 | DQ089778 | DQ377160 | AB241110 | FJ562243 | AB026815 |
| EU916238 | AY206376 | GQ377536 | AF461043 | EU560440 | GQ377576 | EU564820 | FJ787478 |
| GQ377516 | EU939651 | AB471853 | DQ089785 | EU589339 | AB367417 | EU916204 | AF068756 |
| FJ882612 | DQ089758 | GQ377597 | EU871982 | AF533983 | EU589345 | FJ386657 | FJ787485 |

FIG. 6C

| | | | | | | | |
|---|---|---|---|---|---|---|---|
| EF137802 | EU306691 | AB198077 | AB112063 | EU939611 | AF223956 | DQ089799 | AY217373 |
| EU678475 | FJ787439 | EU916219 | EU939566 | FJ562283 | AY217372 | FJ562242 | DQ975274 |
| AB367394 | FJ787465 | EU306690 | FJ882613 | GQ377621 | DQ089765 | EU919169 | AB241111 |
| EU871983 | AB485810 | EU306723 | GQ377517 | FJ787484 | GQ924615 | EU306671 | AY167099 |
| DQ089784 | EU882000 | FJ562310 | EU439008 | FJ787479 | AB111116 | AB205123 | FJ787459 |
| GQ924655 | AB198076 | EU939650 | EF137803 | AB026814 | GQ924649 | GQ475350 | EU939610 |
| GQ924609 | AB471852 | DQ089759 | FJ562330 | FJ023659 | DQ089798 | GQ377577 | EU916225 |
| DQ089779 | GQ377601 | GQ924629 | DQ536412 | EU872002 | AF223957 | AB367416 | EU589338 |
| FJ386616 | GQ475310 | AF411410 | EU916239 | AB112348 | EU589344 | GQ227697 | EU560441 |
| EU939546 | AB300367 | FJ787445 | GQ475330 | AB367395 | EU916205 | EU939587 | EU410079 |
| FJ386581 | NC_003977 | FJ023665 | AB064314 | EU678474 | EU564821 | AB195946 | DQ377161 |
| FJ032346 | EU939559 | EU306672 | AB241112 | DQ377162 | EU522068 | EU939565 | GQ475333 |
| EU305541 | FJ787487 | AY330916 | EU939579 | FJ562261 | GQ475313 | FJ023666 | FJ562280 |
| GQ377557 | EU872001 | GQ377642 | GQ227694 | EU916226 | EU306693 | FJ787446 | AY781184 |
| DQ089766 | GQ259588 | GQ475353 | EU939584 | FJ787466 | AB471851 | AB247916 | FJ562333 |
| AB111115 | FJ032339 | AF223954 | AB195945 | EU939545 | GQ377534 | AY206389 | D16665 |
| GQ924616 | AB367415 | AB116080 | EU305542 | FJ386649 | AB367409 | AB048704 | FJ032359 |
| FJ386609 | GQ377574 | FJ386629 | GQ377554 | EU871980 | EU660228 | EU939653 | AB367429 |
| AB195939 | GQ377528 | EU939613 | AB367435 | DQ089787 | DQ993181 | AY206374 | GQ377548 |
| AB367396 | EU916206 | GQ924636 | FJ032345 | EU306720 | EU939598 | FJ386635 | EU554538 |
| AY217371 | FJ562241 | AY161139 | EU594383 | FJ562313 | EU939539 | FJ562221 | FJ882610 |
| GQ377514 | AY161138 | GQ475352 | GQ377575 | AB367428 | DQ536410 | FJ787447 | EU306692 |
| DQ377163 | AB195944 | EU306673 | EU939558 | EU796069 | FJ562332 | FJ023667 | AB300365 |
| DQ361534 | EU939585 | EU498227 | AB367397 | AB112408 | AY781185 | AF411412 | GQ475312 |
| EU916227 | GQ227695 | EU916207 | AB195938 | GQ377515 | EU939652 | GU385774 | EU522069 |
| AB300359 | EU939578 | EU589346 | EU872000 | EU554539 | AB048705 | GQ377535 | GQ377603 |
| GQ377555 | EU939612 | AB116081 | FJ787486 | FJ882611 | AY206388 | AB471850 | FJ386614 |
| EU439016 | FJ386689 | AF223955 | AB111114 | GQ377623 | EU939564 | AY220699 | DQ089786 |
| DQ478885 | FJ386674 | AB367414 | DQ089767 | FJ562281 | EU787444 | EU660229 | EU871981 |
| AB367434 | FJ386628 | FJ032338 | AY152726 | GQ475332 | EU939538 | AB367408 | FJ787467 |
| AB241113 | AF537371 | GQ377529 | DQ478899 | FJ562220 | EU939599 | EU306721 | EU939544 |
| AY206392 | EU439010 | GQ475328 | FJ787480 | AB246337 | D23681 | FJ787461 | DQ089780 |
| EU939648 | AB367432 | AB111112 | AB367412 | AF473543 | FJ386632 | AY596107 | AY040627 |
| EU939614 | FJ562328 | DQ089761 | EF688062 | AB116087 | EU939608 | FJ386578 | EU871987 |
| FJ386672 | DQ377165 | FJ386652 | GQ475308 | EU562219 | EU939654 | EU939542 | FJ562314 |
| EU414133 | EU594384 | FJ386599 | GQ377619 | FJ562308 | GQ475334 | FJ386585 | DQ377159 |
| AF411408 | EU410080 | AY217376 | GQ475354 | EU939562 | FJ562287 | AB037927 | EU306727 |
| EU939583 | EU916221 | EU678470 | EU306675 | AB176643 | FJ562226 | AB112066 | EU306694 |
| AB195942 | FJ562266 | AB111946 | EU306688 | AB241109 | FJ562334 | FJ386612 | EU916241 |
| GQ227693 | EF494377 | EU872006 | EU589340 | FJ023661 | AB113878 | DQ683578 | GQ205441 |
| GQ377553 | AB493837 | AB485808 | EU560439 | FJ787441 | FJ882617 | EU881999 | AB300363 |
| GQ475348 | GQ377618 | FJ386598 | EU717218 | FJ032343 | AY206393 | FJ386613 | FJ882616 |
| GQ377605 | GQ475355 | FJ787481 | DQ377164 | EU796072 | GQ377593 | EU871986 | FJ562227 |
| GQ475314 | GQ475309 | AB485809 | FJ562329 | EU439011 | DQ980547 | DQ089781 | GQ377624 |
| GQ377533 | EU562218 | AB026811 | GQ475329 | AF411409 | EU554542 | GQ924650 | FJ562286 |
| AP011108 | EU560438 | EU872007 | EF494376 | GQ227692 | EU306726 | FJ787460 | GQ475335 |

FIG. 6D

| | | | | | | | |
|---|---|---|---|---|---|---|---|
| AB112472 | EU589341 | DQ089760 | FJ562267 | AB195943 | FJ562315 | EU882005 | FJ562335 |
| EU306689 | AB367413 | AB111113 | EU916220 | EU939582 | GQ475315 | EU939543 | AB074756 |
| FJ562247 | GQ377572 | FJ386653 | AB288026 | FJ386673 | GQ475349 | FJ386579 | AF462041 |
| EU306674 | EU678471 | EU594385 | GQ377552 | EU939615 | AB300362 | AB113879 | Y18858 |
| EF536065 | AY217377 | EU410081 | AB367433 | EU939649 | EU916240 | AF384371 | EU939655 |
| EU939609 | AB300361 | DQ089782 | AP011099 | GQ377571 | EF536066 | EU872004 | EU916223 |
| AB202072 | FJ562258 | EU871978 | D23683 | AB471848 | GQ475356 | AB367393 | EU594386 |
| FJ386633 | EU306725 | AY707087 | FJ023663 | U87742 | AB205125 | EU678472 | EU306719 |
| AB176642 | GQ377531 | FJ562336 | AY123424 | FJ032360 | EU522071 | AB367430 | GQ924633 |
| EU939563 | EU554541 | AB074755 | FJ787443 | AB367410 | FJ386650 | FJ032340 | FJ386670 |
| D23680 | FJ386587 | FJ562278 | EU939560 | AB116078 | DQ089763 | EU439012 | EU939616 |
| FJ787440 | EU939540 | FJ562285 | EU939656 | EU589342 | GQ924613 | GQ377551 | DQ975272 |
| FJ023660 | FJ787463 | GQ475336 | EU579442 | FJ562244 | EU871999 | FJ562299 | AB195940 |
| GQ475316 | EU882006 | AF384372 | AB202071 | FJ562218 | FJ787482 | FJ562238 | EU939581 |
| GQ377607 | EU871985 | FJ882615 | FJ386630 | AB222714 | AB026812 | FJ562264 | FJ386631 |
| EU579443 | AB205118 | FJ787462 | AB195941 | EU306718 | AY217375 | AB116084 | EU939591 |
| EU939657 | FJ562225 | AB112471 | DQ975273 | EU594387 | EU678473 | EU522070 | AB195950 |
| FJ787442 | FJ562279 | GQ377530 | EU939617 | EU796070 | AB367392 | AB205124 | EU939606 |
| D23682 | EU871979 | EU554540 | FJ386671 | FJ032341 | FJ386651 | GQ475357 | Y18857 |
| EU939561 | DQ089783 | GQ377591 | EU916222 | AB367431 | EU871998 | AB222715 | AB111120 |
| FJ882614 | EU871984 | AB300360 | AY057947 | EU872005 | GQ924612 | FJ562245 | GQ924623 |
| AP011098 | FJ386611 | GQ475317 | FJ562265 | D28880 | EU670263 | AB471849 | AF223961 |
| FJ562337 | AB112065 | FJ562317 | FJ562239 | AB026813 | DQ089762 | GQ377570 | FJ562228 |
| GQ475337 | EU939541 | EU306724 | FJ562298 | FJ787483 | AB116079 | AB367411 | FJ562274 |
| FJ562284 | FJ386586 | EU939580 | AB182589 | AB115417 | EU589343 | FJ032361 | EU916233 |
| GQ377541 | DQ089773 | AP011106 | EU155828 | DQ922651 | GQ872210 | GQ377580 | AB367401 |
| DQ246215 | AB368297 | AB198081 | AY641558 | FJ562268 | DQ089792 | AB116089 | AB198080 |
| FJ032350 | EU871974 | FJ386620 | DQ315783 | EU717217 | FJ904423 | EU562217 | GQ377560 |
| AB299858 | FJ386640 | EU547558 | GQ184325 | EU306715 | EU872008 | FJ562306 | DQ980549 |
| AY220702 | EU939626 | EU939646 | FJ562295 | AB246345 | FJ787473 | FJ562248 | AP011107 |
| AB113876 | GQ475346 | FM209514 | GQ377637 | FJ562326 | AB195930 | EU306686 | AY123041 |
| AB367420 | EU916213 | EU939570 | EF494379 | AB074047 | FJ386597 | GQ475306 | FJ562255 |
| FJ386576 | EU306729 | FJ023673 | AB493839 | GU357843 | AY217378 | GQ377617 | EU916212 |
| EU872014 | AB049609 | FJ787453 | GQ475326 | GQ924643 | EU939550 | EU919163 | AF286594 |
| EU871989 | AB367400 | AJ309369 | AJ344115 | EU871995 | GQ377521 | DQ089804 | GQ475347 |
| EU306728 | EU872015 | FJ562275 | AB246338 | DQ890381 | FJ349225 | DQ922650 | AY641559 |
| EU871975 | GQ377540 | FJ562229 | FJ562307 | GQ377581 | AB195931 | GQ475327 | DQ315782 |
| AB368296 | FJ882618 | FJ386661 | AB231908 | GQ377520 | FJ386601 | AB493838 | FJ518813 |
| EU881996 | AB367421 | Y18856 | EU562216 | FJ032331 | GQ872211 | EF494378 | EU939571 |
| DQ089772 | AB113877 | AY206381 | AB116088 | FJ787472 | DQ089793 | FJ562294 | FM209515 |
| EU871988 | FJ032351 | EU939607 | AB493844 | EU872009 | EU871994 | GQ377636 | EU155829 |
| FJ386641 | AF223960 | GQ924622 | GQ377616 | DQ986375 | GQ924642 | FJ562327 | AY167092 |
| AB037928 | FJ562288 | AB111121 | GQ475307 | AB365451 | EU871969 | AB246344 | FJ787452 |
| FJ386577 | EU916232 | AB195951 | EU306687 | EU939551 | FJ562235 | EU306714 | FJ023672 |
| AY596108 | AY247032 | EU939590 | FJ562249 | FJ386596 | FJ562269 | EU717216 | EU939647 |
| EU547559 | FJ562304 | FJ787471 | GQ475324 | FJ518810 | DQ478900 | EU881995 | GQ377543 |

FIG. 6E

| | | | | | | | |
|---|---|---|---|---|---|---|---|
| FJ386621 | EU562215 | DQ986376 | GQ377635 | EU939572 | AP011104 | DQ089771 | DQ993688 |
| FJ032332 | D50489 | AB365452 | FJ562297 | FJ562318 | AB367402 | AF498266 | AB195952 |
| GQ377523 | DQ089790 | DQ315781 | EU939618 | FJ562256 | FJ787490 | GQ475338 | EU939593 |
| AB206817 | EU871997 | AB042284 | EU939644 | EU916211 | EU872016 | EU916231 | AB111122 |
| AB300373 | FJ386602 | FJ562324 | FJ386622 | GQ475318 | FJ386574 | AY247031 | AF458664 |
| GQ377615 | EU939552 | EU594388 | AB033557 | GQ377609 | AF182802 | FJ562276 | FJ386662 |
| AB493847 | FJ386595 | EU306717 | AY167091 | GQ475344 | FJ386589 | AB367422 | AY206382 |
| EU570072 | AB115418 | EU717215 | FJ023671 | GQ377563 | EU939624 | AY220700 | Y18855 |
| AB116076 | AB195932 | AY057948 | FJ787451 | AB198083 | EU871976 | AP011097 | EU939658 |
| EU939604 | EU306716 | EU871996 | AB206816 | AB195953 | GQ377628 | AM180624 | GQ475319 |
| FJ787450 | AB246346 | DQ089791 | GQ377522 | DQ993689 | FJ562339 | FJ386575 | EU916210 |
| FJ023670 | FJ562325 | FJ386603 | GQ377583 | GQ372968 | FJ386643 | AP011105 | EU717212 |
| AY167090 | AB042285 | EU570073 | GQ924620 | AY220701 | EU939625 | DQ478901 | EU589337 |
| EU939573 | GQ475325 | EU306685 | AB111123 | AB113875 | DQ089770 | AB198082 | FJ562323 |
| FJ386623 | GQ184326 | GQ475305 | AF458665 | AB367423 | EU871977 | GQ377562 | AB042283 |
| EU939645 | FJ386594 | AB300372 | EU939605 | FJ562277 | EU872017 | AB367403 | GQ475323 |
| EU939619 | EU939553 | FJ562305 | EU939659 | AY247030 | AY077736 | FJ562319 | GQ377632 |
| AB033556 | FJ787470 | AB116077 | FJ386663 | EU916230 | FJ386588 | GQ377608 | FJ562290 |
| EU717214 | AJ748098 | FJ032333 | EU939592 | GQ475339 | AF182803 | GQ475345 | FJ386679 |
| FJ386625 | AB367419 | AB111119 | EU439007 | DQ089756 | AP011103 | EU939549 | EU939554 |
| EU939643 | GQ377524 | EU871990 | AB367425 | EU939603 | GQ377599 | AF182805 | AB426467 |
| AB033550 | GQ377578 | DQ089797 | GQ377518 | AY206385 | AB198079 | EU547561 | DQ089796 |
| FJ787456 | GQ377585 | FJ386605 | GQ377544 | FJ386639 | AB198084 | FJ386645 | EU871991 |
| AY167096 | DQ980551 | FJ386659 | AB195955 | FJ386665 | GQ377538 | FJ386619 | AB111118 |
| EU939575 | AB493840 | EU939555 | EU939594 | AY206378 | AB367405 | EU939623 | FJ386604 |
| DQ993693 | EU919166 | FJ386592 | FJ349241 | AB300368 | AY641561 | AY306136 | EU919167 |
| EU939588 | AB298721 | FJ562271 | EU939569 | GQ475343 | DQ089800 | DQ089776 | AB493841 |
| AB195949 | AB049610 | EU916236 | AJ309370 | EU916216 | FJ787436 | EU871971 | EU570074 |
| FJ032335 | AF223958 | FJ032355 | AB111125 | FJ562251 | EU872011 | FJ386593 | AF223959 |
| FJ562302 | AF182804 | FJ787468 | FJ787489 | EU939597 | AB493843 | AB014385 | FJ023643 |
| AB298720 | EU939548 | EU871973 | EU939557 | EU939536 | GQ377611 | AB014389 | FJ023644 |
| AB367418 | AB198078 | GQ924658 | AB195937 | AB367406 | EU919165 | AB014391 | FJ023645 |
| FJ032334 | GQ377598 | GQ924604 | AB367398 | AY641562 | GQ377527 | AB014392 | FJ023646 |
| GQ377584 | AP011102 | DQ089774 | D12980 | DQ089803 | GQ377586 | AB014393 | FJ023647 |
| DQ980550 | DQ089801 | DQ089789 | GQ377526 | AP011100 | FJ032336 | AB014394 | FJ023648 |
| GQ377579 | EU660225 | EU939621 | FJ032337 | EU916215 | FJ787488 | AB014396 | FJ023649 |
| FJ787457 | AY641560 | AB106895 | FJ562301 | FJ562252 | AB367399 | AB014399 | FJ023650 |
| AB195948 | AB367404 | FJ386647 | EU919164 | AY066028 | AB195936 | AB031262 | FJ023653 |
| EU939589 | EU570068 | EU916214 | AF536524 | FJ562340 | EU939556 | AB031265 | FJ023654 |
| DQ993692 | FJ562250 | GQ475341 | AB493842 | DQ089788 | FJ386591 | AB076678 | FJ023656 |
| EU939574 | EU916217 | DQ089802 | EU916208 | DQ089775 | FJ386606 | AB076679 | FJ023657 |
| EU939642 | GQ475342 | EU660226 | AB033552 | EU871972 | GU357845 | AB105172 | FJ023658 |
| FJ386685 | AB300369 | EU439025 | EU939641 | FJ386646 | GQ924619 | AB105173 | FJ023668 |
| FJ386624 | DQ089757 | AY641563 | FJ386686 | EU547562 | DQ089769 | AB105174 | FJ023674 |
| FJ386678 | AB111124 | AB367407 | FJ386627 | EU939620 | EU871993 | AB116085 | FJ023675 |
| AB033551 | AY206379 | AP011101 | DQ993691 | FJ787469 | DQ089794 | AB362931 | FJ023676 |

FIG. 6F

| | | | | | | | |
|---|---|---|---|---|---|---|---|
| AB042282 | FJ386664 | FJ787448 | EU939577 | EU872012 | AB014360 | AB362932 | L08805 |
| EU589336 | FJ386638 | EU939537 | FJ787454 | GQ475320 | AB014362 | AB367800 | L13994 |
| M38636 | AY206384 | EU939596 | FJ562233 | FJ562293 | AB014363 | AB367803 | M38454 |
| EU717213 | EU939602 | AB195957 | EU916228 | GQ377631 | AB014364 | AB367804 | S75184 |
| FJ562230 | EU939568 | FJ386667 | FJ562292 | EU916229 | AB014365 | AF461357 | V00867 |
| GQ377633 | EU939595 | EU939601 | GQ377630 | FJ562232 | AB014367 | AF461358 | X01587 |
| FJ562291 | AB195954 | AF363962 | GQ475321 | EU717211 | AB014369 | AF461359 | X02763 |
| GQ475322 | AJ309371 | EU916234 | AB205152 | EU306713 | AB014370 | AF461361 | X04615 |
| AB050018 | AB367424 | FJ562273 | EU554537 | FJ562320 | AB014371 | AF461363 | X14193 |
| GQ377559 | EU439006 | EU554536 | FJ032356 | EU939576 | AB014372 | AJ012207 | X52939 |
| FJ032348 | EU554535 | GQ377546 | AF241410 | AF330110 | AB014374 | D00630 | X70185 |
| EU939622 | GQ377545 | AB367427 | AB367426 | DQ993690 | AB014376 | D16666 | X75656 |
| FJ386618 | AB117758 | AF241411 | AF363963 | FJ787455 | AB014377 | D16667 | X75665 |
| EU547560 | DQ922649 | EU439005 | FJ562272 | AY167095 | AB014378 | D50517 | Z35717 |
| FJ386644 | EU916237 | FJ386607 | EU916235 | AB033553 | AB014379 | D50518 | Z72478 |
| EU871970 | FJ562270 | DQ089795 | EU939600 | FJ386626 | AB014380 | D50519 | Z72479 |
| DQ089777 | AF363961 | EU871992 | AY206386 | FJ386687 | AB014381 | D50520 | FJ023642 |
| EU872010 | AY148342 | DQ089768 | FJ787449 | EU939640 | AB014382 | FJ023639 | AB014384 |
| FJ787437 | X51970 | GQ924618 | FJ023669 | FJ562300 | AB014383 | FJ023641 | EU916209 |
| AM180623 | EU872013 | FJ787474 | AB195956 | | | | |

Genotype D

| | | | | | | | |
|---|---|---|---|---|---|---|---|
| AY721606 | AF121240 | GU456638 | FJ349214 | EU594409 | EU594389 | GU456672 | AB330369 |
| FJ904397 | GQ377589 | AY161162 | EU787440 | FJ904403 | AJ344116 | M32138 | AB330370 |
| FJ904414 | EU919197 | AB270543 | GQ167302 | AY741797 | AY721612 | FJ904447 | AF280817 |
| EU787447 | AB222711 | AY236163 | AB048701 | AY721611 | DQ315780 | FJ904398 | AJ627215 |
| FJ349213 | EU594400 | GU456644 | DQ111987 | EU414141 | AY741794 | AY721609 | AJ627216 |
| GU456680 | GU456663 | GQ205382 | EU594425 | AY902770 | AY233293 | X59795 | AJ627217 |
| X97848 | EU921418 | EU594427 | GQ205380 | AB119256 | FJ904420 | EU787437 | AJ627218 |
| AJ131956 | DQ315777 | DQ486024 | GU456646 | AB493845 | EU414142 | FJ904438 | AJ627219 |
| FJ349233 | L27106 | AB188245 | FJ349228 | X80925 | AY902773 | AY161157 | AJ627220 |
| AB270546 | AB270544 | AB205127 | AB270541 | AY862864 | GU456649 | GU456651 | AJ627221 |
| FJ562263 | AY236164 | EU787442 | AF121239 | GU456657 | AB119255 | AB090269 | AJ627222 |
| EU414136 | FJ904436 | FJ349216 | AY236161 | EU594434 | AB493846 | EU594432 | AJ627223 |
| GU456661 | AY161159 | AF418687 | GU456666 | AY161151 | GU456675 | EU939680 | AJ627224 |
| AB210821 | AY373430 | GU456678 | AB033559 | AB270550 | EU594416 | EF103276 | DQ336674 |
| EU594402 | EU787439 | AB048703 | EU594405 | EU594397 | FJ904440 | AY796030 | DQ336675 |
| FJ904408 | FJ349231 | EU594398 | FJ349208 | GQ477455 | GQ922000 | AM494716 | DQ336676 |
| AF121242 | EF103285 | FJ904431 | AY161160 | GQ922002 | GQ477457 | FJ904418 | DQ336677 |
| DQ304548 | AY661793 | GU456658 | DQ111986 | GU456677 | EU594436 | FJ904444 | DQ336678 |
| AB222713 | DQ329357 | AB210818 | AF418684 | FJ904442 | GU456655 | GU456671 | DQ336679 |
| EU594422 | FJ349211 | AB471856 | FJ904412 | AF418688 | AY161153 | GQ477453 | DQ336680 |
| AY945307 | EU787445 | DQ304551 | AF418679 | FJ349219 | AB109476 | AY902777 | DQ336681 |
| GU456641 | FJ904416 | AB205126 | EU787441 | AB205128 | AY233295 | FJ904424 | DQ336682 |
| GQ205387 | AF418680 | FJ562309 | FJ349215 | FJ904422 | AB270548 | FJ386590 | DQ336683 |

FIG. 6G

| | | | | | | | |
|---|---|---|---|---|---|---|---|
| FJ904428 | GU456682 | DQ486025 | AF043594 | EU594428 | EU414138 | AB119251 | DQ336684 |
| AY161147 | FJ904395 | AB188244 | GQ477459 | EU414140 | FJ904406 | AY090453 | DQ336685 |
| DQ486021 | EU594382 | GQ205383 | GQ924652 | AY721610 | AF418690 | FJ904404 | DQ336686 |
| Y07587 | DQ315776 | GU456645 | FJ349235 | AY233291 | AB119253 | AF418692 | DQ336687 |
| FJ349232 | AB270545 | EU594426 | FJ904432 | AY741796 | GQ205389 | DQ315779 | DQ336688 |
| FJ904435 | EU921419 | AY236162 | AB109478 | FJ349205 | GU357846 | GQ184322 | DQ336689 |
| X97849 | EU594401 | AY741798 | AB110075 | FJ904402 | FJ349221 | GQ477452 | DQ336690 |
| GU456681 | EU414135 | AB270542 | AB222709 | GU456637 | FJ904426 | GQ922005 | DQ336692 |
| FJ904415 | GU456662 | AY161163 | EF103281 | EU594408 | AY161149 | GU456670 | DQ464164 |
| FJ349212 | AB210822 | AB267090 | FJ349209 | AB119254 | AY721608 | FJ904445 | DQ464165 |
| EU787446 | AB222710 | EU594406 | AY161161 | GU456648 | FJ904399 | EU155893 | DQ464166 |
| AB116266 | AB270539 | GU456639 | AB033558 | AY902772 | FJ904446 | FJ904419 | DQ464167 |
| FJ904396 | AF121241 | GU456665 | GU456667 | EU414143 | GU456673 | DQ991753 | DQ464168 |
| AF043593 | AB078033 | AB471857 | EU594404 | AB090270 | EU594410 | AY796031 | DQ464169 |
| AY721607 | DQ486022 | GQ377532 | AY236160 | FJ904421 | AY796032 | EF103277 | DQ464170 |
| AB188241 | AB188243 | DQ304550 | AB246348 | AY741795 | AY161155 | GU456650 | DQ464172 |
| FJ904429 | GQ205379 | AB210819 | AB270540 | AY233292 | EU594430 | EU594433 | DQ464173 |
| AB078031 | GU456642 | GU456659 | FJ349229 | AJ132335 | GU456653 | AB090268 | DQ464174 |
| EU594423 | GQ205384 | FJ904430 | EU594424 | AB246347 | AY902769 | EU787436 | DQ464175 |
| GQ205386 | EU594421 | EU594399 | GU456647 | AJ344117 | FJ349220 | AY161156 | DQ464178 |
| GU456640 | FJ904394 | GU456684 | GQ205381 | DQ399006 | AY161148 | FJ904439 | DQ464181 |
| AY341335 | AY721605 | GU456679 | AB493848 | GU456668 | FJ904427 | AB126581 | DQ464182 |
| AB222712 | GU456683 | GQ167301 | AF418689 | FJ904401 | AY902774 | AY233296 | GQ922004 |
| DQ304549 | FJ349210 | AB048702 | FJ904443 | FJ349206 | GQ205388 | DQ315778 | X02496 |
| FJ904409 | AF418681 | FJ349217 | FJ349218 | AB109477 | AB119252 | FJ904405 | X65257 |
| AB210820 | FJ904417 | EU787443 | EU594415 | X80926 | DQ304547 | AY090452 | X65258 |
| GU456660 | EF103279 | AF418686 | GU456676 | AY161152 | AF418691 | AB270537 | X65259 |
| EU414137 | AY661792 | FJ904410 | GQ477454 | GU456654 | FJ904407 | FJ904425 | X68292 |
| EU594403 | DQ329356 | EF103280 | EU594396 | GQ922001 | EU414139 | AY902776 | X72702 |
| AB270547 | AY373431 | AB109479 | GQ922003 | FJ562338 | AB270549 | GQ205377 | X85254 |
| GQ205385 | AY161158 | AM422939 | AY161150 | GQ477456 | U95551 | AB104709 | Z35716 |
| GU456643 | FJ904437 | FJ349234 | GU456656 | FJ904441 | AY233294 | AB104710 | V01460 |
| GQ205378 | FJ349230 | FJ904433 | EU594435 | GU456674 | EU594431 | AB104711 | AB330368 |
| DQ486023 | EU787438 | GQ477458 | AF151735 | FJ904400 | AY902768 | AB104712 | EF103275 |
| AB078032 | EU594407 | GQ377627 | X80924 | FJ349207 | GU456652 | AB330366 | GU456635 |
| AB188242 | AB120308 | FJ904413 | AB109475 | GU456669 | AY161154 | AB330367 | GU456636 |
| AB270538 | GU456664 | AF418685 | | | | | |

FIG. 6H

Table 7.Comparision of knockdown efficacies and coverage of HBV genomes for single dsRNAs and combinations thereof.

| dsRNA 1 | | | | dsRNA2 | | | | Combination of dsRNA 1+2 | | | | |
|---|---|---|---|---|---|---|---|---|---|---|---|---|
| SEQ ID NO pair | 1 nM | | % coverage (of 2754 genomes) | SEQ ID NO pair | 1 nM | | % coverage (of 2754 genomes) | 10 nM | 1 nM | | % coverage (of 2754 genomes) | Genomes not matched |
| | [%] rem. Rluc | rank | | | [%] rem. Rluc | rank | | [%] rem. Rluc | [%] rem. Rluc | rank | | |
| 322/486 | 14 | 1 | 96.4 | 333/497 | 21 | 7 | 93.5 | 5 | 25 | 1 | 99.67 | 9 |
| 322/486 | 14 | 1 | 96.4 | 346/510 | 35 | 13 | 94.3 | 7 | 26 | 2 | 99.82 | 5 |
| 322/486 | 14 | 1 | 96.4 | 330/494 | 20 | 5 | 92.2 | 6 | 28 | 3 | 99.67 | 9 |
| 322/486 | 14 | 1 | 96.4 | 324/488 | 15 | 2 | 95.8 | 5 | 29 | 4 | 99.85 | 4 |
| 327/491 | 19 | 4 | 92.6 | 322/486 | 14 | 1 | 96.4 | 5 | 30 | 5 | 99.64 | 10 |
| 327/491 | 19 | 4 | 92.6 | 326/490 | 17 | 3 | 93.3 | 4 | 30 | 6 | 99.35 | 18 |
| 326/490 | 17 | 3 | 93.3 | 333/497 | 21 | 7 | 93.5 | 4 | 30 | 7 | 99.71 | 8 |
| 336/500 | 23 | 8 | 90.2 | 322/486 | 14 | 1 | 96.4 | 5 | 31 | 8 | 99.64 | 10 |
| 324/488 | 15 | 2 | 95.8 | 333/497 | 21 | 7 | 93.5 | 3 | 31 | 9 | 99.56 | 12 |
| 324/488 | 15 | 2 | 95.8 | 339/503 | 25 | 10 | 92.6 | 5 | 31 | 10 | 99.75 | 7 |
| 326/490 | 17 | 3 | 93.3 | 347/511 | 36 | 14 | 96.5 | 6 | 31 | 11 | 99.82 | 5 |
| 326/490 | 17 | 3 | 93.3 | 322/486 | 14 | 1 | 96.4 | 5 | 32 | 12 | 99.85 | 4 |
| 332/496 | 21 | 6 | 94.0 | 322/486 | 14 | 1 | 96.4 | 6 | 32 | 13 | 99.85 | 4 |
| 332/496 | 21 | 6 | 94.0 | 324/488 | 15 | 2 | 95.8 | 4 | 32 | 14 | 99.31 | 19 |
| 327/491 | 19 | 4 | 92.6 | 332/496 | 21 | 6 | 94.0 | 4 | 32 | 15 | 99.38 | 17 |
| 332/496 | 21 | 6 | 94.0 | 347/511 | 36 | 14 | 96.5 | 5 | 32 | 16 | 99.89 | 3 |
| 327/491 | 19 | 4 | 92.6 | 324/488 | 15 | 2 | 95.8 | 4 | 33 | 17 | 99.78 | 6 |
| 336/500 | 23 | 8 | 90.2 | 324/488 | 15 | 2 | 95.8 | 5 | 33 | 18 | 99.49 | 14 |
| 332/496 | 21 | 6 | 94.0 | 333/497 | 21 | 7 | 93.5 | 3 | 34 | 19 | 99.71 | 8 |
| 324/488 | 15 | 2 | 95.8 | 347/511 | 36 | 14 | 96.5 | 5 | 34 | 20 | 99.85 | 4 |
| 332/496 | 21 | 6 | 94.0 | 330/494 | 20 | 5 | 92.2 | 4 | 37 | 21 | 99.24 | 21 |
| 337/501 | 24 | 9 | 95.2 | 322/486 | 14 | 1 | 96.4 | 6 | 42 | 22 | 99.82 | 5 |
| 337/501 | 24 | 9 | 95.2 | 347/511 | 36 | 14 | 96.5 | 6 | 42 | 23 | 99.89 | 3 |

FIG. 7A

| | | | | | | | | | | | | |
|---|---|---|---|---|---|---|---|---|---|---|---|---|
| 337/501 | 24 | 9 | 95.2 | 324/488 | 15 | 2 | 95.8 | 5 | 43 | 24 | 99.60 | 11 |
| 337/501 | 24 | 9 | 95.2 | 333/497 | 21 | 7 | 93.5 | 6 | 44 | 25 | 99.71 | 8 |
| 337/501 | 24 | 9 | 95.2 | 336/500 | 23 | 8 | 90.2 | 7 | 47 | 26 | 99.71 | 8 |
| 341/505 | 31 | 11 | 91.5 | 322/486 | 14 | 1 | 96.4 | 5 | 50 | 27 | 99.85 | 4 |
| 341/505 | 31 | 11 | 91.5 | 324/488 | 15 | 2 | 95.8 | 5 | 57 | 28 | 99.67 | 9 |
| 351/515 | 38 | 15 | 97.7 | 337/501 | 24 | 9 | 95.2 | 6 | 60 | 29 | 99.75 | 7 |
| 351/515 | 38 | 15 | 97.7 | 342/506 | 32 | 12 | 93.2 | 8 | 60 | 30 | 99.93 | 2 |

FIG. 7B

Table 8. Sequences of the negative control ds RNAs used in the psiCHECK™-2 screening assay.

| strand | Sequence | gene |
|---|---|---|
| sense | 5′-cuuAcGcuGAGuAcuucGATsT-3′, SEQ ID No. 789 | LUC(GL3) |
| antisense | 5′-UCGAAGuACUcAGCGuAAGTsT-3′, SEQ ID No. 790 | LUC(GL3) |
| sense | 5′-CcAcAuGAAGcAGcACGACusU-3′, SEQ ID No. 791 | GFP |
| antisense | 5′-AAGUCGUGCUGCUUCAUGUGgsusC -3′, SEQ ID No. 792 | GFP |

FIG. 8

COMPOSITIONS AND METHODS FOR INHIBITING GENE EXPRESSION OF HEPATITIS B VIRUS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This application is a reissue application based on U.S. application Ser. No. 13/535,454 filed on Jun. 28, 2012, which previously issued as U.S. Pat. No. 8,809,293 on Aug. 19, 2014, and claims foreign priority to EP Application No. 11172235 filed on Jun. 30, 2011.*

BACKGROUND OF THE INVENTION

This invention relates to double-stranded ribonucleic acids (dsRNAs), and their use in mediating RNA interference to inhibit the expression of genes, necessary for replication and pathogenesis of Hepatitis B Virus, in particular in the inhibition of viral polymerase, surface antigen, e-antigen and the X protein. Furthermore, the use of said dsRNAs to treat or prevent chronic liver diseases/disorders, inflammations, fibrotic conditions and proliferative disorders, like cancers, as consequence of Hepatitis B Virus infection, is part of this invention.

The Hepatitis B Virus is a strict hepatotrophic, double-stranded DNA containing virus. Although DNA is the genetic material, the replication cycle involves a reverse transcription step to copy a pregenomic RNA into DNA. In order to accomplish this essential step, the viral-encoded polymerase possesses reverse transcriptase activity. Hepatitis B virus is classified as one member of the Hepadnaviruses and belongs to the family of Hepadnaviridae. The primary infection of adult humans with Hepatitis B Virus causes an acute hepatitis with symptoms of organ inflammation, fever, jaundice and increased liver transaminases in blood. About 95% of acute hepatitis resolve without treatment. Those patients, that are not able to overcome the virus infection, suffer a chronic disease progression over many years with increased risk of developing cirrhotic liver or liver cancer. Perinatal transmission from Hepatitis B virus-infected mothers to newborns also leads to chronic hepatitis. The treatment options for chronic Hepatitis B Virus infection are limited and lead only in some cases to complete and lasting remission. Additional clinical and therapeutical complications arise in Hepatitis B Virus patients co-infected with Hepatitis C, Hepatitis D or Human Immunodeficiency Virus.

The Hepatitis B Virus is transmitted via blood or blood products, sperm, vaginal secrets, or saliva. Drug abuse and sexual intercourse are dangerous activities and support spreading the virus. Contact of damaged, mucoid epithelia with contaminated body fluids may be sufficient for infection. Incubation time is between 40 to 200 days. The risk for infection is proportional to the number of transmitted Hepatitis B Virus particles. Babies are often infected perinatally by their Hepatitis B Virus carrying mother, a major health problem in endemic areas.

About 2 billion people are infected with Hepatitis B Virus and 400 million are chronic carriers. Areas with high prevalence are Africa and South-East Asia, with local accumulation of 20-80% infected persons.

Based on sequence homology, Hepatitis B Viruses are classified into genotypes A-H, with genotypes A-D being the most important ones. Genotype A is frequent in North-Western Europe, USA, South and Central America. Genotype B and C are dominant in China, Japan, Indonesia and other countries in East Asia. Genotype D is found in Southern Europe, Northern Africa and South Africa. Disease progression and response to pharmaceutical treatment differ among genotypes.

Infectious Hepatitis B Virus particles have a diameter of about 42 nm. The outer membrane bilayer contains the large, middle and small surface protein. The cognate hepatocellular receptor for virus surface protein binding and internalization is unknown. Many copies of core protein form a spherical nucleocapsid structure inside the virus particle. Each nucleocapsid carries partial double-stranded DNA as genetic material, together with viral polymerase.

Upon uptake by hepatocytes, the nucleocapsid is transferred to the nucleus and DNA is released. There, the DNA strand synthesis is completed and gaps repaired to give the covalently closed circular (ccc) supercoiled DNA of 3.2 kb. The cccDNA serves as template for transcription of four major viral mRNAs, which are 3.5, 2.4, 2.1 and 0.7 kb long. All mRNAs are 5'-capped and polyadenylated at the 3'-end. There is sequence overlap at the 3'-end between all four mRNAs.

The 3.5 kb mRNA serves as template for core protein and polymerase production. In addition, the same transcript serves as a pre-genomic replication intermediate and allows the viral polymerase to initiate the reverse transcription into DNA. Core protein is needed for nucleocapsid formation. In addition, sequential processing activities transforms some core protein into the secretable e-antigen. The abundance of e-antigen in blood correlates with Hepatitis B Virus replication in liver and serves as important diagnostic marker for monitoring the disease progression.

The 2.4 and 2.1 kb mRNAs carry the open reading frames pre-S1, pre-S2 and S2 for expression of viral large, medium and small surface antigen. The s-antigen is associated with infectious, complete particles. In addition, blood of infected patients also contain non-infectious particles derived from s-antigen alone, free of genomic DNA or polymerase. The function of these particles is not fully understood. The complete and lasting depletion of detectable s-antigen in blood is considered as reliable indicator for Hepatitis B Virus clearance and thus, successful cure.

The 0.7 kb mRNA encodes the X protein. This gene product is important for efficient transcription of viral genes and also acts as a transactivator on host gene expression. The latter activity seems to be important for hepatocyte transformation during development of liver cancer.

Recombinant Hepatitis B Virus s-antigen is used for vaccination. The injection of three doses of formulated s-antigen at day 1, at 4 weeks and at 6 months usually induces a sufficient titer of neutralizing antibodies. Vaccinated patients are protected for 10 years or longer. However, the vaccines are no substitute for therapy.

Patients with acute Hepatitis B Virus infection are not treated due to the high, natural remission rate. However, those patients with detectable s-antigen, e-antigen or viral DNA in the blood for more than 6 months are considered chronically infected. Nucleoside analogs as inhibitors of reverse transcriptase activity are the first treatment option for many patients. Lamivudine, Tenofovir, or Entecavir suppress Hepatitis B Virus replication, sometimes to undetectable levels. Improvement of liver function and reduction of liver inflammation are the most important benefits. However, only few patients achieve complete and lasting remission after the end of treatment. Furthermore, the Hepatitis B Virus develops drug resistance with increasing duration of treatment. This is especially difficult for patients co-infected with Hepatitis B and Human Immunodeficiency Virus. Both viruses are susceptible to nucleoside analogue drugs and may co-develop resistance.

The second treatment option is the administration of interferon-alpha. Here, patients receive high doses of interferon-alpha over a period of 6 months. Depending on the virus genotype, up to 50% of chronic infection are curable. However, the Asian genotype B gives very poor response rates. Co-infection with Hepatitis D or Human Immunodeficiency Virus renders interferon-alpha therapy completely ineffective. Patients with strong liver damage and heavy fibrotic conditions are not qualified for interferon-alpha therapy.

Despite significant advances in the field of Hepatitis B Virus treatment, there remains a need for an agent that can selectively and efficiently silence the gene expression of the virus, blocks replication and subsequently reduces viral burden in chronically infected patients.

Double-stranded RNA molecules (dsRNA) have been shown to block gene expression in a highly conserved regulatory mechanism known as RNA interference (RNAi). The invention provides double-stranded ribonucleic acid molecules (dsRNAs), as well as compositions and methods for inhibiting the expression of the Hepatitis B Virus gene, in particular the expression of the Hepatitis B Virus gene, in a cell, tissue or mammal using such dsRNA. The invention also provides compositions and methods for treating or preventing pathological conditions and diseases caused by the infection of the Hepatitis B Virus such as in chronic liver diseases/disorders, inflammations, fibrotic conditions and proliferative disorders, like cancers.

SUMMARY OF THE INVENTION

The invention provides double-stranded ribonucleic acid (dsRNA) molecules able to selectively and efficiently decrease the expression of Hepatitis B Virus gene. The use of Hepatitis B Virus RNAi provides a method for the therapeutic and/or prophylactic treatment of diseases/disorders which are associated with chronic liver diseases/disorders, inflammations, fibrotic conditions and proliferative disorders, like cancers, such method comprises administration of dsRNA targeting Hepatitis B Virus to a human being or animal. In one preferred embodiment the described dsRNA molecule is capable of inhibiting the expression of a Hepatitis B Virus gene by at least 60%, preferably by at least 70%, most preferably by at least 80%.

In one embodiment, the invention provides double-stranded ribonucleic acid (dsRNA) molecules for inhibiting the expression of a Hepatitis B Virus gene, in particular the expression of the genes related to replication or pathogenesis of Hepatitis B Virus. The dsRNA comprises at least two sequences that are complementary to each other. The dsRNA comprises a sense strand comprising a first sequence and an antisense strand comprising a second sequence, see sequences provided in the sequence listing and also the specific dsRNA pairs in the appended Table 1 and Table 2. In one embodiment the sense strand comprises a sequence which has an identity of at least 90% to at least a portion of an Hepatitis B Virus mRNA. Said sequence is located in a region of complementarity of the sense strand to the antisense strand, preferably within nucleotides 2-7 of the 5' terminus of the antisense strand. In one preferred embodiment the dsRNA specifically targets the Hepatitis B Virus gene that encodes core protein, viral polymerase, surface antigen, e-antigen or the X protein. Furthermore, it is preferred that the dsRNA specifically targets a consensus sequence which has a highly conserved nucleic acid sequence among the Hepatitis B Virus genomic sequences of genotype A, B, C and D. Preferably, the consensus sequence is at least 13 contiguous nucleotides in length, more preferably at least 17 contiguous nucleotides, and most preferably at least 19 contiguous nucleotides. Preferred highly conserved nucleic acid sequences are listed in Table 5.

In one embodiment, the antisense strand comprises a nucleotide sequence which is substantially complementary to at least part of an mRNA encoding said Hepatitis B Virus gene, and the region of complementarity is most preferably less than 30 nucleotides in length. Furthermore, it is preferred that the length of the herein described inventive dsRNA molecules (duplex length) is in the range of about 16 to 30 nucleotides, in particular in the range of about 18 to 28 nucleotides. Particularly useful in context of this invention are duplex lengths of about 19, 20, 21, 22, 23 or 24 nucleotides. Most preferred are duplex stretches of 19, 21 or 23 nucleotides. The dsRNA, upon delivery to a cell infected by a Hepatitis B Virus, inhibits the expression of a Hepatitis B Virus gene in vitro by at least 60%, preferably by at least 70%, and most preferably by 80%.

BRIEF DESCRIPTION OF THE DRAWINGS

FIG. 1. Table 1. Core sequences of dsRNAs targeting Hepatitis B Virus gene. Letters in capitals represent RNA nucleotides.

FIG. 2. Table 2. Characterization of dsRNAs targeting Hepatitis B Virus: Activity testing with single dose. Letters in capitals represent RNA nucleotides, lower case letters "c", "g", "a" and "u" represent 2' O-methyl-modified nucleotides, "s" represents phosphorothioate, "dT" represents deoxythymidine, upper case letters A, C, G, U followed by "f" indicates a 2'-fluoro nucleotide. Lower case "p" indicates a 5'-phosphate. (invdT) represents an inverted deoxythimidine (3'-3'-linked).

FIG. 3. Table 3. Characterization of dsRNAs targeting Hepatitis B Virus: Stability. t½: half-life of a strand as defined in examples.

FIG. 4. Table 4. Core sequences of dsRNAs targeting Hepatitis B Virus gene and their modified counterparts. Letters in capitals represent RNA nucleotides, lower case letters "c", "g", "a" and "u" represent 2' O-methyl-modified nucleotides, "s" represents phosphorothioate, "dT" represents deoxythymidine, upper case letters A, C, G, U followed by "t" indicates a 2'-fluoro nucleotide. Lower case "p" indicates a 5'-phosphate. (invdT) represents an inverted deoxythimidine (3'-3'-linked).

FIG. 5. Table 5. Target site sequences of dsRNAs targeting Hepatitis B Virus and their coverage rate with respect to Hepatitis B Virus genotypes A, B, C and D. n=number of available HBV sequences of each genotype FIG. 6. Table 6. NCBI Genbank accession Nos. of Hepatitis B Virus genomic sequences.

FIG. 7. Table 7. Comparison of knockdown efficacies and coverage of HBV genomes for single dsRNAs and combinations thereof. Activity testing for combinations of two dsRNAs was done at final concentrations of 10 nM and at 1 nM with the best performing dsRNAs according to Table 2 and compared with respective data.

FIG. 8. Table 8. Sequences of the negative control ds RNAs used in the psiCHECK™-2 screening assay.

DETAILED DESCRIPTION OF THE INVENTION

Appended Table 1 relates to preferred molecules to be used as dsRNA in accordance with this invention. Also modified dsRNA molecules are provided herein and are in particular disclosed in appended Table 2, providing illustrative examples of modified dsRNA molecules of the present invention. As pointed out herein above, Table 2 provides for illustrative examples of modified dsRNAs of this invention (whereby the corresponding sense strand and antisense strand is provided in this Table). The relation of the unmodified preferred molecules shown in Table 1 to the modified dsRNAs of Table 2 is illustrated in Table 4. Yet, the illustrative modifications of these constituents of the inventive dsRNAs are provided herein as examples of modifications.

Table 3 provides for selective biological, clinical and pharmaceutical relevant parameters of certain dsRNA molecules of this invention.

Some of the preferred dsRNA molecules are provided in the appended Table 1 and, inter alia and preferably, wherein the sense strand is selected from the group consisting of the nucleic acid sequences depicted in SEQ ID NOs: 1, 2, 3, 4, 5, 6, 7, and 26. The antisense strand is selected from the group consisting of the nucleic acid sequences depicted in SEQ ID NOs: 157, 158, 160, 161, 162, 163, 164, and 186. Accordingly, the inventive dsRNA molecule may, inter alia, comprise the sequence pairs selected from the group consisting of SEQ ID NOs: 1/157, 2/158, 3/160, 4/161, 5/162, 6/163, 7/164, and 26/186. In the context of specific dsRNA molecules provided herein, pairs of SEQ ID NOs relate to corresponding sense and antisense strands sequences (5' to 3') as also shown in the Tables.

In one embodiment the dsRNA molecules comprise an antisense strand with a 3' overhang of 1-5 nucleotides in length, preferably 1-2 nucleotides in length. Preferably said overhang of the antisense strand comprises uracil or nucleotides which are complementary to the mRNA encoding a protein necessary for replication or pathogenesis of Hepatitis B Virus, in particular core protein, viral polymerase, surface antigen, e-antigen and X protein. In another preferred embodiment, said dsRNA molecules comprise a sense strand with a 3' overhang of 1-5 nucleotides in length, preferably 1-2 nucleotides in length. Preferably said overhang of the sense strand comprises uracil or nucleotides which are identical to the mRNA encoding a protein necessary for replication or (pathogenesis of Hepatitis B Virus.

In another preferred embodiment, the dsRNA molecules comprise a sense strand with a 3' overhang of 1-5 nucleotides in length, preferably 1-2 nucleotides in length, and an antisense strand with a 3' overhang of 1-5 nucleotides in length, preferably 1-2 nucleotides in length. Preferably said overhang of the sense strand comprises uracil or nucleotides which are at least 90% identical to the pregenomic RNA and/or the mRNA encoding the protein necessary for replication or pathogenesis of Hepatitis B Virus and said overhang of the antisense strand comprises uracil or nucleotides which are at least 90% complementary to the mRNA encoding the protein necessary for replication or pathogenesis of Hepatitis B Virus.

The dsRNA molecules of the invention may be comprised of naturally occurring nucleotides or may be comprised of at least one modified nucleotide, such as a 2'-O-methyl modified nucleotide, inverted deoxythymidine, a nucleotide comprising a 5'-phosphorothioate group, and a terminal nucleotide linked to a cholesteryl derivative or dodecanoic acid bisdecylamide group. 2' modified nucleotides may have the additional advantage that certain immunostimulatory factors or cytokines are suppressed when the inventive dsRNA molecules are employed in vivo, for example in a medical setting. Alternatively and non-limiting, the modified nucleotide may be chosen from the group of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. In one preferred embodiment the dsRNA molecules comprises at least one of the following modified nucleotides: a 2'-β-methyl modified nucleotide, a nucleotide comprising a 5'-phosphorothioate group and a deoxythymidine. Preferred dsRNA molecules comprising modified nucleotides are given in Table 2. In another preferred embodiment one of those deoxythymidine nucleotides at the 3' of both strand is an inverted deoxythymidine.

In a preferred embodiment the inventive dsRNA molecules comprise modified nucleotides as detailed in the sequences given in Table 2. In one preferred embodiment the inventive dsRNA molecule comprises sequence pairs selected from the group consisting of SEQ ID NOs: 1/157, 2/158, 3/160, 4/161, 5/162, 6/163, 7/164, and 26/186, and comprises overhangs at the antisense and/or sense strand of 1-2 deoxythymidines. In one preferred embodiment the inventive dsRNA molecule comprises sequence pairs selected from the group consisting of SEQ ID NOs: 1/157, 2/158, 3/160, 4/161, 5/162, 6/163, 7/164, and 26/186, and comprise modifications as detailed in Table 2. Preferred dsRNA molecules comprising modified nucleotides are listed in Table 2-4, with the most preferred dsRNA molecules depicted in SEQ ID Nos: 321/485, 322/486, 324/488, 325/489, 326/490, 327/491, 328/492, and 350/514.

In another embodiment, the inventive dsRNAs comprise modified nucleotides on positions different from those disclosed in Table 2. In one preferred embodiment two deoxythymidine nucleotides are found at the 3' of both strands of the dsRNA molecule. Preferably said deoxythymidine nucleotides form an overhang.

In one embodiment the dsRNA molecules of the invention comprise a sense and an antisense strand wherein both strands have a half-life of at least 0.9 h. In one preferred embodiment the dsRNA molecules of the invention comprise a sense and an antisense strand wherein both strands have a half-life of at least 48 h, preferably in human serum.

In another embodiment, a nucleic acid sequence encoding a sense strand and/or an antisense strand comprised in the dsRNAs as defined herein are provided.

The invention also provides for cells comprising at least one of the dsRNAs of the invention. The cell is preferably a mammalian cell, such as a human cell. Furthermore, tissues and/or non-human organisms comprising the herein defined dsRNA molecules are an embodiment of this invention, whereby said non-human organisms are particularly useful for research purposes or as research tools, for example in drug testing.

Furthermore, the invention relates to a method for inhibiting the expression of a Hepatitis B Virus gene, in particular a Hepatitis B Virus gene that encodes core protein, viral polymerase, surface antigen, e-antigen or the X protein, in a cell, tissue or organism comprising the following steps:

(a) introducing into the cell, tissue or organism a double-stranded ribonucleic acid (dsRNA) as defined herein; and (b) maintaining said cell, tissue or organism produced in step (a) for a time sufficient to obtain degradation of the mRNA transcript of a Hepatitis B Virus gene, thereby inhibiting expression of a Hepatitis B Virus gene in a given cell.

The invention also relates to pharmaceutical compositions comprising at least one kind of the inventive dsRNAs. These pharmaceutical compositions are particularly useful in the inhibition of the expression of a Hepatitis B Virus gene in a cell, a tissue or an organism.

Preferably said at least one kind of the inventive double-stranded ribonucleic acid molecules target the region of a pregenomic RNA and/or a mRNA encoding a protein necessary for replication or pathogenesis of Hepatitis B Virus gene. More preferably said target region of the inventive double-stranded ribonucleic acid molecules comprises a consensus sequence which is highly conserved among the Hepatitis B Virus genomic sequences of genotype A, B, C and D, and said consensus sequence is at least 13 contiguous nucleotides in length, preferably at least 17 contiguous nucleotides, most preferably at least 19 contiguous nucleotides. Preferred highly conserved nucleic acid sequences are listed in Table 5. The pharmaceutical compositions may be used to treat patients who are infected with any genotype of Hepatitis B Virus or co-infected with different genotypes of Hepatitis B Virus.

In case the pharmaceutical composition comprises at least two kinds of inventive double-stranded ribonucleic acid molecules, it is preferable that the targets of said double-stranded ribonucleic acid molecules are different from each other. The inventive pharmaceutical compositions may be used to treat the patients and to prevent the Hepatitis B Virus from developing resistance to the pharmaceutical compositions. In a preferred embodiment the inventive pharmaceutical compositions comprise the combination of dsRNA molecules as detailed in the sequences given in Table 7. In one preferred embodiment the inventive pharmaceutical compositions comprise combinations of dsRNA pairs selected from the group consisting of SEQ ID NOs: 322/486 and 333/497, 322/486 and 346/510, 322/486 and 330/494, and, 322/486 and 324/488.

The pharmaceutical compositions described above may also comprise (a) pharmaceutically acceptable carrier(s), diluent(s) and/or excipient(s).

In another embodiment, the invention provides methods for treating, preventing or managing chronic liver diseases/disorders, inflammations, fibrotic conditions and/or proliferative disorders like cancers which are associated with Hepatitis B Virus, said method comprising administering to a subject in need of such treatment, prevention or management a therapeutically or prophylactically effective amount of one or more of the dsRNAs of the invention. Preferably, said subject is a mammal, most preferably a human patient.

In one embodiment, the invention provides a method for treating a subject having a pathological condition mediated by the infection of a Hepatitis B Virus. Such conditions comprise disorders associated with chronic liver diseases/disorders, inflammations, fibrotic conditions and/or proliferative disorders like cancers, as described above. In this embodiment, the dsRNA acts as a therapeutic agent for controlling the expression of a Hepatitis B Virus gene. The method comprises administering a pharmaceutical composition of the invention to the patient (e.g., human), such that expression of a Hepatitis B Virus gene is silenced. Because of their high specificity, the dsRNAs of the invention specifically target mRNAs of a Hepatitis B Virus gene. In one preferred embodiment the described dsRNAs specifically decrease Hepatitis B Virus mRNA levels and do not directly affect the expression and/or mRNA levels of off-target genes in the cell.

In one preferred embodiment the described dsRNA decrease Hepatitis B Virus mRNA levels in the liver by at least 60%, preferably by at least 70%, most preferably by at least 80% in vivo. in another embodiment the described dsRNAs decrease Hepatitis B Virus mRNA levels in vivo for at least 4 days. In another preferred embodiment, the dsRNAs of the invention are used for the preparation of a pharmaceutical composition for the treatment of chronic liver diseases/disorders, inflammations, fibrotic conditions and proliferative disorders like cancers. Such diseases to be treated with said pharmaceutical composition comprise but are not limited to: chronic hepatitis (CH), hepatic cirrhosis (HC) and hepatocellular carcinoma (HCC).

In another embodiment, the invention provides vectors for inhibiting the expression of a Hepatitis B Virus gene in a cell, in particular a Hepatitis B Virus gene comprising a regulatory sequence operably linked to a nucleotide sequence that encodes at least one strand of the dsRNA molecules of the invention.

In another embodiment, the invention provides a cell comprising a vector for inhibiting the expression of a Hepatitis B Virus gene in a cell. Said vector comprises a regulatory sequence operably linked to a nucleotide sequence that encodes at least one strand of the dsRNA molecule of the invention. Yet, it is preferred that said vector comprises, besides said regulatory sequence a sequence that encodes at least one "sense strand" of the inventive dsRNA and at least one "antisense strand" of said dsRNA. It is also envisaged that the claimed cell comprises two or more vectors comprising, besides said regulatory sequences, the herein defined sequence(s) that encode(s) at least one strand of the dsRNA molecules of the invention.

In one embodiment, the method comprises administering a composition comprising a dsRNA, wherein the dsRNA comprises a nucleotide sequence which is complementary to at least a part of an RNA transcript of a Hepatitis B Virus gene of the mammal to be treated. As pointed out above, also vectors and cells comprising nucleic acid molecules that encode for at least one strand of the herein defined dsRNA molecules can be used as pharmaceutical compositions and may, therefore, also be employed in the herein disclosed methods of treating a subject in need of medical intervention. It is also of note that these embodiments relating to pharmaceutical compositions and to corresponding methods of treating a (human) subject also relate to approaches like gene therapy approaches.

Hepatitis B Virus specific dsRNA molecules as provided herein or nucleic acid molecules encoding individual strands of these inventive dsRNA molecules may also be inserted into vectors and used as gene therapy vectors for human patients. Gene therapy vectors can be delivered to a subject by, for example, intravenous injection, local administration (see U.S. Pat. No. 5,328,470) or by stereotactic injection (see e.g., Chen et al. Proc. Natl. Acad. Sci. USA (1994) 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

In another aspect of the invention, Hepatitis B Virus specific dsRNA molecules that modulate Hepatitis B Virus gene expression activity are expressed from transcription units inserted into DNA or RNA vectors (see, e.g., Skillern A et al., International PCT Publication No. WO 00/22113). These transgenes can be introduced as a linear construct, a circular plasmid, or a viral vector, which can be incorporated and inherited as a transgene integrated into the host genome. The transgene can also be constructed to permit it to be inherited as an extrachromosomal plasmid (Gassmann et al., Proc. Natl. Acad. Sci. USA (1995) 92:1292).

The individual strands of a dsRNA can be transcribed by promoters on two separate expression vectors and co-transfected into a target cell. Alternatively each individual strand of the dsRNA can be transcribed by promoters both of which are located on the same expression plasmid. In a preferred embodiment, a dsRNA is expressed as an inverted repeat joined by a linker polynucleotide sequence such that the dsRNA has a stem and loop structure.

The recombinant dsRNA expression vectors are preferably DNA plasmids or viral vectors. dsRNA expressing viral vectors can be constructed based on, but not limited to, adeno-associated virus (for a review, see Muzyczka et al., Curr. Topics Micro. Immunol. (1992) 158:97-129); adenovirus (see, for example, Berkner et al., BioTechniques (1998) 6:616; Rosenfeld et al. Science (1991) 252:431-434; and Rosenfeld et al. Cell (1992) 68:143-155); or alphavirus as well as others known in the art. Retroviruses have been used to introduce a variety of genes into many different cell types, including epithelial cells, in vitro and/or in vivo (see, e.g., Danos and Mulligan, Proc. Natl. Acad. Sci. USA (1998) 85:6460-6464). Recombinant retroviral vectors capable of transducing and expressing genes inserted into the genome of a cell can be produced by transfecting the recombinant retro-viral genome into suitable packaging cell lines such as PA317 and Psi-CRIP (Comette et al., Human Gene Therapy (1991) 2:5-10; Cone et al., Proc. Natl. Acad. Sci. USA (1984) 81:6349). Recombinant adenoviral vectors can be used to infect a wide variety of cells and tissues in susceptible hosts (e.g., rat, hamster, dog, and chimpanzee) (Hsu et al., J. Infectious Disease, (1992) 166:769), and also have the advantage of not requiring mitotically active cells for infection.

The promoter driving dsRNA expression in either a DNA plasmid or viral vector of the invention may be a eukaryotic RNA polymerase I (e.g. ribosomal RNA promoter), RNA polymerase II (e.g. CMV early promoter or actin promoter or U1 snRNA promoter) or preferably RNA polymerase III promoter (e.g. U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g. the insulin regulatory sequence for pancreas (Bucchini et al., Proc. Natl. Acad. Sci. USA (1986) 83:2511-2515).

In addition, expression of the transgene can be precisely regulated, for example, by using an inducible regulatory sequence and expression systems such as a regulatory sequence that is sensitive to certain physiological regulators, e.g., circulating glucose levels, or hormones (Docherty et al., FASEB J. (1994) 8:20-24). Such inducible expression systems, suitable for the control of transgene expression in cells or in mammals include regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the dsRNA transgene.

Preferably, recombinant vectors capable of expressing dsRNA molecules are delivered as described below, and persist in target cells. Alternatively, viral vectors can be used that provide for transient expression of dsRNA molecules. Such vectors can be repeatedly administered as necessary. Once expressed, the dsRNAs bind to target RNA and modulate its function or expression. Delivery of dsRNA expressing vectors can be systemic, such as by intravenous or intramuscular administration, by administration to target cells ex-planted from the patient followed by reintroduction into the patient, or by any other means that allows for introduction into a desired target cell.

dsRNA expression DNA plasmids are typically transfected into target cells as a complex with cationic lipid carriers (e.g. Oligofectamine) or non-cationic lipid-based carriers (e.g. Transit-TKO™). Multiple lipid transfections for dsRNA-mediated knockdowns targeting different regions of a single Hepatitis B Virus gene or multiple Hepatitis B Virus genes over a period of a week or more are also contemplated by the invention. Successful introduction of the vectors of the invention into host cells can be monitored using various known methods. For example, transient transfection can be signaled with a reporter, such as a fluorescent marker, such as Green Fluorescent Protein (GFP). Stable transfection of ex vivo cells can be ensured using markers that provide the transfected cell with resistance to specific environmental factors (e.g., antibiotics and drugs), such as hygromycin B resistance.

The following detailed description discloses how to make and use the dsRNA and compositions containing dsRNA to inhibit the expression of a target Hepatitis B Virus gene, as well as compositions and methods for treating diseases and disorders caused by the infection of said Hepatitis B Virus.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A", "U" and "T" or "dT" respectively, each generally stand for a nucleotide that contains guanine, cytosine, adenine, uracil and deoxythymidine as a base, respectively. However, the term "ribonucleotide" or "nucleotide" can also refer to a modified nucleotide, as further detailed below, or a surrogate replacement moiety. Sequences comprising such replacement moieties are embodiments of the invention. As detailed below, the herein described dsRNA molecules may also comprise "overhangs", i.e. unpaired, overhanging nucleotides which are not directly involved in the RNA double helical structure normally formed by the herein defined pair of "sense strand" and "antisense strand". Often, such an overhanging stretch comprises the deoxythymidine nucleotide, in most embodiments, two deoxythymidines in the 3' end. Such overhangs will be described and illustrated below.

The term "Hepatitis B Virus gene" as used herein relates to the genes necessary for replication and pathogenesis of Hepatitis B Virus, in particular to the genes that encode core protein, viral polymerase, surface antigen, e-antigen and the X protein and the genes that encode the functional fragments of the same. The term "Hepatitis B Virus gene/sequence" does not only relate to (the) wild-type sequence(s) but also to mutations and alterations which may be comprised in said gene/sequence. Accordingly, the present invention is not limited to the specific dsRNA molecules provided herein. The invention also relates to dsRNA molecules that comprise an antisense strand that is at least 85% complementary to the corresponding nucleotide stretch of an RNA transcript of a Hepatitis B Virus gene that comprises such mutations/alterations.

As used herein, the term "consensus sequence" refers to at least 13 contiguous nucleotides, preferably at least 17 contiguous nucleotides, most preferably at least 19 contiguous nucleotides, which is highly conserved among the Hepatitis B Virus genomic sequences of genotype A, B, C and D.

As used herein, "target sequence" refers to a contiguous portion of the nucleotide sequence of an mRNA molecule formed during the transcription of a Hepatitis B Virus gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature. However, as detailed herein, such a "strand comprising a sequence" may also comprise modifications, like modified nucleotides.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence. "Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled.

Sequences referred to as "fully complementary" comprise base-pairing of the oligonucleotide or polynucleotide comprising the first nucleotide sequence to the oligonucleotide or polynucleotide comprising the second nucleotide sequence over the entire length of the first and second nucleotide sequence.

However, where a first sequence is referred to as "substantially complementary" with respect to a second sequence herein, the two sequences can be fully complementary, or they may form one or more, but preferably not more than 13 mismatched base pairs upon hybridization.

The terms "complementary", "fully complementary" and "substantially complementary" herein may be used with respect to the base matching between the sense strand and the antisense strand of a dsRNA, or between the antisense strand of a dsRNA and a target sequence, as will be understood from the context of their use.

The term "double-stranded RNA", "dsRNA molecule", or "dsRNA", as used herein, refers to a ribonucleic acid molecule, or complex of ribonucleic acid molecules, having a duplex structure comprising two anti-parallel and substantially complementary nucleic acid strands. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5' end of the respective other strand forming the duplex structure, the connecting RNA chain is referred to as a "hairpin loop". Where the two strands are connected covalently by means other than an uninterrupted chain of nucleotides between the 3'-end of one strand and the 5' end of the respective other strand forming the duplex structure, the connecting structure is referred to as a "linker". The RNA strands may have the same or a different number of nucleotides. In addition to the duplex structure, a dsRNA may comprise one or more nucleotide overhangs. The nucleotides in said "overhangs" may comprise between 0 and 5 nucleotides, whereby "0" means no additional nucleotide(s) that form(s) an "overhang" and whereas "5" means five additional nucleotides on the individual strands of the dsRNA duplex. These optional "overhangs" are located in the 3' end of the individual strands. As will be detailed below, also dsRNA molecules which comprise only an "overhang" in one of the two strands may be useful and even advantageous in context of this invention. The "overhang" comprises preferably between 0 and 2 nucleotides. Most preferably two "dT" (deoxythymidine) nucleotides are found at the 3' end of both strands of the dsRNA. Also two "U" (uracil) nucleotides can be used as overhangs at the 3' end of both strands of the dsRNA. Accordingly, a "nucleotide overhang" refers to the unpaired nucleotide or nucleotides that protrude from the duplex structure of a dsRNA when a 3'-end of one strand of the dsRNA extends beyond the 5'-end of the other strand, or vice versa. For example the antisense strand comprises 23 nucleotides and the sense strand comprises 21 nucleotides, forming a two nucleotide overhang at the 3' end of the antisense strand. Preferably, the two nucleotide overhang is fully complementary to the mRNA of the target gene. "Blunt" or "blunt end" means that there are no unpaired nucleotides at that end of the dsRNA, i.e., no nucleotide overhang. A "blunt ended" dsRNA is a dsRNA that is double-stranded over its entire length, i.e., no nucleotide overhang at either end of the molecule.

The term "antisense strand" refers to the strand of a dsRNA which includes a region that is substantially complementary to a target sequence. As used herein, the term "region of complementarity" refers to the region on the antisense strand that is substantially complementary to a sequence, for example a target sequence. Where the region of complementarity is not fully complementary to the target sequence, the mismatches are most tolerated outside nucleotides 2-7 of the 5' terminus of the antisense strand The term "sense strand," as used herein, refers to the strand of a dsRNA that includes a region that is substantially complementary to a region of the antisense strand. "Substantially complementary" means preferably at least 85% of the overlapping nucleotides in sense and antisense strand are complementary.

"Introducing into a cell", when referring to a dsRNA, means facilitating uptake or absorption into the cell, as is understood by those skilled in the art. Absorption or uptake of dsRNA can occur through unaided diffusive or active cellular processes, or by auxiliary agents or devices. The meaning of this term is not limited to cells in vitro; a dsRNA may also be "introduced into a cell", wherein the cell is part of a living organism. In such instance, introduction into the cell will include the delivery to the organism. For example, for in vivo delivery, dsRNA can be injected into a tissue site or administered systemically. It is, for example envisaged that the dsRNA molecules of this invention be administered to a subject in need of medical intervention. Such an administration may comprise the injection of the dsRNA, the vector or a cell of this invention into a diseased site in said subject, for example into liver tissue/cells or into cancerous tissues/cells, like liver cancer tissue. In addition, the injection is preferably in close proximity to the diseased tissue envisaged. In vitro introduction into a cell includes methods known in the art such as electroporation and lipofection.

As used herein, "chronic liver diseases/disorders" refers to the functional abnormality of liver lasting more than six months which can be caused by the infection of virus. One example of the chronic liver diseases/disorders is chronic hepatitis (CH).

The term "inflammation" as used herein refers to the biologic response of body tissue to injury, irritation, or disease which can be caused by harmful stimuli, for example, pathogens, damaged cells, or irritants. Inflammation is typically characterized by pain and swelling. Inflammation is intended to encompass both acute responses, in which inflammatory processes are active (e.g., neutrophils and leukocytes), and chronic responses, which are marked by slow progress, a shift in the type of cell present at the site of inflammation, and the formation of connective tissue. One example of an inflammation-caused disease is fibrosis.

The term "fibrotic conditions" as used herein refers to the functional problem of organs which can be caused by growth of fibrous tissue. One such example of such kind of disease is hepatic cirrhosis (HC).

The term "proliferating" and "proliferation" as used herein refer to cells undergoing mitosis. Throughout this application, the term "proliferative disorder" refers to any disease/disorder marked by unwanted or aberrant proliferation of tissue. As used herein, the term "proliferative disorder" also refers to conditions in which the unregulated and/or abnormal growth of cells can lead to the development of an unwanted condition or disease, which can be cancerous or non-cancerous.

Cancers to be treated comprise, but are again not limited to liver cancer, whereby said liver cancer may, inter alia, be selected from the group consisting of hepatocellular carcinoma (HCC), hepatoblastoma, a mixed liver cancer, a cancer derived from mesenchymal tissue, a liver sarcoma or a cholangiocarcinoma.

The terms "silence", "inhibit the expression of" and "knock down", in as far as they refer to a Hepatitis B Virus gene, herein refer to the at least partial suppression of the expression of a Hepatitis B Virus gene, as manifested by a reduction of the amount of mRNA transcribed from a Hepatitis B Virus gene which may be isolated from a first cell or group of cells in which a Hepatitis B Virus gene is transcribed and which has or have been treated such that the expression of a Hepatitis B Virus gene is inhibited, as compared to a second cell or group of cells substantially identical to the first cell or group of cells but which has or have not been so treated (control cells). The degree of inhibition is usually expressed in terms of $$\frac{(\text{mRNA in control cells}) - (\text{mRNA in treated cells})}{(\text{mRNA in control cells})} \times 100\%$$

Alternatively, the degree of inhibition may be given in terms of a reduction of a parameter that is functionally linked to the Hepatitis B Virus gene transcription, e.g. the amount of protein encoded by a Hepatitis B Virus gene which is secreted by a cell, or the number of cells displaying a certain phenotype.

As illustrated in the appended examples and in the appended Tables provided herein, the inventive dsRNA molecules are capable of inhibiting the expression of a Hepatitis B Virus by at least about 60%, preferably by at least 70%, most preferably by at least 80% in in vitro assays, i.e. in vitro. The term "in vitro" as used herein includes but is not limited to cell culture assays. The person skilled in the art can readily determine such an inhibition rate and related effects, in particular in light of the assays provided herein.

The term "off target" as used herein refers to all non-target mRNAs of the transcriptome that are predicted by in silico methods to hybridize to the described dsRNAs based on sequence complementarity. The dsRNAs of the present invention preferably do specifically inhibit the expression of Hepatitis B Virus gene, i.e. do not inhibit the expression of any off-target.

The term "half-life" as used herein is a measure of stability of a compound or molecule and can be assessed by methods known to a person skilled in the art, especially in light of the assays provided herein.

The term "non-immunostimulatory" as used herein refers to the absence of any induction of an immune response by the invented dsRNA molecules. Methods to determine immune responses are well known to a person skilled in the art, for example by assessing the release of cytokines, as described in the examples section.

The terms "treat", "treatment", and the like, mean in context of this invention the relief from or alleviation of a disorder related to Hepatitis B Virus infection, like chronic liver diseases/disorders, inflammations, fibrotic conditions and proliferative disorders, like cancers.

As used herein, a "pharmaceutical composition" comprises a pharmacologically effective amount of at least one kind of dsRNAs and a pharmaceutically acceptable carrier. However, such a "pharmaceutical composition" may also comprise individual strands of such dsRNA molecules or the herein described vector(s) comprising a regulatory sequence operably linked to a nucleotide sequence that encodes at least one strand of a sense or an antisense strand comprised in the dsRNAs of this invention. It is also envisaged that cells, tissues or isolated organs that express or comprise the herein defined dsRNAs may be used as "pharmaceutical compositions". As used herein, "pharmacologically effective amount," "therapeutically effective amount," or simply "effective amount" refers to that amount of an RNA effective to produce the intended pharmacological, therapeutic or preventive result.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives as known to persons skilled in the art.

It is in particular envisaged that the pharmaceutically acceptable carrier allows for the systemic administration of the dsRNAs, vectors or cells of this invention. Whereas also the enteric administration is envisaged the parenteral administration and also transdermal or transmucosal (e.g. insufflation, buccal, vaginal, anal) administration as well as inhalation of the drug are feasible ways of administering to a patient in need of medical intervention the compounds of this invention. When parenteral administration is employed, this can comprise the direct injection of the compounds of this invention into the diseased tissue or at least in close proximity. However, also intravenous, intraarterial, subcutaneous, intramuscular, intraperitoneal, intradermal, intrathecal and other administrations of the compounds of this invention are within the skill of the artisan, for example the attending physician.

For intramuscular, subcutaneous and intravenous use, the pharmaceutical compositions of the invention will generally be provided in sterile aqueous solutions or suspensions, buffered to an appropriate pH and isotonicity. In a preferred embodiment, the carrier consists exclusively of an aqueous buffer. In this context, "exclusively" means no auxiliary agents or encapsulating substances are present which might affect or mediate uptake of dsRNA in the cells that express a Hepatitis B Virus gene. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. The pharmaceutical compositions useful according to the invention also include encapsulated formulations to protect the dsRNA against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions and bi-specific antibodies can also be used as pharmaceutically acceptable carriers. These can be prepared according to methods known to those skilled in the art, for example, as described in PCT publication WO91/06309 and WO2011/003780 which is incorporated by reference herein.

As used herein, a "transformed cell" is a cell into which at least one vector has been introduced from which a dsRNA molecule or at least one strand of such a dsRNA molecule may be expressed. Such a vector is preferably a vector comprising a regulatory sequence operably linked to nucleotide sequence that encodes at least one sense strand or antisense strand of a dsRNA of the present invention.

It can be reasonably expected that shorter dsRNAs comprising one of the sequences in Table 1 and 4 minus only a few nucleotides on one or both ends may be similarly effective as compared to the dsRNAs described above.

In one preferred embodiment the inventive dsRNA molecules comprise nucleotides 1-19 of the sequences given in Table 1.

As pointed out above, in most embodiments of this invention, the dsRNA molecules provided herein comprise a duplex length (i.e. without "overhangs") of about 16 to about 30 nucleotides. Particular useful dsRNA duplex lengths are about 19 to about 25 nucleotides. Most preferred are duplex structures with a length of 19 nucleotides. In the inventive dsRNA molecules, the antisense strand is at least partially complementary to the sense strand.

The dsRNA of the invention can contain one or more mismatches to the target sequence. In a preferred embodiment, the dsRNA of the invention contains no more than 13 mismatches. If the antisense strand of the dsRNA contains mismatches to a target sequence, it is preferable that the area of mismatch not be located within nucleotides 2-7 of the 5' terminus of the antisense strand. In another embodiment it is preferable that the area of mismatch not be located within nucleotides 2-9 of the 5' terminus of the antisense strand.

As mentioned above, at least one end/strand of the dsRNA may have a single-stranded nucleotide overhang of 1 to 5, preferably 1 or 2 nucleotides. dsRNAs having at least one nucleotide overhang have unexpectedly superior inhibitory properties than their blunt-ended counterparts. Moreover, the present inventors have discovered that the presence of only one nucleotide overhang strengthens the interference activity of the dsRNA, without affecting its overall stability. dsRNA having only one overhang has proven particularly stable and effective in viva, as well as in a variety of cells, cell culture mediums, blood, and serum. Preferably, the single-stranded overhang is located at the 3'-terminal end of the antisense strand or, alternatively, at the 3'-terminal end of the sense strand. The dsRNA may also have a blunt end, preferably located at the 5'-end of the antisense strand. Preferably, the antisense strand of the dsRNA has a nucleotide overhang at the 3'-end, and the 5'-end is blunt. In another embodiment, one or more of the nucleotides in the overhang is replaced with a nucleoside thiophosphate.

The dsRNA of the present invention may also be chemically modified to enhance stability. The nucleic acids of the invention may be synthesized and/or modified by methods well established in the art. Chemical modifications may include, but are not limited to 2' modifications, introduction of non-natural bases, covalent attachment to a ligand, and replacement of phosphate linkages with thiophosphate linkages, inverted deoxythymidines. In this embodiment, the integrity of the duplex structure is strengthened by at least one, and preferably two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues. Preferably, the chemical groups that can be used to modify the dsRNA include, without limitation, methylene blue; bifunctional groups, preferably bis-(2-chloroethyl)amine; N-acetyl-N'-(p-glyoxylbenzoyl) cystamine; 4-thiouracil; and psoralen. In one preferred embodiment, the linker is a hexa-ethylene glycol linker. In this case, the dsRNA are produced by solid phase synthesis and the hexa-ethylene glycol linker is incorporated according to standard methods (e.g., Williams D J and Hall K B, Biochem. (1996) 35:14665-14670). In a particular embodiment, the 5'-end of the antisense strand and the 3'-end of the sense strand are chemically linked via a hexaethylene glycol linker. In another embodiment, at least one nucleotide of the dsRNA comprises a phosphorothioate or phosphorodithioate groups. The chemical bond at the ends of the dsRNA is preferably formed by triple-helix bonds.

In certain embodiments, a chemical bond may be formed by means of one or several bonding groups, wherein such bonding groups are preferably poly-(oxyphosphinicooxy-1, 3-propandiol) and/or polyethylene glycol chains. In other embodiments, a chemical bond may also be formed by means of purine analogs introduced into the double-stranded structure instead of purines. In further embodiments, a chemical bond may be formed by azabenzene units introduced into the double-stranded structure. In still further embodiments, a chemical bond may be formed by branched nucleotide analogs instead of nucleotides introduced into the double-stranded structure. In certain embodiments, a chemical bond may be induced by ultraviolet light.

In yet another embodiment, the nucleotides at one or both of the two single strands may be modified to prevent or inhibit the activation of cellular enzymes, for example certain nucleases. Techniques for inhibiting the activation of cellular enzymes are known in the art including, but not limited to, 2'-amino modifications, 2'-amino sugar modifications, 2'-F sugar modifications, 2'-F modifications, 2'-alkyl sugar modifications, uncharged backbone modifications, morpholino modifications, 2'-O-methyl modifications, and phosphoramidate (see, e.g., Wagner, Nat. Med. (1995) 1:111.6-8). Thus, at least one 2'-hydroxyl group of the nucleotides on a dsRNA is replaced by a chemical group, preferably by a 2'-amino or a 2'-methyl group. Also, at least one nucleotide may be modified to form a locked nucleotide. Such locked nucleotide contains a methylene bridge that connects the 2'-oxygen of ribose the 4'-carbon of ribose. Introduction of a locked nucleotide into an oligonucleotide improves the affinity for complementary sequences and increases the melting temperature by several degrees.

Modifications of dsRNA molecules provided herein may positively influence their stability in vivo as well as in vitro and also improve their delivery to the (diseased) target side. Furthermore, such structural and chemical modifications may positively influence physiological reactions towards the dsRNA molecules upon administration, e.g. the cytokine release which is preferably suppressed. Such chemical and structural modifications are known in the art and are, inter alia, illustrated in Nawrot Current Topics in Med Chem, (2006) 6:913-925.

Conjugating a ligand to a dsRNA can enhance its cellular absorption as well as targeting to a particular tissue. In certain instances, a hydrophobic ligand is conjugated to the dsRNA to facilitate direct permeation of the cellular membrane. Alternatively, the ligand conjugated to the dsRNA is a substrate for receptor-mediated endocytosis. These approaches have been used to facilitate cell permeation of antisense oligonucleotides. For example, cholesterol has been conjugated to various antisense oligonucleotides resulting in compounds that are substantially more active compared to their non-conjugated analogs (See Manoharan M, Antisense & Nucleic Acid Drug Development (2002) 12:103). Other lipophilic compounds that have been conjugated to oligonucleotides include 1-pyrene butyric acid, 1,3-bis-O-(hexadecyl)glycerol, and menthol. One example of a ligand for receptor-mediated endocytosis is folic acid. Folic acid enters the cell by folate-receptor-mediated endocytosis. dsRNA compounds bearing folic acid would be efficiently transported into the cell via the folate-receptor-mediated endocytosis. Attachment of folic acid to the 3'-terminus of an oligonucleotide results in increased cellular uptake of the oligonucleotide (Li S, Deshmukh H M, and Huang L, Pharm. Res. (1998) 15:1540). Other ligands that have been conjugated to oligonucleotides include polyethylene glycols, carbohydrate clusters, cross-linking agents, porphyrin conjugates, and delivery peptides.

In certain instances, conjugation of a cationic ligand to oligonucleotides often results in improved resistance to nucleases. Representative examples of cationic ligands are propylammonium and dimethylpropylammonium. Interestingly, antisense oligonucleotides were reported to retain their high binding affinity to mRNA when the cationic ligand was dispersed throughout the oligonucleotide. See Manoharan M, Antisense & Nucleic Acid Drug Development (2002) 12:103 and references therein.

The ligand-conjugated dsRNA of the invention may be synthesized by the use of a dsRNA that bears a pendant reactive functionality, such as that derived from the attachment of a linking molecule onto the dsRNA. This reactive oligonucleotide may be reacted directly with commercially-available ligands, ligands that are synthesized bearing any of a variety of protecting groups, or ligands that have a linking moiety attached thereto. The methods of the invention facilitate the synthesis of ligand-conjugated dsRNA by the use of, in some preferred embodiments, nucleoside monomers that have been appropriately conjugated with ligands and that may further be attached to a solid-support material. Such ligand-nucleoside conjugates, optionally attached to a solid-support material, are prepared according to some preferred embodiments of the methods of the invention via reaction of a selected serum-binding ligand with a linking moiety located on the 5' position of a nucleoside or oligonucleotide. In certain instances, a dsRNA bearing an aralkyl ligand attached to the 3'-terminus of the dsRNA is prepared by first covalently attaching a monomer building block to a controlled-pore-glass support via a long-chain aminoalkyl group. Then, nucleotides are bonded via standard solid-phase synthesis techniques to the monomer building-block bound to the solid support. The monomer building block may be a nucleoside or other organic compound that is compatible with solid-phase synthesis.

The dsRNA used in the conjugates of the invention may be conveniently and routinely made through the well-known technique of solid-phase synthesis. It is also known to use similar techniques to prepare other oligonucleotides, such as the phosphorothioates and alkylated derivatives.

Teachings regarding the synthesis of particular modified oligonucleotides may be found in the following U.S. patents: U.S. Pat. No. 5,218,105, drawn to polyamine conjugated oligonucleotides; U.S. Pat. No. 5,541,307, drawn to oligonucleotides having modified backbones; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. No. 5,587,361 drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,608,046, both drawn to conjugated 4'-desmethyl nucleoside analogs; U.S. Pat. No. 5,610,289, drawn to backbone-modified oligonucleotide analogs; U.S. Pat. No. 6,262,241 drawn to, inter alia, methods of synthesizing 2'-fluoro-oligonucleotides.

In the ligand-conjugated dsRNA and ligand-molecule bearing sequence-specific linked nucleosides of the invention, the oligonucleotides and oligonucleosides may be assembled on a suitable oligonucleotide synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. Oligonucleotide conjugates bearing a variety of molecules such as steroids, vitamins, lipids and reporter molecules, has previously been described (see Manoharan et al., PCT Application WO 93/07883). In a preferred embodiment, the oligonucleotides or linked nucleosides of the invention are synthesized by an automated synthesizer using phosphoramidites derived from ligand-nucleoside conjugates in addition to commercially available phosphoramidites.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention can be augmented to include either or both a phosphorothioate backbone or a 2'-β-methyl, 2'-O-ethyl, 2'-O-propyl, 2'-O-aminoalkyl, 2'-O-allyl or 2'-deoxy-2'-fluoro group.

In some preferred embodiments, functionalized nucleoside sequences of the invention possessing an amino group at the 5'-terminus are prepared using a DNA synthesizer, and then reacted with an active ester derivative of a selected ligand. Active ester derivatives are well known to those skilled in the art. Representative active esters include N-hydrosuccinimide esters, tetrafluorophenolic esters, pentafluorophenolic esters and pentachlorophenolic esters. The reaction of the amino group and the active ester produces an oligonucleotide in which the selected ligand is attached to the 5'-position through a linking group. The amino group at the 5'-terminus can be prepared utilizing a 5'-Amino-Modifier C6 reagent. In a preferred embodiment, ligand molecules may be conjugated to oligonucleotides at the 5'-position by the use of a ligand-nucleoside phosphoramidite wherein the ligand is linked to the 5'-hydroxy group directly or indirectly via a linker. Such ligand-nucleoside phosphoramidites are typically used at the end of an automated synthesis procedure to provide a ligand-conjugated oligonucleotide bearing the ligand at the 5'-terminus.

In one preferred embodiment of the methods of the invention, the preparation of ligand conjugated oligonucleotides commences with the selection of appropriate precursor molecules upon which to construct the ligand molecule. Typically, the precursor is an appropriately-protected derivative of the commonly-used nucleosides. For example, the synthetic precursors for the synthesis of the ligand-conjugated oligonucleotides of the invention include, but are not limited to, 2'-aminoalkoxy-5'-ODMT-nucleosides, 2'-6-aminoalkylamino-5'-ODMT-nucleosides, 5'-6-aminoalkoxy-2'-deoxynucleosides, 5'-6-aminoalkoxy-2-protected-nucleosides, 3'-6-aminoalkoxy-5'-ODMT-nucleosides, and 3'-aminoalkylamino-5'-ODMT-nucleosides that may be protected in the nucleobase portion of the molecule. Methods for the synthesis of such amino-linked protected nucleoside precursors are known to those of ordinary skill in the art.

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Protecting groups in general and hydroxyl protecting groups in particular are well known in the art (Greene and Wuts, Protective Groups in Organic Synthesis, Chapter 2, 2d ed., John Wiley & Sons, New York, 1991). Amino-protecting groups stable to acid treatment are selectively removed with base treatment, and are used to make reactive amino groups selectively available for substitution. Examples of such groups are the Fmoc and various substituted sulfonylethyl carbamates exemplified by the Nsc group.

Additional amino-protecting groups include, but are not limited to, carbamate protecting groups, such as 2-trimethylsilylethoxycarbonyl (Teoc), 1-methyl-1-(4-biphenylyl)-ethoxycarbonyl (Bpoc), t-butoxycarbonyl (BOC), allyloxycarbonyl (Alloc), 9-fluorenyl-methyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

Many solid supports are commercially available and one of ordinary skill in the art can readily select a solid support to be used in the solid-phase synthesis steps. In certain embodiments, a universal support is used. A universal support, well known in the art, allows for the preparation of oligonucleotides having unusual or modified nucleotides located at the 3-terminus of the oligonucleotide. In addition, it has been reported that the oligonucleotide can be cleaved from the universal support under milder reaction conditions when the oligonucleotide is bonded to the solid support via a syn-1,2-acetoxyphosphate group which more readily undergoes basic hydrolysis. See Guzaev A I, and Manoharan M J. Am. Chem. Soc. (2003) 125:2380.

The nucleosides are linked by phosphorus-containing or non-phosphorus-containing covalent internucleoside linkages. For the purposes of identification, such conjugated nucleosides can be characterized as ligand-bearing nucleosides or ligand-nucleoside conjugates. The linked nucleosides having an aralkyl ligand conjugated to a nucleoside within their sequence will demonstrate enhanced dsRNA activity when compared to like dsRNA compounds that are not conjugated.

The aralkyl-ligand-conjugated oligonucleotides of the invention also include conjugates of oligonucleotides and linked nucleosides wherein the ligand is attached directly to the nucleoside or nucleotide without the intermediacy of a linker group. The ligand may preferably be attached, via linking groups, at a carboxyl, amino or oxo group of the ligand. Typical linking groups may be ester, amide or carbamate groups.

Specific examples of preferred modified oligonucleotides envisioned for use in the ligand-conjugated oligonucleotides of the invention include oligonucleotides containing modified backbones or non-natural internucleoside linkages. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modifications may be incorporated in a single dsRNA compound or even in a single nucleotide thereof.

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included.

Representative United States patents relating to the preparation of the above phosphorus-atom-containing linkages include, but are not limited to, U.S. Pat. Nos. 4,469,863, 5,023,243, 5,264,423, 5,321,131, 5,399,676, 5,405,939, 5,453,496, 5,455,33, and 5,466,677, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents relating to the preparation of the above oligonucleosides include, but are not limited to, U.S. Pat. Nos. 5,034,506, 5,214,134, 5,216,141, 5,264,562, 5,466,677, 5,470,967, 5,489,677, 5,602,240, and 5,663,312, each of which is herein incorporated by reference.

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Teaching of PNA compounds can be found for example in U.S. Pat. No. 5,539,082.

Some preferred embodiments of the invention employ oligonucleotides with phosphorothioate linkages and oligonucleosides with heteroatom backbones, and in particular —$CH_2$—NH—O—$CH_2$, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

The oligonucleotides employed in the ligand-conjugated oligonucleotides of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further nucleobases include those disclosed in U.S. Pat. No. 3,687,808, or otherwise known in the art or commercially available. Certain of these nucleobases are particularly useful for increasing the binding affinity of the oligonucleotides of the invention. These include 5-substituted pyrimidines, 6-azapyrimidines and N-2, N-6 and O-6 substituted purines, including 2-aminopropyladenine, 5-propynyluracil and 5-propynylcytosine. 5-Methylcytosine substitutions have been shown to increase nucleic acid duplex stability by 0.6-1.2° C. and are presently preferred base substitutions, even more particularly when combined with 2'-methoxyethyl sugar modifications.

Representative United States patents relating to the preparation of certain of the above-noted modified nucleobases as well as other modified nucleobases include, but are not limited to, the above noted U.S. Pat. No. 3,687,808, as well as U.S. Pat. Nos. 5,134,066, 5,459,255, 5,552,540, 5,594,121, and 5,596,091 all of which are hereby incorporated by reference.

In certain embodiments, the oligonucleotides employed in the ligand-conjugated oligonucleotides of the invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in U.S. Pat. No. 6,127,533.

Other preferred modifications include 2'-methoxy (2'-O—$CH_3$), 2'-aminopropoxy (2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides.

As used herein, the term . . . sugar substituent group" or "2'-substituent group" includes groups attached to the 2'-position of the ribofuranosyl moiety with or without an oxygen atom. Sugar substituent groups include, but are not limited to, fluoro, O-alkyl, O-alkylamino, O-alkylalkoxy, protected O-alkylamino, O-alkylaminoalkyl, O-alkyl imidazole and polyethers of the formula (O-alkyl)m, wherein m is 1 to about 10. Preferred among these polyethers are linear and cyclic polyethylene glycols (PEGs), and (PEG)-containing groups, such as crown ethers and, inter alia, those which are disclosed by Delgardo et. al. (Critical Reviews in Therapeutic Drug Carrier Systems (1992) 9:249). Further sugar modifications are disclosed by Cook (Anti-fibrosis Drug Design, (1991) 6:585-607). Fluoro, O-alkyl, O-alkylamino, O-alkyl imidazole, O-alkylaminoalkyl, and alkyl amino substitution is described in U.S. Pat. No. 6,166,197, entitled "Oligomeric Compounds having Pyrimidine Nucleotide(s) with 2' and 5' Substitutions," hereby incorporated by reference in its entirety.

Additional sugar substituent groups amenable to the invention include 2'-SR and 2'-$NR_2$ groups, wherein each R is, independently, hydrogen, a protecting group or substituted or unsubstituted alkyl, alkenyl, or alkynyl. 2'-SR Nucleosides are disclosed in U.S. Pat. No. 5,670,633, hereby incorporated by reference in its entirety. The incorporation of 2'-SR monomer synthons is disclosed by Hamm et al. (J. Org. Chem., (1997) 62:3415-3420). 2'-NR nucleosides are disclosed by Thomson J B, J. Org. Chem., (1996) 61:6273-6281; and Polushin et al., Tetrahedron Lett., (1996) 37:3227-3230. Further representative 2'-substituent groups amenable to the invention include those having one of formula I or II:

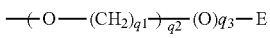

I

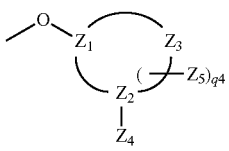

II wherein

E is $C_1$-$C_{10}$ alkyl, N(Q3)(Q4) or N═C(Q3)(Q4); each Q3 and Q4 is, independently, H, $C_1$-$C_{10}$ alkyl, dialkylaminoalkyl, a nitrogen protecting group, a tethered or untethered conjugate group, a linker to a solid support; or Q3 and Q4, together, form a nitrogen protecting group or a ring structure optionally including at least one additional heteroatom selected from N and O;

q1 is an integer from 1 to 10;

q2 is an integer from 1 to 10;

q3 is 0 or 1;

q4 is 0, 1 or 2;

each Z1, Z2, and Z3 is, independently, $C_4$-$C_7$ cycloalkyl, $C_5$-$C_{14}$ aryl or $C_3$-$C_{15}$ heterocyclyl, wherein the heteroatom in said heterocyclyl group is selected from oxygen, nitrogen and sulfur;

Z4 is OM1, SM1, or $N(M1)_2$; each M1 is, independently, H, $C_1$-$C_8$ alkyl, $C_1$-$C_8$ haloalkyl, C(═NH)N(H)M2, C(═O)N(H)M2 or OC(═O)N(H)M2; M2 is H or $C_1$-$C_8$ alkyl; and Z5 is $C_1$-$C_{10}$ alkyl, $C_1$-$C_{10}$ haloalkyl, $C_2$-$C_{10}$ alkenyl, $C_2$-$C_{10}$ alkynyl, $C_6$-$C_{14}$ aryl, N(Q3)(Q4), OQ3, halo, SQ3 or CN.

Representative 2'-O-sugar substituent groups of formula I are disclosed in U.S. Pat. No. 6,172,209, entitled "Capped 2'-Oxyethoxy Oligonucleotides," hereby incorporated by reference in its entirety. Representative cyclic 2'-O-sugar substituent groups of formula II are disclosed in U.S. Pat. No. 6,271,358, entitled "RNA Targeted 2'-Modified Oligonucleotides that are Conformationally Preorganized," hereby incorporated by reference in its entirety.

Sugars having O-substitutions on the ribosyl ring are also amenable to the invention. Representative substitutions for ring O include, but are not limited to, S, $CH_2$, CHF, and $CF_2$.

Oligonucleotides may also have sugar mimetics, such as cyclobutyl moieties, in place of the pentofuranosyl sugar. Representative United States patents relating to the preparation of such modified sugars include, but are not limited to, U.S. Pat. Nos. 5,359,044, 5,466,786, 5,519,134, 5,591,722, 5,597,909, 5,646,265, and 5,700,920, all of which are hereby incorporated by reference.

Additional modifications may also be made at other positions on the oligonucleotide, particularly the 3' position of the sugar on the 3' terminal nucleotide. For example, one additional modification of the ligand-conjugated oligonucleotides of the invention involves chemically linking to the oligonucleotide one or more additional non-ligand moieties or conjugates which enhance the activity, cellular distribution or cellular uptake of the oligonucleotide. Such moieties include but are not limited to lipid moieties, such as a cholesterol moiety (Letsinger et al., Proc. Natl. Acad. Sci. USA, (1989) 86:6553), cholic acid (Manoharan et al., Bioorg. Med. Chem. Lett., (1994) 4:1053), a thioether, e.g., hexyl-S-tylthiol (Manoharan et al., Ann, N.Y. Acad. Sci., (1992) 660:306; Manoharan et al., Bioorg. Med. Chem. Let., (1993) 3:2765), a thiocholesterol (Oberhauser et al., Nucl. Acids Res, (1992) 20:533), an aliphatic chain, e.g., dodecandiol or undecyl residues (Saison-Behmoaras et al., EMBO J., (1991) 10:111; Kabanov et al., FEBS Lett., (1990) 259:327; Svinarchuk et al., Biochimie, (1993) 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., (1995) 36:3651; Shea et al., Nucl. Acids Res., (1990) 18:3777), a polyamine or a polyethylene glycol chain (Manoharan et al., Nucleosides & Nucleotides, (1995) 14:969), or adamantane acetic acid (Manoharan et al., Tetrahedron Lett., (1995) 36:3651), a palmityl moiety (Mishra et al., Biochim. Biophys. Acta, (1995) 1264:229), or an octadecylamine or hexylamino-carbonyl-oxycholesterol moiety (Crooke et al., J. Pharmacol. Exp. Ther., (1996) 277:923).

The invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoramidate or phosphotriester linkages (Cook, U.S. Pat. Nos. 5,212,295 and 5,521,302).

In certain instances, the oligonucleotide may be modified by a non-ligand group. A number of non-ligand molecules have been conjugated to oligonucleotides in order to enhance the activity, cellular distribution or cellular uptake of the oligonucleotide, and procedures for performing such conjugations are available in the scientific literature. Such non-ligand moieties have included lipid moieties, such as cholesterol (Letsinger et al., Proc. Natl. Acad. Sci. USA, (1989, 86:6553), cholic acid (Manoharan et al., Bioorg. Med. Chem. Lett., (1994, 4:1053), a thioether, e.g., hexyl-S-tritylthiol (Manoharan et al., Ann. N.Y. Acad. Sci., (1992, 660:306; Manoharan et al., Bioorg. Med. Chem. Lett., (1993, 3:2765), a thiocholesterol (Oberhauser et al., Nucl. Acids Res., (1992, 20:533), an aliphatic chain, e.g., dodecandiol or undecyl residues (Saison-Behmoaras et al., EMBO J., (1991) 10:111; Kabanov et al., FEBS Lett., (1990) 259:327; Svinarchuk et al., Biochimie, (1993) 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., (1995) 36:3651; Shea et al., Nucl. Acids Res., (1990) 18:3777), a polyamine or a polyethylene glycol chain (Manoharan et al., Nucleosides & Nucleotides, (1995) 14:969), or adamantane acetic acid (Manoharan et al., Tetrahedron Lett., (1995) 36:3651), a palmityl moiety (Mishra et al., Biochim. Biophys. Acta, (1995) 1264:229), or an octadecylamine or hexylamino-carbonyl-oxycholesterol moiety (Crooke et al., J. Pharmacol. Exp. Ther., (1996) 277:923). Typical conjugation protocols involve the synthesis of oligonucleotides bearing an aminolinker at one or more positions of the sequence. The amino group is then reacted with the molecule being conjugated using appropriate coupling or activating reagents. The conjugation reaction may be performed either with the oligonucleotide still bound to the solid support or following cleavage of the oligonucleotide in solution phase. Purification of the oligonucleotide conjugate by HPLC typically affords the pure conjugate.

Alternatively, the molecule being conjugated may be converted into a building block, such as a phosphoramidite, via an alcohol group present in the molecule or by attachment of a linker bearing an alcohol group that may be phosphorylated.

Importantly, each of these approaches may be used for the synthesis of ligand conjugated oligonucleotides. Amino linked oligonucleotides may be coupled directly with ligand via the use of coupling reagents or following activation of the ligand as an NHS or pentfluorophenolate ester. Ligand phosphoramidites may be synthesized via the attachment of an aminohexanol linker to one of the carboxyl groups followed by phosphitylation of the terminal alcohol functionality. Other linkers, such as cysteamine, may also be utilized for conjugation to a chloroacetyl linker present on a synthesized oligonucleotide.

The person skilled in the art is readily aware of methods to introduce the molecules of this invention into cells, tissues or organisms. Corresponding examples have also been provided in the detailed description of the invention above. For example, the nucleic acid molecules or the vectors of this invention, encoding for at least one strand of the inventive dsRNAs may be introduced into cells or tissues by methods known in the art, like transfections etc.

Also for the introduction of dsRNA molecules, means and methods have been provided. For example, targeted delivery by glycosylated and folate-modified molecules, including the use of polymeric carriers with ligands, such as galactose and lactose or the attachment of folic acid to various macromolecules allows the binding of molecules to be delivered to folate receptors. Targeted delivery by peptides and proteins other than antibodies, for example, including RGD-modified nanoparticles to deliver siRNA in vivo or multicomponent (nonviral) delivery systems including short cyclodextrins, adamantine-PEG are known. Yet, also the targeted delivery using antibodies or antibody fragments, including (monovalent) Fab-fragments of an antibody (or other fragments of such an antibody) or single-chain antibodies are envisaged. Injection approaches for target directed delivery comprise, inter alia, hydrodynamic i.v. injection. Also cholesterol conjugates of dsRNA may be used for targeted delivery, whereby the conjugation to lipohilic groups enhances cell uptake and improve pharmacokinetics and tissue biodistribution of oligonucleotides. Also cationic delivery systems are known, whereby synthetic vectors with net positive (cationic) charge to facilitate the complex formation with the polyanionic nucleic acid and interaction with the negatively charged cell membrane. Such cationic delivery systems comprise also cationic liposomal delivery systems, cationic polymer and peptide delivery systems. Other delivery systems for the cellular uptake of dsRNA/siRNA are aptamer-ds/siRNA. Also gene therapy approaches can be used to deliver the inventive dsRNA molecules or nucleic acid molecules encoding the same. Such systems comprise the use of non-pathogenic virus, modified viral vectors, as well as deliveries with nanoparticles or liposomes. Other delivery methods for the cellular uptake of dsRNA are extracorporeal, for example ex vivo treatments of cells, organs or tissues. Certain of these technologies are described and summarized in publications, like Akhtar, Journal of Clinical Investigation (2007) 117: 3623-3632, Nguyen et al., Current Opinion in Molecular Therapeutics (2008) 10:158-167, Zamboni, Clin Cancer Res (2005) 11:8230-8234 or Ikeda et al., Pharmaceutical Research (2006) 23:1631-1640.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, and patents are incorporated by reference in their entirety. In case of conflict, the present specification, including definitions, will control. In addition, the materials, methods, and examples are illustrative only and not intended to be limiting.

The above provided embodiments and items of the present invention are now illustrated with the following, non-limiting examples.

EXAMPLES

Identification of dsRNAs for therapeutic use. dsRNA design was carried out to identify dsRNAs specifically targeting Hepatitis B Virus genotypes A, B, C and D for therapeutic use. First, the known Hepatitis B Virus genomic sequences were downloaded from NCBI Genbank (accessions listed in Table. 6). The genotype information was either extracted form NCBI Genbank files or determined by computer aided comparison with reference genomes (accessions listed in Table. 6).

The Hepatitis B Virus genomic sequences of genotype A-D were examined by computer analysis to identify optimal target regions for RNAi agents, namely highly conserved 17nucleotide long sequence stretches that were identical in at least 90% of all sequences.

In identifying RNAi agents, the selection was limited to 17mer sequences having at least two mismatches to any sequence in the human RefSeq database (release 41), which we assumed to represent the comprehensive human transcriptome, by using a proprietary algorithm.

All 17mer sequences containing four or more consecutive G's (poly-G sequences) were further excluded from the synthesis.

Sequences of 19 nucleotides length were defined that harbor the selected 17mers in position 2 to 18.

These 19mer sequences yield RNA interference (RNAi) agents cross-reactive to Hepatitis B Virus genomic sequences of genotype A-D and formed the basis for the synthesis of the RNAi agents in appended Tables 1 and 2.

dsRNA synthesis. Oligoribonucleotides were synthesized according to the phosphoramidite technology on solid phase. Depending on the scale either an ABI 394 synthesizer (Applied Biosystems) or an AKTA oligopilot 100 (GE Healthcare, Freiburg, Germany) was used. Syntheses were performed on a solid support made of controlled pore glass (CPG, 520 Å, with a loading of 75 μmol/g, obtained from Prime Synthesis, Aston, Pa., USA). All 2'-modified RNA phosphoramidites as well as ancillary reagents were purchased from SAFC (Hamburg, Germany). Specifically, the following 2'-O-Methyl phosphoramidites were used: (5'-O-dimethoxytrityl-$N^6$-(benzoyl)-2'-O-methyl-adenosine-3'-O-(2-cyanoethyl-N,N-diisopropylamino) phosphoramidite, 5'-O—dimethoxytrityl-$N^4$-(acetyl)-2'-O-methyl-cytidine-3'-O-(2-cyanoethyl-N,N-diisopropylamino) phosphoramidite, (5'-O-dimethoxytrityl-$N^2$-(isobutyryl)-2'-O-methyl-guanosine-3'-O-(2-cyanoethyl-N,N-diisopropylamino)phosphoramidite, and 5'-O-dimethoxy-trityl-2'-O-methyl-uridine-3'-O-(2-cyanoethyl-N,N-diisopropylamino) phosphoramidite. The 2'-Deoxy-2'-fluoro-phosphoramidites carried the same protecting groups as the 2'-O-methyl RNA amidites. All amidites were dissolved in anhydrous acetonitrile (100 mM) and molecular sieves (3 Å) were added. To generate the 5'-phosphate the 2-[2-(4,4'-Dimethoxytrityloxy)ethylsulfonyl]ethyl-(2-cyanoethyl)-(N,N-diisopropyl)-phosphoramidite from Glen Research (Sterling, Va., USA) was used. In order to introduce the C-6 aminolinker at the 5'-end of the oligomers the 6-(Trifluoroacetylamino)-hexyl-(2-cyanoethyl)-(N,N-diisopropyl)-phosphoramidite from Thermo Fisher Scientific (Milwaukee, Wis., USA) was employed. The 5'-modifications were introduced without any modification of the synthesis cycle. 5-Ethyl thiotetrazole (ETT, 500 mM in acetonitrile) was used as activator solution. Coupling times were 6 min. In order to introduce phosphorothioate linkages, a 50 mM solution of 3-((Dimethylamino-methylidene)amino)-3H-1,2,4-dithiazole-3-thione (DDTT, obtained from AM Chemicals, Oceanside, Calif., USA) in anhydrous Acetonitrile/pyridine (1:1 v/v) was employed.

Cleavage and deprotection of support bound oligomer. After finalization of the solid phase synthesis, cyanoethyl protecting groups were removed by a 30 min treatment with 20% Diethyl amine in ACN without cleaving the oligonucleotides from the support. Subsequently, the dried solid support was transferred to a 15 mL tube and treated with concentrated aqueous ammonia (Aldrich) for 18 h at 40° C. After centrifugation the supernatant was transferred to a new tube and the CPG was washed with aqueous ammonia. The combined solutions were evaporated and the solid residue was reconstituted in buffer A (see below).

Purification of oligoribonucleotides. Crude oligomers were purified by anionic exchange HPLC using a column packed with Source Q15 (GE Helthcare) and an AKTA Explorer system (GE Helthcare). Buffer A was 10 mM sodium perchlorate, 20 mM Tris, 1 mM EDTA, pH 7.4 (Fluka, Buchs, Switzerland) and contained 20% Acetonitrile and buffer B was the same as buffer A with the exception of 500 mM sodium perchlorate. A gradient of 22% B to 42% B within 32 column volumes (CV) was employed. UV traces at 280 nm were recorded Appropriate fractions were pooled and precipitated with 3M NaOAc, pH=5.2 and 70% Ethanol. Finally, the pellet was washed with 70% Ethanol. Alternatively, desalting was carried out using Sephadex HiTrap columns (GE Helthcare) according to the manufacturer's recommendation.

Annealing of oligoribonucleotides to generate siRNA. Complementary strands were mixed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 80° C. which was cooled to RT within 3 h.

In Vitro screening of HBV mRNA-targeting dsRNA. The psiCHECK™-2 vector (Promega) contains two reporter genes for monitoring RNAi activity: a synthetic version of the renilla luciferase (hRluc) gene and a synthetic firefly luciferase gene (hluc+). Measurement of firefly luciferase activity permits determination of changes unrelated to the RNAi activity of tested dsRNA. Renilla and firefly luciferase activities were measured using the Dual-Glo® Luciferase Assay System (Promega). HBV target sites of interest were inserted into the psiCHECK™-2 vector, after cloning into the multiple cloning region located 3' of the synthetic renilla luciferase gene's translational stop codon and the polyA tail. Cell line COS-7 was transfected with the vector, and subsequently treated with dsRNA-lipofectamine 2000 lipoplexes targeting the HBV sequences. The RNAi effect conferred by the dsRNA towards the cloned HBV target site was determined by measuring activity of the renilla luciferase fusion gene.

Generation of psiCHECK Vectors Containing Target Sequences. In order to test the activity of the HBV dsRNAs, a Dual-Luciferase HBV reporter was constructed. Regions 84 to 805, 1075 to 1992, 2165 to 2530, and 2718 to 2940 of Hepatitis B Virus genomic sequence accession number EU554538.1 (genotype C) were joined in silico. Two mutations were inserted intentionally (128 A→T, 598 T→C, positions relative to EU554538.1). One was needed to remove an internal XhoI site. The second mutation led to removal of a single mismatch to a dsRNA. This HBV target construct was extended by adding restriction sites at both the 5' and 3' end. The artificial DNA sequence was chemically synthesized by Geneart (Regensburg, Germany) and cloned into the XhoI/NotI site of psiCHECK™-2 Dual-Luciferase vector.

Transfection and Luciferase Quantification. Cos-7 cells (DSMZ. Braunschweig, Germany, cat. No. ACC-60) were seeded at a density of $2.25\times10^4$ cells/well in 96-well plates. Plasmid transfection was carried out at a concentration of 50 ng/well with 0.5 μL/well Lipofectamine 2000 (invitrogen GmbH, Karlsruhe, Germany, cat. No. 11668-019) as described by the manufacturer. 4 h after vector transfection, the medium was discarded and fresh medium was added. After this period, the dsRNAs were added to the cells in a concentration of 10 nM or 1 nM using Lipofectamine 2000 as described above. In order to optimize the HBV genotype coverage and to minimize development of resistance against dsRNAs, two different dsRNAs can be used simultaneously in combination. For demonstrating the feasibility of such approach, pairs of two different dsRNAs were selected among the most efficient dsRNAs with additional bias towards optimized genotype coverage.

The dsRNAs were added to the cells in a concentration of 5 nM or 0.5 nM for each dsRNA, resulting in 10 nM or 1 nM total dsRNA concentration, using Lipofectamine 2000 as described above. The cells were lysed 48 hours later using luciferase reagents as described by the manufacturer. Renilla luciferase protein levels were normalized to firefly luciferase levels to consider transfection efficiency. For each dsRNA four individual data points were collected. At least one dsRNA unrelated to all target sites was used as a control to determine the relative renilla luciferase protein levels in cells treated with dsRNA (Table 8). For comparison of silencing activity under full-match conditions, dsRNAs with full match to the renilla open reading frame were synthesized and tested in parallel to the HBV dsRNAs.

Inhibition data are given in appended Table 2.

Stability of dsRNAs. Stability of dsRNAs targeting human Hepatitis B Virus was determined in in vitro assays with any one of human, cynomolgous monkey or mouse serum by measuring the half-life of each single strand.

Measurements were carried out in triplicates for each time point, using 3 μL 50 μM dsRNA sample mixed with 30 μL human serum (Sigma), cynomolgous monkey serum (Sigma) or mouse serum (Sigma). Mixtures were incubated for either 0 min, 30 min, 1 h, 3 h, 6 h, 24 h, or 48 h at 37° C. As control for unspecific degradation dsRNA was incubated with 30 μL 1×PBS pH 6.8 for 48 h. Reactions were stopped by the addition of 4 μL proteinase K (20 mg/ml), 25 μL of "Tissue and Cell Lysis Solution" (Epicentre) and 38 μL Millipore water for 30 min at 65° C. Samples were afterwards spin filtered through a 0.2 μm 96 well filter plate at 1400 rpm for 8 min, washed with 55 μL Millipore water twice and spin filtered again.

For separation of single strands and analysis of remaining full length product (FLP), samples were run through an ion exchange Dionex Summit HPLC under denaturing conditions using as eluent A 20 mM $Na_3PO^4$ in 10% ACN pH=11 and for eluent B 1M NaBr in eluent A.

The following gradient was applied:

| Time (min) | % A | % B |
|---|---|---|
| −1.0 | 75 | 25 |
| 1.00 | 75 | 25 |
| 19.0 | 38 | 62 |
| 19.5 | 0 | 100 |
| 21.5 | 0 | 100 |
| 22.0 | 75 | 25 |
| 24.0 | 75 | 25 |

For every injection, the chromatograms were integrated automatically by the Dionex Chromeleon 6.60 HPLC software, and were adjusted manually if necessary. All peak areas were corrected to the internal standard (IS) peak and normalized to the incubation at t=0 min. The area under the peak and resulting remaining FLP was calculated for each single strand and triplicate separately. Half-life (t½) of a strand was defined by the average time point (h) for triplicates at which half of the FLP was degraded. Results are given in appended Table 3.

SEQUENCE LISTING

```
<160> NUMBER OF SEQ ID NOS: 792

<210> SEQ ID NO 1
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 1

caagguaugu ugcccguuu                                                19


<210> SEQ ID NO 2
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"

<400> SEQUENCE: 2

cuguaggcau aaauuggua                                                19


<210> SEQ ID NO 3
<211> LENGTH: 19
<212> TYPE: RNA
<213> ORGANISM: Artificial sequence
<220> FEATURE:
<223> OTHER INFORMATION: Description of the artificial sequence: sense
      strand of dsRNA
```

<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 3 ucugcggcgu uuuaucaua 19

<210> SEQ ID NO 4
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 4 accucugccu aaucaucuc 19

<210> SEQ ID NO 5
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 5 uuuacuagug ccauuugua 19

<210> SEQ ID NO 6
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 6 accucugccu aaucaucua 19

<210> SEQ ID NO 7
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 7 cuguaggcau aaauugguc 19

<210> SEQ ID NO 8
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 8 ugucugcggc guuuuauca 19

<210> SEQ ID NO 9
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 9 uacuagugcc auuuguuca 19

<210> SEQ ID NO 10
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 10 caacuuuuuc accucugca 19

<210> SEQ ID NO 11
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 11 ccauuuguuc agugguucg 19

<210> SEQ ID NO 12
<211> LENGTH: 19
<212> TYPE: RNA

<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 12 ccaaguguuu gcugacgca 19

<210> SEQ ID NO 13
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 13 ccauuuguuc agugguuca 19

<210> SEQ ID NO 14
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 14 uuuacuagug ccauuuguu 19

<210> SEQ ID NO 15
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 15 caccucugcc uaaucauca 19

<210> SEQ ID NO 16
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1

<223> OTHER INFORMATION: /mod_base = "nucleoside: lacks 5'-phosphate group"

<400> SEQUENCE: 16 cuggcucagu uuacuagug 19

<210> SEQ ID NO 17
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 17 caagguaugu ugcccguua 19

<210> SEQ ID NO 18
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 18 cuggcucagu uuacuagua 19

<210> SEQ ID NO 19
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 19 gaggcuguag gcauaaauu 19

<210> SEQ ID NO 20
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 20 caguuuacua gugccauuu 19

<210> SEQ ID NO 21
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 21 agguauguug cccguuugu 19

<210> SEQ ID NO 22
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 22 uauguugccc guuugucca 19

<210> SEQ ID NO 23
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 23 gaggcuguag gcauaaaua 19

<210> SEQ ID NO 24
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 24 gucugcggcg uuuuaucau 19

<210> SEQ ID NO 25
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 25 caacuuuuuc accucugcc 19

<210> SEQ ID NO 26
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 26 ccgugugcac uucgcuuca 19

<210> SEQ ID NO 27
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 27 ucaagguaug uugcccgua 19

<210> SEQ ID NO 28
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 28 caguuuacua gugccauua 19

<210> SEQ ID NO 29
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 29 ugguggacuu cucucaauu 19

<210> SEQ ID NO 30
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 30 agguauguug cccguuuga 19

<210> SEQ ID NO 31
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 31 cugcucgugu uacaggcgg 19

<210> SEQ ID NO 32
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 32 uauguugccc guuuguccu 19

<210> SEQ ID NO 33
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 33 ucaagguaug uugcccguu 19

<210> SEQ ID NO 34
<211> LENGTH: 19

<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 34 ucuuaucaac acuuccgga 19

<210> SEQ ID NO 35
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 35 caccucugcc uaaucaucu 19

<210> SEQ ID NO 36
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 36 auaagaggac ucuuggacu 19

<210> SEQ ID NO 37
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 37 gucugcggcg uuuuaucaa 19

<210> SEQ ID NO 38
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base <222> LOCATION: 1
<223> OTHER INFORMATION: /mod_base = "nucleoside: lacks 5'-phosphate group"

<400> SEQUENCE: 38 ggcgcugaau cccgcggac 19

<210> SEQ ID NO 39
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 39 cgcgucgcag aagaucuca 19

<210> SEQ ID NO 40
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 40 aaugucaacg accgaccuu 19

<210> SEQ ID NO 41
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 41 gcucaguuua cuagugcca 19

<210> SEQ ID NO 42
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 42 ugguggacuu cucucaaua 19

<210> SEQ ID NO 43
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 43 aucgccgcgu cgcagaaga 19

<210> SEQ ID NO 44
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 44 gccauuuguu cagugguuc 19

<210> SEQ ID NO 45
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 45 cgauccauac ugcggaacu 19

<210> SEQ ID NO 46
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 46 ucaccucugc cuaaucauc 19

<210> SEQ ID NO 47
<211> LENGTH: 19
<212> TYPE: RNA
<213> ORGANISM: Artificial sequence
<220> FEATURE:

<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 47 guggacuucu cucaauuuu 19

<210> SEQ ID NO 48
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 48 gggucaccau auucuuggg 19

<210> SEQ ID NO 49
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 49 gccgcgucgc agaagaucu 19

<210> SEQ ID NO 50
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 50 ucaaucgccg cgucgcaga 19

<210> SEQ ID NO 51
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 51 uggauguguc ugcggcguu 19

<210> SEQ ID NO 52
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 52 uacuguucaa gccuccaag 19

<210> SEQ ID NO 53
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 53 guuuacuagu gccauuugu 19

<210> SEQ ID NO 54
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 54 acuagugcca uuuguucag 19

<210> SEQ ID NO 55
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 55 ccgcgucgca gaagaucuc 19

<210> SEQ ID NO 56

<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 56 uaucuuauca acacuuccg 19

<210> SEQ ID NO 57
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 57 ggccaaaauu cgcaguccc 19

<210> SEQ ID NO 58
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 58 uucaccucug ccuaaucau 19

<210> SEQ ID NO 59
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 59 cucaguuuac uagugccau 19

<210> SEQ ID NO 60
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:

<221> NAME/KEY: modified_base
<222> LOCATION: 1
<223> OTHER INFORMATION: /mod_base = "nucleoside: lacks 5'-phosphate group"

<400> SEQUENCE: 60 uguugcccgu uuguccucu 19

<210> SEQ ID NO 61
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 61 uagugccauu uguucagug 19

<210> SEQ ID NO 62
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 62 aggcuguagg cauaaauug 19

<210> SEQ ID NO 63
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 63 augugucugc ggcguuuua 19

<210> SEQ ID NO 64
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 64 acuucgcuuc accucugca 19

<210> SEQ ID NO 65
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 65 cgugugcacu ucgcuucac 19

<210> SEQ ID NO 66
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 66 gugguggacu ucucucaau 19

<210> SEQ ID NO 67
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 67 ugugucugcg gcguuuuau 19

<210> SEQ ID NO 68
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 68 aagguauguu gcccguuug 19

<210> SEQ ID NO 69
<211> LENGTH: 19
<212> TYPE: RNA
<213> ORGANISM: Artificial sequence <220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 69 ucaacgaccg accuugagg 19

<210> SEQ ID NO 70
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 70 cauaagagga cucuuggac 19

<210> SEQ ID NO 71
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 71 gucaacgacc gaccuugag 19

<210> SEQ ID NO 72
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 72 auauucuugg gaacaagag 19

<210> SEQ ID NO 73
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 73 ugcucguguu acaggcggg 19

<210> SEQ ID NO 74
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 74 caaucgccgc gucgcagaa 19

<210> SEQ ID NO 75
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 75 acuguucaag ccuccaagc 19

<210> SEQ ID NO 76
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 76 cgccgcgucg cagaagauc 19

<210> SEQ ID NO 77
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 77 cauuuguuca gugguucgu 19

<210> SEQ ID NO 78
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 78 cgcugaaucc cgcggacga 19

<210> SEQ ID NO 79
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 79 ugggucacca uauucuugg 19

<210> SEQ ID NO 80
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 80 uccucugccg auccauacu 19

<210> SEQ ID NO 81
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 81 augucaacga ccgaccuug 19

<210> SEQ ID NO 82
<211> LENGTH: 19
<212> TYPE: RNA
<213> ORGANISM: Artificial sequence
<220> FEATURE:
<223> OTHER INFORMATION: Description of the artificial sequence: sense
strand of dsRNA <220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 82 ccucugccua aucaucuca 19

<210> SEQ ID NO 83
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 83 accgugugca cuucgcuuc 19

<210> SEQ ID NO 84
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 84 ugccgaucca uacugcgga 19

<210> SEQ ID NO 85
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 85 cagagucuag acucguggu 19

<210> SEQ ID NO 86
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 86 cuguucaagc cuccaagcu 19

<210> SEQ ID NO 87
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 87 ggaggcugua ggcauaaau 19

<210> SEQ ID NO 88
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 88 aggaggcugu aggcauaaa 19

<210> SEQ ID NO 89
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 89 gguggacuuc ucucaauuu 19

<210> SEQ ID NO 90
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 90 gcaacuuuuu caccucugc 19

<210> SEQ ID NO 91
<211> LENGTH: 19
<212> TYPE: RNA

<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 91 cugcucgugu uacaggcga 19

<210> SEQ ID NO 92
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 92 cuagugccau uuguucagu 19

<210> SEQ ID NO 93
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 93 cugccgaucc auacugcgg 19

<210> SEQ ID NO 94
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 94 gugugcacuu cgcuucacc 19

<210> SEQ ID NO 95
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1

<223> OTHER INFORMATION: /mod_base = "nucleoside: lacks 5'-phosphate group"

<400> SEQUENCE: 95 gcucguguua caggcgggc 19

<210> SEQ ID NO 96
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 96 ccuaucuuau caacacuuc 19

<210> SEQ ID NO 97
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 97 ucucaaucgc cgcgucgca 19

<210> SEQ ID NO 98
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 98 gcccgucugu gccuucuca 19

<210> SEQ ID NO 99
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 99 cuaucuuauc aacacuucc 19

<210> SEQ ID NO 100
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 100 auguugcccg uuuguccuc 19

<210> SEQ ID NO 101
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 101 guauguugcc cguuugucc 19

<210> SEQ ID NO 102
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 102 cuucgcuuca ccucugcac 19

<210> SEQ ID NO 103
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 103 ugugcacuuc gcuucaccu 19

<210> SEQ ID NO 104
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 104 gccaaaauuc gcagucccg 19

<210> SEQ ID NO 105
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 105 ccugcucgug uuacaggcg 19

<210> SEQ ID NO 106
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 106 uggagugugg auucgcacu 19

<210> SEQ ID NO 107
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 107 aacgaccgac cuugaggca 19

<210> SEQ ID NO 108
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 108 acagagucua gacucgugg 19

<210> SEQ ID NO 109
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 109 aaucgccgcg ucgcagaag 19

<210> SEQ ID NO 110
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 110 gguauguugc ccguuuguc 19

<210> SEQ ID NO 111
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 111 gccgauccau acugcggaa 19

<210> SEQ ID NO 112
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 112 gcccuaucuu aucaacacu 19

<210> SEQ ID NO 113
<211> LENGTH: 19

<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 113 aguuuacuag ugccauuug 19

<210> SEQ ID NO 114
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 114 ugucaacgac cgaccuuga 19

<210> SEQ ID NO 115
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 115 acuucucuca auuuucuag 19

<210> SEQ ID NO 116
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 116 gcgcgggacg uccuuuguc 19

<210> SEQ ID NO 117
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base <222> LOCATION: 1
<223> OTHER INFORMATION: /mod_base = "nucleoside: lacks 5'-phosphate group"

<400> SEQUENCE: 117 ucuagacucg ugguggacu 19

<210> SEQ ID NO 118
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 118 gauccauacu gcggaacuc 19

<210> SEQ ID NO 119
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 119 cucugccgau ccauacugc 19

<210> SEQ ID NO 120
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 120 ucugccgauc cauacugcg 19

<210> SEQ ID NO 121
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 121 ccucugccga uccauacug 19

<210> SEQ ID NO 122
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 122 gcaccucucu uuacgcggu 19

<210> SEQ ID NO 123
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 123 aagaacuccc ucgccucgc 19

<210> SEQ ID NO 124
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 124 gaacucccuc gccucgcag 19

<210> SEQ ID NO 125
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 125 ucucucaauu uucuagggc 19

<210> SEQ ID NO 126
<211> LENGTH: 19
<212> TYPE: RNA
<213> ORGANISM: Artificial sequence
<220> FEATURE:

<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 126 gggcgcaccu cucuuuacg 19

<210> SEQ ID NO 127
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 127 ccgauccaua cugcggaac 19

<210> SEQ ID NO 128
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 128 aacucccucg ccucgcaga 19

<210> SEQ ID NO 129
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 129 cuccucugcc gauccauac 19

<210> SEQ ID NO 130
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 130 ggagugugga uucgcacuc 19

<210> SEQ ID NO 131
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 131 cgggcgcacc ucucuuuac 19

<210> SEQ ID NO 132
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 132 gucucaaucg ccgcgucgc 19

<210> SEQ ID NO 133
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 133 auccauacug cggaacucc 19

<210> SEQ ID NO 134
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 134 cgcaccucuc uuuacgcgg 19

<210> SEQ ID NO 135

<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 135 caacgaccga ccuugaggc 19

<210> SEQ ID NO 136
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 136 ccauacugcg gaacuccua 19

<210> SEQ ID NO 137
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 137 ugaaucccgc ggacgaccc 19

<210> SEQ ID NO 138
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 138 agaacucccu cgccucgca 19

<210> SEQ ID NO 139
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:

<221> NAME/KEY: modified_base
<222> LOCATION: 1
<223> OTHER INFORMATION: /mod_base = "nucleoside: lacks 5'-phosphate group"

<400> SEQUENCE: 139 ggcgcaccuc ucuuuacgc 19

<210> SEQ ID NO 140
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 140 gcgcaccucu cuuuacgcg 19

<210> SEQ ID NO 141
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 141 gcugaauccc gcggacgac 19

<210> SEQ ID NO 142
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 142 cacuucgcuu caccucugc 19

<210> SEQ ID NO 143
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 143 cucaaucgcc gcgucgcag 19

<210> SEQ ID NO 144
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 144 ucccgucggc gcugaaucc 19

<210> SEQ ID NO 145
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 145 cugaaucccg cggacgacc 19

<210> SEQ ID NO 146
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 146 agagucuaga cucguggug 19

<210> SEQ ID NO 147
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 147 uccauacugc ggaacuccu 19

<210> SEQ ID NO 148
<211> LENGTH: 19
<212> TYPE: RNA
<213> ORGANISM: Artificial sequence <220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 148 gcgcugaauc ccgcggacg 19

<210> SEQ ID NO 149
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 149 aguguggauu cgcacuccu 19

<210> SEQ ID NO 150
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 150 cccugcucgu guuacaggc 19

<210> SEQ ID NO 151
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 151 gaaucccgcg gacgacccg 19

<210> SEQ ID NO 152
<211> LENGTH: 19
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 152 aagcugugcc uuggguggc 19

<210> SEQ ID NO 153
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 153 gcccugcucg uguuacagg 19

<210> SEQ ID NO 154
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 154 gucccgucgg cgcugaauc 19

<210> SEQ ID NO 155
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 155 aucuuaucaa cacuuccgg 19

<210> SEQ ID NO 156
<211> LENGTH: 19
<212> TYPE: RNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 156 cuuaucaaca cuuccggaa 19

<210> SEQ ID NO 157
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 157 aaacgggcaa cauaccuug 19

<210> SEQ ID NO 158
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 158 taccaauuua ugccuacag 19

<210> SEQ ID NO 159
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 159 uaugauaaaa cgccgcaga 19

<210> SEQ ID NO 160
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 160 taugauaaaa cgccgcaga 19

<210> SEQ ID NO 161
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 161 gagaugauua ggcagaggu 19

<210> SEQ ID NO 162
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 162 tacaaauggc acuaguaaa 19

<210> SEQ ID NO 163
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 163 tagaugauua ggcagaggu 19

<210> SEQ ID NO 164
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 164 gaccaauuua ugccuacag 19

<210> SEQ ID NO 165
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 165 ugauaaaacg ccgcagaca 19

<210> SEQ ID NO 166
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 166 tgauaaaacg ccgcagaca 19

<210> SEQ ID NO 167
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 167 ugaacaaaug gcacuagua 19

<210> SEQ ID NO 168
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base <222> LOCATION: 2..19
<223> OTHER INFORMATION: /mod_base = "2'-hydroxy corresponding
nucleoside"

<400> SEQUENCE: 168 tgaacaaaug gcacuagua 19

<210> SEQ ID NO 169
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 169 tgcagaggug aaaaaguug 19

<210> SEQ ID NO 170
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 170 cgaaccacug aacaaaugg 19

<210> SEQ ID NO 171
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 171 ugcgucagca aacacuugg 19

<210> SEQ ID NO 172
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2..19
<223> OTHER INFORMATION: /mod_base = "2'-hydroxy corresponding nucleoside"

<400> SEQUENCE: 172 tgcgucagca aacacuugg 19

<210> SEQ ID NO 173
<211> LENGTH: 19
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2..19
<223> OTHER INFORMATION: /mod_base = "2'-hydroxy corresponding nucleoside"

<400> SEQUENCE: 173 tgaaccacug aacaaaugg 19

<210> SEQ ID NO 174
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 174 aacaaauggc acuaguaaa 19

<210> SEQ ID NO 175
<211> LENGTH: 19
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2..19
<223> OTHER INFORMATION: /mod_base = "2'-hydroxy corresponding nucleoside"

<400> SEQUENCE: 175 tgaugauuag gcagaggug 19

<210> SEQ ID NO 176
<211> LENGTH: 19
<212> TYPE: RNA

<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 176 cacuaguaaa cugagccag 19

<210> SEQ ID NO 177
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 177 taacgggcaa cauaccuug 19

<210> SEQ ID NO 178
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 178 tacuaguaaa cugagccag 19

<210> SEQ ID NO 179
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 179 aauuuaugcc uacagccuc 19

<210> SEQ ID NO 180
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 180 aaauggcacu aguaaacug 19

<210> SEQ ID NO 181
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 181 acaaacgggc aacauaccu 19

<210> SEQ ID NO 182
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 182 uggacaaacg ggcaacaua 19

<210> SEQ ID NO 183
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 183 tauuuaugcc uacagccuc 19

<210> SEQ ID NO 184
<211> LENGTH: 19

<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 184 augauaaaac gccgcagac 19

<210> SEQ ID NO 185
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 185 ggcagaggug aaaaaguug 19

<210> SEQ ID NO 186
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 186 ugaagcgaag ugcacacgg 19

<210> SEQ ID NO 187
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 187 tgaagcgaag ugcacacgg 19

<210> SEQ ID NO 188
<211> LENGTH: 19
<212> TYPE: DNA
<213> ORGANISM: Artificial sequence <220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 188 tacgggcaac auaccuuga 19

<210> SEQ ID NO 189
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 189 taauggcacu aguaaacug 19

<210> SEQ ID NO 190
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 190 aauugagaga aguccacca 19

<210> SEQ ID NO 191
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 191 tcaaacgggc aacauaccu 19

<210> SEQ ID NO 192
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 192 ccgccuguaa cacgagcag 19

<210> SEQ ID NO 193
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 193 aggacaaacg ggcaacaua 19

<210> SEQ ID NO 194
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 194 aacgggcaac auaccuuga 19

<210> SEQ ID NO 195
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 195 uccggaagug uugauaaga 19

<210> SEQ ID NO 196
<211> LENGTH: 19
<212> TYPE: DNA

<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 196 tccggaagug uugauaaga 19

<210> SEQ ID NO 197
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 197 agaugauuag gcagaggug 19

<210> SEQ ID NO 198
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 198 aguccaagag uccucuuau 19

<210> SEQ ID NO 199
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 199 tugauaaaac gccgcagac 19

<210> SEQ ID NO 200
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 200 guccgcggga uucagcgcc 19

<210> SEQ ID NO 201
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 201 ugagaucuuc ugcgacgcg 19

<210> SEQ ID NO 202
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 202 aaggucgguc guugacauu 19

<210> SEQ ID NO 203
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 203 uggcacuagu aaacugagc 19

<210> SEQ ID NO 204
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA <220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2..19
<223> OTHER INFORMATION: /mod_base = "2'-hydroxy corresponding nucleoside"

<400> SEQUENCE: 204 tauugagaga aguccacca 19

<210> SEQ ID NO 205
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 205 ucuucugcga cgcggcgau 19

<210> SEQ ID NO 206
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 206 gaaccacuga acaaauggc 19

<210> SEQ ID NO 207
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 207 aguuccgcag uauggaucg 19

<210> SEQ ID NO 208
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base <222> LOCATION: 1
<223> OTHER INFORMATION: /mod_base = "nucleoside: lacks 5'-phosphate group"

<400> SEQUENCE: 208 gaugauuagg cagagguga 19

<210> SEQ ID NO 209
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 209 aaaauugaga gaaguccac 19

<210> SEQ ID NO 210
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 210 cccaagaaua uggugaccc 19

<210> SEQ ID NO 211
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 211 agaucuucug cgacgcggc 19

<210> SEQ ID NO 212
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 212 ucugcgacgc ggcgauuga 19

<210> SEQ ID NO 213
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 213 aacgccgcag acacaucca 19

<210> SEQ ID NO 214
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 214 cuuggaggcu ugaacagua 19

<210> SEQ ID NO 215
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 215 acaaauggca cuaguaaac 19

<210> SEQ ID NO 216
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 216 cugaacaaau ggcacuagu 19

<210> SEQ ID NO 217
<211> LENGTH: 19
<212> TYPE: RNA
<213> ORGANISM: Artificial sequence
<220> FEATURE:

<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 217 gagaucuucu gcgacgcgg 19

<210> SEQ ID NO 218
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 218 cggaaguguu gauaagaua 19

<210> SEQ ID NO 219
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 219 gggacugcga auuuuggcc 19

<210> SEQ ID NO 220
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 220 augauuaggc agaggugaa 19

<210> SEQ ID NO 221
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 221 auggcacuag uaaacugag 19

<210> SEQ ID NO 222
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 222 agaggacaaa cgggcaaca 19

<210> SEQ ID NO 223
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 223 cacugaacaa auggcacua 19

<210> SEQ ID NO 224
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 224 caauuuaugc cuacagccu 19

<210> SEQ ID NO 225
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 225 uaaaacgccg cagacacau 19

<210> SEQ ID NO 226

<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 226 taaaacgccg cagacacau 19

<210> SEQ ID NO 227
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 227 ugcagaggug aagcgaagu 19

<210> SEQ ID NO 228
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 228 gugaagcgaa gugcacacg 19

<210> SEQ ID NO 229
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 229 auugagagaa guccaccac 19

<210> SEQ ID NO 230
<211> LENGTH: 19
<212> TYPE: RNA

<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 230 auaaaacgcc gcagacaca 19

<210> SEQ ID NO 231
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 231 caaacgggca acauaccuu 19

<210> SEQ ID NO 232
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 232 ccucaagguc ggucguuga 19

<210> SEQ ID NO 233
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 233 guccaagagu ccucuuaug 19

<210> SEQ ID NO 234
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1

<223> OTHER INFORMATION: /mod_base = "nucleoside: lacks 5'-phosphate group"

<400> SEQUENCE: 234 cucaaggucg gucguugac 19

<210> SEQ ID NO 235
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 235 cucuuguucc caagaauau 19

<210> SEQ ID NO 236
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 236 cccgccugua acacgagca 19

<210> SEQ ID NO 237
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 237 uucugcgacg cggcgauug 19

<210> SEQ ID NO 238
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 238 gcuuggaggc uugaacagu 19

<210> SEQ ID NO 239
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 239 gaucuucugc gacgcggcg 19

<210> SEQ ID NO 240
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 240 acgaaccacu gaacaaaug 19

<210> SEQ ID NO 241
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 241 ucguccgcgg gauucagcg 19

<210> SEQ ID NO 242
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 242 ccaagaauau ggugaccca 19

<210> SEQ ID NO 243
<211> LENGTH: 19
<212> TYPE: RNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 243 aguauggauc ggcagagga 19

<210> SEQ ID NO 244
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 244 caaggucggu cguugacau 19

<210> SEQ ID NO 245
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 245 ugagaugauu aggcagagg 19

<210> SEQ ID NO 246
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 246 gaagcgaagu gcacacggu 19

<210> SEQ ID NO 247
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 247 uccgcaguau ggaucggca 19

<210> SEQ ID NO 248
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 248 accacgaguc uagacucug 19

<210> SEQ ID NO 249
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 249 agcuuggagg cuugaacag 19

<210> SEQ ID NO 250
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 250 auuuaugccu acagccucc 19

<210> SEQ ID NO 251
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 251 uuuaugccua cagccuccu 19

<210> SEQ ID NO 252
<211> LENGTH: 19

<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 252 aaauugagag aaguccacc 19

<210> SEQ ID NO 253
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 253 gcagagguga aaaaguugc 19

<210> SEQ ID NO 254
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 254 tcgccuguaa cacgagcag 19

<210> SEQ ID NO 255
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 255 acugaacaaa uggcacuag 19

<210> SEQ ID NO 256
<211> LENGTH: 19
<212> TYPE: RNA
<213> ORGANISM: Artificial sequence <220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 256 ccgcaguaug gaucggcag 19

<210> SEQ ID NO 257
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 257 ggugaagcga agugcacac 19

<210> SEQ ID NO 258
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 258 gcccgccugu aacacgagc 19

<210> SEQ ID NO 259
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 259 gaaguguuga uaagauagg 19

<210> SEQ ID NO 260
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 260 ugcgacgcgg cgauugaga 19

<210> SEQ ID NO 261
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 261 ugagaaggca cagacgggc 19

<210> SEQ ID NO 262
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 262 ggaaguguug auaagauag 19

<210> SEQ ID NO 263
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 263 gaggacaaac gggcaacau 19

<210> SEQ ID NO 264
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 264 ggacaaacgg gcaacauac 19

<210> SEQ ID NO 265
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 265 gugcagaggu gaagcgaag 19

<210> SEQ ID NO 266
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 266 aggugaagcg aagugcaca 19

<210> SEQ ID NO 267
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 267 cgggacugcg aauuuuggc 19

<210> SEQ ID NO 268
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 268 cgccuguaac acgagcagg 19

<210> SEQ ID NO 269
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA <220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 269 agugcgaauc cacacucca 19

<210> SEQ ID NO 270
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 270 ugccucaagg ucggucguu 19

<210> SEQ ID NO 271
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 271 ccacgagucu agacucugu 19

<210> SEQ ID NO 272
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 272 cuucugcgac gcggcgauu 19

<210> SEQ ID NO 273
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 273 gacaaacggg caacauacc 19

<210> SEQ ID NO 274
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 274 uuccgcagua uggaucggc 19

<210> SEQ ID NO 275
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 275 aguguugaua agauagggc 19

<210> SEQ ID NO 276
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 276 caaauggcac uaguaaacu 19

<210> SEQ ID NO 277
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 277 ucaaggucgg ucguugaca 19

<210> SEQ ID NO 278
<211> LENGTH: 19
<212> TYPE: RNA

<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 278 cuagaaaauu gagagaagu 19

<210> SEQ ID NO 279
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 279 gacaaaggac gucccgcgc 19

<210> SEQ ID NO 280
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 280 aguccaccac gagucuaga 19

<210> SEQ ID NO 281
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 281 gaguuccgca guauggauc 19

<210> SEQ ID NO 282
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1

<223> OTHER INFORMATION: /mod_base = "nucleoside: lacks 5'-phosphate group"

<400> SEQUENCE: 282 gcaguaugga ucggcagag 19

<210> SEQ ID NO 283
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 283 cgcaguaugg aucggcaga 19

<210> SEQ ID NO 284
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 284 caguauggau cggcagagg 19

<210> SEQ ID NO 285
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 285 accgcguaaa gagaggugc 19

<210> SEQ ID NO 286
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 286 gcgaggcgag ggaguucuu 19

<210> SEQ ID NO 287
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 287 cugcgaggcg agggaguuc 19

<210> SEQ ID NO 288
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 288 gcccuagaaa auugagaga 19

<210> SEQ ID NO 289
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 289 cguaaagaga ggugcgccc 19

<210> SEQ ID NO 290
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 290 guuccgcagu auggaucgg 19

<210> SEQ ID NO 291
<211> LENGTH: 19
<212> TYPE: RNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 291 ucugcgaggc gagggaguu 19

<210> SEQ ID NO 292
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 292 guauggaucg gcagaggag 19

<210> SEQ ID NO 293
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 293 gagugcgaau ccacacucc 19

<210> SEQ ID NO 294
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 294 guaaagagag gugcgcccg 19

<210> SEQ ID NO 295
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 295 gcgacgcggc gauugagac 19

<210> SEQ ID NO 296
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 296 ggaguuccgc aguauggau 19

<210> SEQ ID NO 297
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 297 ccgcguaaag agaggugcg 19

<210> SEQ ID NO 298
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 298 gccucaaggu cggucguug 19

<210> SEQ ID NO 299
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 299 uaggaguucc gcaguaugg 19

<210> SEQ ID NO 300
<211> LENGTH: 19

<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 300 gggucguccg cgggauuca 19

<210> SEQ ID NO 301
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 301 ugcgaggcga gggaguucu 19

<210> SEQ ID NO 302
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 302 gcguaaagag aggugcgcc 19

<210> SEQ ID NO 303
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 303 cgcguaaaga gaggugcgc 19

<210> SEQ ID NO 304
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base <222> LOCATION: 1
<223> OTHER INFORMATION: /mod_base = "nucleoside: lacks 5'-phosphate group"

<400> SEQUENCE: 304 gucguccgcg ggauucagc 19

<210> SEQ ID NO 305
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 305 gcagagguga agcgaagug 19

<210> SEQ ID NO 306
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 306 cugcgacgcg gcgauugag 19

<210> SEQ ID NO 307
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 307 ggauucagcg ccgacggga 19

<210> SEQ ID NO 308
<211> LENGTH: 19
<212> TYPE: RNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<400> SEQUENCE: 308 ggucguccgc gggauucag 19

<210> SEQ ID NO 309
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 309 caccacgagu cuagacucu 19

<210> SEQ ID NO 310
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 310 aggaguuccg caguaugga 19

<210> SEQ ID NO 311
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 311 cguccgcggg auucagcgc 19

<210> SEQ ID NO 312
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 312 aggagugcga auccacacu 19

<210> SEQ ID NO 313
<211> LENGTH: 19
<212> TYPE: RNA
<213> ORGANISM: Artificial sequence
<220> FEATURE:

<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 313 gccuguaaca cgagcaggg 19

<210> SEQ ID NO 314
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 314 cgggucgucc gcgggauuc 19

<210> SEQ ID NO 315
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 315 gccacccaag gcacagcuu 19

<210> SEQ ID NO 316
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 316 ccuguaacac gagcagggc 19

<210> SEQ ID NO 317
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 317 gauucagcgc cgacgggac 19

<210> SEQ ID NO 318
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 318 ccggaagugu ugauaagau 19

<210> SEQ ID NO 319
<211> LENGTH: 19
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<400> SEQUENCE: 319 uuccggaagu guugauaag 19

<210> SEQ ID NO 320
<211> LENGTH: 19
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2..19
<223> OTHER INFORMATION: /mod_base = "2'-hydroxy corresponding
nucleoside"

<400> SEQUENCE: 320 tuccggaagu guugauaag 19

<210> SEQ ID NO 321
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base <222> LOCATION: 1, 2, 6, 8, 10, 11, 13, 14, 15, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 7, 9, 12, 16
<223> OTHER INFORMATION: /mod_base = "2'-hydroxy corresponding
nucleoside"

<400> SEQUENCE: 321 caagguaugu ugcccguuut t 21

<210> SEQ ID NO 322
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 322 cuguaggcau aaauugguat 20

<210> SEQ ID NO 323
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 8, 10, 11, 12, 13, 15, 16, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 7, 9, 14, 17, 19
<223> OTHER INFORMATION: /mod_base = "2'-hydroxy corresponding
nucleoside"

<400> SEQUENCE: 323 ucugcggcgu uuuaucauat t 21

<210> SEQ ID NO 324
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 324 ucugcggcgu uuuaucauat 20

<210> SEQ ID NO 325
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 6, 8, 9, 10, 13, 14, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 11, 12, 15
<223> OTHER INFORMATION: /mod_base = "2'-hydroxy corresponding
nucleoside"

<400> SEQUENCE: 325 accucugccu aaucaucuct t 21

<210> SEQ ID NO 326
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 326 uuuacuagug ccauuuguat 20

<210> SEQ ID NO 327
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 327 accucugccu aaucaucuat 20

<210> SEQ ID NO 328
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 8, 10, 14, 15, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 9, 11, 12, 13, 16, 17
<223> OTHER INFORMATION: /mod_base = "2'-hydroxy corresponding nucleoside"

<400> SEQUENCE: 328 cuguaggcau aaauugguct t 21

<210> SEQ ID NO 329
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 10, 12, 13, 14, 15, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 8, 9, 11, 16, 19
<223> OTHER INFORMATION: /mod_base = "2'-hydroxy corresponding nucleoside"

<400> SEQUENCE: 329 ugucugcggc guuuuaucat t 21

<210> SEQ ID NO 330
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 330 ugucugcggc guuuuaucat 20

<210> SEQ ID NO 331
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1

<223> OTHER INFORMATION: /mod_base = "nucleoside: lacks 5'-phosphate group"
<220> FEATURE:
<221> NAME/KEY: modified_base
<222> LOCATION: 1, 2, 3, 4, 7, 9, 10, 12, 13, 14, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 8, 11, 15, 19
<223> OTHER INFORMATION: /mod_base = "2'-hydroxy corresponding nucleoside"

<400> SEQUENCE: 331 uacuagugcc auuuguucat t 21

<210> SEQ ID NO 332
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 332 uacuagugcc auuuguucat 20

<210> SEQ ID NO 333
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20

<223> OTHER INFORMATION: /mod_base = "3'-3'-linked desoxythymidine"

<400> SEQUENCE: 333 caacuuuuuc accucugcat 20

<210> SEQ ID NO 334
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 6, 8, 9, 10, 13, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 11, 12, 14, 15, 19
<223> OTHER INFORMATION: /mod_base = "2'-hydroxy corresponding nucleoside"

<400> SEQUENCE: 334 ccauuuguuc agugguucgt t 21

<210> SEQ ID NO 335
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 6, 8, 9, 10, 12, 13, 16, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 7, 11, 14, 15, 17, 19
<223> OTHER INFORMATION: /mod_base = "2'-hydroxy corresponding nucleoside"

<400> SEQUENCE: 335 ccaaguguuu gcugacgcat t 21

<210> SEQ ID NO 336
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:

<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 336 ccaaguguuu gcugacgcat 20

<210> SEQ ID NO 337
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 337 ccauuuguuc agugguucat 20

<210> SEQ ID NO 338
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 9, 11, 12, 14, 15, 16, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base <222> LOCATION: 4, 7, 8, 10, 13, 17
<223> OTHER INFORMATION: /mod_base = "2'-hydroxy corresponding
nucleoside"

<400> SEQUENCE: 338 uuuacuagug ccauuuguut t 21

<210> SEQ ID NO 339
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 339 caccucugcc uaaucaucat 20

<210> SEQ ID NO 340
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 6, 7, 10, 11, 12, 14, 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 8, 9, 13, 16, 17, 19
<223> OTHER INFORMATION: /mod_base = "2'-hydroxy corresponding
nucleoside"

<400> SEQUENCE: 340 cuggcucagu uuacuagugt t 21

<210> SEQ ID NO 341
<211> LENGTH: 20
<212> TYPE: DNA
<213> ORGANISM: Artificial sequence
<220> FEATURE:
<223> OTHER INFORMATION: Description of the artificial sequence: sense

```
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 341

caagguaugu ugcccguuat                                                20


<210> SEQ ID NO 342
<211> LENGTH: 20
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
      nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
      nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 342

cuggcucagu uuacuaguat                                                20


<210> SEQ ID NO 343
<211> LENGTH: 21
<212> TYPE: DNA
<213> ORGANISM: Artificial sequence
<220> FEATURE:
<223> OTHER INFORMATION: Description of the artificial sequence: sense
      strand of dsRNA
<220> FEATURE:
<221> NAME/KEY: modified_base
<222> LOCATION: 1
<223> OTHER INFORMATION: /mod_base = "nucleoside: lacks 5'-phosphate
      group"
<220> FEATURE:
<221> NAME/KEY: modified_base
<222> LOCATION: 1, 2, 5, 6, 8, 12, 14, 18, 19
<223> OTHER INFORMATION: /mod_base = "2'-O-methyl corresponding
      nucleoside"
<220> FEATURE:
<221> NAME/KEY: modified_base
<222> LOCATION: 21
<223> OTHER INFORMATION: /mod_base = "5'-phosphorothioate thymidine"
```

<220> FEATURE:
<221> NAME/KEY: modified_base
<222> LOCATION: 3, 4, 7, 9, 10, 11, 13, 15, 16, 17
<223> OTHER INFORMATION: /mod_base = "2'-hydroxy corresponding
nucleoside"

<400> SEQUENCE: 343 gaggcuguag gcauaaauut t 21

<210> SEQ ID NO 344
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 8, 9, 12, 14, 15, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 10, 11, 13, 16
<223> OTHER INFORMATION: /mod_base = "2'-hydroxy corresponding
nucleoside"

<400> SEQUENCE: 344 caguuuacua gugccauuut t 21

<210> SEQ ID NO 345
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 6, 8, 9, 11, 12, 13, 15, 16, 17, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 10, 14, 18
<223> OTHER INFORMATION: /mod_base = "2'-hydroxy corresponding
nucleoside"

<400> SEQUENCE: 345 agguauguug cccguuugut t 21

<210> SEQ ID NO 346
<211> LENGTH: 20
<212> TYPE: DNA
<213> ORGANISM: Artificial sequence <220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 346 uauguugccc guuuguccat 20

<210> SEQ ID NO 347
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 347 gaggcuguag gcauaaauat 20

<210> SEQ ID NO 348
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 6, 9, 11, 12, 13, 14, 16, 17, 19
<223> OTHER INFORMATION: /mod_base = "2'-O-methyl corresponding nucleoside"
<220> FEATURE:
<221> NAME/KEY: modified_base <222> LOCATION: 21
<223> OTHER INFORMATION: /mod_base = "5'-phosphorothioate thymidine"
<220> FEATURE:
<221> NAME/KEY: modified_base
<222> LOCATION: 5, 7, 8, 10, 15, 18
<223> OTHER INFORMATION: /mod_base = "2'-hydroxy corresponding
nucleoside"

<400> SEQUENCE: 348 gucugcggcg uuuuaucaut t 21

<210> SEQ ID NO 349
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 7, 8, 9, 10, 12, 13, 14, 15, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 11, 17
<223> OTHER INFORMATION: /mod_base = "2'-hydroxy corresponding
nucleoside"

<400> SEQUENCE: 349 caacuuuuuc accucugcct t 21

<210> SEQ ID NO 350
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 6, 8, 10, 11, 12, 13, 15, 16, 17, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 9, 14, 19
<223> OTHER INFORMATION: /mod_base = "2'-hydroxy corresponding
nucleoside"

<400> SEQUENCE: 350 ccgugugcac uucgcuucat t 21

<210> SEQ ID NO 351
<211> LENGTH: 20

<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 351 ccgugugcac uucgcuucat 20

<210> SEQ ID NO 352
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 352 ucaagguaug uugcccguat 20

<210> SEQ ID NO 353
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"

<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 353 caguuuacua gugccauuat 20

<210> SEQ ID NO 354
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 8, 9, 10, 11, 12, 13, 14, 15, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 16, 17
<223> OTHER INFORMATION: /mod_base = "2'-hydroxy corresponding nucleoside"

<400> SEQUENCE: 354 ugguggacuu cucucaauut t 21

<210> SEQ ID NO 355
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 355 agguauguug cccguuugat 20

<210> SEQ ID NO 356
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 8, 10, 11, 13, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 9, 12, 14, 15, 16, 18, 19
<223> OTHER INFORMATION: /mod_base = "2'-hydroxy corresponding
nucleoside"

<400> SEQUENCE: 356 cugcucgugu uacaggcggt t 21

<210> SEQ ID NO 357
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 6, 8, 9, 10, 12, 13, 14, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 11, 15
<223> OTHER INFORMATION: /mod_base = "2'-hydroxy corresponding
nucleoside"

<400> SEQUENCE: 357 uauguugccc guuuguccut t 21

<210> SEQ ID NO 358
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 7, 9, 11, 12, 14, 15, 16, 18, 19

<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 8, 10, 13, 17
<223> OTHER INFORMATION: /mod_base = "2'-hydroxy corresponding
nucleoside"

<400> SEQUENCE: 358 ucaagguaug uugcccguut t 21

<210> SEQ ID NO 359
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 7, 10, 12, 13, 14, 15, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 11, 17, 18, 19
<223> OTHER INFORMATION: /mod_base = "2'-hydroxy corresponding
nucleoside"

<400> SEQUENCE: 359 ucuuaucaac acuuccggat t 21

<210> SEQ ID NO 360
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 360 ucuuaucaac acuuccggat 20

<210> SEQ ID NO 361
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 6, 7, 9, 10, 11, 14, 15, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 8, 12, 13, 16
<223> OTHER INFORMATION: /mod_base = "2'-hydroxy corresponding
nucleoside"

<400> SEQUENCE: 361 caccucugcc uaaucaucut t 21

<210> SEQ ID NO 362
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 10, 11, 12, 13, 14, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 7, 8, 9, 15, 16, 17
<223> OTHER INFORMATION: /mod_base = "2'-hydroxy corresponding
nucleoside"

<400> SEQUENCE: 362 auaagaggac ucuuggacut t 21

<210> SEQ ID NO 363
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:

<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 363 gucugcggcg uuuuaucaat 20

<210> SEQ ID NO 364
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 10, 11, 12, 13, 15, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 9, 14, 16, 17, 18
<223> OTHER INFORMATION: /mod_base = "2'-hydroxy corresponding nucleoside"

<400> SEQUENCE: 364 ggcgcugaau cccgcggact t 21

<210> SEQ ID NO 365
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 8, 15, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 9, 10, 11, 12, 13, 14, 19
<223> OTHER INFORMATION: /mod_base = "2'-hydroxy corresponding nucleoside"

<400> SEQUENCE: 365 cgcgucgcag aagaucucat t 21

<210> SEQ ID NO 366
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 9, 12, 13, 16, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 10, 11, 14, 15
<223> OTHER INFORMATION: /mod_base = "2'-hydroxy corresponding nucleoside"

<400> SEQUENCE: 366 aaugucaacg accgaccuut t 21

<210> SEQ ID NO 367
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 7, 8, 9, 11, 12, 15, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 10, 13, 14, 16, 19
<223> OTHER INFORMATION: /mod_base = "2'-hydroxy corresponding nucleoside"

<400> SEQUENCE: 367 gcucaguuua cuagugccat t 21

<210> SEQ ID NO 368
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 368 ugguggacuu cucucaauat 20

<210> SEQ ID NO 369
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 8, 10, 11, 13
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 9, 12, 14, 15, 16, 17, 18, 19
<223> OTHER INFORMATION: /mod_base = "2'-hydroxy corresponding nucleoside"

<400> SEQUENCE: 369 aucgccgcgu cgcagaagat t 21

<210> SEQ ID NO 370
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 7, 9, 10, 11, 14, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 12, 13, 15, 16
<223> OTHER INFORMATION: /mod_base = "2'-hydroxy corresponding nucleoside"

<400> SEQUENCE: 370 gccauuuguu cagugguuct t 21

<210> SEQ ID NO 371
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 8, 10, 11, 13, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 9, 12, 14, 15, 16, 17
<223> OTHER INFORMATION: /mod_base = "2'-hydroxy corresponding
nucleoside"

<400> SEQUENCE: 371 cgauccauac ugcggaacut t 21

<210> SEQ ID NO 372
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 7, 8, 10, 11, 12, 15, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 9, 13, 14, 17
<223> OTHER INFORMATION: /mod_base = "2'-hydroxy corresponding
nucleoside"

<400> SEQUENCE: 372 ucaccucugc cuaaucauct t 21

<210> SEQ ID NO 373
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base <222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 6, 7, 8, 9, 10, 11, 12, 13, 16, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 14, 15
<223> OTHER INFORMATION: /mod_base = "2'-hydroxy corresponding nucleoside"

<400> SEQUENCE: 373 guggacuucu cucaauuuut t 21

<210> SEQ ID NO 374
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 7, 8, 10, 12, 13, 14, 15, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 9, 11, 17, 18, 19
<223> OTHER INFORMATION: /mod_base = "2'-hydroxy corresponding nucleoside"

<400> SEQUENCE: 374 gggucaccau auucuugggt t 21

<210> SEQ ID NO 375
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 7, 8, 10, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 9, 11, 12, 13, 14, 15, 16

<223> OTHER INFORMATION: /mod_base = "2'-hydroxy corresponding
nucleoside"

<400> SEQUENCE: 375 gccgcgucgc agaagaucut t 21

<210> SEQ ID NO 376
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 6, 8, 9, 11, 13, 14, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 7, 10, 12, 15, 17, 18, 19
<223> OTHER INFORMATION: /mod_base = "2'-hydroxy corresponding
nucleoside"

<400> SEQUENCE: 376 ucaaucgccg cgucgcagat t 21

<210> SEQ ID NO 377
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 7, 9, 10, 11, 13, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 12, 14, 15, 17
<223> OTHER INFORMATION: /mod_base = "2'-hydroxy corresponding
nucleoside"

<400> SEQUENCE: 377 uggauguguc ugcggcguut t 21

<210> SEQ ID NO 378
<211> LENGTH: 21
<212> TYPE: DNA
<213> ORGANISM: Artificial sequence
<220> FEATURE:
<223> OTHER INFORMATION: Description of the artificial sequence: sense
strand of dsRNA <220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 6, 7, 8, 12, 13, 14, 15, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 10, 11, 17, 18, 19
<223> OTHER INFORMATION: /mod_base = "2'-hydroxy corresponding nucleoside"

<400> SEQUENCE: 378 uacuguucaa gccuccaagt t 21

<210> SEQ ID NO 379
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 6, 7, 10, 12, 13, 15, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 11, 14, 18
<223> OTHER INFORMATION: /mod_base = "2'-hydroxy corresponding nucleoside"

<400> SEQUENCE: 379 guuuacuagu gccauuugut t 21

<210> SEQ ID NO 380
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 6, 8, 9, 11, 12, 13, 15, 16, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:

<221> NAME/KEY: modified_base
<222> LOCATION: 4, 5, 7, 10, 14, 18, 19
<223> OTHER INFORMATION: /mod_base = "2'-hydroxy corresponding nucleoside"

<400> SEQUENCE: 380 acuagugcca uuuguucagt t 21

<210> SEQ ID NO 381
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 6, 7, 9, 16, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 10, 11, 12, 13, 14, 15
<223> OTHER INFORMATION: /mod_base = "2'-hydroxy corresponding nucleoside"

<400> SEQUENCE: 381 ccgcgucgca gaagaucuct t 21

<210> SEQ ID NO 382
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 6, 8, 9, 12, 14, 15, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 10, 11, 13, 19
<223> OTHER INFORMATION: /mod_base = "2'-hydroxy corresponding nucleoside"

<400> SEQUENCE: 382 uaucuuauca acacuuccgt t 21

<210> SEQ ID NO 383
<211> LENGTH: 21
<212> TYPE: DNA
<213> ORGANISM: Artificial sequence
<220> FEATURE:

<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 9, 10, 11, 13, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 7, 8, 12, 14, 15
<223> OTHER INFORMATION: /mod_base = "2'-hydroxy corresponding
nucleoside"

<400> SEQUENCE: 383 ggccaaaauu cgcaguccct t 21

<210> SEQ ID NO 384
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 6, 7, 8, 9, 11, 12, 13, 16, 17, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 10, 14, 15, 18
<223> OTHER INFORMATION: /mod_base = "2'-hydroxy corresponding
nucleoside"

<400> SEQUENCE: 384 uucaccucug ccuaaucaut t 21

<210> SEQ ID NO 385
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 6, 7, 8, 10, 11, 14, 16, 17, 19
<223> OTHER INFORMATION: /mod_base = "2'-O-methyl corresponding
nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 4, 5, 9, 12, 13, 15, 18
<223> OTHER INFORMATION: /mod_base = "2'-hydroxy corresponding
nucleoside"

<400> SEQUENCE: 385 cucaguuuac uagugccaut t 21

<210> SEQ ID NO 386
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 7, 8, 10, 11, 12, 14, 15, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 13
<223> OTHER INFORMATION: /mod_base = "2'-hydroxy corresponding
nucleoside"

<400> SEQUENCE: 386 uguugcccgu uuguccucut t 21

<210> SEQ ID NO 387
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 6, 7, 9, 10, 11, 13, 14, 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 12, 16, 17, 19
<223> OTHER INFORMATION: /mod_base = "2'-hydroxy corresponding
nucleoside"

<400> SEQUENCE: 387 uagugccauu uguucagugt t 21

<210> SEQ ID NO 388
<211> LENGTH: 21
<212> TYPE: DNA

<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 7, 11, 13, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 8, 9, 10, 12, 14, 15, 16, 19
<223> OTHER INFORMATION: /mod_base = "2'-hydroxy corresponding nucleoside"

<400> SEQUENCE: 388 aggcuguagg cauaaauugt t 21

<210> SEQ ID NO 389
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 6, 7, 8, 10, 13, 15, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 9, 11, 12, 14, 19
<223> OTHER INFORMATION: /mod_base = "2'-hydroxy corresponding nucleoside"

<400> SEQUENCE: 389 augugucugc ggcguuuuat t 21

<210> SEQ ID NO 390
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:

<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 390 augugucugc ggcguuuuat 20

<210> SEQ ID NO 391
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 9, 10, 12, 13, 14, 15, 16, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 11, 17, 19
<223> OTHER INFORMATION: /mod_base = "2'-hydroxy corresponding nucleoside"

<400> SEQUENCE: 391 acuucgcuuc accucugcat t 21

<210> SEQ ID NO 392
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 7, 9, 10, 11, 12, 14, 15, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 8, 13, 18
<223> OTHER INFORMATION: /mod_base = "2'-hydroxy corresponding nucleoside"

<400> SEQUENCE: 392 cgugugcacu ucgcuucact t 21

<210> SEQ ID NO 393

<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 9, 10, 11, 12, 13, 14, 15, 16, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 7, 8, 17, 18
<223> OTHER INFORMATION: /mod_base = "2'-hydroxy corresponding
nucleoside"

<400> SEQUENCE: 393 gugguggacu ucucucaaut t 21

<210> SEQ ID NO 394
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 6, 7, 9, 12, 14, 15, 16, 17, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 10, 11, 13, 18
<223> OTHER INFORMATION: /mod_base = "2'-hydroxy corresponding
nucleoside"

<400> SEQUENCE: 394 ugugucugcg gcguuuuaut t 21

<210> SEQ ID NO 395
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 7, 9, 10, 12, 13, 14, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 11, 15, 19
<223> OTHER INFORMATION: /mod_base = "2'-hydroxy corresponding
nucleoside"

<400> SEQUENCE: 395 aagguauguu gcccguuugt t 21

<210> SEQ ID NO 396
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 8, 9, 12, 13, 14, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 7, 10, 11, 16, 17, 18, 19
<223> OTHER INFORMATION: /mod_base = "2'-hydroxy corresponding
nucleoside"

<400> SEQUENCE: 396 ucaacgaccg accuugaggt t 21

<210> SEQ ID NO 397
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 11, 12, 13, 14, 15, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 7, 8, 9, 10, 16, 17, 18
<223> OTHER INFORMATION: /mod_base = "2'-hydroxy corresponding
nucleoside"

<400> SEQUENCE: 397 cauaagagga cucuuggact t 21

<210> SEQ ID NO 398
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 6, 9, 10, 13, 14, 15, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 7, 8, 11, 12, 17, 18, 19
<223> OTHER INFORMATION: /mod_base = "2'-hydroxy corresponding
nucleoside"

<400> SEQUENCE: 398 gucaacgacc gaccuugagt t 21

<210> SEQ ID NO 399
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 7, 8, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 9, 10, 11, 12, 13, 15, 16, 17, 18, 19
<223> OTHER INFORMATION: /mod_base = "2'-hydroxy corresponding
nucleoside"

<400> SEQUENCE: 399 auauucuugg gaacaagagt t 21

<210> SEQ ID NO 400
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base <222> LOCATION: 1, 2, 3, 4, 5, 7, 9, 10, 12, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 8, 11, 13, 14, 15, 17, 18, 19
<223> OTHER INFORMATION: /mod_base = "2'-hydroxy corresponding
nucleoside"

<400> SEQUENCE: 400 ugcucguguu acaggcgggt t 21

<210> SEQ ID NO 401
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 7, 8, 10, 12, 13, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 9, 11, 14, 16, 17, 18, 19
<223> OTHER INFORMATION: /mod_base = "2'-hydroxy corresponding
nucleoside"

<400> SEQUENCE: 401 caaucgccgc gucgcagaat t 21

<210> SEQ ID NO 402
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 6, 7, 11, 12, 13, 14, 15, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 9, 10, 16, 17, 18
<223> OTHER INFORMATION: /mod_base = "2'-hydroxy corresponding
nucleoside"

<400> SEQUENCE: 402 acuguucaag ccuccaagct t 21

<210> SEQ ID NO 403
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 6, 8, 9, 11, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 7, 10, 12, 13, 14, 15, 16, 17
<223> OTHER INFORMATION: /mod_base = "2'-hydroxy corresponding nucleoside"

<400> SEQUENCE: 403 cgccgcgucg cagaagauct t 21

<210> SEQ ID NO 404
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 9, 12, 15, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 10, 11, 13, 14, 18
<223> OTHER INFORMATION: /mod_base = "2'-hydroxy corresponding nucleoside"

<400> SEQUENCE: 404 cauuuguuca gugguucgut t 21

<210> SEQ ID NO 405
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<220> FEATURE:
<221> NAME/KEY: modified_base
<222> LOCATION: 1, 2, 3, 4, 8, 9, 10, 11, 13, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 7, 12, 14, 15, 16, 18, 19
<223> OTHER INFORMATION: /mod_base = "2'-hydroxy corresponding
nucleoside"

<400> SEQUENCE: 405 cgcugaaucc cgcggacgat t 21

<210> SEQ ID NO 406
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 6, 8, 9, 11, 13, 14, 15, 16, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 7, 10, 12, 18, 19
<223> OTHER INFORMATION: /mod_base = "2'-hydroxy corresponding
nucleoside"

<400> SEQUENCE: 406 uggguacacca uauucuuggt t 21

<210> SEQ ID NO 407
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 6, 8, 9, 12, 13, 14, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 10, 11, 15, 17
<223> OTHER INFORMATION: /mod_base = "2'-hydroxy corresponding
nucleoside"

<400> SEQUENCE: 407 uccucugccg auccauacut t 21

<210> SEQ ID NO 408
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 8, 11, 12, 15, 16, 17, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 7, 9, 10, 13, 14, 19
<223> OTHER INFORMATION: /mod_base = "2'-hydroxy corresponding
nucleoside"

<400> SEQUENCE: 408 augucaacga ccgaccuugt t 21

<210> SEQ ID NO 409
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 7, 8, 9, 12, 13, 15, 16, 17, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 10, 11, 14, 19
<223> OTHER INFORMATION: /mod_base = "2'-hydroxy corresponding
nucleoside"

<400> SEQUENCE: 409 ccucugccua aucaucucat t 21

<210> SEQ ID NO 410
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1

<223> OTHER INFORMATION: /mod_base = "nucleoside: lacks 5'-phosphate group"
<220> FEATURE:
<221> NAME/KEY: modified_base
<222> LOCATION: 1, 2, 3, 5, 7, 9, 11, 12, 13, 14, 16, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 8, 10, 15
<223> OTHER INFORMATION: /mod_base = "2'-hydroxy corresponding nucleoside"

<400> SEQUENCE: 410 accgugugca cuucgcuuct t 21

<210> SEQ ID NO 411
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 7, 8, 9, 11, 13, 14, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 10, 12, 15, 17, 18, 19
<223> OTHER INFORMATION: /mod_base = "2'-hydroxy corresponding nucleoside"

<400> SEQUENCE: 411 ugccgaucca uacugcggat t 21

<210> SEQ ID NO 412
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 6, 7, 8, 12, 13, 14, 16, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 9, 10, 11, 15, 17, 18
<223> OTHER INFORMATION: /mod_base = "2'-hydroxy corresponding nucleoside"

<400> SEQUENCE: 412 cagagucuag acucguggut t 21

<210> SEQ ID NO 413
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 6, 10, 11, 12, 13, 14, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 7, 8, 9, 15, 16, 17
<223> OTHER INFORMATION: /mod_base = "2'-hydroxy corresponding nucleoside"

<400> SEQUENCE: 413 cuguucaagc cuccaagcut t 21

<210> SEQ ID NO 414
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 6, 7, 9, 13, 15, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 8, 10, 11, 12, 14, 16, 17, 18
<223> OTHER INFORMATION: /mod_base = "2'-hydroxy corresponding nucleoside"

<400> SEQUENCE: 414 ggaggcugua ggcauaaaut t 21

<210> SEQ ID NO 415
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:

<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 7, 8, 10, 14, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 9, 11, 12, 13, 15, 17, 18, 19
<223> OTHER INFORMATION: /mod_base = "2'-hydroxy corresponding nucleoside"

<400> SEQUENCE: 415 aggaggcugu aggcauaaat t 21

<210> SEQ ID NO 416
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 7, 8, 9, 10, 11, 12, 13, 14, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 15, 16
<223> OTHER INFORMATION: /mod_base = "2'-hydroxy corresponding nucleoside"

<400> SEQUENCE: 416 gguggacuuc ucucaauuut t 21

<210> SEQ ID NO 417
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 5, 6, 7, 8, 9, 10, 11, 13, 14, 15, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base <222> LOCATION: 3, 4, 12, 18
<223> OTHER INFORMATION: /mod_base = "2'-hydroxy corresponding
nucleoside"

<400> SEQUENCE: 417 gcaacuuuuu caccucugct t 21

<210> SEQ ID NO 418
<211> LENGTH: 20
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding
nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding
nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 418 cugcucgugu uacaggcgat 20

<210> SEQ ID NO 419
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 7, 8, 10, 11, 12, 14, 15, 16, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 9, 13, 17, 18
<223> OTHER INFORMATION: /mod_base = "2'-hydroxy corresponding
nucleoside"

<400> SEQUENCE: 419 cuagugccau uuguucagut t 21

<210> SEQ ID NO 420
<211> LENGTH: 21
<212> TYPE: DNA
<213> ORGANISM: Artificial sequence
<220> FEATURE:

<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 8, 9, 10, 12, 14, 15, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 7, 11, 13, 16, 18, 19
<223> OTHER INFORMATION: /mod_base = "2'-hydroxy corresponding
nucleoside"

<400> SEQUENCE: 420 cugccgaucc auacugcggt t 21

<210> SEQ ID NO 421
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 6, 8, 9, 10, 11, 13, 14, 15, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 12, 17
<223> OTHER INFORMATION: /mod_base = "2'-hydroxy corresponding
nucleoside"

<400> SEQUENCE: 421 gugugcacuu cgcuucacct t 21

<210> SEQ ID NO 422
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 8, 9, 11, 15, 19
<223> OTHER INFORMATION: /mod_base = "2'-O-methyl corresponding
nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 5, 7, 10, 12, 13, 14, 16, 17, 18
<223> OTHER INFORMATION: /mod_base = "2'-hydroxy corresponding
nucleoside"

<400> SEQUENCE: 422 gcucguguua caggcgggct t 21

<210> SEQ ID NO 423
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 6, 7, 8, 10, 11, 14, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 9, 12, 13, 15
<223> OTHER INFORMATION: /mod_base = "2'-hydroxy corresponding
nucleoside"

<400> SEQUENCE: 423 ccuaucuuau caacacuuct t 21

<210> SEQ ID NO 424
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 7, 8, 10, 11, 13, 15, 16, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 9, 12, 14, 17, 19
<223> OTHER INFORMATION: /mod_base = "2'-hydroxy corresponding
nucleoside"

<400> SEQUENCE: 424 ucucaaucgc cgcgucgcat t 21

<210> SEQ ID NO 425
<211> LENGTH: 21
<212> TYPE: DNA

<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 6, 7, 8, 10, 12, 13, 14, 15, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 11, 19
<223> OTHER INFORMATION: /mod_base = "2'-hydroxy corresponding nucleoside"

<400> SEQUENCE: 425 gcccgucugu gccuucucat t 21

<210> SEQ ID NO 426
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 6, 7, 9, 10, 13, 15, 16, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 8, 11, 12, 14
<223> OTHER INFORMATION: /mod_base = "2'-hydroxy corresponding nucleoside"

<400> SEQUENCE: 426 cuaucuuauc aacacuucct t 21

<210> SEQ ID NO 427
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 7, 8, 9, 11, 12, 13, 15, 16, 17, 18, 19
<223> OTHER INFORMATION: /mod_base = "2'-O-methyl corresponding nucleoside"
<220> FEATURE:

<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 10, 14
<223> OTHER INFORMATION: /mod_base = "2'-hydroxy corresponding
nucleoside"

<400> SEQUENCE: 427 auguugcccg uuuguccuct t 21

<210> SEQ ID NO 428
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 6, 7, 9, 10, 11, 13, 14, 15, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 12, 16
<223> OTHER INFORMATION: /mod_base = "2'-hydroxy corresponding
nucleoside"

<400> SEQUENCE: 428 guauguugcc cguuugucct t 21

<210> SEQ ID NO 429
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 7, 8, 9, 11, 12, 13, 14, 15, 17, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 10, 16, 18
<223> OTHER INFORMATION: /mod_base = "2'-hydroxy corresponding
nucleoside"

<400> SEQUENCE: 429 cuucgcuuca ccucugcact t 21

<210> SEQ ID NO 430

<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 7, 8, 9, 10, 12, 13, 14, 15, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 11, 16
<223> OTHER INFORMATION: /mod_base = "2'-hydroxy corresponding nucleoside"

<400> SEQUENCE: 430 ugugcacuuc gcuucaccut t 21

<210> SEQ ID NO 431
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 8, 9, 10, 12, 15, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 7, 11, 13, 14, 19
<223> OTHER INFORMATION: /mod_base = "2'-hydroxy corresponding nucleoside"

<400> SEQUENCE: 431 gccaaaauuc gcagucccgt t 21

<210> SEQ ID NO 432
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 7, 9, 11, 12, 14, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 8, 10, 13, 15, 16, 17, 19
<223> OTHER INFORMATION: /mod_base = "2'-hydroxy corresponding
nucleoside"

<400> SEQUENCE: 432 ccugcucgug uuacaggcgt t 21

<210> SEQ ID NO 433
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 6, 8, 12, 13, 14, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 7, 9, 10, 11, 15, 17
<223> OTHER INFORMATION: /mod_base = "2'-hydroxy corresponding
nucleoside"

<400> SEQUENCE: 433 uggagugugg auucgcacut t 21

<210> SEQ ID NO 434
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 6, 7, 10, 11, 12, 13, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 8, 9, 14, 15, 16, 17, 19
<223> OTHER INFORMATION: /mod_base = "2'-hydroxy corresponding
nucleoside"

<400> SEQUENCE: 434 aacgaccgac cuugaggcat t 21

<210> SEQ ID NO 435
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 7, 8, 9, 13, 14, 15, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 6, 10, 11, 12, 16, 18, 19
<223> OTHER INFORMATION: /mod_base = "2'-hydroxy corresponding
nucleoside"

<400> SEQUENCE: 435 acagagucua gacucguggt t 21

<210> SEQ ID NO 436
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 7, 9, 11, 12, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 10, 13, 15, 16, 17, 18, 19
<223> OTHER INFORMATION: /mod_base = "2'-hydroxy corresponding
nucleoside"

<400> SEQUENCE: 436 aaucgccgcg ucgcagaagt t 21

<210> SEQ ID NO 437
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base <222> LOCATION: 1, 2, 3, 5, 7, 8, 10, 11, 12, 14, 15, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 9, 13, 17
<223> OTHER INFORMATION: /mod_base = "2'-hydroxy corresponding
nucleoside"

<400> SEQUENCE: 437 gguauguugc ccguuuguct t 21

<210> SEQ ID NO 438
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 6, 7, 8, 10, 12, 13, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 9, 11, 14, 16, 17, 18, 19
<223> OTHER INFORMATION: /mod_base = "2'-hydroxy corresponding
nucleoside"

<400> SEQUENCE: 438 gccgauccau acugcggaat t 21

<210> SEQ ID NO 439
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 7, 8, 9, 10, 12, 13, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 11, 14, 15, 17
<223> OTHER INFORMATION: /mod_base = "2'-hydroxy corresponding
nucleoside"

<400> SEQUENCE: 439 gcccuaucuu aucaacacut t 21

<210> SEQ ID NO 440
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 11, 13, 14, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 12, 15, 19
<223> OTHER INFORMATION: /mod_base = "2'-hydroxy corresponding nucleoside"

<400> SEQUENCE: 440 aguuuacuag ugccauuugt t 21

<210> SEQ ID NO 441
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 7, 10, 11, 14, 15, 16, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 6, 8, 9, 12, 13, 18, 19
<223> OTHER INFORMATION: /mod_base = "2'-hydroxy corresponding nucleoside"

<400> SEQUENCE: 441 ugucaacgac cgaccuugat t 21

<210> SEQ ID NO 442
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"

<220> FEATURE:
<221> NAME/KEY: modified_base
<222> LOCATION: 1, 2, 3, 4, 5, 6, 7, 8, 9, 12, 13, 14, 15, 16, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 10, 11, 18, 19
<223> OTHER INFORMATION: /mod_base = "2'-hydroxy corresponding
nucleoside"

<400> SEQUENCE: 442 acuucucuca auuuucuagt t 21

<210> SEQ ID NO 443
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 9, 11, 12, 13, 14, 15, 16, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 7, 8, 10, 17
<223> OTHER INFORMATION: /mod_base = "2'-hydroxy corresponding
nucleoside"

<400> SEQUENCE: 443 gcgcgggacg uccuuuguct t 21

<210> SEQ ID NO 444
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 7, 8, 9, 11, 14, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 10, 12, 13, 15, 16, 17
<223> OTHER INFORMATION: /mod_base = "2'-hydroxy corresponding
nucleoside"

<400> SEQUENCE: 444 ucuagacucg ugguggacut t 21

<210> SEQ ID NO 445
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 9, 10, 12, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 8, 11, 13, 14, 15, 16
<223> OTHER INFORMATION: /mod_base = "2'-hydroxy corresponding nucleoside"

<400> SEQUENCE: 445 gauccauacu gcggaacuct t 21

<210> SEQ ID NO 446
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 6, 7, 10, 11, 12, 14, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 13, 15, 18
<223> OTHER INFORMATION: /mod_base = "2'-hydroxy corresponding nucleoside"

<400> SEQUENCE: 446 cucugccgau ccauacugct t 21

<210> SEQ ID NO 447
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1

<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 9, 10, 11, 13, 15, 16, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 12, 14, 17, 19
<223> OTHER INFORMATION: /mod_base = "2'-hydroxy corresponding nucleoside"

<400> SEQUENCE: 447 ucugccgauc cauacugcgt t 21

<210> SEQ ID NO 448
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 11, 12, 13, 15, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 14, 16, 19
<223> OTHER INFORMATION: /mod_base = "2'-hydroxy corresponding nucleoside"

<400> SEQUENCE: 448 ccucugccga uccauacugt t 21

<210> SEQ ID NO 449
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 6, 7, 8, 9, 10, 11, 12, 14, 16, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 13, 15, 17, 18
<223> OTHER INFORMATION: /mod_base = "2'-hydroxy corresponding nucleoside"

<400> SEQUENCE: 449 gcaccucucu uuacgcggut t 21

<210> SEQ ID NO 450
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 6, 7, 8, 9, 10, 11, 12, 14, 15, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 13, 18
<223> OTHER INFORMATION: /mod_base = "2'-hydroxy corresponding nucleoside"

<400> SEQUENCE: 450 aagaacuccc ucgccucgct t 21

<210> SEQ ID NO 451
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 5, 6, 7, 8, 9, 10, 12, 13, 14, 15, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 11, 16, 18, 19
<223> OTHER INFORMATION: /mod_base = "2'-hydroxy corresponding nucleoside"

<400> SEQUENCE: 451 gaacucccuc gccucgcagt t 21

<210> SEQ ID NO 452
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:

<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 6, 9, 10, 11, 12, 13, 14, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 8, 15, 16, 17, 18
<223> OTHER INFORMATION: /mod_base = "2'-hydroxy corresponding nucleoside"

<400> SEQUENCE: 452 ucucucaauu uucuagggct t 21

<210> SEQ ID NO 453
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 6, 8, 9, 10, 11, 12, 13, 14, 15, 16, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 7, 17, 19
<223> OTHER INFORMATION: /mod_base = "2'-hydroxy corresponding nucleoside"

<400> SEQUENCE: 453 gggcgcaccu cucuuuacgt t 21

<210> SEQ ID NO 454
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 5, 6, 7, 9, 11, 12, 14, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base <222> LOCATION: 3, 4, 8, 10, 13, 15, 16, 17, 18
<223> OTHER INFORMATION: /mod_base = "2'-hydroxy corresponding
nucleoside"

<400> SEQUENCE: 454 ccgauccaua cugcggaact t 21

<210> SEQ ID NO 455
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 6, 7, 8, 9, 11, 12, 13, 14, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 10, 15, 17, 18, 19
<223> OTHER INFORMATION: /mod_base = "2'-hydroxy corresponding
nucleoside"

<400> SEQUENCE: 455 aacucccucg ccucgcagat t 21

<210> SEQ ID NO 456
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 5, 6, 7, 9, 10, 13, 14, 15, 17, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 8, 11, 12, 16, 18
<223> OTHER INFORMATION: /mod_base = "2'-hydroxy corresponding
nucleoside"

<400> SEQUENCE: 456 cuccucugcc gauccauact t 21

<210> SEQ ID NO 457
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 5, 7, 11, 12, 13, 15, 17, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 9, 10, 14, 16
<223> OTHER INFORMATION: /mod_base = "2'-hydroxy corresponding nucleoside"

<400> SEQUENCE: 457 ggagugugga uucgcacuct t 21

<210> SEQ ID NO 458
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 5, 7, 9, 10, 11, 12, 13, 14, 15, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 6, 8, 18
<223> OTHER INFORMATION: /mod_base = "2'-hydroxy corresponding nucleoside"

<400> SEQUENCE: 458 cgggcgcacc ucucuuuact t 21

<210> SEQ ID NO 459
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 8, 9, 11, 12, 14, 16, 17, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"

<220> FEATURE:
<221> NAME/KEY: modified_base
<222> LOCATION: 6, 7, 10, 13, 15, 18
<223> OTHER INFORMATION: /mod_base = "2'-hydroxy corresponding
nucleoside"

<400> SEQUENCE: 459 gucucaaucg ccgcgucgct t 21

<210> SEQ ID NO 460
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 8, 9, 11, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 7, 10, 12, 13, 14, 15
<223> OTHER INFORMATION: /mod_base = "2'-hydroxy corresponding
nucleoside"

<400> SEQUENCE: 460 auccauacug cggaacucct t 21

<210> SEQ ID NO 461
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 6, 7, 8, 9, 10, 11, 12, 13, 15, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 14, 16, 18, 19
<223> OTHER INFORMATION: /mod_base = "2'-hydroxy corresponding
nucleoside"

<400> SEQUENCE: 461 cgcaccucuc uuuacgcggt t 21

<210> SEQ ID NO 462
<211> LENGTH: 21
<212> TYPE: DNA
<213> ORGANISM: Artificial sequence <220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 7, 8, 11, 12, 13, 14, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 6, 9, 10, 15, 16, 17, 18
<223> OTHER INFORMATION: /mod_base = "2'-hydroxy corresponding nucleoside"

<400> SEQUENCE: 462 caacgaccga ccuugaggct t 21

<210> SEQ ID NO 463
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 6, 7, 9, 14, 15, 16, 17, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 8, 10, 11, 12, 13, 19
<223> OTHER INFORMATION: /mod_base = "2'-hydroxy corresponding nucleoside"

<400> SEQUENCE: 463 ccauacugcg gaacuccuat t 21

<210> SEQ ID NO 464
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 5, 6, 7, 8, 10, 14, 17, 18, 19
<223> OTHER INFORMATION: /mod_base = "2'-O-methyl corresponding nucleoside"
<220> FEATURE:
<221> NAME/KEY: modified_base <222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 9, 11, 12, 13, 15, 16
<223> OTHER INFORMATION: /mod_base = "2'-hydroxy corresponding
nucleoside"

<400> SEQUENCE: 464 ugaaucccgc ggacgaccct t 21

<210> SEQ ID NO 465
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 6, 7, 8, 9, 10, 11, 13, 14, 15, 16, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 12, 17, 19
<223> OTHER INFORMATION: /mod_base = "2'-hydroxy corresponding
nucleoside"

<400> SEQUENCE: 465 agaacucccu cgccucgcat t 21

<210> SEQ ID NO 466
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 7, 8, 9, 10, 11, 12, 13, 14, 15, 17, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 16, 18
<223> OTHER INFORMATION: /mod_base = "2'-hydroxy corresponding
nucleoside"

<400> SEQUENCE: 466 ggcgcaccuc ucuuuacgct t 21

<210> SEQ ID NO 467
<211> LENGTH: 21

<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 4, 6, 7, 8, 9, 10, 11, 12, 13, 14, 16, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 5, 15, 17, 19
<223> OTHER INFORMATION: /mod_base = "2'-hydroxy corresponding nucleoside"

<400> SEQUENCE: 467 gcgcaccucu cuuuacgcgt t 21

<210> SEQ ID NO 468
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 7, 8, 9, 10, 12, 16, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 6, 11, 13, 14, 15, 17, 18
<223> OTHER INFORMATION: /mod_base = "2'-hydroxy corresponding nucleoside"

<400> SEQUENCE: 468 gcugaauccc gcggacgact t 21

<210> SEQ ID NO 469
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 6, 8, 9, 10, 11, 13, 14, 15, 16, 17, 19
<223> OTHER INFORMATION: /mod_base = "2'-O-methyl corresponding nucleoside"

<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 7, 12, 18
<223> OTHER INFORMATION: /mod_base = "2'-hydroxy corresponding
nucleoside"

<400> SEQUENCE: 469 cacuucgcuu caccucugct t 21

<210> SEQ ID NO 470
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 6, 7, 9, 10, 12, 14, 15, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 5, 8, 11, 13, 16, 18, 19
<223> OTHER INFORMATION: /mod_base = "2'-hydroxy corresponding
nucleoside"

<400> SEQUENCE: 470 cucaaucgcc gcgucgcagt t 21

<210> SEQ ID NO 471
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 7, 10, 12, 13, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 8, 9, 11, 14, 15, 16
<223> OTHER INFORMATION: /mod_base = "2'-hydroxy corresponding
nucleoside"

<400> SEQUENCE: 471 ucccgucggc gcugaaucct t 21

<210> SEQ ID NO 472
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 6, 7, 8, 9, 11, 15, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 5, 10, 12, 13, 14, 16, 17
<223> OTHER INFORMATION: /mod_base = "2'-hydroxy corresponding
nucleoside"

<400> SEQUENCE: 472 cugaaucccg cggacgacct t 21

<210> SEQ ID NO 473
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 5, 6, 7, 11, 12, 13, 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 4, 8, 9, 10, 14, 16, 17, 19
<223> OTHER INFORMATION: /mod_base = "2'-hydroxy corresponding
nucleoside"

<400> SEQUENCE: 473 agagucuaga cucguggugt t 21

<210> SEQ ID NO 474
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 7, 8, 10, 15, 16, 17, 18, 19

<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 9, 11, 12, 13, 14
<223> OTHER INFORMATION: /mod_base = "2'-hydroxy corresponding
nucleoside"

<400> SEQUENCE: 474 uccauacugc ggaacuccut t 21

<210> SEQ ID NO 475
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 9, 10, 11, 12, 14, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 7, 8, 13, 15, 16, 17, 19
<223> OTHER INFORMATION: /mod_base = "2'-hydroxy corresponding
nucleoside"

<400> SEQUENCE: 475 gcgcugaauc ccgcggacgt t 21

<210> SEQ ID NO 476
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 5, 9, 10, 11, 13, 15, 16, 17, 18, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 6, 7, 8, 12, 14
<223> OTHER INFORMATION: /mod_base = "2'-hydroxy corresponding
nucleoside"

<400> SEQUENCE: 476 aguguggauu cgcacuccut t 21

<210> SEQ ID NO 477
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 3, 4, 6, 7, 8, 10, 12, 13, 15, 19
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 5, 9, 11, 14, 16, 17, 18
<223> OTHER INFORMATION: /mod_base = "2'-hydroxy corresponding
nucleoside"

<400> SEQUENCE: 477 cccugcucgu guuacaggct t 21

<210> SEQ ID NO 478
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 2, 4, 5, 6, 7, 9, 13, 16, 17, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 8, 10, 11, 12, 14, 15, 19
<223> OTHER INFORMATION: /mod_base = "2'-hydroxy corresponding
nucleoside"

<400> SEQUENCE: 478 gaaucccgcg gacgacccgt t 21

<210> SEQ ID NO 479
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:

<221> NAME/KEY: modified_base
<222> LOCATION: 1, 2, 4, 5, 7, 9, 10, 11, 12, 16, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 3, 6, 8, 13, 14, 15, 17, 18
<223> OTHER INFORMATION: /mod_base = "2'-hydroxy corresponding nucleoside"

<400> SEQUENCE: 479 aagcugugcc uuggguggct t 21

<210> SEQ ID NO 480
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 9, 11, 13, 14, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 10, 12, 15, 17, 18, 19
<223> OTHER INFORMATION: /mod_base = "2'-hydroxy corresponding nucleoside"

<400> SEQUENCE: 480 gcccugcucg uguuacaggt t 21

<210> SEQ ID NO 481
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 11, 13, 14, 18, 19
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 12, 15, 16, 17
<223> OTHER INFORMATION: /mod_base = "2'-hydroxy corresponding nucleoside"

<400> SEQUENCE: 481 gucccgucgg cgcugaauct t 21

<210> SEQ ID NO 482
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 4, 5, 7, 8, 11, 13, 14, 15, 16, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 6, 9, 10, 12, 18, 19
<223> OTHER INFORMATION: /mod_base = "2'-hydroxy corresponding nucleoside"

<400> SEQUENCE: 482 aucuuaucaa cacuuccggt t 21

<210> SEQ ID NO 483
<211> LENGTH: 21
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 2, 3, 5, 6, 9, 11, 12, 13, 14, 15
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 4, 7, 8, 10, 16, 17, 18, 19
<223> OTHER INFORMATION: /mod_base = "2'-hydroxy corresponding nucleoside"

<400> SEQUENCE: 483 cuuaucaaca cuuccggaat t 21

<210> SEQ ID NO 484
<211> LENGTH: 20
<212> TYPE: DNA
<213> ORGANISM: Artificial sequence
<220> FEATURE:
<223> OTHER INFORMATION: Description of the artificial sequence: sense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 4, 6, 8, 10, 12, 14, 16, 18
<223> OTHER INFORMATION: /mod_base = "2'-O-methyl corresponding nucleoside"
<220> FEATURE:
<221> NAME/KEY: modified_base
<222> LOCATION: 1, 3, 5, 7, 9, 11, 13, 15, 17, 19
<223> OTHER INFORMATION: /mod_base = "2'-deoxy-2'-fluoro corresponding nucleoside"
<220> FEATURE:
<221> NAME/KEY: modified_base
<222> LOCATION: 20
<223> OTHER INFORMATION: /mod_base = "3'-3'-linked desoxythymidine"

<400> SEQUENCE: 484 cuuaucaaca cuuccggaat 20

<210> SEQ ID NO 485
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 8, 11, 13
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 12, 14, 15, 16, 17, 18, 19
<223> OTHER INFORMATION: /mod_base = "2'-hydroxy corresponding nucleoside"

<400> SEQUENCE: 485 aaacgggcaa cauaccuugt t 21

<210> SEQ ID NO 486
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 486 taccaauuua ugccuacagt t 21

<210> SEQ ID NO 487
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 6, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 7, 8, 9, 10, 11, 12, 13, 14, 15, 17, 18, 19
<223> OTHER INFORMATION: /mod_base = "2'-hydroxy corresponding
nucleoside"

<400> SEQUENCE: 487 uaugauaaaa cgccgcagat t 21

<210> SEQ ID NO 488
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 488 taugauaaaa cgccgcagat t 21

<210> SEQ ID NO 489
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 9, 13
<223> OTHER INFORMATION: /mod_base = "2'-O-methyl corresponding
nucleoside"
<220> FEATURE:
<221> NAME/KEY: modified_base <222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 12, 14, 15, 16, 17, 18, 19
<223> OTHER INFORMATION: /mod_base = "2'-hydroxy corresponding nucleoside"

<400> SEQUENCE: 489 gagaugauua ggcagaggut t 21

<210> SEQ ID NO 490
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 490 tacaaauggc acuaguaaat t 21

<210> SEQ ID NO 491
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 491 tagaugauua ggcagaggut t 21

<210> SEQ ID NO 492
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 4, 9, 15, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 10, 11, 12, 13, 14, 16, 18, 19
<223> OTHER INFORMATION: /mod_base = "2'-hydroxy corresponding nucleoside"

<400> SEQUENCE: 492 gaccaauuua ugccuacagt t 21

<210> SEQ ID NO 493
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 4, 14, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 15, 16, 17, 19
<223> OTHER INFORMATION: /mod_base = "2'-hydroxy corresponding nucleoside"

<400> SEQUENCE: 493 ugauaaaacg ccgcagacat t 21

<210> SEQ ID NO 494
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 494 tgauaaaacg ccgcagacat t 21

<210> SEQ ID NO 495
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 12, 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 13, 14, 16, 17, 19
<223> OTHER INFORMATION: /mod_base = "2'-hydroxy corresponding
nucleoside"

<400> SEQUENCE: 495 ugaacaaaug gcacuaguat t 21

<210> SEQ ID NO 496
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 496 tgaacaaaug gcacuaguat t 21

<210> SEQ ID NO 497
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base <222> LOCATION: 21
<223> OTHER INFORMATION: /mod_base = "5'-phosphorothioate thymidine"

<400> SEQUENCE: 497 tgcagaggug aaaaaguugt t 21

<210> SEQ ID NO 498
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6, 13
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 14, 15, 16, 17, 18,
19
<223> OTHER INFORMATION: /mod_base = "2'-hydroxy corresponding
nucleoside"

<400> SEQUENCE: 498 cgaaccacug aacaaauggt t 21

<210> SEQ ID NO 499
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6, 9, 13
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 10, 11, 12, 14, 15, 16, 17, 18, 19
<223> OTHER INFORMATION: /mod_base = "2'-hydroxy corresponding
nucleoside"

<400> SEQUENCE: 499 ugcgucagca aacacuuggt t 21

<210> SEQ ID NO 500
<211> LENGTH: 21
<212> TYPE: DNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 500 tgcgucagca aacacuuggt t 21

<210> SEQ ID NO 501
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 501 tgaaccacug aacaaauggt t 21

<210> SEQ ID NO 502
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3, 10, 13, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 11, 12, 14, 15, 17, 18, 19
<223> OTHER INFORMATION: /mod_base = "2'-hydroxy corresponding nucleoside"

<400> SEQUENCE: 502 aacaaauggc acuaguaaat t 21

<210> SEQ ID NO 503
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 503 tgaugauuag gcagaggugt t 21

<210> SEQ ID NO 504
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 4, 7, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 5, 6, 8, 9, 10, 11, 12, 13, 14, 15, 16, 18, 19
<223> OTHER INFORMATION: /mod_base = "2'-hydroxy corresponding
nucleoside"

<400> SEQUENCE: 504 cacuaguaaa cugagccagt t 21

<210> SEQ ID NO 505
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base <222> LOCATION: 21
<223> OTHER INFORMATION: /mod_base = "5'-phosphorothioate thymidine"

<400> SEQUENCE: 505 taacgggcaa cauaccuugt t 21

<210> SEQ ID NO 506
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 506 tacuaguaaa cugagccagt t 21

<210> SEQ ID NO 507
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 11, 13
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 12, 14, 15, 16, 17, 18, 19
<223> OTHER INFORMATION: /mod_base = "2'-hydroxy corresponding
nucleoside"

<400> SEQUENCE: 507 aauuuaugcc uacagccuct t 21

<210> SEQ ID NO 508
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"

<220> FEATURE:
<221> NAME/KEY: modified_base
<222> LOCATION: 7, 10, 13
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 12, 14, 15, 16, 17, 18, 19
<223> OTHER INFORMATION: /mod_base = "2'-hydroxy corresponding
nucleoside"

<400> SEQUENCE: 508 aaauggcacu aguaaacugt t 21

<210> SEQ ID NO 509
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 10, 13, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 11, 12, 14, 16, 17, 18, 19
<223> OTHER INFORMATION: /mod_base = "2'-hydroxy corresponding
nucleoside"

<400> SEQUENCE: 509 acaaacgggc aacauaccut t 21

<210> SEQ ID NO 510
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 510 tggacaaacg ggcaacauat t 21

<210> SEQ ID NO 511
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 511 tauuuaugcc uacagccuct t 21

<210> SEQ ID NO 512
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 16, 17, 18,
19
<223> OTHER INFORMATION: /mod_base = "2'-hydroxy corresponding
nucleoside"

<400> SEQUENCE: 512 augauaaaac gccgcagact t 21

<210> SEQ ID NO 513
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 3
<223> OTHER INFORMATION: /mod_base = "2'-O-methyl corresponding
nucleoside"
<220> FEATURE:
<221> NAME/KEY: modified_base <222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 513 ggcagaggug aaaaaguugt t 21

<210> SEQ ID NO 514
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 13, 15
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 16, 17, 18, 19
<223> OTHER INFORMATION: /mod_base = "2'-hydroxy corresponding nucleoside"

<400> SEQUENCE: 514 ugaagcgaag ugcacacggt t 21

<210> SEQ ID NO 515
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 515 tgaagcgaag ugcacacggt t 21

<210> SEQ ID NO 516
<211> LENGTH: 21
<212> TYPE: DNA
<213> ORGANISM: Artificial sequence
<220> FEATURE:

<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 516 tacgggcaac auaccuugat t 21

<210> SEQ ID NO 517
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 517 taauggcacu aguaaacugt t 21

<210> SEQ ID NO 518
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
19
<223> OTHER INFORMATION: /mod_base = "2'-hydroxy corresponding
nucleoside"

<400> SEQUENCE: 518 aauugagaga aguccaccat t 21

<210> SEQ ID NO 519
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 519 tcaaacgggc aacauaccut t 21

<210> SEQ ID NO 520
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 8, 11, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 12, 13, 14, 15, 16, 18, 19
<223> OTHER INFORMATION: /mod_base = "2'-hydroxy corresponding
nucleoside"

<400> SEQUENCE: 520 ccgccuguaa cacgagcagt t 21

<210> SEQ ID NO 521
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 13, 16, 18
<223> OTHER INFORMATION: /mod_base = "2'-O-methyl corresponding
nucleoside"

<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 14, 15, 17, 19
<223> OTHER INFORMATION: /mod_base = "2'-hydroxy corresponding
nucleoside"

<400> SEQUENCE: 521 aggacaaacg ggcaacauat t 21

<210> SEQ ID NO 522
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 7, 10, 12
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 13, 14, 15, 16, 17, 18, 19
<223> OTHER INFORMATION: /mod_base = "2'-hydroxy corresponding
nucleoside"

<400> SEQUENCE: 522 aacgggcaac auaccuugat t 21

<210> SEQ ID NO 523
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
18, 19
<223> OTHER INFORMATION: /mod_base = "2'-hydroxy corresponding
nucleoside"

<400> SEQUENCE: 523 uccggaagug uugauaagat t 21

<210> SEQ ID NO 524
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 524 tccggaagug uugauaagat t 21

<210> SEQ ID NO 525
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 8, 12
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 11, 13, 14, 15, 16, 17, 18,
19
<223> OTHER INFORMATION: /mod_base = "2'-hydroxy corresponding
nucleoside"

<400> SEQUENCE: 525 agaugauuag gcagaggugt t 21

<210> SEQ ID NO 526
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 17
<223> OTHER INFORMATION: /mod_base = "2'-O-methyl corresponding
nucleoside"
<220> FEATURE:

<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16, 18, 19
<223> OTHER INFORMATION: /mod_base = "2'-hydroxy corresponding nucleoside"

<400> SEQUENCE: 526 aguccaagag uccucuuaut t 21

<210> SEQ ID NO 527
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 527 tugauaaaac gccgcagact t 21

<210> SEQ ID NO 528
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 13
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 15, 16, 17, 18, 19
<223> OTHER INFORMATION: /mod_base = "2'-hydroxy corresponding nucleoside"

<400> SEQUENCE: 528 guccgcggga uucagcgcct t 21

<210> SEQ ID NO 529
<211> LENGTH: 21
<212> TYPE: DNA
<213> ORGANISM: Artificial sequence <220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 529 ugagaucuuc ugcgacgcgt t 21

<210> SEQ ID NO 530
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
18, 19
<223> OTHER INFORMATION: /mod_base = "2'-hydroxy corresponding
nucleoside"

<400> SEQUENCE: 530 aaggucgguc guugacauut t 21

<210> SEQ ID NO 531
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 4, 7, 10
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base <222> LOCATION: 1, 2, 3, 5, 6, 8, 9, 11, 12, 13, 14, 15, 16, 17, 18, 19
<223> OTHER INFORMATION: /mod_base = "2'-hydroxy corresponding
nucleoside"

<400> SEQUENCE: 531 uggcacuagu aaacugagct t 21

<210> SEQ ID NO 532
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 532 tauugagaga aguccaccat t 21

<210> SEQ ID NO 533
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 533 ucuucugcga cgcggcgaut t 21

<210> SEQ ID NO 534
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 12
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 13, 14, 15, 16, 17, 18, 19
<223> OTHER INFORMATION: /mod_base = "2'-hydroxy corresponding nucleoside"

<400> SEQUENCE: 534 gaaccacuga acaaauggct t 21

<210> SEQ ID NO 535
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 8, 11
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 12, 13, 14, 15, 16, 17, 18, 19
<223> OTHER INFORMATION: /mod_base = "2'-hydroxy corresponding nucleoside"

<400> SEQUENCE: 535 aguuccgcag uauggaucgt t 21

<210> SEQ ID NO 536
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 7, 11
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 12, 13, 14, 15, 16, 17, 18, 19
<223> OTHER INFORMATION: /mod_base = "2'-hydroxy corresponding nucleoside"

<400> SEQUENCE: 536 gaugauuagg cagaggugat t 21

<210> SEQ ID NO 537
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16,
18, 19
<223> OTHER INFORMATION: /mod_base = "2'-hydroxy corresponding
nucleoside"

<400> SEQUENCE: 537 aaaauugaga gaaguccact t 21

<210> SEQ ID NO 538
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 3, 9
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 10, 11, 12, 13, 14, 15, 16, 17, 18,
19
<223> OTHER INFORMATION: /mod_base = "2'-hydroxy corresponding
nucleoside"

<400> SEQUENCE: 538 cccaagaaua uggugaccct t 21

<210> SEQ ID NO 539
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base <222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 539 agaucuucug cgacgcggct t 21

<210> SEQ ID NO 540
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 540 ucugcgacgc ggcgauugat t 21

<210> SEQ ID NO 541
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 8, 12, 14, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 9, 10, 11, 13, 15, 16, 17, 19
<223> OTHER INFORMATION: /mod_base = "2'-hydroxy corresponding nucleoside"

<400> SEQUENCE: 541 aacgccgcag acacauccat t 21

<210> SEQ ID NO 542
<211> LENGTH: 21

<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17,
19
<223> OTHER INFORMATION: /mod_base = "2'-hydroxy corresponding
nucleoside"

<400> SEQUENCE: 542 cuuggaggcu ugaacaguat t 21

<210> SEQ ID NO 543
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 9, 12, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 10, 11, 13, 14, 16, 17, 18, 19
<223> OTHER INFORMATION: /mod_base = "2'-hydroxy corresponding
nucleoside"

<400> SEQUENCE: 543 acaaauggca cuaguaaact t 21

<210> SEQ ID NO 544
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6, 13, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 14, 15, 17, 18, 19
<223> OTHER INFORMATION: /mod_base = "2'-hydroxy corresponding
nucleoside"

<400> SEQUENCE: 544 cugaacaaau ggcacuagut t 21

<210> SEQ ID NO 545
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 545 gagaucuucu gcgacgcggt t 21

<210> SEQ ID NO 546
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 13, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 14, 15, 16, 17,
19
<223> OTHER INFORMATION: /mod_base = "2'-hydroxy corresponding
nucleoside"

<400> SEQUENCE: 546 cggaaguguu gauaagauat t 21

<210> SEQ ID NO 547
<211> LENGTH: 21
<212> TYPE: DNA

<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 547 gggacugcga auuuuggcct t 21

<210> SEQ ID NO 548
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6, 10
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 11, 12, 13, 14, 15, 16, 17, 18,
19
<223> OTHER INFORMATION: /mod_base = "2'-hydroxy corresponding
nucleoside"

<400> SEQUENCE: 548 augauuaggc agaggugaat t 21

<210> SEQ ID NO 549
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 8, 11
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:

<221> NAME/KEY: modified_base
<222> LOCATION: 1, 2, 3, 4, 6, 7, 9, 10, 12, 13, 14, 15, 16, 17, 18, 19
<223> OTHER INFORMATION: /mod_base = "2'-hydroxy corresponding
nucleoside"

<400> SEQUENCE: 549 auggcacuag uaaacugagt t 21

<210> SEQ ID NO 550
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 7, 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 14, 16, 17, 19
<223> OTHER INFORMATION: /mod_base = "2'-hydroxy corresponding
nucleoside"

<400> SEQUENCE: 550 agaggacaaa cgggcaacat t 21

<210> SEQ ID NO 551
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 8, 15, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 9, 10, 11, 12, 13, 14, 16, 17, 19
<223> OTHER INFORMATION: /mod_base = "2'-hydroxy corresponding
nucleoside"

<400> SEQUENCE: 551 cacugaacaa auggcacuat t 21

<210> SEQ ID NO 552
<211> LENGTH: 21
<212> TYPE: DNA
<213> ORGANISM: Artificial sequence
<220> FEATURE:

<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 6, 12, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 7, 8, 9, 10, 11, 13, 15, 16, 17, 18, 19
<223> OTHER INFORMATION: /mod_base = "2'-hydroxy corresponding
nucleoside"

<400> SEQUENCE: 552 caauuuaugc cuacagccut t 21

<210> SEQ ID NO 553
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 11, 15, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 9, 10, 12, 13, 14, 16, 18, 19
<223> OTHER INFORMATION: /mod_base = "2'-hydroxy corresponding
nucleoside"

<400> SEQUENCE: 553 uaaaacgccg cagacacaut t 21

<210> SEQ ID NO 554
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21

<223> OTHER INFORMATION: /mod_base = "5'-phosphorothioate thymidine"

<400> SEQUENCE: 554 taaaacgccg cagacacaut t 21

<210> SEQ ID NO 555
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 3
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 555 ugcagaggug aagcgaagut t 21

<210> SEQ ID NO 556
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 14, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 17, 18,
19
<223> OTHER INFORMATION: /mod_base = "2'-hydroxy corresponding
nucleoside"

<400> SEQUENCE: 556 gugaagcgaa gugcacacgt t 21

<210> SEQ ID NO 557
<211> LENGTH: 21
<212> TYPE: DNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 14, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 16, 18, 19
<223> OTHER INFORMATION: /mod_base = "2'-hydroxy corresponding nucleoside"

<400> SEQUENCE: 557 auugagagaa guccaccact t 21

<210> SEQ ID NO 558
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 12, 16, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 13, 14, 15, 17, 19
<223> OTHER INFORMATION: /mod_base = "2'-hydroxy corresponding nucleoside"

<400> SEQUENCE: 558 auaaaacgcc gcagacacat t 21

<210> SEQ ID NO 559
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 9, 12, 14
<223> OTHER INFORMATION: /mod_base = "2'-O-methyl corresponding nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 10, 11, 13, 15, 16, 17, 18, 19
<223> OTHER INFORMATION: /mod_base = "2'-hydroxy corresponding
nucleoside"

<400> SEQUENCE: 559 caaacgggca acauaccuut t 21

<210> SEQ ID NO 560
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 4
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 560 ccucaagguc ggucguugat t 21

<210> SEQ ID NO 561
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 4, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 17, 18,
19
<223> OTHER INFORMATION: /mod_base = "2'-hydroxy corresponding
nucleoside"

<400> SEQUENCE: 561 guccaagagu ccucuuaugt t 21

<210> SEQ ID NO 562

<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 3
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 562 cucaaggucg gucguugact t 21

<210> SEQ ID NO 563
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 11, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 13, 14, 15, 16, 18,
19
<223> OTHER INFORMATION: /mod_base = "2'-hydroxy corresponding
nucleoside"

<400> SEQUENCE: 563 cucuuguucc caagaauaut t 21

<210> SEQ ID NO 564
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base <222> LOCATION: 9, 12, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 13, 14, 15, 16, 17, 19
<223> OTHER INFORMATION: /mod_base = "2'-hydroxy corresponding nucleoside"

<400> SEQUENCE: 564 cccgccugua acacgagcat t 21

<210> SEQ ID NO 565
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 565 uucugcgacg cggcgauugt t 21

<210> SEQ ID NO 566
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17, 18, 19
<223> OTHER INFORMATION: /mod_base = "2'-hydroxy corresponding nucleoside"

<400> SEQUENCE: 566 gcuuggaggc uugaacagut t 21

<210> SEQ ID NO 567

<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 567 gaucuucugc gacgcggcgt t 21

<210> SEQ ID NO 568
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 7, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 15, 16, 17, 18,
19
<223> OTHER INFORMATION: /mod_base = "2'-hydroxy corresponding
nucleoside"

<400> SEQUENCE: 568 acgaaccacu gaacaaaugt t 21

<210> SEQ ID NO 569
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 15
<223> OTHER INFORMATION: /mod_base = "2'-O-methyl corresponding
nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 17, 18, 19
<223> OTHER INFORMATION: /mod_base = "2'-hydroxy corresponding nucleoside"

<400> SEQUENCE: 569 ucguccgcgg gauucagcgt t 21

<210> SEQ ID NO 570
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 8, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 9, 10, 11, 12, 13, 14, 15, 16, 17, 19
<223> OTHER INFORMATION: /mod_base = "2'-hydroxy corresponding nucleoside"

<400> SEQUENCE: 570 ccaagaauau ggugacccat t 21

<210> SEQ ID NO 571
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3, 13
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 14, 15, 16, 17, 18, 19
<223> OTHER INFORMATION: /mod_base = "2'-hydroxy corresponding nucleoside"

<400> SEQUENCE: 571 aguauggauc ggcagaggat t 21

<210> SEQ ID NO 572

<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 9, 10, 11, 12, 13, 14, 15, 16, 18,
19
<223> OTHER INFORMATION: /mod_base = "2'-hydroxy corresponding
nucleoside"

<400> SEQUENCE: 572 caaggucggu cguugacaut t 21

<210> SEQ ID NO 573
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 10, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 11, 12, 13, 15, 16, 17, 18,
19
<223> OTHER INFORMATION: /mod_base = "2'-hydroxy corresponding
nucleoside"

<400> SEQUENCE: 573 ugagaugauu aggcagaggt t 21

<210> SEQ ID NO 574
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base <222> LOCATION: 12, 14
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 13, 15, 16, 17, 18, 19
<223> OTHER INFORMATION: /mod_base = "2'-hydroxy corresponding nucleoside"

<400> SEQUENCE: 574 gaagcgaagu gcacacggut t 21

<210> SEQ ID NO 575
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 5, 8, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 11, 12, 13, 14, 15, 16, 17, 19
<223> OTHER INFORMATION: /mod_base = "2'-hydroxy corresponding nucleoside"

<400> SEQUENCE: 575 uccgcaguau ggaucggcat t 21

<210> SEQ ID NO 576
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3, 11
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 12, 13, 14, 15, 16, 17, 18, 19
<223> OTHER INFORMATION: /mod_base = "2'-hydroxy corresponding nucleoside"

<400> SEQUENCE: 576 accacgaguc uagacucugt t 21

<210> SEQ ID NO 577
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 17
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16,
18, 19
<223> OTHER INFORMATION: /mod_base = "2'-hydroxy corresponding
nucleoside"

<400> SEQUENCE: 577 agcuuggagg cuugaacagt t 21

<210> SEQ ID NO 578
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 4, 10, 12
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 11, 13, 14, 15, 16, 17, 18, 19
<223> OTHER INFORMATION: /mod_base = "2'-hydroxy corresponding
nucleoside"

<400> SEQUENCE: 578 auuuaugccu acagccucct t 21

<210> SEQ ID NO 579
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base <222> LOCATION: 1
<223> OTHER INFORMATION: /mod_base = "nucleoside: lacks 5'-phosphate group"
<220> FEATURE:
<221> NAME/KEY: modified_base
<222> LOCATION: 3, 9, 11
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 10, 12, 13, 14, 15, 16, 17, 18, 19
<223> OTHER INFORMATION: /mod_base = "2'-hydroxy corresponding nucleoside"

<400> SEQUENCE: 579 uuuaugccua cagccuccut t 21

<210> SEQ ID NO 580
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17, 18, 19
<223> OTHER INFORMATION: /mod_base = "2'-hydroxy corresponding nucleoside"

<400> SEQUENCE: 580 aaauugagag aaguccacct t 21

<210> SEQ ID NO 581
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base <222> LOCATION: 1, 3, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 581 gcagagguga aaaaguugct t 21

<210> SEQ ID NO 582
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 582 tcgccuguaa cacgagcagt t 21

<210> SEQ ID NO 583
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 7, 14, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 15, 16, 18, 19
<223> OTHER INFORMATION: /mod_base = "2'-hydroxy corresponding nucleoside"

<400> SEQUENCE: 583 acugaacaaa uggcacuagt t 21

<210> SEQ ID NO 584
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1

<223> OTHER INFORMATION: /mod_base = "nucleoside: lacks 5'-phosphate group"
<220> FEATURE:
<221> NAME/KEY: modified_base
<222> LOCATION: 4, 7, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 8, 9, 10, 11, 12, 13, 14, 15, 16, 18, 19
<223> OTHER INFORMATION: /mod_base = "2'-hydroxy corresponding nucleoside"

<400> SEQUENCE: 584 ccgcaguaug gaucggcagt t 21

<210> SEQ ID NO 585
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 15, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 16, 18, 19
<223> OTHER INFORMATION: /mod_base = "2'-hydroxy corresponding nucleoside"

<400> SEQUENCE: 585 ggugaagcga agugcacact t 21

<210> SEQ ID NO 586
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 10, 13
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 11, 12, 14, 15, 16, 17, 18, 19
<223> OTHER INFORMATION: /mod_base = "2'-hydroxy corresponding nucleoside"

<400> SEQUENCE: 586 gcccgccugu aacacgagct t 21

<210> SEQ ID NO 587
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 11, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 13, 14, 15, 17, 18, 19
<223> OTHER INFORMATION: /mod_base = "2'-hydroxy corresponding nucleoside"

<400> SEQUENCE: 587 gaaguguuga uaagauaggt t 21

<210> SEQ ID NO 588
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 588 ugcgacgcgg cgauugagat t 21

<210> SEQ ID NO 589
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1

<223> OTHER INFORMATION: /mod_base = "nucleoside: lacks 5'-phosphate group"
<220> FEATURE:
<221> NAME/KEY: modified_base
<222> LOCATION: 9, 11
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 12, 13, 14, 15, 16, 17, 18, 19
<223> OTHER INFORMATION: /mod_base = "2'-hydroxy corresponding nucleoside"

<400> SEQUENCE: 589 ugagaaggca cagacgggct t 21

<210> SEQ ID NO 590
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 12, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 13, 14, 15, 16, 18, 19
<223> OTHER INFORMATION: /mod_base = "2'-hydroxy corresponding nucleoside"

<400> SEQUENCE: 590 ggaaguguug auaagauagt t 21

<210> SEQ ID NO 591
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 6, 14, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base <222> LOCATION: 1, 2, 3, 4, 5, 7, 8, 9, 10, 11, 12, 13, 15, 16, 18, 19
<223> OTHER INFORMATION: /mod_base = "2'-hydroxy corresponding nucleoside"

<400> SEQUENCE: 591 gaggacaaac gggcaacaut t 21

<210> SEQ ID NO 592
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 4, 12, 15, 17
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 13, 14, 16, 18, 19
<223> OTHER INFORMATION: /mod_base = "2'-hydroxy corresponding nucleoside"

<400> SEQUENCE: 592 ggacaaacgg gcaacauact t 21

<210> SEQ ID NO 593
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 4
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 593 gugcagaggu gaagcgaagt t 21

<210> SEQ ID NO 594
<211> LENGTH: 21
<212> TYPE: DNA
<213> ORGANISM: Artificial sequence
<220> FEATURE:

<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 16, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
19
<223> OTHER INFORMATION: /mod_base = "2'-hydroxy corresponding
nucleoside"

<400> SEQUENCE: 594 aggugaagcg aagugcacat t 21

<210> SEQ ID NO 595
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 595 cgggacugcg aauuuuggct t 21

<210> SEQ ID NO 596
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 7, 10, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 12, 13, 14, 15, 17, 18, 19

<223> OTHER INFORMATION: /mod_base = "2'-hydroxy corresponding
nucleoside"

<400> SEQUENCE: 596 cgccuguaac acgagcaggt t 21

<210> SEQ ID NO 597
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 11, 13, 18
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 14, 15, 16, 17, 19
<223> OTHER INFORMATION: /mod_base = "2'-hydroxy corresponding
nucleoside"

<400> SEQUENCE: 597 agugcgaauc cacacuccat t 21

<210> SEQ ID NO 598
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 598 ugccucaagg ucggucguut t 21

<210> SEQ ID NO 599
<211> LENGTH: 21
<212> TYPE: DNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 10
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 11, 12, 13, 14, 15, 16, 17, 18, 19
<223> OTHER INFORMATION: /mod_base = "2'-hydroxy corresponding nucleoside"

<400> SEQUENCE: 599 ccacgagucu agacucugut t 21

<210> SEQ ID NO 600
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 600 cuucugcgac gcggcgauut t 21

<210> SEQ ID NO 601
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3, 11, 14, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 12, 13, 15, 17, 18, 19
<223> OTHER INFORMATION: /mod_base = "2'-hydroxy corresponding nucleoside"

<400> SEQUENCE: 601 gacaaacggg caacauacct t 21

<210> SEQ ID NO 602
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6, 9
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 10, 11, 12, 13, 14, 15, 16, 17, 18,
19
<223> OTHER INFORMATION: /mod_base = "2'-hydroxy corresponding
nucleoside"

<400> SEQUENCE: 602 uuccgcagua uggaucggct t 21

<210> SEQ ID NO 603
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 9, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 12, 13, 15, 16, 17, 18,
19
<223> OTHER INFORMATION: /mod_base = "2'-hydroxy corresponding
nucleoside"

<400> SEQUENCE: 603 aguguugaua agauagggct t 21

<210> SEQ ID NO 604
<211> LENGTH: 21
<212> TYPE: DNA
<213> ORGANISM: Artificial sequence
<220> FEATURE:
<223> OTHER INFORMATION: Description of the artificial sequence:

antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 8, 11, 14
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 9, 10, 12, 13, 15, 16, 17, 18, 19
<223> OTHER INFORMATION: /mod_base = "2'-hydroxy corresponding nucleoside"

<400> SEQUENCE: 604 caaauggcac uaguaaacut t 21

<210> SEQ ID NO 605
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2, 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17, 19
<223> OTHER INFORMATION: /mod_base = "2'-hydroxy corresponding nucleoside"

<400> SEQUENCE: 605 ucaaggucgg ucguugacat t 21

<210> SEQ ID NO 606
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2
<223> OTHER INFORMATION: /mod_base = "2'-O-methyl corresponding nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 606 cuagaaaauu gagagaagut t 21

<210> SEQ ID NO 607
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 607 gacaaaggac gucccgcgct t 21

<210> SEQ ID NO 608
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 5, 8, 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 11, 12, 13, 14, 15, 17, 18, 19
<223> OTHER INFORMATION: /mod_base = "2'-hydroxy corresponding nucleoside"

<400> SEQUENCE: 608 aguccaccac gagucuagat t 21

<210> SEQ ID NO 609

<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 9, 12
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 10, 11, 13, 14, 15, 16, 17, 18,
19
<223> OTHER INFORMATION: /mod_base = "2'-hydroxy corresponding
nucleoside"

<400> SEQUENCE: 609 gaguuccgca guauggauct t 21

<210> SEQ ID NO 610
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 5, 15
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 6, 7, 8, 9, 10, 11, 12, 13, 14, 16, 17, 18, 19
<223> OTHER INFORMATION: /mod_base = "2'-hydroxy corresponding
nucleoside"

<400> SEQUENCE: 610 gcaguaugga ucggcagagt t 21

<210> SEQ ID NO 611
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 3, 6, 16

<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 7, 8, 9, 10, 11, 12, 13, 14, 15, 17, 18, 19
<223> OTHER INFORMATION: /mod_base = "2'-hydroxy corresponding
nucleoside"

<400> SEQUENCE: 611 cgcaguaugg aucggcagat t 21

<210> SEQ ID NO 612
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 1, 4, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 5, 6, 7, 8, 9, 10, 11, 12, 13, 15, 16, 17, 18, 19
<223> OTHER INFORMATION: /mod_base = "2'-hydroxy corresponding
nucleoside"

<400> SEQUENCE: 612 caguauggau cggcagaggt t 21

<210> SEQ ID NO 613
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 7
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 613 accgcguaaa gagaggugct t 21

<210> SEQ ID NO 614
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 614 gcgaggcgag ggaguucuut t 21

<210> SEQ ID NO 615
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 615 cugcgaggcg agggaguuct t 21

<210> SEQ ID NO 616
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:

<221> NAME/KEY: modified_base
<222> LOCATION: 1, 2, 3, 4, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 616 gcccuagaaa auugagagat t 21

<210> SEQ ID NO 617
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 617 cguaaagaga ggugcgccct t 21

<210> SEQ ID NO 618
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 7, 10
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 8, 9, 11, 12, 13, 14, 15, 16, 17, 18, 19
<223> OTHER INFORMATION: /mod_base = "2'-hydroxy corresponding nucleoside"

<400> SEQUENCE: 618 guuccgcagu auggaucggt t 21

<210> SEQ ID NO 619
<211> LENGTH: 21

<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 619 ucugcgaggc gagggaguut t 21

<210> SEQ ID NO 620
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 2, 12
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 13, 14, 15, 16, 17, 18,
19
<223> OTHER INFORMATION: /mod_base = "2'-hydroxy corresponding
nucleoside"

<400> SEQUENCE: 620 guauggaucg gcagaggagt t 21

<210> SEQ ID NO 621
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 12, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"

<220> FEATURE:
<221> NAME/KEY: modified_base
<222> LOCATION: 1, 2, 3, 4, 5, 6, 7, 8, 9, 10, 11, 13, 15, 16, 17, 18, 19
<223> OTHER INFORMATION: /mod_base = "2'-hydroxy corresponding nucleoside"

<400> SEQUENCE: 621 gagugcgaau ccacacucct t 21

<210> SEQ ID NO 622
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 622 guaaagagag gugcgcccgt t 21

<210> SEQ ID NO 623
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 623 gcgacgcggc gauugagact t 21

<210> SEQ ID NO 624
<211> LENGTH: 21
<212> TYPE: DNA
<213> ORGANISM: Artificial sequence
<220> FEATURE:
<223> OTHER INFORMATION: Description of the artificial sequence: antisense strand of dsRNA <220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 10, 13
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 11, 12, 14, 15, 16, 17, 18, 19
<223> OTHER INFORMATION: /mod_base = "2'-hydroxy corresponding nucleoside"

<400> SEQUENCE: 624 ggaguuccgc aguauggaut t 21

<210> SEQ ID NO 625
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 6
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 625 ccgcguaaag agaggugcgt t 21

<210> SEQ ID NO 626
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 5
<223> OTHER INFORMATION: /mod_base = "2'-O-methyl corresponding nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 626 gccucaaggu cggucguugt t 21

<210> SEQ ID NO 627
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 12, 15
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 4, 5, 6, 7, 8, 9, 10, 11, 13, 14, 16, 17, 18, 19
<223> OTHER INFORMATION: /mod_base = "2'-hydroxy corresponding nucleoside"

<400> SEQUENCE: 627 uaggaguucc gcaguauggt t 21

<210> SEQ ID NO 628
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 18
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16, 17, 19
<223> OTHER INFORMATION: /mod_base = "2'-hydroxy corresponding nucleoside"

<400> SEQUENCE: 628 gggucguccg cgggauucat t 21

<210> SEQ ID NO 629

<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 629 ugcgaggcga gggaguucut t 21

<210> SEQ ID NO 630
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 4
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 5, 6, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 630 gcguaaagag aggugcgcct t 21

<210> SEQ ID NO 631
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5
<223> OTHER INFORMATION: /mod_base = "2'-O-methyl corresponding
nucleoside"
<220> FEATURE:
<221> NAME/KEY: modified_base
<222> LOCATION: 21

<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 631 cgcguaaaga gaggugcgct t 21

<210> SEQ ID NO 632
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 16
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17, 18, 19
<223> OTHER INFORMATION: /mod_base = "2'-hydroxy corresponding nucleoside"

<400> SEQUENCE: 632 gucguccgcg ggauucagct t 21

<210> SEQ ID NO 633
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 2
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 3, 4, 5, 6, 7, 8, 9, 10, 11, 12, 13, 14, 15, 16, 17, 18, 19
<223> OTHER INFORMATION: /mod_base = "2'-hydroxy corresponding nucleoside"

<400> SEQUENCE: 633 gcagagguga agcgaagugt t 21

<210> SEQ ID NO 634
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding
nucleoside"

<400> SEQUENCE: 634 cugcgacgcg gcgauugagt t 21

<210> SEQ ID NO 635
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 6
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 635 ggauucagcg ccgacgggat t 21

<210> SEQ ID NO 636
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 17
<223> OTHER INFORMATION: /mod_base = "2'-O-methyl corresponding
nucleoside"
<220> FEATURE:
<221> NAME/KEY: modified_base <222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 16, 18, 19
<223> OTHER INFORMATION: /mod_base = "2'-hydroxy corresponding nucleoside"

<400> SEQUENCE: 636 ggucguccgc gggauucagt t 21

<210> SEQ ID NO 637
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 1, 4, 12
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 2, 3, 5, 6, 7, 8, 9, 10, 11, 13, 14, 15, 16, 17, 18, 19
<223> OTHER INFORMATION: /mod_base = "2'-hydroxy corresponding nucleoside"

<400> SEQUENCE: 637 caccacgagu cuagacucut t 21

<210> SEQ ID NO 638
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 11, 14
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 12, 13, 15, 16, 17, 18, 19
<223> OTHER INFORMATION: /mod_base = "2'-hydroxy corresponding nucleoside"

<400> SEQUENCE: 638 aggaguuccg caguauggat t 21

<210> SEQ ID NO 639
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 16, 17,
18, 19
<223> OTHER INFORMATION: /mod_base = "2'-hydroxy corresponding
nucleoside"

<400> SEQUENCE: 639 cguccgcggg auucagcgct t 21

<210> SEQ ID NO 640
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 14, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 17, 18,
19
<223> OTHER INFORMATION: /mod_base = "2'-hydroxy corresponding
nucleoside"

<400> SEQUENCE: 640 aggagugcga auccacacut t 21

<210> SEQ ID NO 641
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:

<221> NAME/KEY: modified_base
<222> LOCATION: 6, 9, 15
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 7, 8, 10, 11, 12, 13, 14, 16, 17, 18, 19
<223> OTHER INFORMATION: /mod_base = "2'-hydroxy corresponding nucleoside"

<400> SEQUENCE: 641 gccuguaaca cgagcagggt t 21

<210> SEQ ID NO 642
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1..19
<223> OTHER INFORMATION: /mod_base = "2'-hydroxy corresponding nucleoside"

<400> SEQUENCE: 642 cgggucgucc gcgggauuct t 21

<210> SEQ ID NO 643
<211> LENGTH: 21
<212> TYPE: DNA
<213> ORGANISM: Artificial sequence
<220> FEATURE:
<223> OTHER INFORMATION: Description of the artificial sequence: antisense strand of dsRNA
<220> FEATURE:
<221> NAME/KEY: modified_base
<222> LOCATION: 1
<223> OTHER INFORMATION: /mod_base = "nucleoside: lacks 5'-phosphate group"
<220> FEATURE:
<221> NAME/KEY: modified_base
<222> LOCATION: 3, 7, 12, 14
<223> OTHER INFORMATION: /mod_base = "2'-O-methyl corresponding nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 4, 5, 6, 8, 9, 10, 11, 13, 15, 16, 17, 18, 19
<223> OTHER INFORMATION: /mod_base = "2'-hydroxy corresponding nucleoside"

<400> SEQUENCE: 643 gccacccaag gcacagcuut t 21

<210> SEQ ID NO 644

<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5, 8, 14
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 9, 10, 11, 12, 13, 15, 16, 17, 18, 19
<223> OTHER INFORMATION: /mod_base = "2'-hydroxy corresponding
nucleoside"

<400> SEQUENCE: 644 ccuguaacac gagcagggct t 21

<210> SEQ ID NO 645
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 5
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 6, 7, 8, 9, 10, 11, 12, 13, 14, 15, 16, 17,
18, 19
<223> OTHER INFORMATION: /mod_base = "2'-hydroxy corresponding
nucleoside"

<400> SEQUENCE: 645 gauucagcgc cgacgggact t 21

<210> SEQ ID NO 646
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 14

<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 15, 16, 17,
18, 19
<223> OTHER INFORMATION: /mod_base = "2'-hydroxy corresponding
nucleoside"

<400> SEQUENCE: 646 ccggaagugu ugauaagaut t 21

<210> SEQ ID NO 647
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1
<223> OTHER INFORMATION: /mod_base = "nucleoside: lacks 5'-phosphate
group"
<220> FEATURE:
<221> NAME/KEY: modified_base
<222> LOCATION: 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"
<220> FEATURE:
<221> NAME/KEY: modified_base
<222> LOCATION: 1, 2, 3, 4, 5, 6, 7, 8, 9, 10, 11, 12, 13, 14, 15, 17,
18, 19
<223> OTHER INFORMATION: /mod_base = "2'-hydroxy corresponding
nucleoside"

<400> SEQUENCE: 647 uuccggaagu guugauaagt t 21

<210> SEQ ID NO 648
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 3, 5, 7, 9, 11, 13, 15, 17, 19
<223> OTHER INFORMATION: /mod_base = "2'-O-methyl corresponding
nucleoside"
<220> FEATURE:
<221> NAME/KEY: modified_base
<222> LOCATION: 2, 4, 6, 8, 10, 12, 14, 16, 18
<223> OTHER INFORMATION: /mod_base = "2'-deoxy-2'-fluoro corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 648 tuccggaagu guugauaagt t 21

<210> SEQ ID NO 649

<211> LENGTH: 17
<212> TYPE: RNA
<213> ORGANISM: Hepatitis B virus

<400> SEQUENCE: 649 aagguauguu gcccguu 17

<210> SEQ ID NO 650
<211> LENGTH: 17
<212> TYPE: RNA
<213> ORGANISM: Hepatitis B virus

<400> SEQUENCE: 650 cugcggcguu uuaucau 17

<210> SEQ ID NO 651
<211> LENGTH: 17
<212> TYPE: RNA
<213> ORGANISM: Hepatitis B virus

<400> SEQUENCE: 651 ccucugccua aucaucu 17

<210> SEQ ID NO 652
<211> LENGTH: 17
<212> TYPE: RNA
<213> ORGANISM: Hepatitis B virus

<400> SEQUENCE: 652 uguaggcaua aauuggu 17

<210> SEQ ID NO 653
<211> LENGTH: 17
<212> TYPE: RNA
<213> ORGANISM: Hepatitis B virus

<400> SEQUENCE: 653 gucugcggcg uuuuauc 17

<210> SEQ ID NO 654
<211> LENGTH: 17
<212> TYPE: RNA
<213> ORGANISM: Hepatitis B virus

<400> SEQUENCE: 654 acuagugcca uuuguuc 17

<210> SEQ ID NO 655
<211> LENGTH: 17
<212> TYPE: RNA
<213> ORGANISM: Hepatitis B virus

<400> SEQUENCE: 655 cauuuguuca gugguuc 17

<210> SEQ ID NO 656
<211> LENGTH: 17
<212> TYPE: RNA
<213> ORGANISM: Hepatitis B virus

<400> SEQUENCE: 656 caaguguuug cugacgc 17

<210> SEQ ID NO 657
<211> LENGTH: 17
<212> TYPE: RNA
<213> ORGANISM: Hepatitis B virus

<400> SEQUENCE: 657 uuacuagugc cauuugu 17

<210> SEQ ID NO 658
<211> LENGTH: 17
<212> TYPE: RNA
<213> ORGANISM: Hepatitis B virus

<400> SEQUENCE: 658 uggcucaguu uacuagu 17

<210> SEQ ID NO 659
<211> LENGTH: 17
<212> TYPE: RNA
<213> ORGANISM: Hepatitis B virus

<400> SEQUENCE: 659 aggcuguagg cauaaau 17

<210> SEQ ID NO 660
<211> LENGTH: 17
<212> TYPE: RNA
<213> ORGANISM: Hepatitis B virus

<400> SEQUENCE: 660 aguuuacuag ugccauu 17

<210> SEQ ID NO 661
<211> LENGTH: 17
<212> TYPE: RNA
<213> ORGANISM: Hepatitis B virus

<400> SEQUENCE: 661 gguauguugc ccguuug 17

<210> SEQ ID NO 662
<211> LENGTH: 17
<212> TYPE: RNA
<213> ORGANISM: Hepatitis B virus

<400> SEQUENCE: 662 ucugcggcgu uuuauca 17

<210> SEQ ID NO 663
<211> LENGTH: 17
<212> TYPE: RNA
<213> ORGANISM: Hepatitis B virus

<400> SEQUENCE: 663 aacuuuuuca ccucugc 17

<210> SEQ ID NO 664
<211> LENGTH: 17
<212> TYPE: RNA
<213> ORGANISM: Hepatitis B virus

<400> SEQUENCE: 664 cgugugcacu ucgcuuc 17

<210> SEQ ID NO 665
<211> LENGTH: 17
<212> TYPE: RNA
<213> ORGANISM: Hepatitis B virus

<400> SEQUENCE: 665 gguggacuuc ucucaau 17

<210> SEQ ID NO 666
<211> LENGTH: 17
<212> TYPE: RNA
<213> ORGANISM: Hepatitis B virus

<400> SEQUENCE: 666 ugcucguguu acaggcg 17

<210> SEQ ID NO 667
<211> LENGTH: 17
<212> TYPE: RNA
<213> ORGANISM: Hepatitis B virus

<400> SEQUENCE: 667 auguugcccg uuugucc 17

<210> SEQ ID NO 668
<211> LENGTH: 17
<212> TYPE: RNA
<213> ORGANISM: Hepatitis B virus

<400> SEQUENCE: 668 caagguaugu ugcccgu 17

<210> SEQ ID NO 669
<211> LENGTH: 17
<212> TYPE: RNA
<213> ORGANISM: Hepatitis B virus

<400> SEQUENCE: 669 cuuaucaaca cuuccgg 17

<210> SEQ ID NO 670
<211> LENGTH: 17
<212> TYPE: RNA
<213> ORGANISM: Hepatitis B virus

<400> SEQUENCE: 670 accucugccu aaucauc 17

<210> SEQ ID NO 671
<211> LENGTH: 17
<212> TYPE: RNA
<213> ORGANISM: Hepatitis B virus

<400> SEQUENCE: 671 uaagaggacu cuuggac 17

<210> SEQ ID NO 672
<211> LENGTH: 17
<212> TYPE: RNA
<213> ORGANISM: Hepatitis B virus

<400> SEQUENCE: 672 gcgcugaauc ccgcgga 17

<210> SEQ ID NO 673
<211> LENGTH: 17
<212> TYPE: RNA
<213> ORGANISM: Hepatitis B virus

<400> SEQUENCE: 673 gcgucgcaga agaucuc 17

<210> SEQ ID NO 674
<211> LENGTH: 17
<212> TYPE: RNA
<213> ORGANISM: Hepatitis B virus

<400> SEQUENCE: 674 augucaacga ccgaccu 17

<210> SEQ ID NO 675
<211> LENGTH: 17
<212> TYPE: RNA
<213> ORGANISM: Hepatitis B virus

<400> SEQUENCE: 675 cucaguuuac uagugcc 17

<210> SEQ ID NO 676
<211> LENGTH: 17
<212> TYPE: RNA
<213> ORGANISM: Hepatitis B virus

<400> SEQUENCE: 676 ucgccgcguc gcagaag 17

<210> SEQ ID NO 677
<211> LENGTH: 17
<212> TYPE: RNA
<213> ORGANISM: Hepatitis B virus

<400> SEQUENCE: 677 ccauuuguuc agugguu 17

<210> SEQ ID NO 678
<211> LENGTH: 17
<212> TYPE: RNA
<213> ORGANISM: Hepatitis B virus

<400> SEQUENCE: 678 gauccauacu gcggaac 17

<210> SEQ ID NO 679
<211> LENGTH: 17
<212> TYPE: RNA
<213> ORGANISM: Hepatitis B virus

<400> SEQUENCE: 679 caccucugcc uaaucau 17

<210> SEQ ID NO 680
<211> LENGTH: 17
<212> TYPE: RNA
<213> ORGANISM: Hepatitis B virus

<400> SEQUENCE: 680 uggacuucuc ucaauuu 17

<210> SEQ ID NO 681
<211> LENGTH: 17
<212> TYPE: RNA
<213> ORGANISM: Hepatitis B virus

<400> SEQUENCE: 681 ggucaccaua uucuugg 17

<210> SEQ ID NO 682
<211> LENGTH: 17
<212> TYPE: RNA
<213> ORGANISM: Hepatitis B virus

<400> SEQUENCE: 682 ccgcgucgca gaagauc 17

<210> SEQ ID NO 683
<211> LENGTH: 17
<212> TYPE: RNA
<213> ORGANISM: Hepatitis B virus

<400> SEQUENCE: 683 caaucgccgc gucgcag 17

<210> SEQ ID NO 684
<211> LENGTH: 17
<212> TYPE: RNA
<213> ORGANISM: Hepatitis B virus

<400> SEQUENCE: 684 ggaugugucu gcggcgu 17

<210> SEQ ID NO 685
<211> LENGTH: 17
<212> TYPE: RNA
<213> ORGANISM: Hepatitis B virus

<400> SEQUENCE: 685 acuguucaag ccuccaa 17

<210> SEQ ID NO 686
<211> LENGTH: 17
<212> TYPE: RNA
<213> ORGANISM: Hepatitis B virus

<400> SEQUENCE: 686 uuuacuagug ccauuug 17

<210> SEQ ID NO 687
<211> LENGTH: 17
<212> TYPE: RNA
<213> ORGANISM: Hepatitis B virus

<400> SEQUENCE: 687 cuagugccau uuguuca 17

<210> SEQ ID NO 688
<211> LENGTH: 17
<212> TYPE: RNA
<213> ORGANISM: Hepatitis B virus

<400> SEQUENCE: 688 cgcgucgcag aagaucu 17

<210> SEQ ID NO 689
<211> LENGTH: 17
<212> TYPE: RNA
<213> ORGANISM: Hepatitis B virus

<400> SEQUENCE: 689 aucuuaucaa cacuucc 17

<210> SEQ ID NO 690
<211> LENGTH: 17
<212> TYPE: RNA
<213> ORGANISM: Hepatitis B virus

<400> SEQUENCE: 690 gccaaaauuc gcagucc 17

<210> SEQ ID NO 691
<211> LENGTH: 17
<212> TYPE: RNA
<213> ORGANISM: Hepatitis B virus

<400> SEQUENCE: 691 ucaccucugc cuaauca 17

<210> SEQ ID NO 692
<211> LENGTH: 17
<212> TYPE: RNA
<213> ORGANISM: Hepatitis B virus

<400> SEQUENCE: 692 ucaguuuacu agugcca 17

<210> SEQ ID NO 693
<211> LENGTH: 17
<212> TYPE: RNA
<213> ORGANISM: Hepatitis B virus

<400> SEQUENCE: 693 guugcccguu uguccuc 17

<210> SEQ ID NO 694
<211> LENGTH: 17
<212> TYPE: RNA
<213> ORGANISM: Hepatitis B virus

<400> SEQUENCE: 694 agugccauuu guucagu 17

<210> SEQ ID NO 695
<211> LENGTH: 17
<212> TYPE: RNA
<213> ORGANISM: Hepatitis B virus

<400> SEQUENCE: 695 ggcuguaggc auaaauu 17

<210> SEQ ID NO 696
<211> LENGTH: 17
<212> TYPE: RNA
<213> ORGANISM: Hepatitis B virus

<400> SEQUENCE: 696 ugugucugcg gcguuuu 17

<210> SEQ ID NO 697
<211> LENGTH: 17
<212> TYPE: RNA
<213> ORGANISM: Hepatitis B virus

<400> SEQUENCE: 697 cuucgcuuca ccucugc 17

<210> SEQ ID NO 698
<211> LENGTH: 17
<212> TYPE: RNA
<213> ORGANISM: Hepatitis B virus

<400> SEQUENCE: 698 gugugcacuu cgcuuca 17

<210> SEQ ID NO 699
<211> LENGTH: 17
<212> TYPE: RNA
<213> ORGANISM: Hepatitis B virus

<400> SEQUENCE: 699 ugguggacuu cucucaa 17

<210> SEQ ID NO 700
<211> LENGTH: 17
<212> TYPE: RNA
<213> ORGANISM: Hepatitis B virus

<400> SEQUENCE: 700 gugucugcgg cguuuua 17

<210> SEQ ID NO 701
<211> LENGTH: 17
<212> TYPE: RNA
<213> ORGANISM: Hepatitis B virus

<400> SEQUENCE: 701 agguauguug cccguuu 17

<210> SEQ ID NO 702
<211> LENGTH: 17
<212> TYPE: RNA
<213> ORGANISM: Hepatitis B virus

<400> SEQUENCE: 702 caacgaccga ccuugag 17

<210> SEQ ID NO 703
<211> LENGTH: 17
<212> TYPE: RNA
<213> ORGANISM: Hepatitis B virus

<400> SEQUENCE: 703 auaagaggac ucuugga 17

<210> SEQ ID NO 704
<211> LENGTH: 17
<212> TYPE: RNA
<213> ORGANISM: Hepatitis B virus

<400> SEQUENCE: 704 ucaacgaccg accuuga 17

<210> SEQ ID NO 705
<211> LENGTH: 17
<212> TYPE: RNA
<213> ORGANISM: Hepatitis B virus

<400> SEQUENCE: 705 uauucuuggg aacaaga 17

<210> SEQ ID NO 706
<211> LENGTH: 17
<212> TYPE: RNA
<213> ORGANISM: Hepatitis B virus

<400> SEQUENCE: 706 gcucguguua caggcgg 17

<210> SEQ ID NO 707
<211> LENGTH: 17
<212> TYPE: RNA
<213> ORGANISM: Hepatitis B virus

<400> SEQUENCE: 707 aaucgccgcg ucgcaga 17

<210> SEQ ID NO 708
<211> LENGTH: 17
<212> TYPE: RNA
<213> ORGANISM: Hepatitis B virus

<400> SEQUENCE: 708 cuguucaagc cuccaag 17

<210> SEQ ID NO 709
<211> LENGTH: 17
<212> TYPE: RNA
<213> ORGANISM: Hepatitis B virus

<400> SEQUENCE: 709 gccgcgucgc agaagau 17

<210> SEQ ID NO 710
<211> LENGTH: 17
<212> TYPE: RNA
<213> ORGANISM: Hepatitis B virus

<400> SEQUENCE: 710 auuuguucag ugguucg 17

<210> SEQ ID NO 711
<211> LENGTH: 17
<212> TYPE: RNA
<213> ORGANISM: Hepatitis B virus

<400> SEQUENCE: 711 gcugaauccc gcggacg 17

<210> SEQ ID NO 712
<211> LENGTH: 17
<212> TYPE: RNA

<213> ORGANISM: Hepatitis B virus

<400> SEQUENCE: 712 gggucaccau auucuug 17

<210> SEQ ID NO 713
<211> LENGTH: 17
<212> TYPE: RNA
<213> ORGANISM: Hepatitis B virus

<400> SEQUENCE: 713 ccucugccga uccauac 17

<210> SEQ ID NO 714
<211> LENGTH: 17
<212> TYPE: RNA
<213> ORGANISM: Hepatitis B virus

<400> SEQUENCE: 714 ugucaacgac cgaccuu 17

<210> SEQ ID NO 715
<211> LENGTH: 17
<212> TYPE: RNA
<213> ORGANISM: Hepatitis B virus

<400> SEQUENCE: 715 cucugccuaa ucaucuc 17

<210> SEQ ID NO 716
<211> LENGTH: 17
<212> TYPE: RNA
<213> ORGANISM: Hepatitis B virus

<400> SEQUENCE: 716 ccgugugcac uucgcuu 17

<210> SEQ ID NO 717
<211> LENGTH: 17
<212> TYPE: RNA
<213> ORGANISM: Hepatitis B virus

<400> SEQUENCE: 717 gccgauccau acugcgg 17

<210> SEQ ID NO 718
<211> LENGTH: 17
<212> TYPE: RNA
<213> ORGANISM: Hepatitis B virus

<400> SEQUENCE: 718 agagucuaga cucgugg 17

<210> SEQ ID NO 719
<211> LENGTH: 17
<212> TYPE: RNA
<213> ORGANISM: Hepatitis B virus

<400> SEQUENCE: 719 uguucaagcc uccaagc 17

<210> SEQ ID NO 720
<211> LENGTH: 17

<212> TYPE: RNA
<213> ORGANISM: Hepatitis B virus

<400> SEQUENCE: 720 gaggcuguag gcauaaa 17

<210> SEQ ID NO 721
<211> LENGTH: 17
<212> TYPE: RNA
<213> ORGANISM: Hepatitis B virus

<400> SEQUENCE: 721 ggaggcugua ggcauaa 17

<210> SEQ ID NO 722
<211> LENGTH: 17
<212> TYPE: RNA
<213> ORGANISM: Hepatitis B virus

<400> SEQUENCE: 722 guggacuucu cucaauu 17

<210> SEQ ID NO 723
<211> LENGTH: 17
<212> TYPE: RNA
<213> ORGANISM: Hepatitis B virus

<400> SEQUENCE: 723 caacuuuuuc accucug 17

<210> SEQ ID NO 724
<211> LENGTH: 17
<212> TYPE: RNA
<213> ORGANISM: Hepatitis B virus

<400> SEQUENCE: 724 uagugccauu uguucag 17

<210> SEQ ID NO 725
<211> LENGTH: 17
<212> TYPE: RNA
<213> ORGANISM: Hepatitis B virus

<400> SEQUENCE: 725 ugccgaucca uacugcg 17

<210> SEQ ID NO 726
<211> LENGTH: 17
<212> TYPE: RNA
<213> ORGANISM: Hepatitis B virus

<400> SEQUENCE: 726 ugugcacuuc gcuucac 17

<210> SEQ ID NO 727
<211> LENGTH: 17
<212> TYPE: RNA
<213> ORGANISM: Hepatitis B virus

<400> SEQUENCE: 727 cucguguuac aggcggg 17

<210> SEQ ID NO 728

<211> LENGTH: 17
<212> TYPE: RNA
<213> ORGANISM: Hepatitis B virus

<400> SEQUENCE: 728 cuaucuuauc aacacuu 17

<210> SEQ ID NO 729
<211> LENGTH: 17
<212> TYPE: RNA
<213> ORGANISM: Hepatitis B virus

<400> SEQUENCE: 729 cucaaucgcc gcgucgc 17

<210> SEQ ID NO 730
<211> LENGTH: 17
<212> TYPE: RNA
<213> ORGANISM: Hepatitis B virus

<400> SEQUENCE: 730 cccgucugug ccuucuc 17

<210> SEQ ID NO 731
<211> LENGTH: 17
<212> TYPE: RNA
<213> ORGANISM: Hepatitis B virus

<400> SEQUENCE: 731 uaucuuauca acacuuc 17

<210> SEQ ID NO 732
<211> LENGTH: 17
<212> TYPE: RNA
<213> ORGANISM: Hepatitis B virus

<400> SEQUENCE: 732 uguugcccgu uuguccu 17

<210> SEQ ID NO 733
<211> LENGTH: 17
<212> TYPE: RNA
<213> ORGANISM: Hepatitis B virus

<400> SEQUENCE: 733 uauguugccc guuuguc 17

<210> SEQ ID NO 734
<211> LENGTH: 17
<212> TYPE: RNA
<213> ORGANISM: Hepatitis B virus

<400> SEQUENCE: 734 uucgcuucac cucugca 17

<210> SEQ ID NO 735
<211> LENGTH: 17
<212> TYPE: RNA
<213> ORGANISM: Hepatitis B virus

<400> SEQUENCE: 735 gugcacuucg cuucacc 17

<210> SEQ ID NO 736
<211> LENGTH: 17
<212> TYPE: RNA
<213> ORGANISM: Hepatitis B virus

<400> SEQUENCE: 736 ccaaaauucg caguccc 17

<210> SEQ ID NO 737
<211> LENGTH: 17
<212> TYPE: RNA
<213> ORGANISM: Hepatitis B virus

<400> SEQUENCE: 737 cugcucgugu uacaggc 17

<210> SEQ ID NO 738
<211> LENGTH: 17
<212> TYPE: RNA
<213> ORGANISM: Hepatitis B virus

<400> SEQUENCE: 738 ggagugugga uucgcac 17

<210> SEQ ID NO 739
<211> LENGTH: 17
<212> TYPE: RNA
<213> ORGANISM: Hepatitis B virus

<400> SEQUENCE: 739 acgaccgacc uugaggc 17

<210> SEQ ID NO 740
<211> LENGTH: 17
<212> TYPE: RNA
<213> ORGANISM: Hepatitis B virus

<400> SEQUENCE: 740 cagagucuag acucgug 17

<210> SEQ ID NO 741
<211> LENGTH: 17
<212> TYPE: RNA
<213> ORGANISM: Hepatitis B virus

<400> SEQUENCE: 741 aucgccgcgu cgcagaa 17

<210> SEQ ID NO 742
<211> LENGTH: 17
<212> TYPE: RNA
<213> ORGANISM: Hepatitis B virus

<400> SEQUENCE: 742 guauguugcc cguuugu 17

<210> SEQ ID NO 743
<211> LENGTH: 17
<212> TYPE: RNA
<213> ORGANISM: Hepatitis B virus

<400> SEQUENCE: 743 ccgauccaua cugcgga 17

<210> SEQ ID NO 744
<211> LENGTH: 17
<212> TYPE: RNA
<213> ORGANISM: Hepatitis B virus

<400> SEQUENCE: 744 cccuaucuuaucaacac 17

<210> SEQ ID NO 745
<211> LENGTH: 17
<212> TYPE: RNA
<213> ORGANISM: Hepatitis B virus

<400> SEQUENCE: 745 guuuacuagu gccauuu 17

<210> SEQ ID NO 746
<211> LENGTH: 17
<212> TYPE: RNA
<213> ORGANISM: Hepatitis B virus

<400> SEQUENCE: 746 gucaacgacc gaccuug 17

<210> SEQ ID NO 747
<211> LENGTH: 17
<212> TYPE: RNA
<213> ORGANISM: Hepatitis B virus

<400> SEQUENCE: 747 cuucucucaa uuuucua 17

<210> SEQ ID NO 748
<211> LENGTH: 17
<212> TYPE: RNA
<213> ORGANISM: Hepatitis B virus

<400> SEQUENCE: 748 cgcgggacgu ccuuugu 17

<210> SEQ ID NO 749
<211> LENGTH: 17
<212> TYPE: RNA
<213> ORGANISM: Hepatitis B virus

<400> SEQUENCE: 749 cuagacucgu gguggac 17

<210> SEQ ID NO 750
<211> LENGTH: 17
<212> TYPE: RNA
<213> ORGANISM: Hepatitis B virus

<400> SEQUENCE: 750 auccauacugcggaacu 17

<210> SEQ ID NO 751
<211> LENGTH: 17
<212> TYPE: RNA
<213> ORGANISM: Hepatitis B virus

<400> SEQUENCE: 751 ucugccgauc cauacug 17

<210> SEQ ID NO 752
<211> LENGTH: 17
<212> TYPE: RNA
<213> ORGANISM: Hepatitis B virus

<400> SEQUENCE: 752 cugccgauccauacugc 17

<210> SEQ ID NO 753
<211> LENGTH: 17
<212> TYPE: RNA
<213> ORGANISM: Hepatitis B virus

<400> SEQUENCE: 753 cucugccgau ccauacu 17

<210> SEQ ID NO 754
<211> LENGTH: 17
<212> TYPE: RNA
<213> ORGANISM: Hepatitis B virus

<400> SEQUENCE: 754 caccucucuu uacgcgg 17

<210> SEQ ID NO 755
<211> LENGTH: 17
<212> TYPE: RNA
<213> ORGANISM: Hepatitis B virus

<400> SEQUENCE: 755 agaacucccu cgccucg 17

<210> SEQ ID NO 756
<211> LENGTH: 17
<212> TYPE: RNA
<213> ORGANISM: Hepatitis B virus

<400> SEQUENCE: 756 aacucccucg ccucgca 17

<210> SEQ ID NO 757
<211> LENGTH: 17
<212> TYPE: RNA
<213> ORGANISM: Hepatitis B virus

<400> SEQUENCE: 757 cucucaauuu ucuaggg 17

<210> SEQ ID NO 758
<211> LENGTH: 17
<212> TYPE: RNA
<213> ORGANISM: Hepatitis B virus

<400> SEQUENCE: 758 ggcgcaccuc ucuuuac 17

<210> SEQ ID NO 759
<211> LENGTH: 17
<212> TYPE: RNA
<213> ORGANISM: Hepatitis B virus

<400> SEQUENCE: 759 cgauccauac ugcggaa 17

<210> SEQ ID NO 760
<211> LENGTH: 17
<212> TYPE: RNA
<213> ORGANISM: Hepatitis B virus

<400> SEQUENCE: 760 acucccucgc cucgcag 17

<210> SEQ ID NO 761
<211> LENGTH: 17
<212> TYPE: RNA
<213> ORGANISM: Hepatitis B virus

<400> SEQUENCE: 761 uccucugccg auccaua 17

<210> SEQ ID NO 762
<211> LENGTH: 17
<212> TYPE: RNA
<213> ORGANISM: Hepatitis B virus

<400> SEQUENCE: 762 gaguguggau ucgcacu 17

<210> SEQ ID NO 763
<211> LENGTH: 17
<212> TYPE: RNA
<213> ORGANISM: Hepatitis B virus

<400> SEQUENCE: 763 gggcgcaccu cucuuua 17

<210> SEQ ID NO 764
<211> LENGTH: 17
<212> TYPE: RNA
<213> ORGANISM: Hepatitis B virus

<400> SEQUENCE: 764 ucucaaucgc cgcgucg 17

<210> SEQ ID NO 765
<211> LENGTH: 17
<212> TYPE: RNA
<213> ORGANISM: Hepatitis B virus

<400> SEQUENCE: 765 uccauacugc ggaacuc 17

<210> SEQ ID NO 766
<211> LENGTH: 17
<212> TYPE: RNA
<213> ORGANISM: Hepatitis B virus

<400> SEQUENCE: 766 gcaccucucu uuacgcg 17

<210> SEQ ID NO 767
<211> LENGTH: 17
<212> TYPE: RNA
<213> ORGANISM: Hepatitis B virus

<400> SEQUENCE: 767 aacgaccgac cuugagg 17

<210> SEQ ID NO 768
<211> LENGTH: 17
<212> TYPE: RNA
<213> ORGANISM: Hepatitis B virus

<400> SEQUENCE: 768 cauacugcgg aacuccu 17

<210> SEQ ID NO 769
<211> LENGTH: 17
<212> TYPE: RNA
<213> ORGANISM: Hepatitis B virus

<400> SEQUENCE: 769 gaaucccgcg gacgacc 17

<210> SEQ ID NO 770
<211> LENGTH: 17
<212> TYPE: RNA
<213> ORGANISM: Hepatitis B virus

<400> SEQUENCE: 770 gaacucccuc gccucgc 17

<210> SEQ ID NO 771
<211> LENGTH: 17
<212> TYPE: RNA
<213> ORGANISM: Hepatitis B virus

<400> SEQUENCE: 771 gcgcaccucu cuuuacg 17

<210> SEQ ID NO 772
<211> LENGTH: 17
<212> TYPE: RNA
<213> ORGANISM: Hepatitis B virus

<400> SEQUENCE: 772 cgcaccucuc uuuacgc 17

<210> SEQ ID NO 773
<211> LENGTH: 17
<212> TYPE: RNA
<213> ORGANISM: Hepatitis B virus

<400> SEQUENCE: 773 cugaaucccg cggacga 17

<210> SEQ ID NO 774
<211> LENGTH: 17
<212> TYPE: RNA
<213> ORGANISM: Hepatitis B virus

<400> SEQUENCE: 774 acuucgcuuc accucug 17

<210> SEQ ID NO 775
<211> LENGTH: 17
<212> TYPE: RNA
<213> ORGANISM: Hepatitis B virus

<400> SEQUENCE: 775 ucaaucgccg cgucgca 17

<210> SEQ ID NO 776
<211> LENGTH: 17
<212> TYPE: RNA
<213> ORGANISM: Hepatitis B virus

<400> SEQUENCE: 776 cccgucggcg cugaauc 17

<210> SEQ ID NO 777
<211> LENGTH: 17
<212> TYPE: RNA
<213> ORGANISM: Hepatitis B virus

<400> SEQUENCE: 777 ugaaucccgc ggacgac 17

<210> SEQ ID NO 778
<211> LENGTH: 17
<212> TYPE: RNA
<213> ORGANISM: Hepatitis B virus

<400> SEQUENCE: 778 gagucuagac ucguggu 17

<210> SEQ ID NO 779
<211> LENGTH: 17
<212> TYPE: RNA
<213> ORGANISM: Hepatitis B virus

<400> SEQUENCE: 779 ccauacugcg gaacucc 17

<210> SEQ ID NO 780
<211> LENGTH: 17
<212> TYPE: RNA
<213> ORGANISM: Hepatitis B virus

<400> SEQUENCE: 780 cgcugaaucc cgcggac 17

<210> SEQ ID NO 781
<211> LENGTH: 17
<212> TYPE: RNA
<213> ORGANISM: Hepatitis B virus

<400> SEQUENCE: 781 guguggauuc gcacucc 17

<210> SEQ ID NO 782
<211> LENGTH: 17
<212> TYPE: RNA
<213> ORGANISM: Hepatitis B virus

<400> SEQUENCE: 782 ccugcucgug uuacagg 17

<210> SEQ ID NO 783
<211> LENGTH: 17
<212> TYPE: RNA
<213> ORGANISM: Hepatitis B virus

<400> SEQUENCE: 783 aaucccgcgg acgaccc 17

<210> SEQ ID NO 784
<211> LENGTH: 17
<212> TYPE: RNA
<213> ORGANISM: Hepatitis B virus

<400> SEQUENCE: 784 agcugugccu ugggugg 17

<210> SEQ ID NO 785
<211> LENGTH: 17
<212> TYPE: RNA
<213> ORGANISM: Hepatitis B virus

<400> SEQUENCE: 785 cccugcucgu guuacag 17

<210> SEQ ID NO 786
<211> LENGTH: 17
<212> TYPE: RNA
<213> ORGANISM: Hepatitis B virus

<400> SEQUENCE: 786 ucccgucggc gcugaau 17

<210> SEQ ID NO 787
<211> LENGTH: 17
<212> TYPE: RNA
<213> ORGANISM: Hepatitis B virus

<400> SEQUENCE: 787 ucuuaucaac acuuccg 17

<210> SEQ ID NO 788
<211> LENGTH: 17
<212> TYPE: RNA
<213> ORGANISM: Hepatitis B virus

<400> SEQUENCE: 788 uuaucaacac uuccgga 17

<210> SEQ ID NO 789
<211> LENGTH: 21
<212> TYPE: DNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 1, 2, 3, 5, 7, 8, 12, 14, 15, 16, 17
<223> OTHER INFORMATION: /mod_base = "2'-O-methyl corresponding
nucleoside"
<220> FEATURE:
<221> NAME/KEY: modified_base
<222> LOCATION: 4, 5, 9, 10, 11, 13, 18, 19
<223> OTHER INFORMATION: /mod_base = "2'-hydroxy corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 789 cuuacgcuga guacuucgat t 21

<210> SEQ ID NO 790
<211> LENGTH: 21
<212> TYPE: DNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 1, 2, 3, 4, 5, 6, 8, 9, 10, 12, 13, 14, 15, 17, 18, 19
<223> OTHER INFORMATION: /mod_base = "2'-hydroxy corresponding
nucleoside"
<220> FEATURE:
<221> NAME/KEY: modified_base
<222> LOCATION: 7, 11, 16
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate thymidine"

<400> SEQUENCE: 790 ucgaaguacu cagcguaagt t 21

<210> SEQ ID NO 791
<211> LENGTH: 21
<212> TYPE: RNA
<213> ORGANISM: Artificial sequence
<220> FEATURE:
<223> OTHER INFORMATION: Description of the artificial sequence: sense
strand of dsRNA
<220> FEATURE:
<221> NAME/KEY: modified_base
<222> LOCATION: 2, 4, 6, 11, 14, 20
<223> OTHER INFORMATION: /mod_base = "2'-O-methyl corresponding
nucleoside"
<220> FEATURE:
<221> NAME/KEY: modified_base
<222> LOCATION: 21
<223> OTHER INFORMATION: /mod_base = "5'-phosphorothioate uridine"

<400> SEQUENCE: 791 ccacaugaag cagcacgacu u 21

<210> SEQ ID NO 792
<211> LENGTH: 23
<212> TYPE: RNA
<213> ORGANISM: Artificial sequence
<220> FEATURE:
<223> OTHER INFORMATION: Description of the artificial sequence:
antisense strand of dsRNA
<220> FEATURE:
<221> NAME/KEY: modified_base
<222> LOCATION: 21, 22
<223> OTHER INFORMATION: /mod_base = "2'-O-methyl corresponding
nucleoside"
<220> FEATURE:
<221> NAME/KEY: modified_base
<222> LOCATION: 22
<223> OTHER INFORMATION: /mod_base = "5'-phosphorothioate uridine"
<220> FEATURE:
<221> NAME/KEY: modified_base
<222> LOCATION: 23
<223> OTHER INFORMATION: /mod_base = "5'-phosphorothioate cytidine"

<400> SEQUENCE: 792 aagucgugcu gcuucaugug guc 23

The invention claimed is:

1. A double-stranded ribonucleic acid molecule capable of inhibiting the expression of a Hepatitis B Virus gene in vitro wherein said double-stranded ribonucleic acid molecule comprises a sense strand comprising, in order, nucleotides 1-19 of SEQ ID 2[,] or 6 and an antisense strand at least partially complementary to the sense strand, wherein said sense strand and said antisense strand are each less than 30 nucleotides in length.

2. The double-stranded ribonucleic acid molecule of claim 1, wherein said antisense strand comprises in order nucleotides 1-19 of SEQ ID 158 or 163.

3. The double-stranded ribonucleic acid molecule of claim 2, wherein said double-stranded ribonucleic acid molecule comprises sequence pairs selected from the group consisting of SEQ ID NOs: 2/158 and 6/163.

4. The double-stranded ribonucleic acid molecule of claim 1, wherein the sense strand or the antisense strand further comprises a 3' overhang of 1-5 nucleotides in length.

5. The double-stranded ribonucleic acid molecule of claim 4, wherein the 3' overhang of the antisense strand comprises uracil or nucleotides which are complementary to the pregenomic RNA and/or the mRNA encoding the protein necessary for replication or pathogenesis of Hepatitis B Virus.

6. The double-stranded ribonucleic acid molecule of claim 4, wherein the 3' overhang of the sense strand comprises uracil or nucleotides [which] *that* are identical to the pregenomic RNA and/or the mRNA encoding the protein necessary for replication or pathogenesis of Hepatitis B Virus.

7. The double-stranded ribonucleic acid molecule of claim 1, wherein said double-stranded ribonucleic acid molecule comprises at least one modified nucleotide selected from the group consisting of: 2'-O-methyl modified nucleotide, nucleotide comprising a 5'-phosphorothioate group, terminal nucleotide linked to a cholesteryl derivative, terminal nucleotide linked to a dodecanoic acid bisdecylamide group, 2'-deoxy- 2'-fluoro modified nucleotide, [2-deoxy-nucleotide] *2'-deoxy-nucleotide*, locked nucleotide, abasic nucleotide, deoxythymidine, inverted deoxythymidine, 2'-amino-modified nucleotide, 2'-alkyl-modified nucleotide, morpholino nucleotide, phosphoramidate, and non-natural base comprising nucleotide.

8. The double-stranded ribonucleic acid molecule of claim 7, wherein said double-stranded ribonucleic acid molecule contains a 2'-O-methyl modified nucleotide, a nucleotide comprising a [5'-phosphomthioate] *5'-phosphorothioate* group, and a deoxythymidine.

9. The double-stranded ribonucleic acid molecule of claim 8, wherein said sense strand or said antisense strand *further* comprises an overhang of 1-2 deoxythymidines.

10. The double-stranded ribonucleic acid molecule of claim 9, wherein said double-stranded ribonucleic acid molecule comprises [the sequence pairs] *a sequence pair* selected from the group consisting of SEQ ID NOs: 322/486 and 327/491.

11. The double-stranded ribonucleic acid molecule of claim 1, wherein said double-stranded ribonucleic acid molecule comprises a nucleic acid sequence encoding said sense strand or said antisense strand.

12. A pharmaceutical composition comprising:

a) *a* first and *a* second double-stranded ribonucleic acid molecules each as defined in claim 1;

b) at least one nucleic acid sequence encoding sense strands or antisense strands comprising *a* first and *a* second double-stranded ribonucleic acid molecules each as defined in claim 1; or, c) a cell, tissue or non-human organism comprising *a* first and *a* second double-stranded ribonucleic acid molecules each as defined in claim 1.

13. [The] *A* pharmaceutical composition [of claim 12 wherein] *comprising*:

a) [said] *a* first [double stranded] *double-stranded* ribonucleic acid [has] *comprising* a sense strand comprising, in order, nucleotides 1-19 of SEQ ID *NO:* 2 and [said] *a* second double-stranded ribonucleic acid [has] *comprising* a sense strand comprising, in order, nucleotides 1-19 of SEQ ID *NO:* 4 or 6*;* or b) [said] *a* first [double stranded] *double-stranded* ribonucleic acid [has] *comprising* a sense strand comprising, in order, nucleotides 1-19 of SEQ ID *NO:* 6 and [said] *a* second double-stranded ribonucleic acid [has] *comprising* a sense strand comprising, in order, nucleotides 1-19 of SEQ ID *NO:* 2 or 7.

14. The pharmaceutical composition of claim 12, further comprising a pharmaceutically acceptable carrier, stabilizer, and/or diluent.

15. A method for inhibiting the expression of *a* Hepatitis B Virus gene in a cell, a tissue, or an organism, *the method* comprising:

a) introducing into the cell, tissue, or organism the double-stranded ribonucleic acid molecule as defined in claim 1; and b) maintaining the cell, tissue, or organism produced in step a) for a time sufficient to obtain degradation of the mRNA transcript of [a] *the* Hepatitis B Virus gene[, thereby inhibiting expression of a Hepatitis B Virus gene] in the cell, *tissue, or organism*.

16. The method of claim 15, wherein inhibiting *the* expression of *the* Hepatitis B Virus gene in an organism treats or manages a pathological condition or disease caused by infection with [the] Hepatitis B Virus.

17. The method *of* claim 16, wherein the pathological condition and disease caused by the infection with the Hepatitis B Virus is selected from the group consisting of: chronic liver disorder, inflammation, fibrotic condition, and proliferative disorder.

*18. The double-stranded ribonucleic acid molecule of claim 1, wherein the sense strand comprises, in order, nucleotides 1-19 of SEQ ID NO: 2, wherein the antisense strand is at least partially complementary to the sense strand, and wherein the sense strand and the antisense strand are each less than 30 nucleotides in length.*

*19. The double-stranded ribonucleic acid molecule of claim 18, wherein the double-stranded ribonucleic acid molecule contains at least one modified nucleotide.*

*20. The double-stranded ribonucleic acid molecule of claim 19, wherein the one or more modified nucleotides are independently selected from the group consisting of: a 2'-O-methyl modified nucleotide, a nucleotide comprising a 5'-phosphorothioate group, a terminal nucleotide linked to a cholesteryl derivative, a terminal nucleotide linked to a dodecanoic acid bisdecylamide group, a 2'-deoxy-2'-fluoro-modified nucleotide, a 2'-deoxy-nucleotide, a locked nucleotide, an abasic nucleotide, a deoxythymidine, an inverted deoxythymidine, a 2'-amino-modified nucleotide, a 2'-alkyl-modified nucleotide, a morpholino nucleotide, a phosphoroamidate, and a non-natural base comprising a nucleotide.*

*21. The double-stranded ribonucleic acid molecule of claim 19, wherein the double-stranded ribonucleic acid molecule comprises at least one 2'-O-methyl-modified*

*nucleotide, at least one nucleotide comprising a 5'-phosphorothioate group, and at least one deoxythymidine.*

*22. The double-stranded ribonucleic acid molecule of claim 21, wherein the sense strand or the antisense strand further comprises an overhang of 1 or 2 deoxythymidine(s).*

*23. The double-stranded ribonucleic acid molecule of claim 18, wherein the double-stranded ribonucleic acid molecule comprises the sequence pair of SEQ ID NOs: 2/158.*

*24. The double-stranded ribonucleic acid molecule of claim 19, wherein the sense strand, or the antisense strand, or both the sense strand and the antisense strand, further comprises a 3' overhang of 1-5 nucleotides in length.*

*25. A pharmaceutical composition comprising:*

*a) a double-stranded ribonucleic acid molecule of claim 19; or*

*b) a cell, tissue, or non-human organism comprising a double-stranded ribonucleic acid molecule of claim 19.*

*26. A pharmaceutical composition comprising:*

*a) a first double-stranded ribonucleic acid molecule of claim 19 and a second double-stranded ribonucleic acid molecule that is different from the first double-stranded ribonucleic acid molecule and inhibits the expression of a Hepatitis B Virus gene; or*

*b) a cell, tissue, or non-human organism comprising a first double-stranded ribonucleic acid molecule of claim 19 and a second double-stranded ribonucleic acid molecule that is different from the first double-stranded ribonucleic acid molecule and inhibits the expression of a Hepatitis B Virus gene.*

*27. The pharmaceutical composition of claim 26, wherein the second double-stranded ribonucleic acid has a sense strand comprising, in order, nucleotides 1-19 of SEQ ID NO: 3.*

*28. The pharmaceutical composition of claim 26, wherein the second double-stranded ribonucleic acid has a sense strand comprising, in order, nucleotides 1-19 of SEQ ID NO: 6.*

*29. The pharmaceutical composition of claim 27, wherein the first double-stranded ribonucleic acid molecule and the second double-stranded ribonucleic acid molecule each comprise at least one 2'-O-methyl modified nucleotide and at least one nucleotide comprising a 5'-phosphorothioate group.*

*30. The pharmaceutical composition of claim 26, wherein the first double-stranded ribonucleic acid molecule comprises the sequence pair of SEQ ID NOs: 322/486; and the second double-stranded ribonucleic acid molecule comprises the sequence pair of SEQ ID NOs: 323/487, 324/488, or 327/491.*

*31. The pharmaceutical composition of claim 25, wherein the double-stranded ribonucleic acid molecule comprises the sequence pair of SEQ ID NOs: 322/486.*

*32. The pharmaceutical composition of claim 26, wherein the first double-stranded ribonucleic acid molecule comprises the sequence pair of SEQ ID NOs: 322/486.*

*33. A method for inhibiting the expression of a Hepatitis B Virus gene in a cell, a tissue, or an organism, the method comprising:*

*a) introducing into the cell, tissue, or organism a double-stranded ribonucleic acid molecule of claim 19; and*

*b) maintaining the cell, tissue or organism produced in step a) for a time sufficient to obtain degradation of an mRNA transcript of the Hepatitis B Virus gene in the cell, tissue, or organism.*

*34. The method of claim 33, wherein the double-stranded ribonucleic acid molecule comprises the sequence pair of SEQ ID NOs: 2/158.*

*35. The method of claim 33, wherein inhibiting expression of a Hepatitis B Virus gene in an organism treats or manages a pathological condition or disease caused by infection with a Hepatitis B Virus.*

*36. The method of claim 35, wherein the pathological condition and disease caused by the infection with a Hepatitis B Virus is selected from the group consisting of: chronic liver disorder, inflammation, fibrotic condition, and proliferative disorder.*

*37. A method of treating a subject having a pathological condition or disease caused by infection with a Hepatitis B Virus, the method comprising administering to the subject a therapeutically effective amount of the pharmaceutical composition of claim 12.*

*38. The method of claim 37, wherein the pathological condition or disease caused by infection with a Hepatitis B Virus is selected from the group consisting of: chronic liver disorder, inflammation, fibrotic condition, and proliferative disorder.*

*39. A method of treating a subject having a pathological condition or disease caused by infection with a Hepatitis B Virus, the method comprising administering to the subject a therapeutically effective amount of the pharmaceutical composition of claim 13.*

*40. The method of claim 39, wherein the pathological condition or disease caused by infection with a Hepatitis B Virus is selected from the group consisting of: chronic liver disorder, inflammation, fibrotic condition, and proliferative disorder.*

*41. A method of treating a subject having a pathological condition or disease caused by infection with a Hepatitis B Virus, the method comprising administering to the subject a therapeutically effective amount of the pharmaceutical composition of claim 25.*

*42. The method of claim 41, wherein the pathological condition or disease caused by infection with a Hepatitis B Virus is selected from the group consisting of: chronic liver disorder, inflammation, fibrotic condition, and proliferative disorder.*

*43. A method of treating a subject having a pathological condition or disease caused by infection with a Hepatitis B Virus, the method comprising administering to the subject a therapeutically effective amount of the pharmaceutical composition of claim 26.*

*44. The method of claim 43, wherein the first double-stranded ribonucleic acid in the pharmaceutical composition has a sense strand comprising, in order, nucleotides 1-19 of SEQ ID NO: 2 and the second double-stranded ribonucleic acid in the pharmaceutical composition has a sense strand comprising, in order, nucleotides 1-19 of SEQ ID NO: 3.*

*45. The method of claim 43, wherein the first double-stranded ribonucleic acid in the pharmaceutical composition has a sense strand comprising, in order, nucleotides 1-19 of SEQ ID NO: 2 and the second double-stranded ribonucleic acid in the pharmaceutical composition has a sense strand comprising, in order, nucleotides 1-19 of SEQ ID NO: 6.*

*46. The method of claim 43, wherein the pathological condition or disease caused by infection with a Hepatitis B Virus is selected from the group consisting of: chronic liver disorder, inflammation, fibrotic condition, and proliferative disorder.*

*47. The method of claim 43, further comprising administering to the subject a different second pharmaceutical composition.*

*48. A double-stranded ribonucleic acid molecule that inhibits the expression of a Hepatitis B Virus gene, wherein the double-stranded ribonucleic acid molecule comprises an antisense strand comprising, in order, nucleotides 1-19 of SEQ ID NO: 158 and a sense strand at least partially complementary to the antisense strand, wherein the sense strand and the antisense strand are each less than 30 nucleotides in length.*

*49. The double-stranded ribonucleic acid molecule of claim 48, wherein the double-stranded ribonucleic acid molecule contains at least one modified nucleotide.*

*50. The double-stranded ribonucleic acid molecule of claim 49, wherein the one or more modified nucleotides are independently selected from the group consisting of: a 2'-O-methyl modified nucleotide, a nucleotide comprising a 5'-phosphorothioate group, a terminal nucleotide linked to a cholesteryl derivative, a terminal nucleotide linked to a dodecanoic acid bisdecylamide group, a 2'-deoxy-2'-fluoro-modified nucleotide, a 2'-deoxy-nucleotide, a locked nucleotide, an abasic nucleotide, a deoxythymidine, an inverted deoxythymidine, a 2'-amino-modified nucleotide, a 2'-alkyl-modified nucleotide, a morpholino nucleotide, a phosphoroamidate, and a non-natural base comprising nucleotide.*

*51. The double-stranded ribonucleic acid molecule of claim 40, wherein the double-stranded ribonucleic acid molecule comprises at least one 2'-O-methyl-modified nucleotide, at least one nucleotide comprising a 5'-phosphorothioate group, and at least one deoxythymidine.*

*52. The double-stranded ribonucleic acid molecule of claim 51, wherein the sense strand or the antisense strand further comprises an overhang of 1 or 2 deoxythymidine(s).*

*53. The double-stranded ribonucleic acid molecule of claim 49, wherein the sense strand, or the antisense strand, or both the sense strand and the antisense strand, further comprises a 3' overhang of 1-5 nucleotides in length.*

*54. A pharmaceutical composition comprising:*

*a) a double-stranded ribonucleic acid molecule of claim 49; or*

*b) a cell, tissue, or non-human organism comprising a double-stranded ribonucleic acid molecule of claim 49.*

*55. A pharmaceutical composition comprising:*

*a) a first double-stranded ribonucleic acid molecule of claim 49 and a second double-stranded ribonucleic acid molecule that is different from the first double-stranded ribonucleic acid molecule and inhibits the expression of a Hepatitis B Virus gene; or*

*b) a cell, tissue, or non-human organism comprising a first double-stranded ribonucleic acid molecule of claim 49 and a second double-stranded ribonucleic acid molecule that is different from the first double-stranded ribonucleic acid molecule and inhibits the expression of a Hepatitis B Virus gene.*

*56. The pharmaceutical composition of claim 55, wherein the first double-stranded ribonucleic acid has an antisense strand comprising, in order, nucleotides 1-19 of SEQ ID NO: 158 and the second double-stranded ribonucleic acid has an antisense strand comprising, in order, nucleotides 1-19 of SEQ ID NO: 159 or 160.*

*57. The pharmaceutical composition of claim 55, wherein the first double-stranded ribonucleic acid has an antisense strand comprising, in order, nucleotides 1-19 of SEQ ID NO: 158 and the second double-stranded ribonucleic acid has an antisense strand comprising, in order, nucleotides 1-19 of SEQ ID NO: 163.*

*58. The pharmaceutical composition of claim 56, wherein the first double-stranded ribonucleic acid molecule and the second double-stranded ribonucleic acid molecule each comprise at least one 2'-O-methyl modified nucleotide and at least one nucleotide comprising a 5'-phosphorothioate group.*

*59. The pharmaceutical composition of claim 57, wherein the first double-stranded ribonucleic acid molecule and the second double-stranded ribonucleic acid molecule each comprise at least one 2'-O-methyl modified nucleotide and at least one nucleotide comprising a 5'-phosphorothioate group.*

*60. A method for inhibiting the expression of a Hepatitis B Virus gene in a cell, a tissue, or an organism, the method comprising:*

*a) introducing into the cell, tissue, or organism the double-stranded ribonucleic acid molecule of claim 49; and*

*b) maintaining the cell, tissue or organism produced in step a) for a time sufficient to obtain degradation of the mRNA transcript of the Hepatitis B Virus gene in the cell, tissue, or organism.*

*61. The method of claim 60, wherein inhibiting the expression of the Hepatitis B Virus gene in an organism treats a pathological condition or disease caused by infection with the Hepatitis B Virus.*

*62. The method of claim 61, wherein the pathological condition and disease caused by the infection with the Hepatitis B Virus is selected from the group consisting of: chronic liver disorder, inflammation, fibrotic condition, and proliferative disorder.*

*63. A method of treating a subject having a pathological condition or disease caused by infection with a Hepatitis B Virus, the method comprising administering to the subject a therapeutically effective amount of the pharmaceutical composition of claim 54.*

*64. The method of claim 63, wherein the pathological condition or disease caused by infection with a Hepatitis B Virus is selected from the group consisting of: chronic liver disorder, inflammation, fibrotic condition, and proliferative disorder.*

*65. A method of treating a subject having a pathological condition or disease caused by infection with a Hepatitis B Virus, the method comprising administering to the subject a therapeutically effective amount of the pharmaceutical composition of claim 55.*

*66. The method of claim 65, wherein the first double-stranded ribonucleic acid in the pharmaceutical composition has an antisense strand comprising, in order, nucleotides 1-19 of SEQ ID NO: 158 and the second double-stranded ribonucleic acid in the pharmaceutical composition has an antisense strand comprising, in order, nucleotides 1-19 of SEQ ID NO: 159 or 160.*

*67. The method of claim 65, wherein the first double-stranded ribonucleic acid in the pharmaceutical composition has an antisense strand comprising, in order, nucleotides 1-19 of SEQ ID NO: 158 and the second double-stranded ribonucleic acid in the pharmaceutical composition has an antisense strand comprising, in order, nucleotides 1-19 of SEQ ID NO: 163.*

*68. The method of claim 65, wherein the pathological condition or disease caused by infection with a Hepatitis B Virus is selected from the group consisting of: chronic liver disorder, inflammation, fibrotic condition, and proliferative disorder.*

*69. The method of claim 65, further comprising administering to the subject a different second pharmaceutical composition for treating a subject having a pathological condition or disease caused by infection with a Hepatitis B Virus.*

* * * * *